US008188259B2

(12) United States Patent
Dale et al.

(10) Patent No.: US 8,188,259 B2
(45) Date of Patent: May 29, 2012

(54) OLIGONUCLEOTIDE-CONTAINING PHARMACOLOGICAL COMPOSITIONS AND THEIR USE

(75) Inventors: Roderic M. K. Dale, Wilsonville, OR (US); Amy Arrow, Bethel, ME (US); Terry Thompson, Wilsonville, OR (US)

(73) Assignee: Lakewood-Amedex, Inc., Lakewood Ranch, FL (US)

( * ) Notice: Subject to any disclaimer, the term of this patent is extended or adjusted under 35 U.S.C. 154(b) by 185 days.

(21) Appl. No.: 11/673,508

(22) Filed: Feb. 9, 2007

(65) Prior Publication Data

US 2008/0234214 A1 Sep. 25, 2008

Related U.S. Application Data

(63) Continuation of application No. 10/191,997, filed on Jul. 10, 2002, now abandoned.

(60) Provisional application No. 60/303,820, filed on Jul. 10, 2001.

(51) Int. Cl.
*C07H 21/04* (2006.01)

(52) U.S. Cl. ...................................................... 536/24.5

(58) Field of Classification Search .................. 536/24.5
See application file for complete search history.

(56) References Cited

U.S. PATENT DOCUMENTS

| | | | | |
|---|---|---|---|---|
| 4,897,355 | A | 1/1990 | Eppstein et al. | |
| 5,217,866 | A | 6/1993 | Summerton et al. | |
| 5,256,649 | A | 10/1993 | Le Fur et al. | |
| 5,474,796 | A * | 12/1995 | Brennan | 427/2.13 |
| 5,514,788 | A | 5/1996 | Bennett et al. | |
| 5,576,208 | A | 11/1996 | Monia et al. | |
| 5,591,840 | A | 1/1997 | Narayanan et al. | |
| 5,603,915 | A | 2/1997 | Nelson et al. | |
| 5,652,131 | A * | 7/1997 | Beavo et al. | 435/196 |
| 5,734,039 | A | 3/1998 | Calabretta et al. | |
| 5,776,905 | A | 7/1998 | Gibbons et al. | |
| 5,821,234 | A | 10/1998 | Dzau | |
| 5,830,140 | A | 11/1998 | Dillinger et al. | |
| 5,834,443 | A | 11/1998 | Masiello | |
| 5,849,902 | A | 12/1998 | Arrow et al. | |
| 5,948,768 | A | 9/1999 | McMichael et al. | |
| 5,951,455 | A | 9/1999 | Cowsert | |
| 5,989,912 | A | 11/1999 | Arrow et al. | |
| 5,998,203 | A | 12/1999 | Matulic-Adamic et al. | |
| 6,008,048 | A | 12/1999 | Monia et al. | |
| 6,015,886 | A | 1/2000 | Dale et al. | |
| 6,037,346 | A * | 3/2000 | Doherty et al. | 514/252.03 |
| 6,087,112 | A * | 7/2000 | Dale | 435/6 |
| 6,211,162 | B1 | 4/2001 | Dale et al. | |
| 6,211,349 | B1 | 4/2001 | Dale et al. | |
| 6,344,323 | B1 | 2/2002 | Seifert | |
| 6,395,736 | B1 * | 5/2002 | Parks et al. | 514/248 |
| 6,403,597 | B1 * | 6/2002 | Wilson et al. | 514/256 |
| 6,440,723 | B1 | 8/2002 | Dale | |
| 6,562,569 | B1 | 5/2003 | Dale | |
| 6,582,908 | B2 * | 6/2003 | Fodor et al. | 506/9 |
| 6,627,215 | B1 | 9/2003 | Dale et al. | |
| 6,656,717 | B1 | 12/2003 | Xin et al. | |
| 6,844,151 | B1 | 1/2005 | Dale | |
| 2002/0032164 | A1 | 3/2002 | Dale et al. | |
| 2002/0142980 | A1 * | 10/2002 | Thompson et al. | 514/44 |
| 2003/0045490 | A1 | 3/2003 | Dale et al. | |
| 2003/0083477 | A1 | 5/2003 | Arrow et al. | |
| 2003/0180789 | A1 | 9/2003 | Dale | |
| 2003/0207834 | A1 | 11/2003 | Dale et al. | |
| 2004/0121352 | A1 | 6/2004 | Dale | |
| 2005/0025815 | A1 | 2/2005 | Dale et al. | |
| 2005/0107344 | A1 | 5/2005 | Dale et al. | |
| 2005/0118618 | A1 | 6/2005 | Dale | |
| 2008/0161257 | A1 | 7/2008 | Dale et al. | |
| 2008/0167257 | A1 | 7/2008 | Dale et al. | |
| 2008/0234214 | A1 | 9/2008 | Dale et al. | |

FOREIGN PATENT DOCUMENTS

| | | | |
|---|---|---|---|
| WO | WO 90/14074 | A1 | 11/1990 |
| WO | WO 91/16024 | A1 | 10/1991 |
| WO | WO 91/17424 | A1 | 11/1991 |
| WO | WO 92/03568 | | 3/1992 |
| WO | WO-94/15619 | A1 | 7/1994 |
| WO | WO 94/28144 | A1 | 12/1994 |
| WO | WO 95/10938 | | 4/1995 |
| WO | WO 95/15761 | A1 | 6/1995 |
| WO | WO-97/47325 | A1 | 12/1997 |
| WO | WO 98/03533 | A1 | 1/1998 |
| WO | WO 98/13526 | A1 | 4/1998 |
| WO | WO 98/49348 | A1 | 11/1998 |
| WO | WO 99/14346 | | 3/1999 |
| WO | WO-99/53101 | A1 | 10/1999 |
| WO | WO 00/40525 | A2 | 7/2000 |
| WO | WO 00/40591 | A1 | 7/2000 |
| WO | WO 00/40592 | A | 7/2000 |
| WO | WO 00/40714 | A2 | 7/2000 |
| WO | WO 00/57890 | A1 | 10/2000 |
| WO | WO 00/70093 | A1 | 11/2000 |

(Continued)

OTHER PUBLICATIONS

Galym, et al., "Complex Host Cell Responses to Antisense Suppression of ACHE Gene Expression", Antisese & Nucleic Acid Drug Development, 11:51-57 (2001).

Rubenstein, et al., "A Review of Various Antisense Oligonucleotide Therapeutic Approaches for Prostate Cancer" *Prostate Journal*, 2(4):179-188 (2000).

Shohami, et al., "Antisense Prevention of Neuronal Damages Following a Head Injury in Mice" *J. Mol. Med.*, 78:228-236 (2000).

Bost et al., "The jun kinase 2 isoform is preferentially required for epidermal growth factor-induced transformation of human A549 lung carcinoma cells", *Mol. Cell. Biol*, 19(3):1938-1949 (1999).

Lisziewicz et al., "Specific inhibition of human immunodeficiency virus type 1 replication by antisense oligonucleotides: an in vitro model for treatment", *Proc. Natl. Acad. Sci. USA*, 89:11209-11213 (1992).

(Continued)

*Primary Examiner* — Brian Whiteman

(74) *Attorney, Agent, or Firm* — Mintz Levin Cohn Ferris Glovsky and Popeo, P.C.; Ingrid A. Beattie

(57) ABSTRACT

The present invention relates to methods and compositions containing oligonucleotides suitable for administration to humans and other mammals.

16 Claims, No Drawings

FOREIGN PATENT DOCUMENTS

| | | | |
|---|---|---|---|
| WO | WO-00/70093 | A1 | 11/2000 |
| WO | WO 01/23620 | A2 | 4/2001 |
| WO | WO 02/000854 | A1 | 11/2002 |
| WO | WO 02/089581 | A1 | 11/2002 |
| WO | WO 03/006478 | A1 | 11/2003 |

OTHER PUBLICATIONS

Normanno et al., "Growth inhibition of human colon carcinoma cellsby combinations of anti-epidermal growth factor-related growth factor antisense oligonucleotides", *Clin. Cancer Res.*, 2:601-609 (1996).

Agrawal et al., "Absorption, Tissue Distribution and In Vivo Stability in Rats of a Hybrid Antisense Oligonucleotide Following Oral Administration", Biochemical Pharmacology, v50 n4, pp. 571-576 (1995).

Agrawal et al., "Modified Oligonucleotides As Therapeutic and Diagnostic Agents", Current Opinion in Biotechnology, v 6 n1, pp. 12-19 (1995).

Agrawal et al., "Antisense Therapeutics: Is It As Simple As Simple As Complementary Base Recognition", Molecular Medicine Today, v 6 n2, pp. 72-81 (2000).

Altschul et al., "Issues in Searching Molecular Sequence Databases", Nature Genetics, v6, pp. 119-129 (1994).

Altschul et al., "Gapped BLAST and PSI-BLAST: A New Generation of Protein Database Search Programs", Nucleic Acid Research, v25 n17, pp. 3389-3402 (1997).

Belikova et al., Synthesis of Rebonucleosides and Diribonucleoside Phosphates Containing 2-Chloro-Ethylamine and Nitrogen Mustard Residues, Tetrahedron Letters, v37, pp. 3557-3562 (1967).

Bennett et al., "Parmacology of Antisense Therapeutic Agents", Methods in Molecular Medicine: Antisense Therapeutics, pp. 13-46 (1996).

Branch., "A Good Antisense Molecule Is Hard to Find", Trends in Biochemical Sciences, v23, pp. 45-50 (1998).

Chen et al., "In Vivo Expression of Single-Stranded DNA in Mammalian Cells With DNA Enzyme Sequences Targeted to C-raf", Antisense & Nucleic Acid Drug Development, v10. pp. 415-422 (2000).

Cohen et al., "Phosphorothioate Oligodeoxynucleotide Analogues", CRC Press:Boca Raton, FL, pp. 82-92, 97-117 (1989).

Dagle et al., "Oligonucleotide-Based Strategies to Reduce Gene Expression", Differentiation v69, pp. 75-82 (2001).

Egholm et al., "Peptide Nucleic Acids (PNA) Oligonucleotide Analogues With an Achiral Peptide Backbone", Journal American Chemical Society, v114, pp. 1895-1897 (1992).

Flanagan et al., "Cellular Penetration and Antisense Activity by a Phenoxazine-Substituted Heptanucleotide", Nature Biotechnology, v17 n1, pp. 48-52 (1999).

Froehler et al., "Phosporamidate Analogues of DNA: Synthesis and Thermal Stability of Heteroduplexes", Nucleic Acids Research, v16 n11, pp. 4831-4839 (1988).

Ghosh et al., "Evaluation of Some Properties of a Phosphorodithioate Oligodeoxyribonucleotide for Antisense Application", Nucleic Acids Research, v21 n24, pp. 5761-5765 (1993).

Green et al., "Antisense Oligonucleotides: An Evolving Technology for The Modulation of Gene Expression in Human Disease", Journal American College of Surgeons, v191 n1, pp. 93-105 (2000).

Henikoff et al., "Amino Acid Substitution Matrices From Protein Blocks", Proceedings of The National Academy of Sciences USA, v89, pp. 10915-10919 (1992).

Huang et al., "Acyclic Nucleic Acid Analogues: Synthesis and Oligomerization of Gamma, 4-Diamino-2oxo-1(2H)-pyrimidinepentanoic Acid and Delta, 4-Diamino-2-oxo-1(2H)-pyrimidinehexanoic Acid", Journal Organic Chemistry, v56, pp. 6007-6017 (1991).

Jen et al., "Suppression of Gene Expression by Targeted Disruption of Messenger RNA: Available Options and Current Strategies", Stem Cells, v18 n5, pp. 307-319 (2000).

Karlin et al., "Methods for Assessing the Statistical Significance of Molecular Sequence Features by Using General Scoring Schemes", Proceedings of the National Academy of Sciences USA, v 87:2264-2268 (1990).

Kushner et al., "Antisense Cancer Therapy: The State of the Science", Current Oncology Reports, v2, pp. 23-30 (2000).

Lesnick et al., "Ologiodeoxynucleotides Containing 2'-O-Modified Adeosine: Synthesis and Effects on Stability of DNA:RNA Duplexes", Biochemistry, v32 n30, pp. 7832-7838 (1993).

Ma et al., "Synthetic Oligonucleotides As Therapeutics: The Coming of Age", Biotechnology Annual Review, v5, pp. 155-196 (2000).

Marcus-Sekura et al., "Comparative Inhibition of Chloramphenicol Acetyltranserase Gene Expression by Antisense Oligonucleotide Analogus Having Alkyl Phospotriester, Methylphosphonate and Phosphothioate Linkages", Nucleic Acids Research, v15 n14, pp. 5749-5763 (1987).

Matthews et al., "Expanded Sequence Dependence of Thermodynamic Parameters Improves Prediction of RNA Secondary Structure", Journal Molecular Biology, v288, pp. 911-940 (1999).

Matthews et al., "Predicting Oligonucleotide Affinity to Nucleic Acid Targets", RNA, v5, pp. 1458-1469 (1999).

Micklefield., "Backbone Modification of Nucleic Acids: Synthesis, Structure and Therapeutic Applications", Current Medicinal Chemistry, v8 n10, pp. 1157-1179 (2001).

Milligan et al., "Current concepts in Antisense Drug Design", Journal of Medicinal Chemistry, v36 n14, pp. 1923-1937 (1993).

Miraglia et al., "Variations in mRNA Contect Have No Effect on the Potency of Antisense Oligonucleotides", Antisense & Nucleic Acid Drug Development, v10, pp. 453-461 (2000).

Neurath et al., "Cytokine Gene Transcription by NF-Kappa B Family Members in Patients With Inflammatory Bowel Disease", Annals of the New York Academy of Sciences, v859, pp. 149-159 (1998).

Neurath et al., "Local Administration of Antisense Phosphorothioate Oligonucleotides to the p65 Subunit of NF-Kappa B Abrogates Established Experimental Colitis in Mice", Nature Medicine, v2 n9, pp. 998-1004 (1996).

Rudin et al., "Phase I Trial of ISIS 5132, An Antisense Oligonucleotide Inhibitor of c-raf-1, Administered by 24-Hour Weekly Infusion to Patients With Advance Cancer", Clinical Cancer Research, v7, pp. 1214-1220 (2001).

Sambrook et al., "Molecular Cloning: A Laboratory Manual", Cold Spring Harbor Laboratory Press (1989).

Shibahara et al., "Inhibition of Human Immunodeficiency Virus (HIV-1) Replication by Synthetic Oligo-RNA Derivatives", Nucleic Acids Research, v17 n1, pp. 239-252 (1989).

Summerton., "Intracellular Inactivation of Specific Nucleotide Sequences: A General Approach to the Treatment of Viral Diseases and Virally-Mediated Cancers", Journal of Theoretical Biology, v78, pp. 77-99 (1979).

Summerton et al., "Sequence-specific Crosslinking Agents for Nucleic Acids", Journal of Molecular Biology, v122, pp. 145-162 (1978).

Vlassov et al., "Penetration of Oligonucleotides Into Mouse Organism Through Mucosa and Skin", Federation of European Biochemical Societies, v327 n3, pp. 271-274 (1993).

Weller et al., "Molecular Modeling of Acyclic Polyamide Oligonucleotide Analogues", Journal Organic Chemistry, v56 n21, pp. 6000-6006 (1991).

Zamecnik et al., "Inhibition of Rous Sarcoma Virus Replication and Cell Transformation by a Specific Oligodeoxynucleotide", Proceedings of the National Academy of Science USA, v75 n1, pp. 280-284 (1978).

Zhu et al., "Inhibition of the expression of Phosphodiesterase 5 by Antisense Inhibits the Growth of Human colon Carcinoma (HT-29) Cells in Culture", Journal for the Federation of American Societies for Experimental Biology, v15 n5, p. A924 (2001).

Zhu et al., "Stable Expression of Phospodiesterase (PDE) 5 Antisense in Human Colon Turmor HT29 Cell is Associated With Delayed G2/M Cell Cycle Progression", Proceedings of the American Association for Cancer Research Annual Meeting, v43, p. 64 (2002).

Francischi, et al., "Anti-inflammatory and analgesic effects of the phosphodiesterase 4 inhibitor rolipram in a rat model of arthritis", *Eur J. Pharmacol*., 2000, vol. 399, No. 2-3, pp. 243-249.

Higashi, et al., "Enhanced Expression of Cyclooxygenase (COX)-2 in Human Skin Epidermal Cancer Cells: Evidence for Growth Suppression by Inhibiting COX-2 Expression", *Int. J. Cancer*, vol. 86, pp. 667-671, 2000, ISSN: 0020-7136.

Khan, et al., "In Vivo Inhibition of Cyclooxygenase-2 by a Selective Phosphorothioated Oligonucleotide", *Antisense & Nucleic Acid Drug Development*, vol. 11, pp. 199-207, 2001, ISSN: 1087-2906.

Lazzeri, et al., "Effects of Prostaglandin $E_2$ and cAMP Elevating Drugs on GM-CSF Release by Cultured Human Airway Smooth Muscle Cells", *Am. J. Respir. Cell Mol. Biol.*, vol. 24, pp. 44-48 2001, XP001180092ISSN: 1044-1549.

Mardini, et al., "Selective Inhibitors of Cyclooxygenase-2: A Growing Class of Anti-Inflammatory Drugs," *Mol. Interv.*, 2001, vol. 1, No. 1, pp. 30-38.

Sano, H. Journal of Clinical and Experimental Medicine (IGAKU NO AYUMI), 2000, vol. 195, No. 7, pp. 463-468.

Seibert, et al., "Pharmacological and biochemical demonstration of the role of cyclooxygenase 2 in inflammation and pain", *Proc. Natl. Acad. Sci. USA*, vol. 91, pp. 12013-12017, 1994, ISSN: 0027-8424.

Sumitani, et al., "Specific inhibition of cyclooxygenase-2 results in inhibition of proliferation of oral cancer cell lines via suppression of prostaglandin $E_2$ production", *J. Oral Pathol. Med.*, vol. 30, pp. 41-47, 2001, ISSN: 0904-2512.

Yamada, et al., "Selective Inhibition of Cyclooxygenase-2 with Antisense Oligodeoxynucleotide Restricts Induction of Rat Adjuvant-Induced Arthritis", *Biochemical and Biophysical Research Communications*, vol. 269, pp. 415-421, 2000, ISSN: 0006-291X.

Dobashi et al. "Simultaneous Suppression of cdc2 and cdk2 Activities Induces Neuronal Differentiation of PC12 Cells." *J. Biol. Chem.* 275.17(Apr. 2000):12572-12580.

Miyake et al. "Inhibition of Progression to Androgen-Independence by Combined Adjuvant Treatment with Antisense BCL-XL and Antisense BCL-2 Oligonucleotides plus Taxol After Castration in the Shionogi Tumor Model." *Int. J. Cancer*. 86.6(Jun. 2000):855-862.

Agrawal et al. "Antisense Therapeutics." *Curr. Opin. Chem. Biol.* 2.4(1998):519-528.

Hughes et al. "The Cellular Delivery of Antisense Oligonucleotides and Ribozymes." *Drug Disc. Today.* 6.6(2001):303-315.

Okamoto et al. "Attempt for Liver-Targeted Delivery of Antisense Oligonucleotides by Cholesterol Modification and Oral Administration." *Clin. Cancer Res.* 6.1(2000):2506-2512.

Tortora et al. "Oral Antisense That Targets Protein Kinase a Cooperates With Taxol and Inhibits Tumor Growth, Antiogenesis and Growth Factor Production." *Clin. Cancer Res.* 6.1(2000):2506-2512.

Wang. "Antitumor Activity and Pharmacokineticc of a Mixed-Backbone Antisense Oligonucleotide Targeted to the RIα Subunit of Protein Kinase a After Oral Administration." *PNAS.* 96.24(1999):13989-13994.

* cited by examiner

OLIGONUCLEOTIDE-CONTAINING PHARMACOLOGICAL COMPOSITIONS AND THEIR USE

This application is a Continuation of U.S. patent application Ser. No. 10/191,997, "Oligonucleotide-Containing Pharmacological Compositions and Their Use", Roderic M.K. Dale, first author, filed Jul. 10, 2002 (abandoned), and claims the benefit of U.S. Provisional Application No. 60/303,820, filed on Jul. 10, 2001.

FIELD OF THE INVENTION

The present invention relates to compositions containing oligonucleotides, and particularly to oligonucleotide-containing compositions suitable for administration to humans and other mammals.

BACKGROUND OF THE INVENTION

Oligonucleotides, oligonucleotide analogs and other sequence-specific binding polymers designed to block translation of selected messenger RNA (the sense strand) are commonly called antisense oligonucleotides. Development of such oligonucleotides, for therapeutic applications entails selecting a target genetic sequence unique and critical to the pathogen or pathogenic state one wishes to treat. One then assembles an oligomer of genetic bases (adenine, cytosine, guanine, and thymine or uracil) complementary to that selected sequence. When such an antisense oligonucleotide binds to its targeted disease-causing sequence, it can inactivate that target and thereby alleviate the disease.

Antisense oligonucleotides offer the prospect of safe and effective therapeutics for a broad range of intractable diseases. Nonetheless, developing therapeutics that function by a true antisense mechanism presents a number of forbidding challenges. The oligonucleotides should achieve adequate efficacy at a concentration attainable within the cells of the patient. They should inhibit their selected target sequences without concomitant attack on any other sequences in the patient's pool of approximately 200 million bases of unique-sequence RNA. They should be stable in extracellular compartments and within cells. They must be deliverable into the cellular compartments containing their targeted sequences. They should be adequately soluble in aqueous solution. Finally, they should exhibit little or no toxicity at therapeutic concentrations.

First-generation antisense oligonucleotides comprised natural genetic material (Belikova et al. (1967) Tetrahedron Lett. 37, 3557-3562; Zamecnik et al. (1978) Proc. Natl. Acad. Sci. USA 75, 280-284; Summerton (1979) J. Theor. Biol. 78, 77-99) and often contained crosslinking agents for binding their targets irreversibly (Summerton et al. (1978) J. Mol. Biol. 122, 145-162). As the design challenges became more fully appreciated, a number of non-natural antisense structural types were developed in an effort to improve efficacy, stability and delivery. Of particular note are the early non-ionic DNA analogs including phosphotriester-linked DNA and methylphosphonate-linked DNA (Cohen (1989) Oligodeoxynucleotides: Antisense Inhibitors of Gene Expression, CRC Press, pp. 82-92). Other nucleic acid analogs of note include carbamate-linked DNA (Cohen (1989) Oligodeoxynucleotides Antisense Inhibitors of Gene Expression, CRC Press, pp. 97-117), phosphoroamidate-linked DNA (Froehler et al. (1988) Nucleic Acids Res. 16, 4831-4839) and 2'-O-methyl RNA (Shibahara et al. (1989) Nucleic Acids Res. 17, 239-252). These second generation oligonucleotides include oligonucleotides containing acyclic backbone moieties, including nylon (Weller et al. (1991) J. Org. Chem. 56, 6000-6006; Huang et al. (1991) J. Org. Chem. 56, 6007-6018), the exceptionally high-affinity peptide nucleic acids (PNA) (Egholm et al. (1992) J. Am. Chem. Soc. 114, 1895-1897) and related types (U.S. Pat. No. 5,217,866).

One approach to improving the potency of antisense oligonucleotides is to enhance the affinity or the efficiency with which the antisense oligonucleotides interact with their targets and induce RNase degradation of their target gene transcripts. The doses at which effects have been observed generally range from 10 to 30 mg/kg i.v. (Miragha et al. (2000) Antisense Nuc. Acid Drug Devel. 10, 453-461). Some clinical studies, however, have not demonstrated antisense activity at doses up to 30 mg/kg i.v. (Rudin et al. (2001) Clin. Cancer Res. 7, 1214-1220; Kushner et al. (2000) Curr. Oncol. Reports 2, 23-30), indicating that results vary based on the structure of the oligonucleotide administered. Typical dose-response curves for antisense oligonucleotides both in vivo and in vitro, often reveal that less than a factor of ten often separates the concentration producing antisense activity from the concentration producing no activity (Branch (1998) Trends Biochem. Sci. 23, 45-50). Since the ratio of antisense to non-antisense effects drops sharply outside a restricted concentration range, it remains challenging to identify common structural features for any antisense oligonucleotide that will enhance affinity and efficiency of the oligonucleotide for its target. Furthermore, no studies to date have identified common structural features of antisense oligonucleotides that would make them suitable for oral administration, thus necessitating intravenous administration (Chen et al. (2000) Antisense Nuc. Acid. Drug Develop. 10, 415-422). Identification of common structural modifications of antisense oligonucleotides that facilitate oral or topical administration would therefore also be advantageous.

Although each of these newer structural types provides one or more significant advantages over the first-generation oligonucleotides, none yet appear to provide the full combination of properties needed in antisense therapeutics for successful therapeutic applications.

SUMMARY OF THE INVENTION

The invention encompasses a composition suitable for administration in a mammal comprising a modified oligonucleotide of about seven to seventy-five nucleotides containing seven or more contiguous ribose groups linked by achiral 5' to 3' internucleoside phosphate linkages, wherein the modified oligonucleotide is complementary to a region of a gene associated with a pathological disorder. In some embodiments, the mammal is a human and the oligonucleotide is a ribonucleotide or deoxyribonucleotide. The modified oligonucleotide can be complementary to a region of the gene selected from the group consisting of the 5' UTR region, translational start site, the 3' UTR, and translational termination site.

In some embodiments, the gene is a gene selected from Table 1 and the pathological disorder is selected from the group consisting of abnormal appetite, hypertension, hypercholesterolemia, hyperlipidemia, erectile dysfunction, eczema, depression, anxiety, stress, inflammatory bowel syndrome, ulcerative colitis, Crohn's disease, renal stones, gall stones, constipation, migraine headache, seizure, multiple sclerosis, polymyositis, fibromyalgia, Parkinson's disease, ALS, chronic pain, pre-menstrual syndrome, sinusitis, colds, trauma, carpal tunnel syndrome, chronic fatigue syndrome, rosacea, arthritis, psoriasis, prostatitis, inflammation, heartburn, infection, poison ivy, colon cancer, malignant melanoma and malignant nasal polyps. In preferred embodiments, the modified oligonucleotide is selected from the group consisting of SEQ ID NO: 1-81

In some embodiments, the modified oligonucleotide is present in the composition at a concentration effective to reduce the expression of the gene when administered. When the composition is administered, the modified oligonucleotide is administered at a dose of less than 100 μg/kg, preferably less than 50 μg/kg, more preferably less than 5.0 μg/kg, even more preferably less than 0.50 μg/kg, yet even more preferably less than 0.050 μg/kg, and most preferably less than 0.0050 μg/kg. Furthermore, the modified oligonucleotide present in the composition may be suitable for oral administration.

The modified oligonucleotides present in the compositions of the invention preferably have a Tm of about 75-115° C. at a concentration of 1 mM and a length of 10 to 26 bases, or a Tm of 40° C. to 85° C. at a concentration of 1 pM and a length of 10 to 26 bases. In one embodiment, the ribose group has a modified 2' substituent selected from the group consisting of hydrogen, methoxy, propoxy, methoxy-ethoxy, flourine, chlorine, bromine and iodine. In another embodiment, the modified oligonucleotide is 3' or 5' end-blocked.

The compositions of the invention may be formulated as pharmaceutical compositions, nutritional or dietary supplement compositions, or as cosmetic compositions. In some embodiments, the compositions of the invention comprise two or more different modified oligonucleotides, while in other embodiments, three or more different modified oligonucleotides.

The invention also encompasses a method of treating a patient with a pathological disorder comprising administering one or more of the aforementioned modified oligonucleotides of the invention, wherein the modified oligonucleotides are about seven to seventy-five nucleotides, contain seven or more contiguous ribose groups linked by achiral 5' to 3' internucleoside phosphate linkages. Preferably, the modified oligonucleotide is complementary to a region of a gene associated with the pathological disorder. More preferably, the gene is selected from Table 1 and the aforementioned pathological disorders are selected from the group consisting of abnormal appetite, hypertension, hypercholesterolemia, hyperlipidemia, erectile dysfunction, eczema, depression, anxiety, stress, inflammatory bowel syndrome, ulcerative colitis, Crohn's disease, renal stones, gall stones, constipation, migraine headache, seizure, multiple sclerosis, polymyositis, fibromyalgia, Parkinson's disease, ALS, chronic pain, pre-menstrual syndrome, sinusitis, colds, trauma, carpal tunnel syndrome, chronic fatigue syndrome, rosacea, arthritis, psoriasis, prostatitis, inflammation, heart burn, infection, poison ivy, colon cancer, malignant melanoma and malignant nasal polyps.

As mentioned above, the invention includes a nutritional supplement comprising a modified oligonucleotide of about seven to seventy-file nucleotides containing seven or more contiguous ribose groups linked by achiral 5' to 3' internucleoside phosphate linkages. The invention also includes a method of supplementing the diet of an individual comprising administering this nutritional supplement, wherein administration of the nutritional supplement improves the health of the individual.

The invention further includes a cosmetic composition comprising a modified oligonucleotide of about seven to seventy-file nucleotides containing seven or more contiguous ribose groups linked by achiral 5' to 3' internucleoside phosphate linkages, wherein the modified oligonucleotide is complementary to a region of a gene associated with a skin disorder. The invention also includes a method of improving the appearance of the skin in an individual with a skin disorder comprising administering this cosmetic composition.

DETAILED DESCRIPTION

The present invention relates to compositions that comprise oligonucleotide molecules, and the use of such compositions to treat the symptoms of diseases/conditions such as acroparaesthsia, allergic (psoric) conditions, allergic reactions, alopecia, amnesia, anaphrodisia, angina, arthritis, asthenopia, biliary sycosis, burns, cancerous conditions, such as colon cancer, malignant melanoma and malignant nasal polyps, carpal tunnel syndrome, colds, conjunctivitis, Crohn's disease, depression, depressive psychosis, dysthyroidism, epilepsy, erectile dysfunction, excessive appetite (i.e., appetite control and suppression, promotion of healthy weight loss while naturally satisfying the appetite), gingivitis, heart burn (i.e., relief of occasional heartburn or occasional acid indigestion), hemorrhage, hypertension (i.e. helps maintain cardiovascular function, and a healthy heart and circulatory system), high cholesterol (i.e., helps to maintain cholesterol levels that are already within the normal range), hyperthyroidism, infections, inflammatory disease, lack of willpower, laryngitis, leucopenia, liver disorders, mental disorders (i.e., reduces stress, frustration, muscle tension, anxiety, and occasional simple nervous tension; enhances resistance to stress), myopia, neurosis, neurological disorders such as multiple sclerosis and ALS, obesity, pain (i.e., relief of minor or temporary aches and pains), pancreatic disorders, poison ivy, premature senescence, pre-menstrual syndrome (i.e., treatment of common symptoms associated with the menstrual cycle such as edema, breast tenderness, headaches, skin problems, cramps and mild mood changes), prostatitis, psoriasis, rosacea, seborrhea, sinusitis, and trauma.

The Oligonucleotide

Generally

A double-stranded DNA molecule encoding a gene has both a sense and an antisense strand. The transcription of RNA uses the antisense strand to make an exact sequence copy of the sense strand (with the minor changes of employing uridine for thymidine, and an RNA backbone in lieu of a DNA backbone). Thus, the RNA formed in transcription has the same nucleotide sequence as the sense strand of the gene. The RNA transcript is processed in the cell to become mRNA, which may subsequently be used as a template to make protein.

The term "oligonucleotides" as used herein, refers to a molecule comprised of nucleotides (i.e., ribonucleotides, deoxyribonucleotides, or both). The term includes monomers and polymers of ribonucleotides and deoxyribonucleotides, or mixtures thereof, with the nucleotides being connected together via, for example 5' to 3' linkages, 5' to 2' linkages, etc. The nucleotides used in the oligonucleotides may be naturally occurring or may be synthetically produced analogues that are capable of forming base-pair relationships with naturally occurring base pairs. Examples of non-naturally occurring bases that are capable of forming base-pairing relationships include, but are not limited to, aza and deaza pyrimidine analogues, aza and deaza purine analogues, and other heterocyclic base analogues, wherein one or more of the carbon and nitrogen atoms of the purine and pyrimidine rings have been substituted by heteroatoms, e.g., oxygen, sulfur, selenium, phosphorus, etc.

The oligonucleotides of the present invention are at least five contiguous nucleotides in length. For example, the oligonucleotide can be five to seventy-five nucleotides in length.

The oligonucleotide can also be at least ten sequential nucleotides and alternatively, at least fifteen sequential nucleotides in length. In one embodiment, the oligonucleotide is twelve to twenty-six nucleotides in length. The oligonucleotide sequence can be derived from any of the genes listed in Table 1 (SEQ ID NO: 82-132). Examples of suitable antisense oligonucleotide sequences for the compositions of the present invention are described in Table 1 below.

TABLE 1

Representative antisense oligonucleotides

| Oligo Name(s) | Gene Target (Accession #) | Nucleic Acid Sequence | SEQ ID |
|---|---|---|---|
| Asm | PDE-4 phosphodiesterase 4 (U50158) (SEQ ID NO: 82) | CGTGTCAGGAGAAC | 1 |
| Ace1, Ace12 | angiotensin I converting enzyme (J04144.1) (SEQ ID NO: 83) | CATGACGCGGTGCG | 2 |
| Acid-2 | ATP4A H+/K+ ATPase alpha (NM_000704) (SEQ ID NO: 84) | GGCAGTCGTCCCTCTA | 3 |
| Acid B2 | ATP4B H+/K+ ATPase beta (NM_000705) (SEQ ID NO: 85) | AACGTTTCAC1TCTCA | 4 |
| cd18-1 | Cd-18 (M15395) (SEQ ID NO: 86) | TTGCTACCAGTCT | 5 |
| COX2 CX2 | cyclooxygenase 2 (M90100) (SEQ ID NO: 87) | TCTACAGTTCAGTCGA | 6 |
| Mg44 | HMGCoA reductase 3-hydroxy-3-methylglutaryl-coenzyme A reductase (NM_000859) (SEQ ID NO: 88) | TGACAACATTGTAGCTAC, AGCTACAGAATCCTTGGA, GTCGGGCTATTCAGGC | 7 8 9 |
| P65-2M 65 | NfkappaB p65 (NM_021975) (SEQ ID NO: 89) | GAACAGTTCGTCCATG | 10 |
| IL-501 | IL-5 (NM_000879) (SEQ ID NO: 90) | CCTCATGGCTCTGAA | 11 |
| LO5 | lipoxygenase 5 (J03571) (SEQ ID NO: 91) | GGAGGGCATGGCGCGG | 12 |
| MPB-19 | SRD5A2 steroid 5-alpha-reductase-2 (M74047) (SEQ ID NO: 92) | CCTGCATCGCGCCGTG | 13 |
| NEP-1 CALLA | neutral endopeptidase (NM_000902) (SEQ ID NO: 93) | GACTTGCCCATCACCT | 14 |
| NPY-1 | Neuropeptide Y (K01911) (SEQ ID NO: 94) | ACCTAGCATGGTGGCT | 15 |
| D5 PDE5.1 | phosphodiesterase 5 (SEG_AB001615) (SEQ ID NO: 95) | CGCTCCATGGTTGGC | 16 |
| D7 | phosphodiesterase 7A (L12052) (SEQ ID NO: 96) | CTTCCATTGAATACGC | 17 |

TABLE 1-continued

| Representative antisense oligonucleotides | | | |
|---|---|---|---|
| Oligo Name(s) | Gene Target (Accession #) | Nucleic Acid Sequence | SEQ ID |
| Per | Perilipin (AB005293) (SEQ ID NO: 97) | ACTGCCATCCTCGCTC | 18 |
| TTP TTPII | tripeptidyl peptidase II (M73047) (SEQ ID NO: 98) | CGGTGGCCATGGACGC, AAGTTCATGGTTTCGGA | 19 20 |
| MTP | Microsomal trigylceride protein (X59657) (SEQ ID NO: 99) | GAATCATATTTGACCAGCA | 21 |
| HisR1 | Histamine receptor 1 (D14436) (SEQ ID NO: 100) | GGCTCATTGGCGCAAG, AGAGCCTCCCTTAGGA | 22 23 |
| CRP | C-reactive protein (M11880) (SEQ ID NO: 101) | CATGGTCACGTCCTGC | 24 |
| CETP | Cholesteryl ester transfer protein (XM_008050) (SEQ ID NO: 102) | ATGGTTATCAGGCAGTGG, CATGGTTATCAGGCAGTGG, CTGAAGAATTGACCAC | 25 26 27 |
| ICAM | ICAM-1 (303132) (SEQ ID NO: 103) | CATAGCGAGGCTGAGG | 28 |
| TNF-α | Tumor necrosis factor-alpha (X02910) (SEQ ID NO: 104) | GTGCTCATGGTGTCC | 29 |
| BMP-4 | Bone morphogenic protein-4 (U43842) (SEQ ID NO: 105) | CGACCATCAGCATTC | 30 |
| BAR-1, BB1 | beta adrenergic receptor-I (NM_000684) (SEQ ID NO: 106) | GCCCATGCCGAGCTGC | 31 |
| IL-6 | Interleukin-6 (X04430) (SEQ ID NO: 107) | AGGAGTTCATAGCTGG | 32 |
| FAAH, $FA_2H$ | fatty acid amid hydrolase (U82535) (SEQ ID NO: 108) | GCACCATGATCCCTTC | 33 |
| ACAT-I | sterol-O-acyl-transferase (XM_031119) (SEQ ID NO: 109) | CTTCACCCACCATTGT | 34 |
| IBAT | ileal sodium dependent bile acid transporter (NM_000452) (SEQ ID NO: 110) | CATTCATTGCTGGGTCTG | 35 |
| HMGIC | High mobility group phosphor-protein isoform C (U28749) (SEQ ID NO: 111) | CGTGCGCTCATCCTG, AACGTTGCGCCCCCTA | 36 37 |
| Ghre | Ghrelin (NM_016362) (SEQ ID NO: 112) | TGCAGACAGGTGGGCC, GCATGGCCTCAGCTGGG, TGGGCGATCACTTGTC | 38 39 40 |

TABLE 1-continued

| Representative antisense oligonucleotides | | | |
|---|---|---|---|
| Oligo Name(s) | Gene Target (Accession #) | Nucleic Acid Sequence | SEQ ID |
| AATIR | angiotensin II receptor (S77410) (SEQ ID NO: 113) | CATTTTGATCACCTGGGT, CGAACATGTCACTCAA | 41 42 |
| VEGF | vascular endothelial growth factor (XM_166457) (SEQ ID NO: 114) | AAGTTCATGGTTTCGGA, TCACCGCCTCGGCTTGT | 43 44 |
| FAS | fatty acid synthase (U29344) (SEQ ID NO: 115) | CCTCCTCCATGGCTG, GCCTAGCCCTCCCGC | 45 46 |
| AmP | amyloid P (NM_001639) (SEQ ID NO: 116) | GCAGCGGCTTGTTCAT, GAGTCAAGACCTCAG | 47 48 |
| PanLip | pancreatic lipase (NM_000936) (SEQ ID NO: 117) | GTGGCAGCATCGTGGC, CCTAACACGGTGTGAG | 49 50 |
| ACC2 | Acetyl-CoA carboxylase (U89344) (SEQ ID NO: 118) | GAAGCAAGACCATTCAG, TCAGGTGGAGGCCGGGC | 51 52 |
| PKARIIbeta | cAMP dependent protein kinase subunit RII-beta (M31158) (SEQ ID NO: 119) | TGCTCATCCTGCCTCC, GCTTCATGCAGTGGGT | 53 54 |
| VR1R | vanilloid receptor subtype 1 (XM_008512) (SEQ ID NO: 120) | TCTTCATCCTTGCTGG, CTCACTTCTCCCCGGA | 55 56 |
| ADAMTS | disintegrin-like and metalloprotease with thrombospodin type 1 motif 4 (NM_005099) (SEQ ID NO: 121) | GGGACATGGCACTGGT, TTATTTCCTGCCCGCC | 57 58 |
| NPY-Y5R | neuropeptide Y5 receptor (U94320) (SEQ ID NO: 122) | TGTGGCAGGTCAGTTG, ATCCATATTATAGTCT, TATTACATATGAAGAC | 59 60 61 |
| GNTV | mannosyl (alpha-1,6)glycoprotein beta-1,6-N-acetyl glucosaminyl transferase (SEQ ID NO: 123) | AGCCATTGCTCTCTGG, TGCTATAGGCAGTCTT | 62 63 |
| FCRG3 | FC-gamma receptor III-1 (X16863) (SEQ ID NO: 124) | TGCCACATGATGCCAC, GTTGAGCTTCAAATGT | 64 65 |
| CD40L | tumor necrosis factor (ligand) superfamily, member 5 (XM_042961) (SEQ ID NO: 125) | TCGATCATGCTGTGTT, AGGTGACACTGTTCAG | 66 67 |
| ETS-1 | erythorblastosis virus oncogene honiolog 1 (J04101) (SEQ ID NO: 126) | ACGGCCGCCTTCATGG, GCCATCACTCGTCGGC | 68 69 |
| ADAMTS-5 | disintegrin-like metalloprotease with throbospondin type 1, motif 5 (XM_047802) (SEQ ID NO: 127) | CCGAGCAGCATAGTGC, TCATAACCACAGGGTA | 70 71 |
| PTP-1B | protein tyrosine phosphatase, non-receptor | CATGACGGGCCAGGGC, GGGTCAGGCTATGTGT | 72 73 |

TABLE 1-continued

Representative antisense oligonucleotides

| Oligo Name(s) | Gene Target (Accession #) | Nucleic Acid Sequence | SEQ ID |
|---|---|---|---|
| | type 1 (NM_002827) (SEQ ID NO: 128) | | |
| MMP-1 | matrix metalloproteinase 1 (NM_002421) (SEQ ID NO: 129) | GCATACTGGCCTTTGTC, TCAATTTTTCCTGCAGT | 74 75 |
| Cat | catalase (NM_001752) (SEQ ID NO: 130) | GCCATAGCGTGCGGTT, CCCGGCCTCACAGATT | 76 77 |
| MMP-17 | matrix metalloproteinase 17 (NM_016155) (SEQ ID NO: 131) | CATGGCGCTCACATGGG, TGTCATAGCGTCAGGGC | 78 79 |
| OPG | osteoprotegerin (U94332) (SEQ ID NO: 132) | TCATTGTGGTCCCCGG, TCCAGTTATAAGCAGC | 80 81 |
| Nu-3 | | 3'5'-dibutyl-diphospho-thymidine | |

In one embodiment, the oligonucleotide composition of the present invention comprises at least about two oligonucleotides of differing sequence. In another embodiment, the oligonucleotide composition of the present invention comprises at least about three, four, five, six, seven, eight, nine, or ten oligonucleotides of differing sequences. Although Table 1 depicts the sequences as oligonucleotides containing only deoxyribonucleotide residues, it is to be understood that the present invention also includes the embodiments wherein the oligonucleotides are composed of ribonucleotide residues (e.g., by substituting uridine for thymidine, and ribosyl substituents for deoxyribosyl substituents). Moreover, it is to be understood that the present invention also includes the embodiments in which the oligonucleotides are composed of only deoxyribonucleotide residues, of only ribonucleotide residues, or of mixtures of deoxyribonucleotide and ribonucleotide residues.

The oligonucleotides in the present invention display greater than or equal to 80 percent sequence identity to a nucleotide sequence selected from the group of SEQ ID NO: 1-81 (see Table 1). Also preferred, the oligonucleotides display greater than or equal to 85 percent sequence identity to a nucleotide sequence selected from the group of SEQ ID NO: 1-81. Still preferred, the oligonucleotides display 90 percent sequence identity and still more preferred, the oligonucleotides display 95 percent sequence identity. Most preferably, the oligonucleotides of the present invention are selected such that their nucleotide sequence is complementary to the sense strand of a gene.

The degree of similarity between two sequences can be determined using methods well known to the art (e.g., computer programs including Fasta (Oxford Molecular Group Inc.) and BLAST (www.ncbi.nlm.nih.gov) (Altschul et al. (1997) Nucleic Acid Res. 25, 3389-3402). These methods can be employed to take into account gaps in the sequences due to deletions or insertions. Homology or sequence identity at the nucleotide or amino acid sequence level determined by BLAST (Basic Local Alignment Search Tool) analysis uses the algorithm employed by the programs blastp, blastn, blastx, tblastn and tblastx (Altschul et al. (1997) Nucleic Acids Res. 25, 3389-3402 and Karlin et al. (1990) Proc. Natl. Acad. Sci. USA 87, 2264-2268, both fully incorporated by reference) which are tailored for sequence similarity searching. The approach used by the BLAST program is to first consider similar segments, with gaps (non-contiguous) and without gaps (contiguous), between a query sequence and a database sequence, then to evaluate the statistical significance of all matches that are identified and finally to summarize only those matches which satisfy a preselected threshold of significance.

For a discussion of basic issues in similarity searching of sequence databases, see Altschul et al. (1994) Nature Genetics 6, 119-129 which is fully incorporated by reference. The search parameters for histogram, descriptions, alignments, expect (i.e., the statistical significance threshold for reporting matches against database sequences), cutoff, matrix and filter (low complexity) are at the default settings. The default scoring matrix used by blastp, blastx, tblastn, and tblastx is the BLOSUM62 matrix (Henikoff et al. (1992) Proc. Natl. Acad. Sci. USA 89, 10915-10919, fully incorporated by reference), recommended for query sequences over 85 nucleotides or amino acids in length.

For blastn, the scoring matrix is set by the ratios of M (i.e., the reward score for a pair of matching residues) to N (i.e., the penalty score for mismatching residues), wherein the default values for M and N are +5 and −4, respectively. Four blastn parameters were adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In a related vein, the oligonucleotides described herein have a Guanine:Cytosine (GC content) greater than 35 percent. The GC content is preferably greater than 40 percent and most preferably, greater than 45 percent.

The Modified Oligonucleotide

The oligonucleotides that may be employed in accordance with the present invention may be modified. An oligonucleotide that comprises at least one modification has one or more chemical modifications at the molecular level of the natural molecular structures of all or any of the nucleic acid bases, sugar moieties, internucleoside phosphate linkages, as well as molecules having added substituents, such as diamines, cholesteryl or other lipophilic groups, or a combination of modifications at these sites. For example, oligonucleotides can be end-blocked, protonated, exhibit substantial acid resistance, substantial nuclease resistance, and contain achiral internucleoside phosphate linkages and modified ribose or deoxyribose substituents.

The term "end-blocked" as used herein refers to a nucleic acid with a chemical modification at the molecular level that prevents the degradation of selected nucleotides, e.g., by exonuclease action. This chemical modification is positioned such that it protects the integral portion of the nucleic acid, for example the portion of an RNA or DNA that is chemically similar to the gene involved in the physiological condition. An end block may be a 3' end block, a 5' end block, or both. For example, a 3' end block may be at the 3'-most position of the molecule, or it may be internal to the 3' ends, provided it is 3' of the integral sequences of the nucleic acid.

The term "protonated compound" refers to a molecule of the invention that, when dissolved in water having a pH of 7 causes the pH of the solution to fall. Generally, compounds are protonated by adding protons to the reactive sites on the molecule, although other modifications of the molecule are possible, and are intended to be encompassed by this term. Such protonation can be accomplished, for example by incubating the compound in the presence of a strong acid, most preferably one with a volatile conjugate base. The term "protonation" and "acidification" as used interchangeably herein refers to the process by which protons (or positively charged hydrogen ions) are added to proton acceptor sites on a compound of the invention. The proton acceptor sites include the substituted or unsubstituted phosphates of the central group, as well as any additional proton acceptor sites on either the central group or the end blocking groups. As the pH of the solution is decreased, the number of these acceptor sites which are protonated increases, resulting in a more highly protonated compound.

Many nucleic acid backbones are not stable at low pH (e.g., pH 1-3) and experience depurination, although a number of backbones are relatively stable at pH 4-5. One aspect of the present invention reflects the recognition that certain modifications, including 2'-halide, 2'-O-alkyl, 3'-O-alkyl, and 2'-O-alkyl-n(O-alkyl) nucleic acid molecules are stable at the desired pH of 2 to 1. These modifications enhance the ability of the oligonucleotides of the pharmacological compositions of the present invention to affect a condition in vivo. Thus, the composition of the present invention may include nucleic acid molecules that are substantially acid resistant. The compositions of the present invention may also include nucleic acid molecules that are nuclease resistant. This includes nucleic acid molecules completely derivatized by 2'-O-methylphosphodiesters, 2'-O-alkyl, 2'-O-alkyl-n(O-alkyl), 2'-fluoro, 2'-deoxy-erythropentofuranosyl, chimeric linkages, and any other backbone modifications, as well as other modifications, which render the nucleic acid molecules substantially resistant to endogenous nuclease activity. Additional suitable methods of rendering nucleic acid molecules nuclease resistant include, but are not limited to, covalently modifying the purine or pyrimidine bases that comprise the nucleic acid. For example, bases may be methylated, hydroxymethylated, or otherwise substituted (e.g., glycosylated) such that the nucleic acid molecules comprising the modified bases are rendered substantially nuclease resistant. Nuclease resistance also aids the oligonucleotides of the compositions of the present invention in retaining their effect in vivo.

Preferably, the oligonucleotides of the of the present invention remain relatively unchanged chemically upon administration to a subject and retain their activity in acidic conditions (pH less than 6.0) or in the presence of an endonuclease or exonuclease (e.g., in an in vivo setting).

The term "substantially acid resistant" as used herein refers to nucleic acid molecules that are resistant to acid degradation as compared to unmodified nucleic acid molecules. Typically, the relative acid resistance of a nucleic acid will be measured by comparing the percent degradation of a resistant nucleic acid with the percent degradation of its unmodified counterpart (i.e., a corresponding nucleic acid of the same length and sequence having a "normal" backbone and bases). A nucleic acid that is acid resistant is preferably at least one and a half times more resistant to acid degradation, more preferably at least two times more resistant, even more preferably at least five times more resistant, and most preferably at least ten times more resistant than their unmodified counterpart.

Although certain acid resistant nucleic acid molecules exhibit marked acid stability and endonuclease resistance, they are sensitive to 3' exonucleases. In order to enhance the exonuclease resistance of 2'-O-alkyl substituted nucleic acid molecules, the 3' or 5' and 3' ends of the nucleic acid are preferably attached to a chemical moiety that provides an exonuclease blocking function. For example, one or more phosphorothioate nucleotides can be placed at either end of the RNA or DNA. Additionally, one or more inverted bases can be placed on either end of the RNA or DNA, or one or more alkyl or alcohol (e.g., butanol-substituted) nucleotides or chemical groups can be placed on one or both ends. Accordingly, a preferred embodiment of the present invention is a nucleic acid comprising a nucleic acid having the following structure: A-B-C, wherein "B" is a 2'-O-alkyl or 2'-O-alkyl-n(O-alkyl) substituted RNA between about 1 and about 98 bases in length, and "A" and "C" are respective 5' and 3' end blocking groups (e.g., one or more phosphorothioate nucleotides (but typically fewer than six), inverted base linkages, or alkyl, alkenyl, alkynyl, O-alkyl, and O-alkyl-n (O-alkyl) groups or substituted nucleotides). A partial list of blocking groups includes inverted bases, dideoxynucleotides, methylphosphates, alkyl groups, aryl groups, cordycepin, cytosine arabanoside, 2'-methoxy, ethoxy nucleotides, phosphoramidates, a peptide linkage, dinitrophenyl group, 2'- or 3'-O-methyl bases with phosphorothioate linkages, 3'-O-methyl bases, fluorescein, cholesterol, biotin, acridine, rhodamine, psoralen, glyceryl, methyl phosphonates, butanol, butyl, hexanol, and 3'-O-alkyls. An enzyme-resistant butanol preferably has the structure OH—$CH_2CH_2CH_2CH_2$ (4-hydroxybutyl), which is also referred to as a C4 spacer.

The term "substantially nuclease resistant" refers to nucleic acid molecules that are resistant to nuclease degradation, as compared to naturally occurring or unmodified nucleic acid molecules. Modified oligonucleotides of the invention are at least 1.25 times more resistant to nuclease degradation than an unmodified nucleic acid having the same sequence and number of nucleotides, more preferably at least 2 times more resistant, even more preferably at least 5 times more resistant, and most preferably at least 10 times more resistant than their unmodified counterpart. Such substantially nuclease resistant nucleic acid molecules include, but are not limited to, nucleic acid molecules with modified backbones such as ethylphosphotriesters, 2'-O-methylphosphorothioates, 2'-O-methyl-p-ethoxy ribonucleotides, 2'-O-alkyls, 2'-O-alkyl-n(O-alkyl), 2'-fluoros, 2'-deoxy-erythropentofuranosyls, 2'-O-methyl ribonucleosides, 3'-O-methylribonucleotides, inverted bases (e.g., inverted T's), or chimeric versions of these backbones.

The modified oligonucleotide includes RNA or DNA comprising modifications to the sugar moieties such as 2'-substituted or 3'-substituted ribonucleotides, or deoxyribonucleotide monomers, any of which are connected together via internucleoside linkages. Modified RNA or DNA may also be comprised of PNA or morpholino modified backbones where specificity of the sequence is maintained.

The ribose groups and the internucleoside linkages link the bases in a nucleic acid and are referred to as the nucleic acid backbone. A modified backbone includes modifications to the chemical linkage between nucleotides, as well as other modifications that may be used to enhance stability and affinity, such as modifications to the sugar structure. For example, an L-anomer of deoxyribose may be used, where the base is inverted with respect to the natural D-anomer. In one embodiment, the 2'-OH of the sugar group may be altered to 2'-halogen, 2'-O-alkyl or 2'-O-alkyl-n(O-alkyl), which provides resistance to degradation without compromising affinity. Other suitable modified backbones include the following types of internucleotide linkages: 2'-O-methyl-phosphodiesters, 2'-O-alkyl, 2'-O-ethyl, 2'-O-propyl, 2'-O-butyl, 2'-O-alkyl-n(O-alkyl), 2'-methoxyethoxy, 2'-fluoro, 2'-deoxy-erythropentofuranosyl, 3'-O-methyl, p-isopropyl oligonucleotides, 2'-O$(CH_2CH_2O)_xCH_3$, and/or butyne linkages. An oligonucleotide may have combinations of such modified backbones, may be completely modified, or may comprise all or some linkages being phosphodiester linkages.

Preferred internucleoside linkages on the modified oligonucleotide are achiral. The term "achiral" as used herein, refers to a molecule that is superimposable with its mirror image, whereas the term "chiral" refers to a molecule that is not superimposable with its mirror image. Oligonucleotides containing achiral 5' to 3' internucleoside phosphate linkages have internucleotide linkages which are achiral (i.e., no stereochemistry). The achiral oligonucleotides preferably contain at least about three to eight contiguous achiral internucleoside linkages, more preferably, nine to ten contiguous achiral internucleoside linkages, even more preferably, eleven to twelve contiguous achiral internucleoside linkages, and most preferably, is completely comprised of achiral internucleoside linkages through the entire contiguous sequence. In another embodiment, the achiral internucleoside linkages are interspersed with chiral internucleoside linkages (e.g., two contiguous achiral linkages followed by one chiral linkage followed by two contiguous achiral linkages; three contiguous achiral linkages followed by one chiral linkage; four contiguous achiral linkages followed by two achiral linkages, etc.). Examples of achiral internucleoside linkages include, but are not limited to, phosphodiester and diphosphorothioate linkages. Achiral RNA and DNA linkages in the backbone are routinely generated during automated synthesis of oligonucleotides if the final structure is a symmetrical molecule (i.e., a phosphate with the same atom attached to both sides).

The internucleoside phosphate linkages can be phosphodiester, or 3' to 3', 5' to 2' or 5' to 5' linkages, and combinations of such similar linkages (to produce mixed backbone modified RNA or DNA). The modifications can be internal (single or repeated) or at the end(s) of the RNA or DNA molecule. These modifications can include additions to the nucleic acid molecule, such as cholesteryl, diamine compounds with varying numbers of carbon residues between amino groups and terminal ribose, and deoxyribose or phosphate modifications which cleave or cross-link to the opposite chains or to associated enzymes or other proteins. Electrophilic groups such as ribose-dialdehyde could covalently link with an epsilon amino group of the lysyl-residue of such a protein. A nucleophilic group such as n-ethylmaleimide tethered to an RNA or DNA could covalently attach to the 5' end of an mRNA or to another electrophilic site.

Suitable oligonucleotides for the present invention can be determined by evaluating the Delta G or Gibbs Free energy of oligonucleotide binding to the complementary RNA strand at 37° C. and the Tm. The Gibbs Free energy and Tm are measured from the part of the target gene that corresponds to the RNA oligonucleotide that is added. These values can be calculated using the program found on ftp://rna.chem.rochester.edu and are described in Matthews et al. (1999) J. Mol. Biol. 288, 911-940 and Matthews et al. (1999) RNA 5, 1458-1469.

Accordingly, a composition comprising an oligonucleotide, (i) wherein said oligonucleotide is at least 10 nucleotides in length, (ii) the Gibbs Free energy of the binding of said oligonucleotide/RNA target duplex at 37° C. is −15 kCal, (iii) said oligonucleotide is complementary to a region within the target gene selected from the group consisting of 5' UTR, translational start site and translational termination site and (iv) wherein said target gene is a gene as listed in Table 1. The Gibbs free energy is measured between that part of the target gene that corresponds to the oligonucleotide, that part typically being the 5'UTR, translational start site or the translational termination site.

In a preferred embodiment, the Gibbs Free energy of the binding of said oligonucleotide/RNA target duplex at 37° C. is ≦−20 kCal. Also preferred, the Gibbs Free energy is ≦−25 kCal. For 12-14 mer oligonucleotides, the Gibbs Free energy is preferably ≦−15 kCal, for 15-17 mer oligonucleotides, the Gibbs Free energy is preferably ≦−20 kCal, for 18-20 mer oligonucleotides, the Gibbs Free energy is preferably ≦−25 kCal, for 21-23 mer oligonucleotides, the Gibbs Free energy is ≦−30 kCal, and for 24-26 mer oligonucleotides, the Gibbs Free energy is ≦35 kCal.

Further described in the present invention is a composition comprising an oligonucleotide, (i) wherein said oligonucleotide is at least 10 nucleotides in length, (ii) the Tm of said oligonucleotide to a target gene is about 65-90° C., (iii) said oligonucleotide is complementary to a region within the target gene selected from the group consisting of 5' UTR, translational start site an termination site, and (iv) wherein said target gene is selected from a gene as listed in Table 1. Preferably, the oligonucleotide has a Tm of about 75-90° C. Still preferred, the oligonucleotide has a Tm of about 85-90° C. Still preferred, the Tm of said oligonucleotide to a target gene at IM monovalent cation concentration is about 65-90° C. The Gibbs free energy is measured between that part of the target gene that corresponds to the oligonucleotide, that part typically being the 5' UTR, translational start site or the translational termination site.

Nutritional Supplements

As used herein, the term "nutritional supplement" refers to a composition that is intended to supplement the diet. A nutritional supplement includes any dietary substance used in mammals to supplement the diet by increasing total dietary intake; or a concentrate, metabolite, constituent, extract, etc. Nutritional supplement includes any product that is intended for ingestion in tablet, capsule, powder, soft-gel, gel-cap, or liquid form. As used herein, the term "nutritional supplement" is used synomously with the term "dietary supplement" and "nutraceutical" throughout the specification.

The present invention provides a composition which is useful as a nutritional supplement to maintain or improve the an individual's health. Preferred indications for dietary supplements include, hut are not limited to, maintenance of cardiovascular function and a healthy circulatory system, maintenance of cholesterol levels that are already within the normal range, reduction of stress and frustration, relief of occasional simple nervous tension, relief of nervousness due to common everyday overwork and fatigue, alleviation of restlessness, reduction in nervous irritability, relief from anxiety, relief of muscle tension, enhancement of resistance to stress, promotion of emotional balance and a positive outlook, relief of sour stomach or upset stomach, relief of occasional heartburn or occasional acid indigestion, appetite suppression, promotion of healthy weight loss while naturally satisfying the appetite, appetite control, relief of minor or temporary aches and pains, treatment of common symptoms associated with the menstrual cycle, treatment of mild mood changes, cramps, and edema associated with the menstrual cycle, maintenance of a normal, healthy attitude during premenstrual syndrome, diminish the normal symptoms of premenstrual syndrome and maintenance of hormonal balance and alleviation of minor pre-menstrual syndrome symptoms such as cramping, breast tenderness, minor mood changes, headaches, bloating and skin problems.

The nutritional supplement composition of the present invention include compositions with a single oligonucleotide and/or a combination of about two or more oligonucleotides. The use of the nutritional supplement compositions of the present invention can be used to treat any of the aforementioned indications. These agents may be combined in an oral dosage with other well known nutritional supplements and/or non-flavonoid antioxidants (e.g., selenium, vitamin E (tocopherol, particularly alpha-tocopherol), vitamin C (ascorbic acid) and coenzyme Q10). Dietary fiber supplements may also be used in the composition.

Other additives may be incorporated in the nutritional supplement of the present invention. Such additives include minerals, (e.g., boron, etc. and trace metals such as zinc, magnesium, manganese, chromium, molybdenum, copper, iron, calcium, and potassium; and other micronutrients such as thiamine, riboflavin, niacin, pantothenic acid, pyridoxine, choline, biotin, inositol, para-aminobenzoic acid, vitamin D, vitamin K, vitamin A). In another embodiment of the invention a dietary fiber supplement such as oat bran or other natural fiber source may also be added to the composition.

Typically the nutritional supplement will further include a pharmaceutically acceptable carrier such as lactose, glucose, sucrose, corn starch, potato starch, cellulose acetate, ethyl cellulose, etc. Diluents and other additives such as one or more pharmaceutically acceptable binding agents, fillers, supports, thickening agents, taste-improving agents, coloring agents, preservatives, stabilizers, regulators, emulsifiers or mixtures thereof may be used depending on the form of the composition employed.

In addition to providing the aforementioned compositions, the invention also includes a method for orally administering the nutritional supplement composition in dosages effective to aid in the maintenance and improvement of an individual's health. The supplement is preferably administered orally. Suitable forms for the nutritional supplement composition for oral administration include tablets, capsules, lozenges, syrups, granules, solutions and suspensions which contain unit doses of the supplement for administration once or several times a day. The nutritional supplement composition of the invention will typically be administered orally as a liquid, tablet or a capsule. Tablets, gel tabs, capsules, liquid and sustained release formulations can be formulated and prepared according to manufacturing techniques well known in the pharmaceutical industry and in a variety of dosage forms.

In one embodiment, the nutritional supplement is a sports drink comprising one or more modified antisense oligonucleotides capable of hybridizing to one or more of the genes listed in Table 1. In a preferred embodiment, the sport drink comprises the modified oligonucleotides Asm (SEQ ID NO: 1), Pde5 (SEQ ID NO: 16), FAAH (SEQ ID NO: 23), CX2 (SEQ ID NO: 6), CRP (SEQ ID NO: 24), LO5 (SEQ ID NO: 12), P65 (SEQ ID NO: 10), CD18 (SEQ ID NO: 5).

Therapeutic Oligonucleotide Compositions

In a related vein, the present invention includes a pharmaceutical composition comprising at least about one oligonucleotide, wherein said oligonucleotide comprises (i) at least about ten contiguous nucleotides in length, (ii) at least about three to eight contiguous achiral internucleoside linkages, (iii) further comprising a pharmaceutically suitable excipient. In alternative embodiments, other oligonucleotides, described herein, are used in the inventive compositions. In some embodiments, the therapeutic composition can be a pharmaceutical or homeopathic composition.

As used herein, the term "pharmaceutical composition" refers to a therapeutic composition that is used to treat a particular disease or pathological disorder that is suitable for parenteral, oral or topical administration in humans.

The compositions containing the modified oligonucleotides of the invention in an admixture with a pharmaceutically acceptable carrier can be prepared according to known techniques. The carrier may take a wide variety of forms depending on the form of preparation desired for administration, e.g., intravenous, oral, topical, aerosol (for topical or inhalation therapy), suppository, parenteral, or spinal injection. The excipient may contain any number of carriers. In the case of homeopathic pharmaceuticals the carriers would preferably be homeopathic carriers, e.g. homeopathic agents that may increase the efficacy of the homeopathic composition or help to alleviate symptoms associated with a physiological condition. In addition, the composition may contain stabilizers, preservatives, and other ingredients, preferably in amounts from about 0.5 to 2.0 percent by weight, provided they do not adversely affect the ability of the pharmacological composition to treat the physiological condition. It is well within the skill of one in the art to determine an appropriate mode of administration and to select an appropriate delivery system.

Administration of the composition will introduce the modified oligonucleotides to the individual in a diluted amount. Exemplary ranges of dosage for oral or topical administration are between about 0.001 mg and 10 mg per day, and preferably between about 0.010 mg and 1.0 mg per day of oligonucleotide in the composition. When orally administered, it is preferred that one dosage unit be administered one to four times per day until relief is achieved or until the symptoms disappear or are satisfactorily attenuated. Normally, a patient is instructed to orally take two to three dosage units per day. The dosage unit may be placed under the tongue of the patient or simply swallowed for such oral administration.

The pharmaceutical compositions of the present invention may be formulated for administration to humans and animals in liquid form, or in tablets, pills, granules, powders, or in ointments, creams, injectables, or suppositories. Ointments and creams are impregnated with a low liquid potency or, sometimes, mother tinctures and are generally prescribed as specific remedies. Liquid compositions may be supplied in amber glass dropper bottles to protect them from light.

In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs, and solutions); or carriers, such as starches, sugars, diluents, granulating agents, lubricants, binders, disintegrating agents and the like in the case of oral solid preparations (such as, for example, powders, capsules and tablets). For homeopathic preparations for example, RNA can be dissolved in a liquid 1 part by weight to produce a ten volumes of liquid attenuation labeled 1×. To produce lower dilutions 1 ml of the 1× attenuation is used (mixed thoroughly) with 9 ml of diluent to produce 2×. This process is repeated until the desired attenuation is achieved.

For administration by injection, preparations may comprise an aqueous solution of a water soluble, or solubilized, and pharmacologically acceptable form of the nucleic acid in an appropriate liquid, e.g., water or saline solution. Injectable suspensions may also be prepared using appropriate liquid carriers, suspending agents, agents for adjusting the isotonicity, preserving agents, and the like. Actual methods for preparing administrable pharmacological compositions and adjustments necessary for administration to subjects will be known or apparent to those skilled in the art.

For topical administration, the carrier may take a wide variety of forms depending on the preparation, which may be a cream, dressing, gel, lotion, ointment, or liquid. A surfactant can be included in the composition to provide deeper penetration of the ingredients. Although natural surfactants are preferred, others such as isopropyl myristate can be used. In one embodiment, the composition is a cosmetic composition for topical administration to the skin. As used herein, the term "cosmetic composition" refers to a composition that is applied topically to the skin to improve the appearance of the skin.

Aerosols are prepared by dissolving or suspending the nucleic acid in a propellant such as ethyl alcohol or in propellant and solvent phases. The pharmaceutical compositions for topical or aerosol form will generally contain from about 0.001 percent by weight (of the nucleic acid) to about 40 percent by weight, preferably about 0.02 percent to about 10 percent by weight, and more preferably about 0.05 percent to about 5 percent by weight depending on the particular form employed. Suppositories are prepared by mixing the nucleic acid with a lipid vehicle such as theobroma oil, cacao butter, glycerin, gelatin, or polyoxyethylene glycols.

The compositions of the invention may also include plant or herbal extracts. For example, topical compositions may include Paraguay tea, Kola and Guarana which provide a source of methylxanthines, saponius, tannins and glycosides which have been shown to reduce swelling and redness. The extract of Paraguay tea is known as "Mate extract" and is described in the International Cosmetic Ingredient Dictionary, 5th Edition. Mate extract is commercially available in combination with extracts of Kola and Guarana that is sold by Cosmetic Ingredient Resources (Stamford, Conn.) under the "QUENCHT" trademark. Suitable herbs which can be used also include *Symphytum officinale, Moschus moscheferous, Pripalia geniculata, Plantago asiatica, Causticum, Helianthemum canadense, Ornithogalum umbellatum, Clematis crispa, Impatiens pallida, Prunus cerasus*, arnica, etc.

The nucleic acid molecule(s) may be combined with a lipid, cationic lipid, or anionic lipid and the active agent delivered via a nucleic acid/lipid emulsion, or a liposomal suspension. The use of cationic, anionic, and/or neutral lipid compositions or liposomes is generally described in International Publications WO90/14074, WO91/16024, WO91/17424, and U.S. Pat. No. 4,897,355, all herein incorporated by reference. By assembling nucleic acid molecules into lipid-associated structures, the nucleic acid molecules may exhibit an increased half-life in vivo. Examples of suitable anionic lipids for use with RNA or DNA include, but are not limited to, cardiolipin, dimyristoyl, dipalmitoyl, or dioleoyl phosphatidyl choline or phosphatidyl glycerol, palmitoyloleoyl phosphatidyl choline or phosphatidyl glycerol, phosphatidic acid, lysophosphatidic acid, phosphatidyl serine, phosphatidyl inositol, and anionic forms of cholesterol.

Making an Oligonucleotide Composition

The invention includes a method for making an oligonucleotide composition comprising (i) selecting an oligonucleotide that is adjacent to or overlaps a target region of a gene, (ii) determining the Gibbs Free energy value associated with said oligonucleotide in reference to said target gene, (iii) assessing Tm in reference to said target gene, and (iv) performing a sequence database search to determine if said oligonucleotide overlaps the 5' UTR, the translational start sequence, or the translational termination site of an mRNA of a gene different from the target gene.

The oligonucleotide of the present invention can be directed to a translational start site, a 5' UTR or a termination site. Preferably, the oligonucleotide is adjacent to or overlaps the translational start site of the gene by at least about one base. Still preferred, the oligonucleotide overlaps the translational start site by at least about two bases. Still more preferred, the oligonucleotide overlaps the translational start site by at least about three bases.

It is generally preferable to design an RNA or DNA that has the same or similar base sequence as the portion of the complement of a gene that encodes the 5' end of an RNA. However, a nucleic acid may also have, for example, a same or similar base sequence as other regions of the gene, such as the region encoding a translation start site or the 3' untranslated region. In another example, a nucleic acid may be designed to reflect the region around a splice donor or splice acceptor site, either with or without the intervening intron. Of particular interest are nucleic acid molecules whose sequences comprise all or a fragment of the sequence of the complement of a gene that is over-expressed in individuals exhibiting the disease or condition. The identification of over-expression of a gene can be through molecular means, e.g., detection of expression in affected tissue using conventional molecular techniques (e.g., Sambrook et al. (1989) Molecular Cloning: A Laboratory Manual, Cold Spring Harbor Laboratory Press). Overexpression of a gene may also be detected using array technology, or inferred from the results of protein assays, such as ELISA.

Making a Homeopathic Oligonucleotide Composition

A method of making a homeopathic composition comprising (i) triturating solid RNA in a 1/9 ratio with lactose to produce a 1× solid and (ii) repeating the process until the desired attenuation is achieved, is described in the present invention. In a related vein, a method of making a homeopathic composition comprising (i) dissolving 1 part RNA by weight in liquid to produce ten volumes of liquid attenuation labeled 1× and optionally (ii) mixing 1 ml of the 1× attenuation with 9 ml of diluent to produce a lower concentration, is also addressed.

In another embodiment, the invention includes homeopathic compositions containing modified oligonucleotides. In one embodiment, tablets for homeopathic use are preferably produced as placebo tablets that are then medicated by dripping or spraying liquid potencies onto the tablets in such a manner as to ensure a coefficient of impregnation of almost 100 percent. The placebo tablets are preferably formed by compression. Pills or granules are preferably spherical in shape, of about 4 millimeters diameter and 3 to 5 centigrams in weight. They are preferably prepared (form pure lactose) and medicated in the same manner as tablets. For example, solid RNA can be triturated (i.e., ground up) in a 1/9 ratio with lactose (1 gram of RNA+9 grams of lactose) to produce a 1× solid. The process is repeated (1 gram of that material plus 9 grams of lactose) until the desired attenuation is achieved.

For homeopathic compositions, the excipient may contain any number of carriers, and preferably homeopathic carriers, e.g., homeopathic agents that may increase the efficacy of the homeopathic composition or help to alleviate symptoms associated with a physiological condition. For example, RNA can be dissolved in a liquid 1 part by weight to produce a ten volumes of liquid attenuation labeled 1×. To produce lower dilutions 1 ml of the 1× attenuation is used (mixed thoroughly) with 9 ml of diluent to produce 2×. This process is repeated until the desired attenuation is achieved. A homeopathic carrier solution such as that described in U.S. Pat. No. 5,603,915 may be used for increasing the efficacy of the homeopathic agent. This carrier solution is sequentially subjected to an alternating current electrical treatment and a direct current electrical treatment, after which additional ingredients such as seawater, brain hormones, and biologically active enzymes are added. The electrical treatment of the carrier, along with the addition of homeopathically active substances, can be used to increase the efficacy of the homeopathic composition. Alternatively, an electromagnetic carrier, such as described in U.S. Pat. No. 5,830,140 may be employed.

Methods of Treatment

The invention includes a method of treating a disorder comprising administering an oligonucleotide to a patient in a therapeutically effective amount. As used herein, the term "therapeutically effective" amount is meant to refer to an amount of a pharmacological composition that is non-toxic and is the lowest amount necessary to provide a desired physiological effect. Preferably, the oligonucletide compositions of the present invention are administered at concentrations at or below 100 μg per kg of body weight. Also preferred, the concentration is at or below 10 μg per kg of body weight, still preferred, the concentration is at or below 1 μg per kg of body weight, and still more preferred, the concentration is at or below 0.1 μg per kg of body weight. Furthermore, for homeopathic use, the oligonucleotide compositions of the present invention can be combined with any homeopathic drug and still elicit a therapeutic effect.

Preferably, the oligonucleotide comprises at least one modification according to the present invention. A preferred modification is the incorporation of at least about three to eight contiguous achiral internucleoside phosphate linkages into the oligonucleotide backbone. More preferably the oligonucleotide incorporates at least nine to ten continuous achiral internucleoside phosphate linkages, even more preferably, eleven to fifteen achiral internucleoside phosphate linkages, and most preferably, the entire oligonucleotide contains achiral internucleoside phosphate linkages. Also preferred, the oligonucleotide is 3' end-blocked, comprises at least 10 contiguous nucleotides greater than or equal to 80 percent identical to a nucleotide sequence selected from SEQ ID NO: 1-81. Also preferred, the oligonucleotide is at least 85 percent identical to a nucleotide sequence selected from the group of SEQ ID NO: 1-81. Still preferred, the oligonucleotide is at least 90 percent identical and more preferred, at least 95 percent identical. Most preferably, the oligonucleotide comprises a sequence from SEQ ID NO: 1-81.

The methods of the present invention can be used to treat disorders including, but not limited to, acroparaesthsia, allergic (psoric) conditions, allergic reactions, alopecia, amnesia, anaphrodisia, angina, arthritis, asthenopia, biliary sycosis, burns, cancerous conditions, such as colon cancer, malignant melanoma and malignant nasal polyps, carpal tunnel syndrome, colds, conjunctivitis, Crohn's disease, depression, depressive psychosis, dysthyroidism, epilepsy, erectile dysfunction, excessive appetite (i.e., appetite control and suppression, promotion of healthy weight loss while naturally satisfying the appetite), gingivitis, heart burn (i.e., relief of occasional heartburn or occasional acid indigestion), hemorrhage, hypertension (i.e., helps maintain cardiovascular function, and a healthy heart and circulatory system), high cholesterol (i.e., helps to maintain cholesterol levels that are already within the normal range), hyperthyroidism, infections, inflammatory disease, lack of willpower, laryngitis, leucopenia, liver disorders, mental disorders (i.e., reduces stress, frustration, muscle tension, anxiety, and occasional simple nervous tension; enhances resistance to stress), myopia, neurosis, neurological disorders such as multiple sclerosis and ALS, obesity, pain (i.e., relief of minor or temporary aches and pains), pancreatic disorders, poison ivy, premature senescence, pre-menstrual syndrome (i.e., treatment of common symptoms associated with the menstrual cycle such as edema, breast tenderness, headaches, skin problems, cramps and mild mood changes), prostatitis, psoriasis, rosacea, seborrhea, sinusitis, and trauma.

Table 2 lists the oligonucleotides, or combinations of oligonucleotides that are preferably employed in remedies for the treatment of various symptoms and conditions. In Table 2, the use of a combination of oligonucleotides is denoted by a "/" (for example, "A/B/C" denotes the combined use of oligonucleotides A, B and C); where two or more different combinations are preferred, each such combination is presented on a separate line. The oligonucleotides are usually used in a 1:1:1 ratio, but this can vary. For example, a combination of 4×, 5×, and 6× solutions may be used, which deviates from 1:1:1.

TABLE 2

| Indication or Condition | Oligonucleotide Combination |
|---|---|
| Arthritis | Asm/X2/P65-2M |
| | Asm/X2/P65-2M/LO5-38 |
| Carpal Tunnel Syndrome | Asm |
| | Asm/X2/P65-2M |
| Chronic Fatigue/Fibromyalgia | Asm/D5/X2 |
| Colds | Asm |
| Crohn's Disease | X2/P65-2M |
| Depression | Asm/D5 |
| Erectile Dysfunction (ED) | Asm/D5 |
| Heartburn | Acid-2/B2 |
| High Cholesterol Hyperlipidemia | Mg44 |
| | Mg44/Asm/D5 |
| Hypertension | Ace1 |
| | Ace1/Nep-1 |
| Inflammation | Asm/X2 |
| | Asm/X2/P65-2M |
| | Asm/X2/P65-2M/LO5-38 |
| Pain | Asm/X2 |
| | Asm/X2/P65-2M |
| Pre-Menstrual Syndrome (PMS) | Asm/D5/X2 |
| Psoriasis | Asm/D5/P65-2M |
| Rosacea | Asm |
| | Asm/D5 |
| Prostatitis | MBP |
| Stress | Asm/D5 |
| Trauma | Asm |
| | Asm/X2/P65-2M |

TABLE 2-continued

| Indication or Condition | Oligonucleotide Combination |
|---|---|
| Ulcerative colitis | X2/P65-2M/LO5-38 |
| Weight Management | TTP |

The compositions of the present invention are formulated to contain a "nutritionally effective" or "allopathically effective" or "homeopathically effective" amount of one or more nucleic acid molecules. As used herein, the term "nutritionally effective" amount is meant to refer to an amount of a oligonucleotide composition that is non-toxic and greater than the minimum amount necessary to maintain a desired physiological effect. As used herein, the term "allopathically effective" amount is meant to refer to an amount of a oligonucleotide composition that is non-toxic and greater than the minimum amount necessary to produce a desired physiological effect.

As used herein, the term "homeopathically effective" amount is meant to refer to an amount of a oligonucleotide composition that is non-toxic and is the lowest amount necessary to provide a desired physiological effect. A homeopathic effect, in accordance with the present invention, is achieved by a dose of modified nucleic acid that will be effective in treating (i.e., relieving, ameliorating, or preventing) symptoms of a particular condition or disease. Such treatment may be prophylactic in nature (i.e., completely or partially preventing the future occurrence of a symptom) and/or it may be therapeutic in nature (i.e., providing a partial or complete cessation or amelioration of a symptom). The method of treating of the present invention covers any treatment of symptoms of a disorder in a mammal, particularly a human, and includes:

(a) preventing symptoms of a disorder from occurring in a subject that may be predisposed to a condition but has not yet been diagnosed as having it;

(b) inhibiting symptoms of a disorder (i.e., arresting its development); or (c) relieving symptoms of a disorder (i.e., ameliorating and/or causing regression of the condition); and/or (d) maintaining homeostasis (i.e., the normal balance of RNA or DNA in a subject).

One of ordinary skill will appreciate that, from a medical practitioner's or patient's perspective, virtually any alleviation or prevention of an undesirable symptom would be desirable. Homeopathic compositions typically employ substantially less nucleic acid than is employed in allopathic compositions. Exemplary dosages to be employed in accordance with the present invention, are described in Table 3 below.

| Homeopathic RNA/DNA Concentration | |
|---|---|
| Dilution/Potency | μg/kg |
| 2x | 50 |
| 3x | 5 |
| 4x | 0.5 |
| 5x | 0.05 |
| 6x | 0.005 |

When used in the therapeutic treatment of disease, an appropriate dosage of one or more therapeutic compositions of the invention may be determined by any of several well-established methodologies. Additionally, dosages may also be altered depending upon factors such as the severity of infection, and the size or species of the host.

Preferably, animals are treated using compositions of the present invention having agents with compositions containing nucleic acid molecules having a sequence appropriate for the particular animal. Targeted species include, but are not limited to birds, fish, and mammals (especially pigs, goats, sheep, cows, dogs, horses, cats, and most preferably, humans).

Having now generally described the invention, the same will be more readily understood through reference to the following examples, which are provided by way of illustration, and are not intended to be limiting of the present invention, unless specified. The effectiveness of the RNA oligonucleotide compositions according to the preferred embodiments of the present invention is demonstrated in the Examples below.

EXAMPLE 1

Individuals with cancers were typically administered a composition containing oligonucleotides complementary to cyclo-oxygenase 2 and NFκB p65 at concentrations of 3 to 30 $A_{260}$/RNA/ml (1.0-10 μg/kg). Some individuals were additionally administered oligonucleotides complementary to lipoxygenase 5. After approximately one to two months of therapy, the effect of the composition was then evaluated on individuals who completed the study (see Table 4). Treatment efficacy was evaluated by each patient and confirmed by the treating physician. A scaled score of 1 to 10 was used to evaluate treatment efficacy over a period of one to two months where a score=10 represented no improvement and a score=1 represented total alleviation of symptoms.

EXAMPLE 2

Individuals with excessive appetite were orally administered an oligonucleotide composition containing RNA oligonucleotides complementary to the tripeptidyl gene. RNA oligonucleotide concentrations were typically 0.3 to 3.0 $A_{260}$/RNA/ml and given in dosages (0.1-1.0 μg/kg of 0.5 ml twice daily). The effect of the composition was then evaluated after approximately one to two months of therapy (see Table 5). Treatment efficacy was evaluated by each patient and confirmed by the treating physician. A scaled score of 1 to 10 was used to evaluate treatment efficacy where a score=10 represented a voracious appetite and a score=1 represented the absence of hunger and the ability to lose weight.

EXAMPLE 3

Individuals diagnosed with arthritis were orally administered oligonucleotide compositions with RNA oligonucleotides complementary to phosphodiesterase 4 and NFκB p65. Some people were additionally given compositions further containing RNA oligonucleotides complementary to other genes. RNA oligonucleotide concentrations were typically between the range of 0.3 to 300 $A_{260}$/RNA/ml and given in dosages (0.1-100 μg/kg) of 0.5 ml twice daily. The effect of the composition was then evaluated after approximately one to two months of therapy (see Table 6). Treatment efficacy was evaluated by each patient and confirmed by the treating physician. A scaled score of 1 to 10 was used to evaluate treatment efficacy where a score=10 represented severe arthritis characterized by inability to freely move affected joints, restricted movement, pain and inflammation and a score=1 represented reduced inflammation, restoration of movement and the absence of pain.

EXAMPLE 4

Individuals with elevated blood pressure were orally administered oligonucleotide compositions with RNA oligonucleotides complementary to CE and/or neutral endopeptidase genes. Some individuals were additionally given compositions with RNA oligonucleotides complementary to other genes. Concentrations were typically 3.0 to 30 $A_{260}$/RNA/ml and given in dosages (1.0-10 μg/kg) of 0.5 ml twice daily. The effect of the composition was evaluated after approximately one to two months of therapy (see Table 7). Treatment efficacy was determined by measuring changes in blood pressure where a decrease in blood pressure below 160/89 was assessed as a successful treatment because blood pressure above this level has been associated with stroke, heart disease and kidney failure.

EXAMPLE 5

Individuals with elevated cholesterol were orally administered oligonucleotide compositions containing RNA oligonucleotides complementary to the 3-hydroxy-3-methylglutaryl-coenzyme A reductase gene. Some individuals were also given oligonucleotide compositions further containing RNA oligonucleotides complementary to other genes such as phosphodiesterase 4 and phosphodiesterase 5. RNA oligonucleotide concentrations were typically 3.0 to 30 $A_{260}$/RNA/ml and given in dosages (1.0-10 μg/kg) of 0.5 ml twice daily. The effect of the composition on serum cholesterol was evaluated after approximately one to two months of therapy (see Table 8). Treatment efficacy was determined by measuring changes in serum cholesterol where a one-point drop corresponded to a two percent reduction in the probability of heart disease and a twenty-five-point drop corresponded to a fifty percent reduction in the probability of heart disease.

In addition, the effect of compositions containing RNA oligonucleotide with eight or more contiguous achiral internucleoside phosphate linkages on cholesterol levels was also assessed. In a representative individual, oligonucleotide compositions containing achiral RNA oligonucleotides complementary to 3-hydroxy-3-methylglutaryl-coenzyme A reductase, phosphodiesterase 4 and phosphodiesterase 5 were given orally in combination at a concentration of 3.0 $A_{260}$/RNA/ml at dosages of 0.5 ml, twice daily. The achiral RNA oligonucleotides produced a decrease of 46 mg/dL in serum cholesterol. The achiral 2'methoxy-RNA supplements resulted in a 31 mg/dL decrease in serum cholesterol levels. Chiral RNA or DNA did not effect cholesterol levels.

EXAMPLE 6

Individuals with emotional distress were orally administered an oligonucleotide composition containing RNA oligonucleotides complementary to the phosphodiesterase 4 and phosphodiesterase 5 genes. RNA oligonucleotide concentrations were typically 0.3 to 3.0 $A_{260}$/RNA/ml and were given in dosages (0.1-1.0 μg/kg) of 0.5 ml two to six times per day. The effect of the composition was evaluated after approximately one to two months of therapy (see Table 9). A scaled score of 1 to 10 was used to evaluate treatment efficacy where a score=10 represented a severely depressed patient with suicidal tendencies and a score=1 represented a emotionally stable patient.

EXAMPLE 7

Individuals with various gastrointestinal disorders were orally administered oligonucleotide compositions with RNA oligonucleotides complementary to the phosphodiesterase 4 and/or cyclooxygenase 2 genes. Some individuals were given compositions additionally containing RNA oligonucleotides complementary to other genes such as phosphodiesterase 5 and NFκB p65. Oligonucleotide concentrations were typically 0.3 to 3.0 $A_{260}$/RNA/ml and given in 0.5 ml dosages (0.1-1.0 μg/kg) twice per day. The effect of the composition was evaluated after approximately one to two months of therapy (see Table 10). A scaled score of 1 to 10 was used to evaluate treatment efficacy where a score=10 represented a patient with above normal bowel movement frequency and the presence of blood in the feces and a score=1 represented a patient with normal frequency of bowel movements and the absence of blood in the feces.

EXAMPLE 8

Individuals with various types of inflammation were orally or topically (as indicated) administered oligonucleotide compositions containing oligonucleotides complementary to the phosphodiesterase 4 or interleukin 5 genes. Some individuals were given compositions additionally containing RNA oligonucleotides complementary to other genes such as cyclooxygenase 2 and NFκB p65. RNA oligonucleotide concentrations were typically 0.03 to 300 $A_{260}$/RNA/ml given in doses (0.01-100 μg/kg) of 0.5 ml twice per day. The effect of the composition was then evaluated (see Table 11). A scaled score of 1 to 10 was used to evaluate treatment efficacy after approximately one to two months of therapy, where a score=10 represented presence of debilitating inflammation with severe pain and a score=1 represented the absence of inflammation and pain.

EXAMPLE 9

Individuals suffering from migraine headaches were orally administered oligonucleotide compositions containing RNA oligonucleotides complementary to the phosphodiesterase 4, phosphodiesterase 5 cyclooxygenase 2 and 3-hydroxy-3-methylglutaryl-coenzyme A reductase genes. Oligonucleotide concentrations were typically 3.0 to 30 $A_{260}$/RNA/ml taken in dosages (1.0-10 μg/kg) of 0.5 ml two to four times per day. The effect of the composition was evaluated after approximately one to two months of therapy (see Table 12). A scaled score of 1 to 10 was used to evaluate treatment efficacy where a score=10 represented severe debilitating headache pain including facial pain accompanied by nausea and sensitivity to light and a score=1 represented the absence of these conditions.

EXAMPLE 10

Individuals with various neurological disorders were orally administered oligonucleotide compositions containing RNA oligonucleotides complementary to the phosphodiesterase 4, cyclooxygenase 2 and p65 genes. Some individuals were given compositions containing additional RNA oligonucleotides complementary to other genes such as lipoxygenase 5. Oligonucleotide concentrations were typically 3.0 to 30 $A_{260}$/RNA/ml taken in dosages (1-10 μg/kg) of 0.5 ml two to four times per day. The effect of the compositions was evaluated after approximately one to two months of therapy (see Table 13). A scaled score of 1 to 10 was used to evaluate treatment efficacy where a score=10 represented a patient with a debilitating form of the indicated neurological disorder (i.e., amyotrophic lateral sclerosis, multiple sclerosis, alzheimer's disease, parkinson's disease) and a score=1 represented a patient with no symptoms or mild symptoms associated with the indicated neurological disorder.

EXAMPLE 11

Individuals suffering from various types of pain were orally administered oligonucleotide compositions containing RNA oligonucleotides complementary to phosphodiesterase 4 and/or cyclooxygenase 2. Some individuals were given compositions containing additional RNA oligonucleotides complementary to other genes such as phosphodiesterase 5 and p65. Oligonucleotide concentrations were typically 0.3 to 3.0 $A_{260}$/RNA/ml and taken in dosages (0.1-10 μg/kg) of 0.5 ml two to four times a day. The effect of the composition was evaluated after approximately one to two months of therapy (see Table 14). A scaled score of 1 to 10 was used to evaluate treatment efficacy where a score=10 represented a patient with severe pain requiring treatment with a subscription analgesic and a score=1 represented a patient with the absence of pain.

EXAMPLE 12

Female individuals diagnosed with pre-menstrual syndrome were orally administered oligonucleotide compositions containing RNA oligonucleotides complementary to the phosphodiesterase 4 gene. Some individuals were given compositions containing additional RNA oligonucleotides complementary to other genes such as phosphodiesterase 5 and cyclooxygenase 2. RNA oligonucleotide concentrations were typically 0.03 to 3.0 $A_{260}$/RNA/ml taken in doses (0.01-1.0 μg/kg) of 0.5 ml two to four times per day. The effect of the composition was evaluated after approximately one to two months of therapy (see Table 15). A scaled score of 1 to 10 was used to evaluate treatment efficacy where a score=10 represented a patient with cramps, bloating, irritability, nausea and vomiting and a score=1 represented a patient with the absence of these conditions.

EXAMPLE 13

Male individuals diagnosed with prostatitis were orally administered oligonucleotide compositions containing RNA oligonucleotides complementary to the steroid 5-alpha-reductase-2 gene. Some individuals were given compositions containing additional RNA oligonucleotides complementary to other genes such as phosphodiesterase 4 and p65 (Super 8+composition=Asm, X2, D5, P65, cd-18, IL-5, LOS and ICAM). Oligonucleotide concentrations were typically 3.0 $A_{260}$/RNA/ml taken in doses (1.0 μg/kg) of 0.5 ml two to four times per day. The effect of the composition was evaluated after approximately one to two months of therapy (see Table 16). A scaled score of 1 to 10 was used to evaluate treatment efficacy where a score=10 represented a patient with urgent need to urinate three to five times per night and a score=1 represented a patient who slept through the night without urinating.

EXAMPLE 14

Individuals suffering from cold and sinusitis symptoms were administered (intranasal) oligonucleotide compositions containing RNA oligonucleotides complementary to phosphodiesterase 4 and a DNA monomer, Nu 3. Some individuals were given compositions containing additional RNA oligonucleotides complementary to other gene targets such as cyclooxygenase 2 and NFκB p65. RNA and DNA concentrations were typically 0.3 to 30 $A_{260}$/RNA/ml (0.1-10 μg/kg). Treatment efficacy was evaluated after approximately one to two months of therapy (see Table 17). A scaled score of 1 to 10 was used to evaluate treatment efficacy where a score=10 represented a patient with sneezing, stuffy nose and watery eyes and a score=1 represented a patient with the absence of these conditions.

EXAMPLE 15

Individuals with various types of trauma were orally or topically (as indicated) administered oligonucleotide compositions containing RNA oligonucleotides complementary to phosphodiesterase 4. Some individuals were given compositions containing additional RNA oligonucleotides complementary to other genes such as cyclooxygenase 2 and NFκB p65. Oligonucleotide concentrations ranged from 0.3 to 3.0 $A_{260}$/RNA/ml and taken in 0.5 ml doses (0.1-1.0 μg/kg) two to four times per day. The effect of the composition was evaluated after approximately one to two months of therapy (see Table 18). A scaled score of 1 to 10 was used to evaluate treatment efficacy where a score=10 represented a patient with severe inflammation and pain associated with the indicated trauma and a score=1 represented a patient with no inflammation or pain.

EXAMPLE 16

Individuals diagnosed with carpal tunnel syndrome were orally administered oligonucleotide compositions containing RNA oligonucleotides complementary to the phosphodiesterase 4 gene. Some individuals were given compositions containing additional RNA oligonucleotides complementary to other genes such as cyclooxygenase 2, NFκB p65 and other gene targets. Oligonucleotide concentrations were typically 0.03 to 300 $A_{260}$/RNA/ml taken in doses (0.01-100 μg/kg) of 0.5 ml two to four times per day. The effect of the composition was evaluated after approximately one to two months of therapy (see Table 19). A scaled score of 1 to 10 was used to evaluate treatment efficacy where a score=10 represented a patient with pain, tingling and numbness in the wrist area necessitating the use of a wrist brace and a score=1 represented a patient with the absence of these conditions and who did not require the assistance of a wrist brace.

EXAMPLE 17

Individuals diagnosed with chronic fatigue syndrome or fibromyalgia were orally administered oligonucleotide compositions containing RNA oligonucleotides complementary to the phosphodiesterase 4 gene. Some individuals were given compositions containing additional RNA oligonucleotides complementary to other genes such as cyclooxygenase 2 and p65. Oligonucleotide concentrations were typically 3.0 to 30 $A_{260}$/RNA/ml taken in doses (1.0-10 μg/kg) of 0.5 ml two to four times per day. The effect of the composition was evaluated after approximately one to two months of therapy (see Table 20). A scaled score of 1 to 10 was used to evaluate treatment efficacy where a score=10 represented a patient who complained of being chronically exhaustion accompanied by minor aches and pain and a score=1 represented a patient who did not complain of any such symptom.

EXAMPLE 18

Individuals suffering from eczema and atopic dermatitis were orally or topically (as indicated) administered oligonucleotide compositions containing RNA oligonucleotides complementary to the phosphodiesterase 4 gene. Some individuals were given compositions containing additional RNA oligonucleotides complementary to other genes such as cyclooxygenase 2 and p65 and other gene targets. Oligonucleotide concentrations were typically 0.3 to 3.0 $A_{260}$/RNA/ml taken in doses (0.1-1.0 μg/kg) of 0.5 ml two to four times per day. The effect of the composition was evaluated after approximately one to two months of therapy (see Table 21). A scaled score of 1 to 10 was used to evaluate treatment efficacy where a score=10 represented patient with itching, inflamed skin and minor bleeding, and a score=1 represented a patient with normal skin.

EXAMPLE 19

Male individuals suffering from erectile dysfunction were orally administered compositions containing RNA oligonucleotides complementary to the phosphodiesterase 4 gene. Some individuals were given compositions containing additional RNA oligonucleotides complementary to other genes such as phosphodiesterase-5. Oligonucleotide concentrations were typically 3.0 to 3.0 $A_{260}$/RNA/ml taken in doses (1.0-10 μg/kg) of 0.5 ml two to four times per day. The effect of the composition was evaluated after approximately one to two months of therapy (see Table 22). A scaled score of 1 to 10 was used to evaluate treatment efficacy where a score=10 represented a patient who could not obtain or maintain an erection and a score=1 represented a patient who was able to obtain and maintain an erection.

EXAMPLE 20

Individuals suffering from acid reflux were orally administered compositions containing RNA oligonucleotides complementary to the ATP4A gene. Some individuals were given compositions containing additional RNA oligonucleotides complementary to other genes such as ATP4B. Oligonucleotide concentrations were typically 3.0 to 30 $A_{260}$/RNA/ml taken in doses (1.0-10 μg/kg) of 0.5 ml two to four times per day. The effect of the composition was evaluated after approximately one to two months of therapy (see Table 23). A scaled score of 1 to 10 was used to evaluate treatment efficacy where a score=10 represented a patient with heartburn requiring treatment with excessive amounts of antacid medication and a score=1 represented a patient with no heartburn.

EXAMPLE 21

Individuals suffering from poison ivy were orally or topically (as indicated) administered compositions containing RNA oligonucleotides complementary to the phosphodiesterase 4 gene. Oligonucleotide concentrations were typically 0.3 to 300 $A_{260}$/RNA/ml taken in doses 0.1-100 μg/kg) of 0.5 ml two to four times per day. The effect of the composition was evaluated after approximately one to two months of therapy (see Table 24). A scaled score of 1 to 10 was used to evaluate treatment efficacy where a score=10 represented a patient with poison ivy covering up to ninety-five percent of the entire body with dermal discharge and secondary inflammation restricting eye openings and a score=1 represented a patient without these symptoms.

EXAMPLE 22

Individuals with psoriasis were orally or topically administered compositions containing RNA oligonucleotides complementary to the phosphodiesterase 4 gene. Some individuals were given compositions containing additional RNA oligonucleotides complementary to other genes such as phosphodiesterase-5 and p65. Oligonucleotide concentrations were typically 0.3 to 300 $A_{260}$/RNA/ml taken in doses of 0.5 ml (0.1-100 μg/kg) two to four times per day. The effect of the composition was evaluated after approximately one to two months of therapy (see Table 25). A scaled score of 1 to 10 was used to evaluate treatment efficacy where a score=10 represented a patient with thick silvery-colored scaly patches of skin with dermal discharge and bleeding and a score=1 represented a patient with normal skin.

EXAMPLE 23

Ten individuals with rosacea were orally or topically administered compositions containing RNA oligonucleotides complementary to the phosphodiesterase 4 gene. Some individuals were given compositions containing additional RNA oligonucleotides complementary to other genes such as cyclooxygenase 2 and p65. Oligonucleotide concentrations were typically 0.3 to 300 $A_{260}$/RNA/ml taken in doses (0.1-100 μg/kg) of 0.5 ml two to four times per day. The effect of the composition was evaluated after approximately one to two months of therapy (see Table 26). A scaled score of 1 to 10 was used to evaluate treatment efficacy where a score=10 represented a patient with red, inflamed facial skin with pimples (e.g., acne) and a score=1 represented a patient normal skin.

TABLE 4

Cancer Therapy

| | sex | age | condition | oligonucleotides | Severity before | Severity after |
|---|---|---|---|---|---|---|
| 1 | m | 38 | Skin cancer | X2/65 | 7-8 | 1-2 |
| 2 | m | 72 | Skin cancer | X2/65/LO5-38 | 7-8 | stable |
| 3 | f | 52 | Malignant nasal polyps | X2/65/LO5-38/Mg44 | 10 | 1 |
| 4 | f | 47 | Malignant melanoma | X2/65/LO5-38/Mg44 | 10 | stable |
| 5 | f | 56 | Breast cancer | X2/65/LO5-38 | 10 | stable |

TABLE 5

Appetite Control

| | sex | age | condition | oligonucleotide | Efficacy |
|---|---|---|---|---|---|
| 1 | f | 37 | appetite control | Ttp | 7 |
| 2 | f | 52 | appetite control | Ttp | 10 |
| 3 | f | 65 | appetite control | Ttp | 5 |
| 4 | f | 46 | appetite control | Ttp | 8 |
| 5 | f | 44 | appetite control | Ttp | 7 |
| 6 | f | 63 | appetite control | Ttp | 8 |
| 7 | f | 48 | appetite control | Ttp | 6 |
| 8 | f | 59 | appetite control | Ttp | 7 |
| 9 | m | 40 | appetite control | Ttp | 7 |
| 10 | f | 40 | appetite control | Ttp | 8 |
| 11 | f | 54 | appetite control | Ttp | 8 |
| 12 | f | 52 | appetite control | Ttp | 7 |
| 13 | f | 58 | appetite control | Ttp | 7 |

TABLE 5-continued

Appetite Control

| | sex | age | condition | oligonucleotide | Efficacy |
|---|---|---|---|---|---|
| 14 | f | 41 | Appetite control | Ttp | 8 |
| 15 | f | 39 | Appetite control | Ttp | 8 |
| 16 | f | 54 | Appetite control | Ttp | 7 |

TABLE 6

Arthritis Treatment

| | | | | | Severity | |
|---|---|---|---|---|---|---|
| | sex | age | condition | oligonucleotide | before | after |
| 1 | m | 50 | Arthritis (back) | Asm/X2/65 | 5 | 1 |
| 2 | f | 60 | Arthritis (general) | Asm/X2/65 | 6 | 1 |
| 3 | f | 63 | Rheumatoid Arthritis | Asm/X2/65/LO5-38/CRP | 10 | 5 |
| 4 | f | 66 | Arthritis (general) | Asm/X2/65/D5 | 7 | 1 |
| 5 | m | 50 | Arthritis (hands) | Asm/65 | 10 | 2 |
| 6 | f | 28 | Arthritis (knee) | Asm/X2/65 | 7 | 1-2 |
| 7 | f | 74 | Arthritis (knee) | Asm/X2/65 | 8 | 2-3 |
| 8 | f | 82 | Arthritis (general) | Asm/X2/65/LO5-38 | 8 | 2 |
| 9 | m | 65 | Arthritis (back/hand) | Asm/X2/65 | 6 | 2 |
| 10 | f | 63 | Arthritis (knee) | Asm/X2/65/LO5-38/CRP | 10 | 3-4 |
| 11 | f | 55 | Arthritis (back/hands) | Asm/X2/65 | 7 | 1 |
| 12 | m | 48 | Arthritis (general) | Asm/X2/65 | 6 | 1 |
| 13 | m | 46 | Arthritis (general) | Asm/X2/65 | 5 | 1 |
| 14 | f | 90 | Arthritis (hand) | Asm/X2/65 | 9-10 | 1 |
| 15 | m | 53 | Arthritis (fingers) | Asm/X2/65 | 8 | 1 |
| 16 | f | 28 | Arthritis (neck) | Asm/X2/65 | 7-8 | 1 |
| 17 | f | 49 | Arthritis (hands) | 65 | 5-6 | 1 |
| 18 | f | 51 | Arthritis (shoulder) | Asm/X2/65 | 5 | 1 |
| 19 | m | 77 | Arthritis (knee) | Asm/X2/65/LO5-38/CRP/D5 | 10 | 3-4 |
| 20 | m | 52 | Arthritis (knee) | Asm/X2/65/LO5-38/D7/CRP | 7 | 3-4 |
| 21 | f | 53 | Arthritis (back) | Asm/X2/65/LO5-38/CRP | 7 | 4 |
| 22 | f | 64 | Arthritis (thumbs) | Asm/X2/65/LO5-38/CRP | 7 | 3 |
| 23 | f | 47 | Arthritis (general) | Asm/X2/65 | 8-9 | 2 |
| 24 | f | 74 | Arthritis (general) | Asm/X2/65/LO5-38/Mg44 | 10 | 1 |
| 25 | m | 65 | Arthritis (back) | Asm/X2/65 | 9 | 2-3 |
| 26 | f | 61 | Arthritis (knees) | Asm/X2/65 | 8-9 | 2 |

TABLE 7

Blood Pressure

| | | | | | Blood Pressure | |
|---|---|---|---|---|---|---|
| | sex | age | Condition | oligonucleotides | before | after |
| 1 | f | 74 | Untreated hypertension | CE/NEP-1/Asm/D5 | 190/100 | 165/75 |
| 2 | f | 56 | Untreated hypertension | CE/NEP-1/Asm/D5 | 190/100 | 160/80 |
| 3 | f | 62 | Hypertension despite treatment with Zestril. Atenolol & Furosemide | CE/NEP-1/Asm/D5 | 200/90 | 170/75 |
| 4 | f | 63 | Hypertension despite treatment with Atenolol & Prinivil | CE/NEP-1/Asm/D5 | 170/70 | 150/70 |
| 5 | m | 65 | Hypertension despite treatment with Atenolol | CE/NEP-1/Asm/D5 | 190/98 | 150/80 |
| 6 | f | 55 | Untreated Hypertension | CE | 190/100 | 160/100 |
| 7 | m | 76 | Hypertension | NEP-1 | 170/69 | 158/74 |
| 8 | m | 36 | Untreated Hypertension | NEP-1 | 214/144 | 160/80 |

TABLE 8

Elevated Cholesterol

| | | | | | Cholesterol Level | |
|---|---|---|---|---|---|---|
| | sex | age | Condition | oligonucleotides | before | after |
| 1 | f | | Hyperlipidemia | Mg44/Asm/D5 | 244 | 125 |
| 2 | f | | Hyperlipidemia | Mg44/Asm/D5 | 220 | <150 |
| 3 | m | | Hyperlipidemia | Mg44 | 265 | 177 |
| 4 | f | | Hyperlipidemia | Mg44 | 212 | 205 |
| 5 | m | | Hyperlipidemia | Mg44/Asm/D5 | 207 | 168 |
| 6 | f | | Hyperlipidemia | Mg44/Asm/D5 | 229 | 163 |
| 7 | f | | Hyperlipidemia | Mg44/Asm/D5 | 300 | 184 |
| 8 | m | | Hyperlipidemia (shifted from Zocor) | Mg44/Asm/D5/MTP | 213 | <150 |
| 9 | m | | Hyperlipidemia (shifted from Zocor) | Mg44/Asm/D5 | <150 | <150 |
| 10 | m | | Hyperlipidemia | Mg44/Asm/D5 | 201 | 164 |

TABLE 9

Emotional Distress

| | | | | | Severity | |
|---|---|---|---|---|---|---|
| | sex | age | condition | oligonucleotides | before | after |
| 1 | f | 39 | Stress | Asm/D5 | 9 | 1-2 |
| 2 | f | 46 | Stress | Asm/D5 | 8 | 2 |
| 3 | f | 52 | Depression | Asm/D5 | 10 | 1-2 |
| 4 | f | 29 | Stress/depression | Asm/D5 | 10 | 3 |
| 5 | m | 56 | Severe depression | Asm/D5 | 10 | 2 |
| 6 | f | 47 | Spousal abuse | Asm/D5 | 8-9 | 1-2 |
| 7 | f | 57 | stress | Asm/D5 | 10 | 1-2 |
| 8 | f | 40 | stress | Asm/D5 | 9 | 3 |
| 9 | f | 52 | Severe depression | Asm/D5 | 10 | 1 |
| 10 | f | 26 | stress | Asm/D5 | 8-9 | 1 |
| 11 | f | 36 | stress | Asm/D5 | 4-5 | 1 |
| 12 | f | 62 | Severe depression | Asm/D5 | 10 | 1 |
| 13 | m | 31 | stress | Asm/D5 | 8-9 | 1 |
| 14 | f | 52 | Stress/anxiety | Asm/D5 | 9-10 | 2-3 |
| 15 | f | 56 | Mild stress | Asm/D5 | 6 | 1 |
| 16 | f | 51 | mood swings | Asm/D5 | 7 | 1 |
| 17 | m | 47 | High stress | Asm/D5 | 10 | 2-3 |
| 18 | f | 56 | Spousal abuse | Asm/D5 | 10 | 5 |
| 19 | m | 56 | Stress | Asm/D5 | 7 | 2 |
| 20 | f | 63 | Depression | Asm/D5 | 10 | 1-2 |
| 21 | m | 51 | SAD | Asm/D5 | 10 | 1-2 |
| 22 | f | 35 | Suicidal | Asm/D5 | 10 | 1-2 |
| 23 | f | 38 | Severe depression | Asm/D5 | 10 | 1-3 |

TABLE 9-continued

| | sex | age | condition | oligonucleotides | Severity before | Severity after |
|---|---|---|---|---|---|---|
| Emotional Distress | | | | | | |
| 24 | f | 63 | Severe depression | Asm/D5 | 10 | 1-2 |
| 25 | f | 45 | Depression | Asm/D5 | 8-9 | 1-2 |
| 26 | f | 31 | depression | Asm/D5 | 8 | 1-2 |
| 27 | f | 34 | stress | Asm/D5 | 9 | 2 |
| 28 | m | 63 | anxiety | Asm/D5 | 9 | 1 |
| 29 | m | 32 | Stress/anxiety | Asm/D5 | 10 | 1 |
| 30 | f | 60 | Severe depression | Asm/D5 | 10 | 1-2 |
| 31 | f | 25 | OCD/stress | Asm/D5 | 10 | 3 |
| 32 | m | 41 | agoraphobic | Asm/D5 | 10 | 3-4 |
| 33 | f | 42 | Severe anxiety | Asm/D5 | 10 | 1 |
| 34 | f | 36 | depression | Asm/D5 | 9-10 | 1-2 |
| 35 | m | 59 | Spousal abuse | Asm/D5 | 10 | 2 |
| 36 | f | 52 | Depression | Asm/D5 | 8 | 2 |
| 37 | f | 31 | stress | Asm/D5 | 9 | 1 |
| 38 | f | 63 | stress | Asm/D5 | 8 | 1 |
| 39 | m | 55 | Anxiety/stress | Asm/D5 | 7 | 4 |
| 40 | m | 45 | stress | Asm/D5 | 4 | 1 |
| 41 | f | 42 | stress | Asm/D5 | 10 | 1 |
| 42 | f | 38 | Severe depression | Asm/D5 | 10 | 1-2 |
| 43 | m | 50 | Mild stress | Asm/D5 | 4 | 1 |
| 44 | f | 33 | Mild stress | Asm/D5 | 5 | 1 |
| 45 | f | 42 | depression | Asm/D5 | 8 | 1 |
| 46 | f | 65 | depression | Asm/D5 | 9 | 2-3 |
| 47 | f | 63 | Stress/anxiety | Asm/D5 | 10 | 2-3 |
| 48 | f | 44 | Stress/anxiety | Asm/D5 | 9-10 | 1-2 |
| 49 | f | 34 | stress | Asm/D5 | 9 | 2 |
| 50 | f | 50 | Mild stress | Asm/D5 | 7 | 1 |
| 51 | m | 65 | depression | Asm/D5 | 9-10 | 1-2 |
| 52 | f | 38 | stress | Asm/D5 | 8 | 1 |
| 53 | f | 32 | Stress/anxiety | Asm/D5 | 9 | 2-3 |
| 54 | f | 40 | stress | Asm/D5 | 8-9 | 1-2 |
| 55 | f | 54 | stress | Asm/D5 | 7-8 | 1 |
| 56 | f | 33 | anxiety | Asm/D5 | 8 | 1 |
| 57 | f | 54 | Stress/depression | Asm/D5 | 9 | 2-3 |
| 58 | f | 41 | stress | Asm/D5 | 10 | 1-2 |
| 59 | m | 15 | Panic attacks | Asm/D5 | 10 | 1 |
| 60 | f | 44 | stress | Asm/D5 | 6 | 1 |
| 61 | f | 41 | stress | Asm/D5 | 9 | 1 |
| 62 | m | 40 | stress | Asm/D5 | 7-8 | 1-2 |
| 63 | f | 13 | Mood swings | Asm/D5 | 8-9 | 1-2 |

TABLE 9-continued

| | sex | age | condition | oligonucleotides | Severity before | Severity after |
|---|---|---|---|---|---|---|
| Emotional Distress | | | | | | |
| 64 | f | 15 | Mood swings | Asm/D5 | 7-8 | 1 |
| 65 | f | 22 | stress | Asm/D5 | 10 | 1 |
| 66 | f | 51 | anxiety | Asm/D5 | 9 | 1 |
| 67 | m | 54 | Depression | Asm/D5 | 8 | 2 |
| 68 | f | 54 | depression | Asm/D5 | 8-9 | 3 |
| 69 | f | 51 | depression | Asm/D5 | 10 | 1-2 |
| 70 | f | 51 | stress | Asm/D5 | 5 | 1 |
| 71 | f | 56 | stress | Asm/D5 | 10 | 1-2 |
| 72 | f | 58 | depression | Asm/D5 | 8 | 2 |
| 73 | f | 39 | Mild stress | Asm/D5 | 5 | 1 |
| 74 | m | 24 | anxiety | Asm/D5 | 6 | 1 |
| 75 | m | 29 | stress | Asm/D5 | 8 | 4 |
| 76 | f | 43 | anxiety | Asm/D5 | 5 | 1 |
| 77 | m | 21 | Panic attacks | Asm/D5 | 10 | 1 |
| 78 | m | 66 | stress | Asm/D5 | 7-8 | 1-2 |
| 79 | f | 45 | Stress/anxiety | Asm/D5 | 7 | 1 |
| 80 | f | 74 | stress | Asm/D5 | 8-9 | 2 |
| 81 | f | 50 | Mild anxiety | Asm/D5 | 4 | 1 |
| 82 | f | 18 | Severe depression | Asm/D5 | 10 | 1 |
| 83 | f | 53 | stress | Asm/D5 | 9 | 3 |
| 84 | f | 32 | stress | Asm/D5 | 7 | 3 |
| 85 | f | 25 | stress | Asm/D5 | 8 | 1-2 |
| 86 | m | 47 | Severe depression | Asm/D5 | 9 | 1-2 |
| 87 | f | 38 | stress | Asm/D5 | 7 | 2 |
| 88 | m | 52 | stress | Asm/D5 | 5 | 1 |
| 89 | f | 14 | Panic attacks | Asm/D5 | 10 | 1-2 |
| 90 | m | 65 | anxiety | Asm/D5 | 8 | 1 |
| 91 | m | 39 | stress | Asm/D5 | 9 | 2 |
| 92 | m | 11 | stress | Asm/D5 | 7 | 1-2 |
| 93 | f | 31 | Severe depression | Asm/D5 | 10 | 3 |
| 94 | m | 67 | depression | Asm/D5 | 7 | 3 |
| 95 | f | 58 | stress | Asm/D5 | 7 | 2 |
| 96 | m | 67 | stress | Asm/D5 | 9 | 2 |
| 97 | m | 12 | ADD | Asm/D5 | 8 | 1 |
| 98 | f | 58 | stress | Asm/D5 | 9-10 | 2-3 |
| 99 | f | 30 | stress | Asm/D5 | 7 | 1 |
| 100 | m | 45 | stress | Asm/D5 | 6 | 1 |
| 101 | m | 13 | ADD | Asm/D5 | 9-10 | 2-3 |

TABLE 10

| | sex | age | condition | oligonucleotides | Elimination/day b/f | Elimination/day after | Severity b/f | Severity after |
|---|---|---|---|---|---|---|---|---|
| Gastrointestinal Disorders | | | | | | | | |
| 1 | f | 46 | IBS | Asm/X2/65 | 11 | 2 | 10 | 3 |
| 2 | m | 40 | Ulcerative colitis | Asm/X2/65 | 5 | 2 | 7 | 1 |
| 3 | f | 40 | IBS | Asm/X2/65 | 20 | 1-2 | 10 | 1 |
| 4 | f | 38 | Ulcerative colitis | Asm/X2/65 | 10-20 | 1 | 10 | 3 |
| 5 | f | 31 | Crohn's | X2/65 | 22 | 1 | 10 | 1 |
| 6 | f | 34 | Crohn's | X2/65 | 8-10 | 1-2 | 7 | 2 |
| 7 | f | 33 | IBS | Asm/X2/65 | 20 | 1-2 | 8 | 1 |
| 8 | m | 50 | IBS | Asm/X2/65 | 5 | 1-2 | 5 | 1 |
| 9 | f | 22 | Chronic constipation | Asm/X2/65 | 0 | 1-2 | 10 | 2 |
| 10 | f | 26 | Crohn's | X2/65 | 19-20 | 1 | 10 | 1 |
| 11 | f | 57 | Ulcerative colitis | Asm/X2/65 | 5-6 | 1 | 6 | 2 |
| 12 | f | 42 | IBS | Asm/X2/65 | 12 | 1 | 9 | 1 |
| 14 | f | 8 | IBS | Asm/65 (testing + X2) | 8 | 3-4 | 10 | 3 |
| 16 | f | 47 | IBS | Asm/X2/65 | 8 | 1-2 | 9 | 1 |
| 17 | f | 55 | IBS | Asm/X2/65 | 10 | 1 | 10 | 1 |
| 18 | m | 67 | IBS | Asm/X2/65 | 6-7 | 1-2 | 6 | 1 |
| 19 | f | 36 | IBS | Asm/X2/65 | 4 | 1 | 7-8 | 1 |
| 20 | m | 31 | Gall bladder | Asm/D5/Mg44 | nd | nd | 10 | 1 |
| 21 | m | 56 | Kidney stones | Mg44 | nd | nd | 10 | 1 |
| 22 | f | 37 | Gall bladder attack | Asm/X2/65/Mg44 | nd | nd | 4 | 1 |
| 23 | f | 57 | Gall bladder attack | Asm/D5/Mg44 | nd | nd | 7-8 | 1 |
| 25 | f | 54 | IBS | Super 8 | 5 | 1-2 | 5 | 1 |

TABLE 10-continued

| Gastrointestinal Disorders | | | | | | | | |
|---|---|---|---|---|---|---|---|---|
| | | | | | Elimination/day | | Severity | |
| | sex | age | condition | oligonucleotides | b/f | after | b/f | after |
| 26 | f | 7 | IBS | Super 8 | nd | nd | 8 | 2 |
| 27 | f | 38 | Ulcerative colitis | Super 8 | 3 | 1-2 | 4-5 | 1 |

TABLE 11

| Inflammation | | | | | | |
|---|---|---|---|---|---|---|
| | | | | | Severity | |
| | sex | age | condition | oligonucleotides | before | after |
| 1 | f | 39 | Post surgical | Asm/X2/65/cd18-1 | 10 | 4 |
| 2 | f | 64 | Post surgical | Asm | 10 | 2 |
| 3 | m | 55 | Asthma/emphysema | Asm/X2/65 | 9 | 7 |
| 4 | f | 33 | asthma | Asm/X2/65 | 10 | 1-2 |
| 5 | f | 40 | asthma | Asm | 10 | 1 |
| 6 | f | 40 | Bee sting | Asm | 10 | 1 |
| 7 | m | 5 | Bee sting | Asm/topical | 10 | 1 |
| 8 | f | 44 | Black fly bite | IL-501 | 10 | 1 |
| 9 | f | 8 | Black fly bite | IL-501 | 10 | 1 |
| 10 | f | 6 | Black fly bite | IL-501 | 10 | 1 |
| 11 | f | 63 | Hair implants | Asm | 10 | 1 |
| 12 | m | 66 | gout | Asm | 8 | 2 |
| 13 | m | 51 | gout | Asm | 10 | 1 |
| 14 | m | 45 | gout | Asm | 10 | 1 |
| 15 | f | 56 | Polymyalgia rheumatica | Asm/X2/65/D7/CRP | 10 | 3 |
| 16 | f | 31 | Multiple sclerosis | Asm/X2/65 | 9-10 | 2 |
| 17 | f | 67 | polymyositis | Asm/X2/65/D7/CRP | 8-9 | 3-4 |
| 18 | m | 32 | Swollen joints | Asm | 9 | 1-2 |
| 19 | m | 65 | Inner ear inflammation | Asm | 7 | 1 |
| 20 | m | 26 | hemorrhoids | Asm | 10 | 5 |
| 21 | f | 41 | hemorrhoids | Asm | 10 | 1 |
| 22 | m | 75 | shingles | Asm/D7 | 10 | 3 |
| 23 | m | 48 | Sore muscles | Asm | 7 | 1 |
| 24 | f | 36 | Varicose veins | Asm | 7 | 7 |
| 25 | f | 74 | Swollen ankle | Asm/X2/65 | 10 | 2 |
| 26 | f | 41 | Swollen ankle | Asm | 10 | 1 |
| 27 | f | 63 | Swollen knee | Asm/X2/65/cd18-1 | 10 | 2 |
| 28 | f | 45 | Ganglion cyst | Asm/X2/65 | 7 | 1 |
| 29 | f | 73 | sciatica | Asm | 10 | 1 |
| 30 | m | 25 | sciatica | Asm | 10 | 1 |
| 31 | m | 54 | sciatica | Asm/X2/65 | 10 | 6 |
| 32 | m | 47 | sciatica | Asm/X2/65 | 10 | 1 |
| 33 | f | 44 | sciatica | Asm | 10 | 1 |
| 34 | f | 46 | Itchy ears | Asm | 6 | 1 |
| 35 | m | 59 | cellulitis | Asm/Nu-3 | 10 | 3-4 |
| 36 | f | 22 | Stomach inflammation | Asm/X2/65 | 9 | 2 |
| 37 | f | 44 | Pinched nerve | Asm/X2/65 | 10 | 1 |
| 38 | f | 44 | Pinched nerve | Asm/X2/65 | 10 | 1 |
| 39 | m | 46 | Hockey/tennis elbow | Asm/X2/65 | 9 | 1 |
| 40 | m | 40 | Hockey/tennis elbow | Asm/X2/65 | 10 | 1 |
| 41 | m | 16 | Pitcher's arm | Asm | 10 | 1 |
| 42 | f | 58 | Heel spur | Asm | 7 | 1 |
| 43 | f | 46 | Multiple sclerosis | Asm/X2/65 | 8 | 2 |
| 44 | f | 63 | hemorrhoids | Asm/Nu-3 | 10 | 3 |
| 45 | m | 64 | bursitis | Asm/X2/65/LO5-38 | 9 | 1-2 |
| 46 | f | 25 | Interstitial cystitis | Asm/X2/65/LO5-38 | 10 | 2 |
| 47 | m | 67 | Inflamed hands | Asm/D5/X2/65/IL-501 | 10 | 5 |
| 48 | f | 30 | Morning sickness | Asm/D5 | 10 | 7 |
| 49 | f | 12 | Inflamed tonsils | Asm | 10 | 1-2 |
| 50 | f | 33 | Inflamed cat scratch | Asm/topical | 6 | 1 |
| 51 | f | 38 | Allergies | Asm | 10 | 3 |
| 52 | f | 42 | Insect bite | IL-501/topical | 9 | 1 |
| 53 | f | 10 | Severe wasp bites | Asm/topical | 10 | 1 |
| 54 | f | 45 | Black fly bites | IL-501/topical | 9 | 1 |
| 55 | f | 62 | Wasp bite | Asm | 8 | 1 |
| 56 | f | 7 | Ear piercing | Asm | 8 | 1 |
| 57 | f | 9 | Ear piercing | Asm | 8 | 1 |
| 58 | m | 37 | Pinched nerve | Asm/X2/65 | 9-10 | 1 |
| 59 | f | 7 | "goose egg" on forehead | Asm/topical | 8 | 1 |
| 60 | m | 12 | Knee injury | Asm/topical | 6 | 1 |

TABLE 11-continued

Inflammation

| | sex | age | condition | oligonucleotides | Severity before | Severity after |
|---|---|---|---|---|---|---|
| 61 | f | 43 | sciatica | Asm/topical | 9-10 | 1 |
| 62 | f | 45 | Pulled muscle (knee) | Asm/topical | 6 | 1 |
| 63 | m | 43 | Degenerative hip | Asm/topical | 5 | 1-2 |
| 64 | m | 65 | Chronic cough | D7 | 10 | 4 |
| 65 | m | 38 | Extreme autoimmune graft rejection/sinusitis/Erosive Peptic Esophagitis | Asm/X2/65/D7/LO5-38/ICAM/cd-18-1/IL6/HisR1 | 10 | 3 |
| 66 | f | 10 | Seasonal allergies | Asm | 7-8 | 1 |
| 67 | f | 42 | Interstitial cystitis | Asm/X2/65 | 9 | 1 |
| 68 | f | 34 | Chronic allergies | Asm/X2/65/D5 | 8 | 2 |
| 69 | f | 44 | Seasonal allergies/cough | IL-501 | 6 | 1 |
| 70 | f | 61 | Seasonal allergies/cough | IL-501 | 6 | 1 |

TABLE 12

Migraines

| | sex | age | Condition | oligonucleotides | Severity before | Severity after |
|---|---|---|---|---|---|---|
| 1 | f | 42 | migraine | Asm/D5/X2/Mg44 | 10 | 1 |
| 2 | f | 51 | migraine | Asm/D5/X2/Mg44 | 9 | 1-2 |
| 3 | f | 28 | migraine | Asm/D5/X2/Mg44 | 10 | 1 |
| 4 | f | 36 | migraine | Asm/D5/X2/Mg44 | 10 | 2 |
| 5 | f | 46 | migraine | Asm/D5/X2/Mg44 | 10 | 1 |
| 6 | f | 51 | migraine | Asm/D5/X2/Mg44 | 9 | 1 |
| 7 | f | 39 | migraine | Asm/D5/X2/Mg44 | 8 | 1 |
| 8 | f | 30 | migraine | Asm/D5/X2/Mg44 | 9 | 1 |
| 9 | f | 58 | Migraine | Asm/D5/X2/Mg44 | 9 | 1 |
| 10 | f | 57 | Migraine | Asm/D5/X2/Mg44 | 10 | 1 |
| 11 | f | 21 | migraine | Asm/D5/X2/Mg44 | 9 | 2-3 |

TABLE 13

Neurological Disorders

| | sex | age | Condition | oligonucleotides | Severity before | Severity after |
|---|---|---|---|---|---|---|
| 1 | f | 56 | polymyalgia | Asm/X2/65/D7/CRP | 10 | 3 |
| 2 | f | 31 | multiple sclerosis | Asm/X2/65 | 9-10 | 2 |
| 3 | f | 67 | polymyositis | Asm/X2/65/D7/CRP | 8-9 | 3-4 |
| 4 | f | 46 | multiple sclerosis | Asm/X2/65 | 8 | 2 |

TABLE 14

Pain

| | sex | age | Condition | oligonucleotides | Severity before | Severity after |
|---|---|---|---|---|---|---|
| 1 | f | 74 | Back | Asm/X2/65/LO5-38/Mg44 | 10 | 5 |
| 2 | m | 54 | back | Asm/X2/65 | 9 | 2 |
| 3 | f | 37 | shoulder | Asm/X2 | 6-7 | 1 |
| 4 | f | 41 | ankle | X2 | 5 | 1 |
| 5 | f | 61 | knee | X2 | 8 | 3 |
| 6 | f | 41 | ovarian | Asm/X2 | 8-9 | 3 |
| 7 | f | 61 | headache | Asm/X2 | 8 | 1 |
| 8 | f | 54 | headache | Asm/X2/65 | 8 | 5 |
| 9 | m | 26 | headache | Asm/X2 | 9 | 1 |
| 10 | f | 65 | headache | Asm/X2/65 | 8 | 1 |
| 11 | f | 36 | headache | Asm/X2 | 7 | 1 |
| 12 | f | 39 | headache | Asm/X2/D5 | 6 | 1 |

TABLE 14-continued

Pain

| | sex | age | Condition | oligonucleotides | Severity before | Severity after |
|---|---|---|---|---|---|---|
| 13 | f | 62 | headache | Asm/X2/D5 | 10 | 1-2 |
| 14 | f | 46 | knee | Asm/X2/D5 | 6 | 2 |
| 15 | f | 31 | knee | Asm/X2/65 | 7 | 1 |
| 16 | f | 62 | knee | Asm/X2/65 | 7 | 2 |
| 17 | f | 61 | knee | Asm/X2 | 8 | 3 |
| 18 | f | 37 | knee | Asm/X2 | 9 | 1-2 |
| 19 | f | 39 | Surgical pain | Asm/X2/65 | 10 | 4 |
| 20 | m | 56 | Cancer pain | X2 | 10 | 6 |
| 21 | m | 30 | stitches | Asm/X2 | 10 | 1-2 |
| 22 | m | 20 | Tooth extraction | Asm/X2 | 10 | 1 |
| 23 | f | 53 | Tooth extraction | Asm/X2 | 9 | 1-2 |
| 24 | f | 30 | Tooth extraction | Asm/X2 | 10 | 1 |
| 25 | f | 45 | Tooth extraction | Asm/X2 | 8 | 1-2 |
| 26 | f | 74 | Rib soreness | Asm/X2/LO5-38/Mg44 | 10 | 1 |
| 27 | f | 48 | shoulder | Asm/X2/65 | 8 | 1 |
| 28 | f | 43 | headache | X2 | 8-9 | 1-2 |
| 29 | m | 38 | headache | X2 | 7 | 1-2 |
| 30 | m | 76 | Tooth extraction | Asm/X2/65 | 8 | 1-2 |
| 31 | m | 23 | Wisdom tooth pain | Asm/X2/65 | 9 | 2-3 |
| 32 | f | 42 | headaches | Asm/D5/X2 | 7 | 1 |
| 33 | f | 47 | Neck pain | Super 8 | 7 | 1 |
| 34 | f | 31 | Headaches | Asm/D5/X2 | 10 | 3 |
| 35 | f | 59 | Teeth pain | Super 8 | 6 | 1 |
| 36 | f | 31 | Knee pain | Super 8 | 6 | 1 |
| 37 | m | 10 | Ankle pain | Asm/65 | 5 | 1 |
| 38 | f | 13 | Tooth extraction | Asm/X2/65 | 7 | 1 |
| 39 | m | 65 | thyroidectomy | Super 8 | 10 | 1 |
| 40 | f | 46 | Surgical pain | Super 8 | 9 | 1 |

TABLE 15

Premenstrual Syndrome

| | sex | age | Condition | oligonucleotides | Severity before | Severity after |
|---|---|---|---|---|---|---|
| 1 | f | 41 | PMS | Asm/D5/X2 | 10 | 1-2 |
| 2 | f | 34 | PMS | Asm/D5/X2 | 10 | 1 |
| 3 | f | 37 | PMS | Asm/D5/X2 | 10 | 1 |
| 4 | f | 53 | PMS | Asm | 10 | 1 |
| 5 | f | 13 | PMS | Asm/D5/X2 | 10 | 1 |
| 6 | f | 15 | PMS | Asm/D5/X2 | 10 | 1 |
| 7 | f | 47 | PMS | Asm/D5/X2 | 10 | 9 |
| 8 | f | 44 | PMS | Asm | 10 | 1 |
| 9 | f | 20 | PMS | Asm/D5/X2 | 10 | 1 |

TABLE 16

| Prostatitis | | | | | | |
|---|---|---|---|---|---|---|
| | | | | | Severity | |
| | sex | age | Condition | oligonucleotides | before | after |
| 1 | m | 63 | BPH | MPB/Asm/X2/65 | 10 | 1 |
| 2 | m | 77 | BPH | Asm/D5/X2 | 3 | 1 |
| 3 | m | 45 | Inflamed prostate | Asm/D5/X2 | 4 | 1 |
| 4 | m | 69 | BPH | MPB/Asm/X2/65 | 7 | 1-2 |

TABLE 17

| Sinus | | | | | | |
|---|---|---|---|---|---|---|
| | | | | | Severity | |
| | sex | age | Condition | oligonucleotides | before | after |
| 1 | m | 8 | Sinus/cold | Asm/Nu-3 nasal | 5 | 1-2 |
| 2 | f | 60 | Sinus/cold | Asm/Nu-3 nasal | 7 | 2 |
| 3 | f | 42 | Sinus/cold | Asm/Nu-3 nasal | 8 | 1 |
| 4 | f | 41 | Sinus/cold | Asm/Nu-3 nasal | 6 | 4 |
| 5 | m | 55 | Sinus/cold | Asm/Nu-3 nasal | 6 | 1 |
| 6 | f | 47 | Sinus/cold | Asm/Nu-3 nasal | 7 | 1-2 |
| 7 | f | 40 | Sinus/cold | Asm/Nu-3 nasal | 5 | 1-2 |
| 8 | f | 35 | Sinus/cold | Asm/Nu-3 nasal | 7 | 1 |
| 9 | f | 12 | Sinus/cold | Asm/Nu-3 nasal | 5 | 1 |
| 10 | f | 34 | Sinus/cold | Asm/Nu-3 nasal | 9 | 1 |
| 11 | m | 17 | Sinus/cold | Asm/Nu-3 nasal | 7 | 2 |
| 12 | m | 15 | Sinus/cold | Asm/Nu-3 nasal | 6 | 2 |
| 13 | m | 70 | Sinus/cold | Asm/Nu-3 nasal | 5 | 1 |
| 14 | f | 53 | Sinus/cold | Asm/Nu-3/CRP | 7 | 3 |
| 15 | m | 77 | Sinus/cold | Asm/Nu-3 nasal | 8 | 3 |
| 16 | f | 37 | Sinus/cold | Asm/Nu-3 nasal | 8 | 2 |
| 17 | f | 55 | Sinus/cold | Asm/Nu-3 nasal | 9 | 2 |
| 18 | m | 17 | Sinus/cold | Asm/Nu-3 nasal | 7 | 1 |
| 19 | f | 62 | Sinus/cold | Asm/Nu-3 nasal | 7 | 1 |
| 20 | m | 43 | Sinus/cold | Asm/Nu-3 nasal | 9 | 1 |
| 21 | f | 41 | Sinus/cold | Asm/Nu-3 nasal | 6 | 1 |
| 22 | f | 58 | Sinus/cold | Asm/Nu-3 nasal | 6 | 1 |
| 23 | f | 34 | Sinus/cold | Asm/Nu-3 nasal | 8 | 1 |
| 24 | f | 61 | Sinus/cold | Asm/Nu-3 nasal | 6 | 2 |
| 25 | f | 19 | Sinus/cold | Asm/Nu-3 nasal | 8 | 1 |
| 26 | f | 50 | Sinus/cold | Asm/Nu-3 nasal | 6 | 1 |
| 27 | m | 36 | Sinus/cold | Asm/Nu-3 nasal | 7 | 6 |
| 28 | f | 48 | Sinus/cold | Asm/Nu-3 nasal | 8 | 2 |
| 29 | f | 60 | Sinus/cold | Asm/Nu-3 nasal | 7 | 1 |
| 30 | m | 40 | Sinus/cold | Asm/Nu-3 nasal | 8 | 1 |
| 31 | f | 45 | Sinus/cold | Asm/Nu-3 nasal | 8 | 1 |
| 32 | f | 32 | Sinus/cold | Asm/Nu-3 nasal | 6 | 1 |
| 33 | f | 48 | Sinus/cold | Asm/Nu-3 nasal | 9 | 2-3 |
| 34 | f | 37 | Sinus/cold | Asm/Nu-3 nasal | 7 | 2 |
| 35 | f | 49 | Sinus/cold | Asm/Nu-3 nasal | 7 | 1-2 |
| 36 | m | 30 | Sinus/cold | Asm/Nu-3 nasal | 8-9 | 1 |
| 37 | m | 52 | Sinus/cold | Asm/Nu-3 nasal | 7 | 3 |
| 38 | f | 67 | Sinus/cold | Asm/Nu-3 nasal | 8 | 1 |
| 39 | m | 53 | Sinus/cold | Asm/Nu-3 nasal | 7 | 1 |
| 40 | f | 12 | Sinus/cold | Asm/Nu-3 nasal | 9 | 2-3 |
| 41 | f | 8 | Sinus/cold | Asm/Nu-3 nasal | 5 | 1 |
| 42 | f | 25 | Sinus/cold | Asm/Nu-3 nasal | 7 | 1 |
| 43 | f | 42 | Sinus/cold | Asm/Nu-3 nasal | 9 | 1-2 |
| 44 | f | 54 | Sinus/cold | Asm/Nu-3 nasal | 9 | 2-3 |
| 45 | f | 42 | Sinus/cold | Asm/Nu-3 nasal | 7 | 2 |
| 46 | f | 45 | Sinus/cold | Asm/Nu-3 nasal | 6 | 1 |
| 47 | m | 47 | Sinus/cold | Asm/Nu-3 nasal | 7 | 1 |
| 48 | f | 60 | Sinus/cold | Asm/Nu-3 nasal | 8 | 1 |
| 49 | f | 34 | Sinus/cold | Asm/Nu-3 nasal | 9 | 2 |
| 50 | f | 37 | Sinus/cold | Asm/Nu-3 nasal | 9 | 2-3 |
| 51 | f | 49 | Sinus/cold | Asm/Nu-3 nasal | 7 | 1 |
| 52 | f | 39 | Sinus/cold | Asm/Nu-3 nasal | 9 | 1 |
| 53 | f | 51 | Sinus/cold | Asm/Nu-3 nasal | 10 | 1-2 |

TABLE 18

| Trauma | | | | | | |
|---|---|---|---|---|---|---|
| | | | | | Severity | |
| | sex | age | Condition | oligonucleotides | before | after |
| 1 | f | 41 | Broke femur | Asm | 10 | 1 |
| 2 | f | 54 | Torn ligament | Asm | 7 | 1 |
| 3 | m | 57 | Compound fracture/leg | Asm/X2/65 | 10 | 4 |
| 4 | f | 72 | Sprained ankle | Asm/X2/65 | 6 | 1 |
| 5 | f | 47 | Root canal | Asm/X2/65 | 7 | 2 |
| 6 | f | 28 | Neck surgery | Asm/X2/65 | 9 | 1 |
| 7 | f | 47 | Torn rotator cup | Asm/X2/65/LO5-38 | 7 | 2-3 |
| 8 | f | 28 | Fractured ankle | Asm/X2/65 | 10 | 1 |
| 9 | m | 48 | Hyperextended elbow | Asm/X2/65/D7 | 7 | 2 |
| 10 | m | 19 | Motorcycle back injury | Asm/X2/65 | 9 | 2 |
| 11 | f | 64 | Fractured tibia | Asm/X2/65/LO5-38 | 10 | 3 |
| 12 | f | 41 | Cellulitis from impaled object | Asm/X2/65/D7 | 10 | 3-4 |
| 13 | f | 74 | Broken ribs | Asm/X2/65/LO5-38/Mg44 | 10 | 1 |
| 14 | f | 36 | Lumpectomy pain | Asm/topical | 10 | 1 |
| 15 | f | 37 | Torn miniscus | Asm/topical | 10 | 1 |
| 16 | m | 43 | Two broken arms | Asm | 10 | 2-3 |
| 17 | m | 1 | Finger slammed in door | Asm | 9 | 1 |
| 18 | f | 48 | Hysterectomy scar | Asm/topical | 7 | 1 |
| 19 | f | 45 | Broken toe | Asm/topical | 10 | 1-2 |
| 20 | f | 37 | Shoulder injury | Asm/X2 | 6 | 1 |
| 21 | m | 59 | Fluid on knee | Super 8 | 7 | 1 |
| 22 | f | 33 | Broken collarbone | Super 8 | 9 | 2 |
| 23 | m | 12 | Sprained finger | Asm/65 | 8 | 1 |
| 24 | f | 43 | Broken foot | Super 8/Mg44 | 9 | 1 |

TABLE 19

| Carpal tunnel | | | | | | |
|---|---|---|---|---|---|---|
| | | | | | Severity | |
| | sex | age | Condition | oligonucleotides | before | after |
| 1 | m | 36 | Carpal tunnel | Asm | 9 | 1 |
| 2 | f | 42 | Carpal tunnel | Asm | 10 | 1 |
| 3 | f | 56 | Carpal tunnel | Asm | 9 | 1 |
| 4 | m | 75 | Carpal tunnel | Asm | 8 | 1-2 |
| 5 | m | 55 | Carpal tunnel | Asm/X2/65 | 8 | 1 |
| 6 | m | 21 | Carpal tunnel | Asm | 9 | 2 |
| 7 | m | 56 | Carpal tunnel | Asm/X2/65 | 10 | 1-2 |
| 8 | f | 63 | Carpal tunnel | Asm | 10 | 2-3 |
| 9 | f | 45 | Carpal tunnel | Super 8 | 7 | 2 |

TABLE 20

| Chronic Fatigue/Fibromyalgia | | | | | | |
|---|---|---|---|---|---|---|
| | | | | | Severity | |
| | sex | age | Condition | oligonucleotides | before | after |
| 1 | f | 62 | CFS | Asm/D5/X2 | 9 | 1 |
| 2 | f | 60 | Fibromyalgia | Asm/D5/X2 | 10 | 1 |
| 3 | f | 56 | CFS | Asm/D5/X2 | 9 | 1 |
| 4 | m | 36 | CFS | Asm/D5/X2 | 8 | 1-2 |
| 5 | m | 69 | CFS | Asm/D5/X2 | 8 | 1 |
| 6 | m | 51 | CFS | Asm/D5/X2 | 9 | 2 |
| 7 | m | 38 | CFS | Asm/D5/X2 | 10 | 1-2 |
| 8 | f | 40 | Fibromyalgia | Asm/D5/X2 | 10 | 2-3 |

TABLE 21

| | sex | age | Condition | oligonucleotides | Severity before | Severity after |
|---|---|---|---|---|---|---|
| | | | Eczema/Atopic Dermatitis | | | |
| 1 | f | 63 | Foot rash | Asm | 8 | 1 |
| 2 | f | 49 | hives | Asm/X2/65/D7 | 10 | 1-2 |
| 3 | f | 13 | Severe leg rashes | Asm | 10 | 3-4 |
| 4 | m | 36 | eczema | Asm/X2/65 | 7-8 | 3-4 |
| 5 | f | 41 | Non-specific rash | Asm | 8 | 1 |
| 6 | m | 11 | eczema | Asm | 10 | 1-2 |
| 7 | f | 51 | rash | Asm/X2 | 5 | 1 |
| 8 | m | 48 | rash | Asm | 6-7 | 1-2 |
| 9 | f | 30 | Atopic dermatitis | Asm | 9 | 1 |
| 10 | f | 26 | Face rash | Asm | 7 | 2 |
| 11 | m | 42 | Severe rash | Asm/X2/65/D7 | 10 | 1 |
| 12 | f | 8 | Rash | Asm | 4 | 1 |
| 13 | f | 12 | eczema | Asm | 6 | 1 |
| 14 | m | 67 | Severely inflamed fingers | Asm/X2/65/IL-501 | 10 | 3-4 |
| 15 | f | 52 | rash | Asm | 6 | 1 |
| 16 | f | 42 | Severe hives | Asm/X2/65 | 10 | 1 |
| 17 | f | 14 | Chronic eczema | Asm | 7 | 1 |
| 18 | m | 64 | eczema | Asm/X2/65 | 8 | 1 |
| 19 | f | 63 | Non-specific itching | Asm | 7-8 | 1 |
| 20 | f | 58 | Contact dermatitis | Asm/topical | 8 | 1 |
| 21 | m | 47 | Itchy scar | Asm/topical | 5 | 1 |
| 22 | f | 37 | Severe contact dermatitis | Asm/topical | 7 | 2 |
| 23 | m | 36 | Severe atopic dermatitis | Asm | 10 | 1 |
| 24 | m | 1 | Severe diaper rash | Asm/topical | 10 | 1 |
| 25 | f | 40 | Eczema | Asm | 6 | 1-2 |
| 26 | f | 35 | Itchy/scaly patches on feet | Asm | 7-8 | 1 |
| 27 | m | 17 | Atopic dermatitis | Asm | 7 | 1 |
| 28 | f | 19 | Severe razor burn | Asm/topical | 10 | 1 |
| 29 | m | 24 | Severe razor burn | Asm/topical | 10 | 1 |
| 30 | f | 40 | Inflamed hands | Asm/topical | 7 | 1 |
| 31 | m | 19 | split, cracked cuticles | cd18-1 | 7 | 1 |
| 32 | f | 51 | Split lips | cd18-1 | 5 | 1 |
| 33 | f | 30 | Dry, cracked skin on hands | cd18-1/topical | 8 | 1 |
| 34 | f | 60 | rash | Super 8 | 9 | 1 |
| 35 | f | 38 | Spider bite | Super 8 | 10 | 2-3 |
| 36 | f | 15 | rash | Super 8 | 5 | 1 |

TABLE 22

| | sex | age | Condition | oligonucleotides | Severity before | Severity after |
|---|---|---|---|---|---|---|
| | | | Erectile Dysfunction | | | |
| 1 | m | 65 | ED/blood pressure med. | D5 | 10 | 1 |
| 2 | m | 69 | ED/blood pressure med. | Asm/D5 | 9 | 2-3 |
| 3 | m | 52 | ED | Asm/D5 | 10 | 1 |

TABLE 23

| | sex | age | Condition | oligonucleotides | Severity before | Severity after |
|---|---|---|---|---|---|---|
| | | | Heartburn/Acid Reflux | | | |
| 1 | f | 63 | heartburn | Acid-2/Acid B2 | 10 | 1 |
| 2 | f | 49 | heartburn | Acid-2/Acid B2 | 10 | 1 |
| 3 | f | 22 | Heartburn | Acid-2/Acid B2 | 10 | 1 |
| 4 | f | 42 | Heartburn | Acid-2 | 7-8 | 1 |

TABLE 23-continued

| | sex | age | Condition | oligonucleotides | Severity before | Severity after |
|---|---|---|---|---|---|---|
| | | | Heartburn/Acid Reflux | | | |
| 5 | f | 41 | Heartburn | Acid-2/Acid B2 | 9-10 | 1 |
| 6 | f | 70 | Heartburn | Acid-2/Acid B2 | 5 | 1 |
| 7 | f | 47 | heartburn | Acid-2/Acid B2 | 8 | 1 |
| 8 | f | 41 | heartburn | Acid-2/Acid B2 | 10 | 1 |
| 9 | f | 19 | heartburn | Acid-2/Acid B2 | 7 | 1 |
| 10 | m | 77 | heartburn | Acid-2/Acid B2 | 10 | 1 |
| 11 | f | 52 | heartburn | Acid-2/Acid B2 | 10 | 1 |
| 12 | f | 21 | Heartburn | Acid-2/Acid B2 | 10 | 1 |
| 13 | f | 41 | heartburn | Acid-2/Acid B2 | 10 | 1 |
| 14 | f | 46 | heartburn | Acid-2/Acid B2 | 10 | 1 |
| 15 | f | 63 | heartburn | Acid-2/Acid B2 | 10 | 1 |
| 16 | f | 62 | heartburn | Acid-2/Acid B2 | 10 | 1 |

TABLE 24

| | sex | age | Condition | oligonucleotides | Severity before | Severity after |
|---|---|---|---|---|---|---|
| | | | Poison Ivy | | | |
| 1 | m | 10 | Poison ivy | Asm | 7 | 1 |
| 2 | f | 43 | Poison ivy | Asm | 7 | 1 |
| 3 | f | 63 | Poison ivy | Asm | 10 | 1 |
| 4 | f | 42 | Poison ivy | Asm | 6 | 1 |
| 5 | m | 3 | Poison ivy | Asm | 6 | 1 |
| 6 | m | 47 | Poison ivy | Asm | 10 | 1 |
| 7 | f | 53 | Poison ivy | Asm | 10 | 1 |
| 8 | m | 21 | Poison ivy | Asm/topical | 8-9 | 1 |
| 9 | f | 12 | Poison ivy | Asm/topical | 10 | 1 |
| 10 | f | 56 | Poison ivy | Asm/topical | 9 | 1 |
| 11 | f | 40 | Poison ivy | Asm/topical | 7-8 | 1 |
| 12 | f | 49 | Poison ivy | Asm | 10 | 1 |
| 13 | m | 17 | Poison ivy | Asm | 7 | 1 |
| 14 | f | 65 | Poison ivy | Asm | 5-6 | 1 |

TABLE 25

| | sex | age | Condition | oligonucleotides | Severity before | Severity after |
|---|---|---|---|---|---|---|
| | | | Psoriasis | | | |
| 1 | m | 59 | stress induced psoriasis | Asm/D5/X2 | 10 | 3 |
| 2 | f | 77 | psoriasis | Asm/D5/65 | 5 | 1 |
| 3 | f | 34 | psoriasis | Asm/D5/65 | 9-10 | 1 |
| 4 | m | 27 | psoriasis | Asm/D5/65 | 7 | 1 |
| 5 | f | 41 | psoriasis | Asm/D5/65 | 7 | 2-3 |
| 6 | f | 19 | psoriasis | Asm/D5/65 | 9 | 1 |
| 7 | f | 6 | psoriasis | Asm | 6 | 1 |
| 8 | f | 75 | psoriasis | Asm | 4 | 1 |
| 9 | m | 47 | Severe psoriasis | Asm | 10 | 2-3 |
| 10 | m | 36 | psoriasis | Asm/D5/65 | 5 | 1 |
| 11 | f | 24 | psoriasis | Asm/D5/65 | 9 | 1 |

TABLE 26

| | sex | age | Condition | oligonucleotides | Severity before | Severity after |
|---|---|---|---|---|---|---|
| | | | Rosacea | | | |
| 1 | f | 40 | Rosacea | Asm | 6 | 1-2 |
| 2 | f | 38 | Rosacea | Asm | 4 | 1 |

TABLE 26-continued

| Rosacea | | | | | | |
|---|---|---|---|---|---|---|
| | | | | | Severity | |
| | sex | age | Condition | oligonucleotides | before | after |
| 3 | f | 58 | Rosacea | Asm | 7 | 1 |
| 4 | f | 40 | Rosacea | Asm | 8 | 1 |
| 5 | f | 40 | Rosacea | Asm | 8-9 | 1 |
| 6 | f | 36 | Rosacea | Asm | 6 | 3 |
| 7 | f | 48 | Rosacea | Asm/X2/65 | 6-7 | 1 |
| 8 | f | 32 | Rosacea | Asm | 6 | 1 |

TABLE 27

| Average of Results | | | |
|---|---|---|---|
| Condition | # cases | pre-treatment average | post-treatment average |
| elevated cholesterol | 10 | 230 | 166 |
| hypertension | 8 | 190/96 | 159/79 |
| inflammatory bowel | 12 | 10 toilet trips | 1-2 toilet trips |
| crohn's disease | 3 | 17 toilet trips | 1-2 toilet trips |
| ulcerative colitis | 5 | 8 toilet trips | 1-2 toilet trips |
| acid reflux/heartburn | 16 | 9.2 | 1.0 |
| emotional distress | 127 | 8.2 | 1.4 |
| PMS | 9 | 10.0 | 1.0 |
| inflammation | 70 | 9.0 | 1.7 |
| pain | 40 | 8.8 | 2.0 |
| infection | 78 | 7.1 | 1.6 |
| migraine | 14 | 9.4 | 1.3 |
| neurological disorders | 9 | 9.0 | 3.0 |
| poison ivy | 14 | 8.0 | 1.0 |
| prostatitis | 5 | 6.6 | 1.2 |
| psoriasis | 14 | 7.1 | 1.5 |
| rocacea | 10 | 6.3 | 1.1 |
| trauma | 25 | 8.7 | 1.7 |
| sinus/cold | 53 | 7.3 | 1.6 |
| erectile dysfunction | 5 | 9.0 | 1.5 |
| eczema/rash | 36 | 8.5 | 1.4 |
| fibromyalgia | 7 | 10.0 | 1.8 |
| chronic fatigue | 9 | 9.5 | 1.2 |
| carpal tunnel syndrome | 9 | 8.9 | 1.3 |
| arthritis | 30 | 7.6 | 2.0 |
| appetite | 16 | 9.5 | 2.3 |

EXAMPLE 24

For animal studies, animals with different indications were provided with oligonucleotide compositions containing RNA oligonucleotides complementary to the phosphodiesterase 4, phosphodiesterase 5 genes or as indicated in FIG. 24. Some animals were additionally given compositions containing additional RNA oligonucleotides complementary to other genes such as cyclooxygenase 2 and p65. Oligonucleotide concentrations were typically 0.3 to 300 $A_{260}$/RNA/ml taken in doses (0.1-100 μg/kg) of 0.5 ml two to four times per day. The effect of the composition was then evaluated (see Table 27). Treatment efficacy was evaluated by an attending veterinarian.

TABLE 27

| Animal studies | | | | |
|---|---|---|---|---|
| | | | Severity | |
| animal | Condition | oligonucleotides | before | after |
| dog | skin allegry | Asm | 8 | 2 |
| dog | inflammatory bowel disease | Asm, CX2, P65 | 7 | 2 |
| horse | nervous and aigtated | Asm, D5 | 8 | 2 |

EXAMPLE 24

The following is the method for selecting nucleic acid sequences from a known gene sequence for the design of oligonucleotides. Preferred choices are sequences that either are adjacent to, or overlap the start site, followed by sequences that are in the 5' un-translated region, followed by sequences immediately adjacent to or overlapping the termination signal. This method is very effective and when combined with, achiral RNA, it produces oligonucleotides that display therapeutic efficacy consistently.

For example, achiral RNA oligonucleotides (10-30 bases in length), or achiral 2'-methoxy oligonucleotides (10-30 bases in length), or achiral 2'-methoxy oligonucleotides (10-30 bases in length) with (a) 3' or 3' & 5' acid stable end-blocks located in the 5' UTR, or (b) immediately adjacent to or more preferably overlapping at least one of the three bases of the start site and extending either 5' or 3' of the start site, or (c) immediately adjacent to or overlapping one of the three bases of the termination signal and extending 3' or 5' of the termination site that are ten to thirty contiguous bases in length and complementary to a RNA or DNA and that have the following binding characteristics:

(d) AG of the oligonucleotide binding the complementary RNA strand at 37° C.

(i) ($G_{37}$°)≦−15 KCal or less (more negative=more stable) for 10 to 14 mer, (ii) ($G_{37}$°)≦−20 KCal or less (more negative=more stable) for 15 to 17 mer, (iii) ($G_{37}$°)≦−25 KCal or less (more negative=more stable) for 18 to 20 mer, (iv) ($G_{37}$°)≦−30 KCal or less (more negative=more stable) for 21 to 23 mer, (v) ($G_{37}$°)≦−35 KCal or less (more negative=more stable) for 24 to 30 mer, (e) the ΔG of any hairpin structure the oligonucleotide could assume is ≧−3.0, (f) the Tm any hairpin that could form is at least 10° C. lower than the Tm of the oligonucleotide binding to the target RNA or DNA, (g) a melting temperature for the oligonucleotide binding to the target RNA is 45° C. by the percent GC method at 1.0 M salt For composition parameters, the percent G+C of the oligonucleotide to be used is >35 percent and are administered so that each specific RNA is at a concentration (1.0 g/100 ml), or lower in doses not to exceed 100 μg/kg per RNA, or more preferably 10 μg/kg, or more preferably 1 μg/kg, or still more preferably <1 μg/kg. Sequences are then screened to be sure they do not overlap the same regions in other known genes by conducting BLAST searches against the entire GenBank list of human sequences.

Factors contributing to the selective inhibition of gene expression in vivo by the modified oligonucleotides of the invention include the influence of chirality on melting temperature. 2'-O-methyl modified RNA oligonucleotides with achiral linkages resemble backbone linkages that very closely resemble normal unmodified nucleic acids. Typically, oligonucleotides synthesized using phosphoramidite based synthesis of phosphorothioates produces mixed isomers present at each modified phosphorothioate linkage. A measurable result of the presence of these mixed isomers is a decrease in melting temperature of the phosphorothioate oligonucleotide in a primer target duplex as compared to an unmodified oligonucleotide in the same duplex. The melting temperature of a 2'-O-methyl RNA oligonucleotide, however, is not substantially lowered relative to an unmodified oligonucleotide. Thus, the melting temperatures for 2'-O-methyl RNA oligonucleotides closely resemble those for unmodified RNA because the presence of the 2'-O-methyl group does not result in the generation of isomers.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents and patent applications referred to in this application are herein incorporated by reference in their entirety.

We claim:

1. A composition suitable for administration in a mammal suffering from a pathological disorder or disease comprising at least three modified oligonucleotides, wherein a first, a second, and a third modified oligonucleotide each comprises about seven to seventy-five nucleotides containing seven or more contiguous ribose groups linked by achiral 5' to 3' internucleotide phosphate linkages, wherein at least one ribose group of at least one of said modified oligonucleotides has a modified 2' substituent, wherein the 5' and 3' ends of at least one of said modified oligonucleotides are blocked, and wherein said first modified oligonucleotide is complementary to a region of phosphodiesterase 4 (SEQ ID NO: 82); and said second modified oligonucleotide is complementary to a region of phosphodiesterase 5 (SEQ ID NO: 95), and said third modified oligonucleotide is complementary to a region of cyclo-oxygenase 2 (SEQ ID NO: 87).

2. The composition of claim 1, further comprising a fourth modified oligonucleotide, wherein said fourth modified oligonucleotide comprises about seven to seventy-five nucleotides containing seven or more contiguous ribose groups linked by achiral 5' to 3' internucleotide phosphate linkages, and wherein said fourth modified oligonucleotide is complementary to a region of Cd-18 (SEQ ID NO: 86).

3. The composition of claim 2, further comprising a fifth modified oligonucleotide, wherein said fifth modified oligonucleotide comprises about seven to seventy-five nucleotides containing seven or more contiguous ribose groups linked by achiral 5' to 3' internucleotide phosphate linkages, and wherein said fifth modified oligonucleotide is complementary to a region of HMGCoA reductase (SEQ ID NO: 88).

4. The composition of claim 2, wherein said fourth modified oligonucleotide comprises SEQ ID NO: 5.

5. The composition of claim 3, further comprising a sixth modified oligonucleotide, wherein said sixth modified oligonucleotide comprises about seven to seventy-five nucleotides containing seven or more contiguous ribose groups linked by achiral 5' to 3' internucleotide phosphate linkages, and wherein said sixth modified oligonucleotide is complementary to a region of IL-5 (SEQ ID NO: 89).

6. The composition of claim 3, wherein said fifth modified oligonucleotide comprises SEQ ID NO: 7, SEQ ID NO: 8, or SEQ ID NO: 9.

7. The composition of claim 5, wherein said sixth modified oligonucleotide comprises SEQ ID NO: 10.

8. The composition of claim 1, 2, 3, or 5, wherein said at least three modified oligonucleotides are each complementary to a region of said gene selected from the group consisting of the 5' UTR region, translational start site, and transitional termination site.

9. The composition of claim 1, wherein one or more of said at least three modified oligonucleotides is present at a concentration effective to reduce the expression of said gene to which it is complementary.

10. The composition of claim 1, wherein said at least three modified oligonucleotides are suitable for oral administration.

11. The composition of claim 1, wherein said 2' substituent is selected from the group consisting of methoxy, propoxy, methoxy-ethoxy, fluorine, chlorine, bromine and iodine.

12. The composition of claim 1, further comprising a pharmaceutically acceptable excipient.

13. The composition of claim 1, wherein said mammal is a human.

14. The composition of claim 1, wherein said 5' and 3' ends comprise a butanol.

15. The composition of claim 1, wherein said first modified oligonucleotide comprises SEQ ID NO: 1 and said second modified oligonucleotide comprises SEQ ID NO: 16.

16. The composition of claim 1, wherein said third modified oligonucleotide comprises SEQ ID NO: 6.

* * * * *

UNITED STATES PATENT AND TRADEMARK OFFICE

CERTIFICATE OF CORRECTION

PATENT NO. : 8,188,259 B2
APPLICATION NO. : 11/673508
DATED : May 29, 2012
INVENTOR(S) : Dale et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 193 days.

Signed and Sealed this
Fourth Day of September, 2012

David J. Kappos
*Director of the United States Patent and Trademark Office*

SEQUENCE LISTING

```
<160> NUMBER OF SEQ ID NOS: 132

<210> SEQ ID NO 1
<211> LENGTH: 14
<212> TYPE: DNA
<213> ORGANISM: Artificial sequence
<220> FEATURE:
<223> OTHER INFORMATION: ASM oligonucleotide

<400> SEQUENCE: 1

cgtgtcagga gaac                                                        14


<210> SEQ ID NO 2
<211> LENGTH: 14
<212> TYPE: DNA
<213> ORGANISM: Artificial sequence
<220> FEATURE:
<223> OTHER INFORMATION: Ace1 oligonucleotide

<400> SEQUENCE: 2

catgacgcgg tgcg                                                        14


<210> SEQ ID NO 3
<211> LENGTH: 16
<212> TYPE: DNA
<213> ORGANISM: Artificial sequence
<220> FEATURE:
<223> OTHER INFORMATION: Acid-2 oligonucleotide

<400> SEQUENCE: 3

ggcagtcgtc cctcta                                                      16


<210> SEQ ID NO 4
<211> LENGTH: 16
<212> TYPE: DNA
<213> ORGANISM: Artificial sequence
<220> FEATURE:
<223> OTHER INFORMATION: Acid B2 oligonucleotide

<400> SEQUENCE: 4

aacgtttcac ttctca                                                      16


<210> SEQ ID NO 5
<211> LENGTH: 13
<212> TYPE: DNA
<213> ORGANISM: Artificial sequence
<220> FEATURE:
<223> OTHER INFORMATION: cd18-1 oligonucleotide

<400> SEQUENCE: 5

ttgctaccag tct                                                         13


<210> SEQ ID NO 6
<211> LENGTH: 16
<212> TYPE: DNA
```

<213> ORGANISM: Artificial sequence
<220> FEATURE:
<223> OTHER INFORMATION: CX2 (X2) oligonucleotide

<400> SEQUENCE: 6
tctacagttc agtcga 16

<210> SEQ ID NO 7
<211> LENGTH: 18
<212> TYPE: DNA
<213> ORGANISM: Artificial sequence
<220> FEATURE:
<223> OTHER INFORMATION: Mg44 oligonucleotide

<400> SEQUENCE: 7
tgacaacatt gtagctac 18

<210> SEQ ID NO 8
<211> LENGTH: 18
<212> TYPE: DNA
<213> ORGANISM: Artificial sequence
<220> FEATURE:
<223> OTHER INFORMATION: Mg44 oligonucleotide

<400> SEQUENCE: 8
agctacagaa tccttgga 18

<210> SEQ ID NO 9
<211> LENGTH: 16
<212> TYPE: DNA
<213> ORGANISM: Artificial sequence
<220> FEATURE:
<223> OTHER INFORMATION: Mg44 oligonucleotide

<400> SEQUENCE: 9
gtcgggctat tcaggc 16

<210> SEQ ID NO 10
<211> LENGTH: 16
<212> TYPE: DNA
<213> ORGANISM: Artificial sequence
<220> FEATURE:
<223> OTHER INFORMATION: P65-2M (65) oligonucleotide

<400> SEQUENCE: 10
gaacagttcg tccatg 16

<210> SEQ ID NO 11
<211> LENGTH: 15
<212> TYPE: DNA
<213> ORGANISM: Artificial sequence
<220> FEATURE:
<223> OTHER INFORMATION: IL-501 oligonucleotide

<400> SEQUENCE: 11
cctcatggct ctgaa 15

<210> SEQ ID NO 12
<211> LENGTH: 16
<212> TYPE: DNA
<213> ORGANISM: Artificial sequence
<220> FEATURE:
<223> OTHER INFORMATION: L05-38 oligonucleotide

<400> SEQUENCE: 12
ggagggcatg gcgcgg 16

<210> SEQ ID NO 13
<211> LENGTH: 16
<212> TYPE: DNA
<213> ORGANISM: Artificial sequence
<220> FEATURE:
<223> OTHER INFORMATION: MPB-19 oligonucleotide

<400> SEQUENCE: 13
cctgcatcgc gccgtg 16

<210> SEQ ID NO 14
<211> LENGTH: 16
<212> TYPE: DNA
<213> ORGANISM: Artificial sequence
<220> FEATURE:
<223> OTHER INFORMATION: NEP-1 (CALLA) oligonucleotide

<400> SEQUENCE: 14
gacttgccca tcacct 16

<210> SEQ ID NO 15
<211> LENGTH: 16
<212> TYPE: DNA
<213> ORGANISM: Artificial sequence
<220> FEATURE:
<223> OTHER INFORMATION: NPY-1 oligonucleotide

<400> SEQUENCE: 15
acctagcatg gtggct 16

<210> SEQ ID NO 16
<211> LENGTH: 15
<212> TYPE: DNA
<213> ORGANISM: Artificial sequence
<220> FEATURE:
<223> OTHER INFORMATION: D5 (PDE5.1) oligonucleotide

<400> SEQUENCE: 16
cgctccatgg ttggc 15

<210> SEQ ID NO 17
<211> LENGTH: 16
<212> TYPE: DNA
<213> ORGANISM: Artificial sequence
<220> FEATURE:
<223> OTHER INFORMATION: D7 oligonucleotide

<400> SEQUENCE: 17
cttccattga atacgc 16

<210> SEQ ID NO 18
<211> LENGTH: 16
<212> TYPE: DNA
<213> ORGANISM: Artificial sequence
<220> FEATURE:
<223> OTHER INFORMATION: Per oligonucleotide

<400> SEQUENCE: 18
actgccatcc tcgctc 16

<210> SEQ ID NO 19
<211> LENGTH: 16
<212> TYPE: DNA
<213> ORGANISM: Artificial sequence
<220> FEATURE:
<223> OTHER INFORMATION: TTP (TTPII) oligonucleotide

<400> SEQUENCE: 19
cggtggccat ggacgc 16

<210> SEQ ID NO 20
<211> LENGTH: 17
<212> TYPE: DNA
<213> ORGANISM: Artificial sequence
<220> FEATURE:
<223> OTHER INFORMATION: TTPII oligonucleotide

<400> SEQUENCE: 20
aagttcatgg tttcgga 17

<210> SEQ ID NO 21
<211> LENGTH: 19
<212> TYPE: DNA
<213> ORGANISM: Artificial sequence
<220> FEATURE:
<223> OTHER INFORMATION: MTP oligonucleotide

<400> SEQUENCE: 21
gaatcatatt tgaccagca 19

<210> SEQ ID NO 22
<211> LENGTH: 16
<212> TYPE: DNA
<213> ORGANISM: Artificial sequence
<220> FEATURE:
<223> OTHER INFORMATION: HisR1 oligonucleotide

<400> SEQUENCE: 22
ggctcattgg cgcaag 16

<210> SEQ ID NO 23
<211> LENGTH: 16
<212> TYPE: DNA
<213> ORGANISM: Artificial sequence
<220> FEATURE:
<223> OTHER INFORMATION: HisR1 oligonucleotide

<400> SEQUENCE: 23
agagcctccc ttagga 16

<210> SEQ ID NO 24
<211> LENGTH: 16
<212> TYPE: DNA
<213> ORGANISM: Artificial sequence
<220> FEATURE:
<223> OTHER INFORMATION: CRP oligonucleotide

<400> SEQUENCE: 24
catggtcacg tcctgc 16

<210> SEQ ID NO 25
<211> LENGTH: 18
<212> TYPE: DNA
<213> ORGANISM: Artificial sequence
<220> FEATURE:
<223> OTHER INFORMATION: CETP oligonucleotide

<400> SEQUENCE: 25
atggttatca ggcagtgg 18

<210> SEQ ID NO 26
<211> LENGTH: 19
<212> TYPE: DNA

<213> ORGANISM: Artificial sequence
<220> FEATURE:
<223> OTHER INFORMATION: CETP oligonucleotide

<400> SEQUENCE: 26
catggttatc aggcagtgg 19

<210> SEQ ID NO 27
<211> LENGTH: 16
<212> TYPE: DNA
<213> ORGANISM: Artificial sequence
<220> FEATURE:
<223> OTHER INFORMATION: CETP oligonucleotide

<400> SEQUENCE: 27
ctgaagaatt gaccac 16

<210> SEQ ID NO 28
<211> LENGTH: 16
<212> TYPE: DNA
<213> ORGANISM: Artificial sequence
<220> FEATURE:
<223> OTHER INFORMATION: ICAM oligonucleotide

<400> SEQUENCE: 28
catagcgagg ctgagg 16

<210> SEQ ID NO 29
<211> LENGTH: 15
<212> TYPE: DNA
<213> ORGANISM: Artificial sequence
<220> FEATURE:
<223> OTHER INFORMATION: TNF-alpha oligonucleotide

<400> SEQUENCE: 29
gtgctcatgg tgtcc 15

<210> SEQ ID NO 30
<211> LENGTH: 15
<212> TYPE: DNA
<213> ORGANISM: Artificial sequence
<220> FEATURE:
<223> OTHER INFORMATION: Bone morphgenic protein-4 oligonucleotide

<400> SEQUENCE: 30
cgaccatcag cattc 15

<210> SEQ ID NO 31
<211> LENGTH: 16
<212> TYPE: DNA
<213> ORGANISM: Artificial sequence
<220> FEATURE:
<223> OTHER INFORMATION: Beta adrenergic receptor-1 oligonucleotide

<400> SEQUENCE: 31
gcccatgccg agctgc 16

<210> SEQ ID NO 32
<211> LENGTH: 16
<212> TYPE: DNA
<213> ORGANISM: Artificial sequence
<220> FEATURE:
<223> OTHER INFORMATION: IL-6 oligonucleotide

<400> SEQUENCE: 32
aggagttcat agctgg 16

<210> SEQ ID NO 33
<211> LENGTH: 16
<212> TYPE: DNA
<213> ORGANISM: Artificial sequence
<220> FEATURE:
<223> OTHER INFORMATION: FAAH oligonucleotide

<400> SEQUENCE: 33
gcaccatgat cccttc 16

<210> SEQ ID NO 34
<211> LENGTH: 16
<212> TYPE: DNA
<213> ORGANISM: Artificial sequence
<220> FEATURE:
<223> OTHER INFORMATION: ACAT oligonucleotide

<400> SEQUENCE: 34
cttcacccac cattgt 16

<210> SEQ ID NO 35
<211> LENGTH: 18
<212> TYPE: DNA
<213> ORGANISM: Artificial sequence
<220> FEATURE:
<223> OTHER INFORMATION: IBAT oligonucleotide

<400> SEQUENCE: 35
cattcattgc tgggtctg 18

<210> SEQ ID NO 36
<211> LENGTH: 15
<212> TYPE: DNA
<213> ORGANISM: Artificial sequence
<220> FEATURE:
<223> OTHER INFORMATION: HMGIC oligonucleotide

<400> SEQUENCE: 36
cgtgcgctca tcctg 15

<210> SEQ ID NO 37
<211> LENGTH: 16
<212> TYPE: DNA
<213> ORGANISM: Artificial sequence
<220> FEATURE:
<223> OTHER INFORMATION: HMGIC oligonucleotide

<400> SEQUENCE: 37
aacgttgcgc ccccta 16

<210> SEQ ID NO 38
<211> LENGTH: 16
<212> TYPE: DNA
<213> ORGANISM: Artificial sequence
<220> FEATURE:
<223> OTHER INFORMATION: Ghre oligonucleotide

<400> SEQUENCE: 38
tgcagacagg tgggcc 16

<210> SEQ ID NO 39
<211> LENGTH: 17
<212> TYPE: DNA
<213> ORGANISM: Artificial sequence
<220> FEATURE:
<223> OTHER INFORMATION: Ghre oligonucleotide

<400> SEQUENCE: 39
gcatggcctc agctggg 17

<210> SEQ ID NO 40
<211> LENGTH: 16
<212> TYPE: DNA
<213> ORGANISM: Artificial sequence
<220> FEATURE:
<223> OTHER INFORMATION: Ghre oligonucleotide

<400> SEQUENCE: 40
tgggcgatca cttgtc 16

<210> SEQ ID NO 41
<211> LENGTH: 18
<212> TYPE: DNA
<213> ORGANISM: Artificial sequence
<220> FEATURE:
<223> OTHER INFORMATION: AAT1R oligonucleotide

<400> SEQUENCE: 41
cattttgatc acctgggt 18

<210> SEQ ID NO 42
<211> LENGTH: 16
<212> TYPE: DNA
<213> ORGANISM: Artificial sequence
<220> FEATURE:
<223> OTHER INFORMATION: AAT1R oligonucleotide

<400> SEQUENCE: 42
cgaacatgtc actcaa 16

<210> SEQ ID NO 43
<211> LENGTH: 17
<212> TYPE: DNA
<213> ORGANISM: Artificial sequence
<220> FEATURE:
<223> OTHER INFORMATION: VEGF oligonucleotide

<400> SEQUENCE: 43
aagttcatgg tttcgga 17

<210> SEQ ID NO 44
<211> LENGTH: 17
<212> TYPE: DNA
<213> ORGANISM: Artificial sequence
<220> FEATURE:
<223> OTHER INFORMATION: VEGF oligonucleotide

<400> SEQUENCE: 44
tcaccgcctc ggcttgt 17

<210> SEQ ID NO 45
<211> LENGTH: 15
<212> TYPE: DNA
<213> ORGANISM: Artificial sequence
<220> FEATURE:
<223> OTHER INFORMATION: FAS oligonucleotide

<400> SEQUENCE: 45
cctcctccat ggctg 15

<210> SEQ ID NO 46
<211> LENGTH: 15
<212> TYPE: DNA

<213> ORGANISM: Artificial sequence
<220> FEATURE:
<223> OTHER INFORMATION: FAS oligonucleotide

<400> SEQUENCE: 46
gcctagccct cccgc 15

<210> SEQ ID NO 47
<211> LENGTH: 16
<212> TYPE: DNA
<213> ORGANISM: Artificial sequence
<220> FEATURE:
<223> OTHER INFORMATION: AmP oligonucleotide

<400> SEQUENCE: 47
gcagcggctt gttcat 16

<210> SEQ ID NO 48
<211> LENGTH: 15
<212> TYPE: DNA
<213> ORGANISM: Artificial sequence
<220> FEATURE:
<223> OTHER INFORMATION: AmP oligonucleotide

<400> SEQUENCE: 48
gagtcaagac ctcag 15

<210> SEQ ID NO 49
<211> LENGTH: 16
<212> TYPE: DNA
<213> ORGANISM: Artificial sequence
<220> FEATURE:
<223> OTHER INFORMATION: PanLip oligonucleotide

<400> SEQUENCE: 49
gtggcagcat cgtggc 16

<210> SEQ ID NO 50
<211> LENGTH: 16
<212> TYPE: DNA
<213> ORGANISM: Artificial sequence
<220> FEATURE:
<223> OTHER INFORMATION: PanLip oligonucleotide

<400> SEQUENCE: 50
cctaacacgg tgtgag 16

<210> SEQ ID NO 51
<211> LENGTH: 17
<212> TYPE: DNA
<213> ORGANISM: Artificial sequence
<220> FEATURE:
<223> OTHER INFORMATION: ACC2 oligonucleotide

<400> SEQUENCE: 51
gaagcaagac cattcag 17

<210> SEQ ID NO 52
<211> LENGTH: 17
<212> TYPE: DNA
<213> ORGANISM: Artificial sequence
<220> FEATURE:
<223> OTHER INFORMATION: ACC2 oligonucleotide

<400> SEQUENCE: 52
tcaggtggag gccgggc 17

<210> SEQ ID NO 53
<211> LENGTH: 16
<212> TYPE: DNA
<213> ORGANISM: Artificial sequence
<220> FEATURE:
<223> OTHER INFORMATION: PKARIIbeta oligonucleotide

<400> SEQUENCE: 53
tgctcatcct gcctcc 16

<210> SEQ ID NO 54
<211> LENGTH: 16
<212> TYPE: DNA
<213> ORGANISM: Artificial sequence
<220> FEATURE:
<223> OTHER INFORMATION: PKARIIbeta oligonucleotide

<400> SEQUENCE: 54
gcttcatgca gtgggt 16

<210> SEQ ID NO 55
<211> LENGTH: 16
<212> TYPE: DNA
<213> ORGANISM: Artificial sequence
<220> FEATURE:
<223> OTHER INFORMATION: VR1R oligonucleotide

<400> SEQUENCE: 55
tcttcatcct tgctgg 16

<210> SEQ ID NO 56
<211> LENGTH: 16
<212> TYPE: DNA
<213> ORGANISM: Artificial sequence
<220> FEATURE:
<223> OTHER INFORMATION: VR1R oligonucleotide

<400> SEQUENCE: 56
ctcacttctc cccgga 16

<210> SEQ ID NO 57
<211> LENGTH: 16
<212> TYPE: DNA
<213> ORGANISM: Artificial sequence
<220> FEATURE:
<223> OTHER INFORMATION: ADAMTS oligonucleotide

<400> SEQUENCE: 57
gggacatggc actggt 16

<210> SEQ ID NO 58
<211> LENGTH: 16
<212> TYPE: DNA
<213> ORGANISM: Artificial sequence
<220> FEATURE:
<223> OTHER INFORMATION: ADAMTS oligonucleotide

<400> SEQUENCE: 58
ttatttcctg cccgcc 16

<210> SEQ ID NO 59
<211> LENGTH: 16
<212> TYPE: DNA
<213> ORGANISM: Artificial sequence
<220> FEATURE:
<223> OTHER INFORMATION: NPY-Y5R oligonucleotide

<400> SEQUENCE: 59
tgtggcaggt cagttg 16

<210> SEQ ID NO 60
<211> LENGTH: 16
<212> TYPE: DNA
<213> ORGANISM: Artificial sequence
<220> FEATURE:
<223> OTHER INFORMATION: NPY-Y5R oligonucleotide

<400> SEQUENCE: 60
atccatatta tagtct 16

<210> SEQ ID NO 61
<211> LENGTH: 16
<212> TYPE: DNA
<213> ORGANISM: Artificial sequence
<220> FEATURE:
<223> OTHER INFORMATION: NPY-Y5R oligonucleotide

<400> SEQUENCE: 61
tattacatat gaagac 16

<210> SEQ ID NO 62
<211> LENGTH: 16
<212> TYPE: DNA
<213> ORGANISM: Artificial sequence
<220> FEATURE:
<223> OTHER INFORMATION: GNTV oligonucleotide

<400> SEQUENCE: 62
agccattgct ctctgg 16

<210> SEQ ID NO 63
<211> LENGTH: 16
<212> TYPE: DNA
<213> ORGANISM: Artificial sequence
<220> FEATURE:
<223> OTHER INFORMATION: GNTV oligonucleotide

<400> SEQUENCE: 63
tgctataggc agtctt 16

<210> SEQ ID NO 64
<211> LENGTH: 16
<212> TYPE: DNA
<213> ORGANISM: Artificial sequence
<220> FEATURE:
<223> OTHER INFORMATION: FCRG3 oligonucleotide

<400> SEQUENCE: 64
tgccacatga tgccac 16

<210> SEQ ID NO 65
<211> LENGTH: 16
<212> TYPE: DNA
<213> ORGANISM: Artificial sequence
<220> FEATURE:
<223> OTHER INFORMATION: FCRG3 oligonucleotide

<400> SEQUENCE: 65
gttgagcttc aaatgt 16

<210> SEQ ID NO 66
<211> LENGTH: 16
<212> TYPE: DNA

<213> ORGANISM: Artificial sequence
<220> FEATURE:
<223> OTHER INFORMATION: CD40L oligonucleotide

<400> SEQUENCE: 66
tcgatcatgc tgtgtt 16

<210> SEQ ID NO 67
<211> LENGTH: 16
<212> TYPE: DNA
<213> ORGANISM: Artificial sequence
<220> FEATURE:
<223> OTHER INFORMATION: CD40L oligonucleotide

<400> SEQUENCE: 67
aggtgacact gttcag 16

<210> SEQ ID NO 68
<211> LENGTH: 16
<212> TYPE: DNA
<213> ORGANISM: Artificial sequence
<220> FEATURE:
<223> OTHER INFORMATION: ETS-1 oligonucleotide

<400> SEQUENCE: 68
acggccgcct tcatgg 16

<210> SEQ ID NO 69
<211> LENGTH: 16
<212> TYPE: DNA
<213> ORGANISM: Artificial sequence
<220> FEATURE:
<223> OTHER INFORMATION: ETS-1 oligonucleotide

<400> SEQUENCE: 69
gccatcactc gtcggc 16

<210> SEQ ID NO 70
<211> LENGTH: 16
<212> TYPE: DNA
<213> ORGANISM: Artificial sequence
<220> FEATURE:
<223> OTHER INFORMATION: ADAMTS-5 oligonucleotide

<400> SEQUENCE: 70
ccgagcagca tagtgc 16

<210> SEQ ID NO 71
<211> LENGTH: 16
<212> TYPE: DNA
<213> ORGANISM: Artificial sequence
<220> FEATURE:
<223> OTHER INFORMATION: ADAMTS-5 oligonucleotide

<400> SEQUENCE: 71
tcataaccac aggcta 16

<210> SEQ ID NO 72
<211> LENGTH: 16
<212> TYPE: DNA
<213> ORGANISM: Artificial sequence
<220> FEATURE:
<223> OTHER INFORMATION: PTP-1B oligonucleotide

<400> SEQUENCE: 72
catgacgggc cagggc 16

<210> SEQ ID NO 73
<211> LENGTH: 16
<212> TYPE: DNA
<213> ORGANISM: Artificial sequence
<220> FEATURE:
<223> OTHER INFORMATION: PTP-1B oligonucleotide

<400> SEQUENCE: 73
gggtcaggct atgtgt 16

<210> SEQ ID NO 74
<211> LENGTH: 17
<212> TYPE: DNA
<213> ORGANISM: Artificial sequence
<220> FEATURE:
<223> OTHER INFORMATION: MMP-1 oligonucleotide

<400> SEQUENCE: 74
gcatactggc ctttgtc 17

<210> SEQ ID NO 75
<211> LENGTH: 17
<212> TYPE: DNA
<213> ORGANISM: Artificial sequence
<220> FEATURE:
<223> OTHER INFORMATION: MMP-1 oligonucleotide

<400> SEQUENCE: 75
tcaatttttc ctgcagt 17

<210> SEQ ID NO 76
<211> LENGTH: 16
<212> TYPE: DNA
<213> ORGANISM: Artificial sequence
<220> FEATURE:
<223> OTHER INFORMATION: Cat oligonucleotide

<400> SEQUENCE: 76
gccatagcgt gcggtt 16

<210> SEQ ID NO 77
<211> LENGTH: 16
<212> TYPE: DNA
<213> ORGANISM: Artificial sequence
<220> FEATURE:
<223> OTHER INFORMATION: Cat oligonucleotide

<400> SEQUENCE: 77
cccggcctca cagatt 16

<210> SEQ ID NO 78
<211> LENGTH: 17
<212> TYPE: DNA
<213> ORGANISM: Artificial sequence
<220> FEATURE:
<223> OTHER INFORMATION: MMP-17 oligonucleotide

<400> SEQUENCE: 78
catggcgctc acatggg 17

<210> SEQ ID NO 79
<211> LENGTH: 17
<212> TYPE: DNA
<213> ORGANISM: Artificial sequence
<220> FEATURE:
<223> OTHER INFORMATION: MMP-17 oligonucleotide

<400> SEQUENCE: 79
tgtcatagcg tcagggc 17

<210> SEQ ID NO 80
<211> LENGTH: 16
<212> TYPE: DNA
<213> ORGANISM: Artificial sequence
<220> FEATURE:
<223> OTHER INFORMATION: OPG oligonucleotide

<400> SEQUENCE: 80
tcattgtggt ccccgg 16

<210> SEQ ID NO 81
<211> LENGTH: 16
<212> TYPE: DNA
<213> ORGANISM: Artificial sequence
<220> FEATURE:
<223> OTHER INFORMATION: OPG oligonucleotide

<400> SEQUENCE: 81
tccagttata agcagc 16

<210> SEQ ID NO 82
<211> LENGTH: 1684
<212> TYPE: DNA
<213> ORGANISM: Homo sapiens
<220> FEATURE:
<221> NAME/KEY: misc_feature
<223> OTHER INFORMATION: Pde4: Acc. No. U50158

<400> SEQUENCE: 82
aatatgaagg agcagccctc atgtgccggc accgggcatc cgagcatggc gggaggaggc 60
ctaccagaaa ctggccagcg agaccctgga ggagctggac tggtgtctgg accagctaga 120
gaccctacag accaggcact ccgtcagtga gatggcctcc aacaagttta aaaggatgct 180
taatcgggag ctcacccatc tctctgaaat gagtcggtct ggaaatcaag tgtcagagtt 240
tatatcaaac acattcttag ataagcaaca tgaagtggaa attccttctc caactcagaa 300
ggaaaaggag aaaaagaaaa gaccaatgtc tcagatcagt ggagtcaaga aattgatgca 360
cagctctagt ctgactaatt caagtatccc aaggtttgga gttaaaactg aacaagaaga 420
tgtccttgcc aaggaactag aagatgtgaa caaatggggt cttcatgttt tcagaatagc 480
agagttgtct ggtaaccggc ccttgactgt tatcatgcac accatttttc aggaacggga 540
tttattaaaa acatttaaaa ttccagtaga tactttaatt acatatctta tgactctcga 600
agaccattac catgctgatg tggcctatca caacaatatc catgctgcag atgttgtcca 660
gtctactcat gtgctattat ctacacctgc tttggaggct gtgtttacag atttggagat 720
tcttgcagca atttttgcca gtgcaataca tgatgtagat catcctggtg tgtccaatca 780
atttctgatc aatacaaact ctgaacttgc cttgatgtac aatgattcct cagtcttaga 840
gaaccatcat ttggctgtgg gctttaaatt gcttcaggaa gaaaactgtg acattttcca 900
gaatttgacc aaaaaacaaa gacaatcttt aaggaaaatg gtcattgaca tcgtacttgc 960
aacagatatg tcaaaacaca tgaatctact ggctgatttg aagactatgg ttgaaactaa 1020
gaaagtgaca agctctggag ttcttcttct tgataattat tccgatagga ttcaggttct 1080
tcagaatatg gtgcactgtg cagatctgag caacccaaca aagcctctcc agctgtaccg 1140
ccagtggacg gaccggataa tggaggagtt cttccgccaa ggagaccgag agagggaacg 1200
tggcatggag ataagcccca tgtgtgacaa gcacaatgct tccgtggaaa aatcacaggt 1260
gggcttcata gactatattg ttcatcccct ctgggagaca tgggcagacc tcgtccaccc 1320
tgacgcccag gatattttgg acactttgga ggacaatcgt gaatggtacc agagcacaat 1380
ccctcagagc ccctctcctg cacctgatga cccagaggag ggccggcagg gtcaaactga 1440
gaaattccag tttgaactaa ctttagagga agatggtgag tcagacacgg aaaaggacag 1500
tggcagtcaa gtggaagaag acactagctg cagtgactcc aagactcttc gtactcaaga 1560
ctcagagtct actgaaattc cccttgatga acaggttgaa gaggaggcag taggggaaga 1620
agaggaaagc caacctgaag cctgtgtcat agatgatcgt tctcctgaca cgtaacagtg 1680
caaa 1684

<210> SEQ ID NO 83
<211> LENGTH: 4020
<212> TYPE: DNA
<213> ORGANISM: Homo sapiens
<220> FEATURE:
<221> NAME/KEY: misc_feature
<223> OTHER INFORMATION: ACE-1: Acc. No. J04144.1

<400> SEQUENCE: 83
gccgagcacc gcgcaccgcg tcatgggggc cgcctcgggc cgccgggggc cggggctgct 60
gctgccgctg ccgctgctgt tgctgctgcc gccgcagccc gccctggcgt tggaccccgg 120
gctgcagccc ggcaactttt ctgctgacga ggccggggcg cagctcttcg cgcagagcta 180
caactccagc gccgaacagg tgctgttcca gagcgtggcc gccagctggg cgcacgacac 240
caacatcacc gcggagaatg caaggcgcca ggaggaagca gccctgctca gccaggagtt 300
tgcggaggcc tggggccaga aggccaagga gctgtatgaa ccgatctggc agaacttcac 360
ggacccgcag ctgcgcagga tcatcggagc tgtgcgaacc ctgggctctg ccaacctgcc 420
cctggctaag cggcagcagt acaacgccct gctaagcaac atgagcagga tctactccac 480
cgccaaggtc tgcctcccca acaagactgc cacctgctgg tccctggacc cagatctcac 540
caacatcctg gcttcctcgc gaagctacgc catgctcctg tttgcctggg agggctggca 600
caacgctgcg ggcatcccgc tgaaaccgct gtacgaggat ttcactgccc tcagcaatga 660
agcctacaag caggacggct tcacagacac gggggcctac tggcgctcct ggtacaactc 720
ccccaccttc gaggacgatc tggaacacct ctaccaacag ctagagcccc tctacctgaa 780
cctccatgcc ttcgtccgcc gcgcactgca tcgccgatac ggagacagat acatcaacct 840
caggggaccc atccctgctc atctgctggg agacatgtgg gcccagagct gggaaaacat 900
ctacgacatg gtggtgcctt tcccagacaa gcccaacctc gatgtcacca gtactatgct 960
gcagcagggc tggaacgcca cgcacatgtt ccgggtggca gaggagttct tcacctccct 1020
ggagctctcc cccatgcctc ccgagttctg ggaagggtcg atgctggaga agccggccga 1080
cgggcgggaa gtggtgtgcc acgcctcggc ttgggacttc tacaacagga aagacttcag 1140
gatcaagcag tgcacacggg tcacgatgga ccagctctcc acagtgcacc atgagatggg 1200
ccatatacag tactacctgc agtacaagga tctgcccgtc tccctgcgtc ggggggccaa 1260
ccccggcttc catgaggcca ttggggacgt gctggcgctc tcggtctcca ctcctgaaca 1320
tctgcacaaa atcggcctgc tggaccgtgt caccaatgac acggaaagtg acatcaatta 1380
cttgctaaaa atggcactgg aaaaaattgc cttcctgccc tttggctact tggtggacca 1440
gtggcgctgg ggggtcttta gtgggcgtac cccccccttcc cgctacaact tcgactggtg 1500
gtatcttcga accaagtatc aggggatctg tcctcctgtt acccgaaacg aaacccactt 1560

-continued

```
tgatgctgga gctaagtttc atgttccaaa tgtgacacca tacatcaggt actttgtgag   1620
ttttgtcctg cagttccagt tccatgaagc cctgtgcaag gaggcaggct atgagggccc   1680
actgcaccag tgtgacatct accggtccac caaggcaggg gccaagctcc ggaaggtgct   1740
gcaggctggc tcctccaggc cctggcagga ggtgctgaag gacatggtcg gcttagatgc   1800
cctggatgcc cagccgctgc tcaagtactt ccagccagtc acccagtggc tgcaggagca   1860
gaaccagcag aacggcgagg tcctgggctg gcccgagtac cagtggcacc cgccgttgcc   1920
tgacaactac ccggagggca tagacctggt gactgatgag gctgaggcca gcaagtttgt   1980
ggaggaatat gaccggacat cccaggtggt gtggaacgag tatgccgagg ccaactggaa   2040
ctacaacacc aacatcacca cagagaccag caagattctg ctgcagaaga acatgcaaat   2100
agccaaccac accctgaagt acggcaccca ggccaggaag tttgatgtga accagttgca   2160
gaacaccact atcaagcgga tcataaagaa ggttcaggac ctagaacggg cagcgctgcc   2220
tgcccaggag ctggaggagt acaacaagat cctgttggat atggaaacca cctacagcgt   2280
ggccactgtg tgccacccga atggcagctg cctgcagctc gagccagatc tgacgaatgt   2340
gatggccaca tcccggaaat atgaagacct gttatgggca tgggagggct ggcgagacaa   2400
ggcggggaga gccatcctcc agttttaccc gaaatacgtg gaactcatca accaggctgc   2460
ccggctcaat ggctatgtag atgcagggga ctcgtggagg tctatgtacg agacaccatc   2520
cctggagcaa gacctggagc ggctcttcca ggagctgcag ccactctacc tcaacctgca   2580
tgcctacgtg cgccgggccc tgcaccgtca ctacggggcc cagcacatca acctggaggg   2640
gcccattcct gctcacctgc tggggaacat gtgggcgcag acctggtcca acatctatga   2700
cttggtggtg cccttccctt cagccccctc gatggacacc acagaggcta tgctaaagca   2760
gggctggacg cccaggagga tgtttaagga ggctgatgat ttcttcacct ccctggggct   2820
gctgcccgtg cctcctgagt tctggaacaa gtcgatgctg gagaagccaa ccgacgggcg   2880
ggaggtggtc tgccacgcct cggcctggga cttctacaac ggcaaggact tccggatcaa   2940
gcagtgcacc accgtgaact tggaggacct ggtggtggcc caccacgaaa tgggccacat   3000
ccagtatttc atgcagtaca aagacttacc tgtggccttg agggagggtg ccaaccccgg   3060
cttccatgag gccattgggg acgtgctagc cctctcagtg tctacgccca agcacctgca   3120
cagtctcaac ctgctgagca gtgagggtgg cagcgacgag catgacatca actttctgat   3180
gaagatggcc cttgacaaga tcgcctttat ccccttcagc tacctcgtcg atcagtggcg   3240
ctggagggta tttgatggaa gcatcaccaa ggagaactat aaccaggagt ggtggagcct   3300
caggctgaag taccagggcc tctgcccccc agtgcccagg actcaaggtg actttgaccc   3360
aggggccaag ttccacattc cttctagcgt gccttacatc aggtactttg tcagcttcat   3420
catccagttc cagttccacg aggcactgtg ccaggcagct ggccacacgg gcccccctgca  3480
caagtgtgac atctaccagt ccaaggaggc cgggcagcgc ctggcgaccg ccatgaagct   3540
gggcttcagt aggccgtggc cggaagccat gcagctgatc acgggccagc ccaacatgag   3600
cgcctcggcc atgttgagct acttcaagcc gctgctggac tggctccgca cggagaacga   3660
gctgcatggg gagaagctgg gctggccgca gtacaactgg acgccgaact ccgctcgctc   3720
agaagggccc ctcccagaca gcggccgcgt cagcttcctg ggcctggacc tggatgcgca   3780
gcaggcccgc gtgggccagt ggctgctgct cttcctgggc atcgccctgc tggtagccac   3840
cctgggcctc agccagcggc tcttcagcat ccgccaccgc agcctccacc ggcactccca   3900
cgggccccag ttcggctccg aggtggagct gagacactcc tgaggtgacc cggctgggtc   3960
```

ggccctgccc aagggcctcc caccagagac tgggatggga acactggtgg gcagctgagg 4020

<210> SEQ ID NO 84
<211> LENGTH: 3556
<212> TYPE: DNA
<213> ORGANISM: Homo sapiens
<220> FEATURE:
<221> NAME/KEY: misc_feature
<223> OTHER INFORMATION: Acid2: Acc. No. NM_000704

<400> SEQUENCE: 84
tgttgggtgg gagcacaggc accgggcacc atggggaagg ccgagaacta tgagctctac 60
tcggtggagc tgggtcctgg ccctggcggg gacatggctg ccaagatgag caagaagaag 120
aaggcgggtg gcgggggtgg caagaggaag gagaagctgg agaacatgaa gaaggagatg 180
gagattaacg accaccagct gtcagtggcg gagctggaac agaaatacca gaccagtgcc 240
accaagggcc tctctgcgag cctggctgct gagctgctgc tgcgggatgg gcccaacgca 300
ctgcggccac cacggggcac cccagagtac gtcaagttcg cgaggcagct ggccgggggc 360
ctgcagtgcc tcatgtgggt tgccgccgcc atctgcctca tcgcctttgc catccaggct 420
agtgaggggg acctcaccac cgacgacaat ctgtacctgg caatcgctct cattgctgtg 480
gttgtcgtca ccggctgctt tggctactac caggaattca agagcaccaa catcatcgcc 540
agctttaaga accttgtgcc acagcaagcc actgtcatcc gcgatggaga caaattccag 600
atcaacgctg accaactggt ggtgggcgac ctggtggaga tgaaaggtgg ggacagagtg 660
cccgccgaca tccgcatcct ggcggcccag ggctgcaagg tggacaactc ctcgctgaca 720
ggggagtctg agccacaaac ccgctcaccc gagtgcacgc acgagagccc tctggagacc 780
cgcaacatcg ccttcttctc caccatgtgc cttgagggca ccgcgcaggg cctggtggtg 840
aacacgggcg accgcaccat cattgggcgc atcgcatcgc tggcgtcggg ggtggaaaac 900
gagaagacac ccatcgctat cgagatcgag cattttgtgg acatcatcgc gggcctggcc 960
attctcttcg gtgccacatt ttttattgtg gccatgtgca ttggctacac cttcctgcgg 1020
gccatggtct tcttcatggc catcgtggtg gcctatgtgc ctgaggggct gctggccact 1080
gtcacagtct gcctgtccct gacagccaag cgcctggcca gtaagaactg cgtggtcaag 1140
aacctggagg cggtggagac attgggctcc acttcggtga tctgctcgga caagacaggg 1200
actctcactc agaaccgcat gactgtgtcc catctgtggt ttgacaacca catccacaca 1260
gctgacacca cggaagacca gtcagggcag acgtttgacc agtcctcgga gacgtggcgg 1320
gcgctgtgcc gggtgctcac cctgtgcaac cgcgccgcct tcaagtccgg ccaggatgca 1380
gtgcctgtgc ccaagcgcat cgtgattgga gacgcatcgg agacggcgct gctcaagttc 1440
tcggagctga cgctgggcaa cgccatgggc taccgggacc gcttcccaaa agtctgcgag 1500 ataccettca actccaccaa caagttccag ctgtccatcc atacgctgga ggacccgcgg 1560
gacccgcgac acttgctggt gatgaagggc gcccccgagc gcgtgctgga gcgctgcagc 1620
tccatcctta tcaagggcca ggagctgccg ctggacgagc agtggcgcga ggccttccag 1680
accgcctacc tcagcctggg aggcctgggc gaacgcgtgc tcggcttctg ccagctctac 1740
ctgaatgaga aggactaccc gcctggctat gccttcgacg tagaggccat gaactttcca 1800
tctagcggcc tctgctttgc gggacttgta tccatgattg acccaccccg ggccaccgtc 1860
cctgatgctg tgctcaagtg tcgcaccgca ggcatccggg tgatcatggt aacgggtgac 1920
caccccatca ccgccaaggc cattgcagcc agtgtgggca tcatctcgga aggcagcgag 1980
acagtggagg acatcgctgc ccgcctccgt gtgcccgtag accaggttaa tcgcaaggat 2040

```
gcccgtgcct gtgtgatcaa tggcatgcag ctgaaggaca tggacccatc ggaactggtc   2100

gaggccctgc gcacccaccc cgagatggtg tttgcgcgca ccagccccca gcagaagctg   2160

gtgatcgtgg agagctgcca gcggctgggt gcgattgtgg ccgtcacggg ggatggtgtg   2220

aatgactccc cagctctgaa gaaggcagac atcggagtag ccatgggcat cgctggctca   2280

gatgctgcca aaaatgcagc tgacatgatc ctgctggatg acaactttgc ctccattgtg   2340

acaggcgtgg agcagggtcg actgatcttc gacaacctga agaagtctat tgcctacaca   2400

ttgaccaaga acatcccaga gctgacaccc tacctcatct acatcaccgt cagcgtgccc   2460

ctgcccctcg ggtgcatcac catcctcttc atcgaactct gcactgacat tttcccatct   2520

gtgtccctgg catatgaaaa ggccgagagt gacatcatgc acctgcgtcc acgcaaccca   2580

aagcgtgaca gattggtcaa cgagcccctg gctgcctact cctacttcca gattggtgcc   2640

attcagtcct ttgctggctt cactgactac ttcacggcaa tggcccagga gggctggttc   2700

ccactgctgt gcgtggggct gcgggcgcag tgggaggacc accacctaca agatctgcag   2760

gacagctacg gccaggagtg gacattcggg cagcgcctgt accagcagta cacctgctac   2820

accgtgttct tcatcagcat tgaggtgtgc cagatcgccg atgtcctcat ccgcaagacg   2880

cgccgtctct ctgccttcca gcaaggcttc ttcaggaata agatcctggt gatcgccatc   2940

gtgttccagg tctgcatcgg ctgcttcctg tgctactgcc ccggcatgcc caacatcttc   3000

aacttcatgc ccattcggtt ccagtggtgg ctggtccccc tgccctacgg catcctcatc   3060

ttcgtctatg atgagatccg gaagcttgga gttcgctgtt gcccagggag ctggtgggac   3120

caggaactct actattagag ggacgactgc cttcaagcat ccctgcaact gccacagcag   3180

gtgggggcag ggcacgtggg accctctgga cagccaccaa gatatctgag caaccaagag   3240

tcccagcccc accagtatct gcttctgtag cccacggcac ccccaaacttg gagggacctg   3300

cccactcccc tcccccattc ccaaggttcg cacctcctgg agcagcagcg cctgggcagt   3360

cctctgggct ggcctcggga aagccgccac ctgtggtggc ggtggggctc tgacagggag   3420

tacagctgac cgcttctgga gggtgtttct gttcttagga ctccagtcca ggctggacgg   3480

ctgcctgagg gcccttcgtt aaagacacgc ttgtgtcctg ggcgatggta ataaaaccag   3540

ctcatgctga ctgtgc                                                    3556
```

<210> SEQ ID NO 85
<211> LENGTH: 1444
<212> TYPE: DNA
<213> ORGANISM: Homo sapiens
<220> FEATURE:
<221> NAME/KEY: misc_feature
<223> OTHER INFORMATION: AcidB2: Acc. No. NM_000705

<400> SEQUENCE: 85

```
agtctgggcg tagagggtgc agggagcaga cgggaggatc tcaggccagg gacgatggcg     60

gctctgcagg agaagaagac gtgtggccag cgcatggagg agttccagcg ttactgctgg    120

aacccggaca cggggcagat gctgggccgc accctgtccc ggtgggtgtg gatcagcctg    180

tactacgtgg ccttctacgt ggtgatgact gggctcttcg ccctgtgcct ctatgtgctg    240

atgcagacag tggacccgta cacaccggac taccaagacc agctacggtc accaggggta    300

accttaaggc cggatgttta cggggagaaa ggcctggaaa ttgtctacaa cgtctctgat    360

aacagaacct gggcagacct cacacagact ctccacgcct tcctagcagg ctactctcca    420

gcagcccagg aggacagcat caactgcacc tccgagcagt acttcttcca ggagagtttc    480
```

```
cgcgctccca accacaccaa gttctcctgc aagttcacgg cagatatgct gcagaactgc    540

tcaggcctgg cggatcccaa cttcggcttt gaagaaggaa agccatgttt tattattaaa    600

atgaacagga tcgtcaagtt cctccccagc aacggctcgg cccccagagt ggactgcgcc    660

ttcctggacc agccccgcga gctcggccag ccgctgcagg tcaagtacta ccctcccaac    720

ggcaccttca gtctgcacta cttcccttat tacgggaaga aagcccagcc ccactacagc    780

aaccccctgg tggcagcgaa gctcctcaac atccccagga acgctgaggt cgccatcgtg    840

tgcaaggtca tggcagagca cgtgaccttc aacaatcccc acgacccgta tgaagggaaa    900

gtggagttca aactcaagat tgagaagtga aacgtttgcg caggggtcct gggcacgcct    960

gcggggtcgc tcaaggacac cctcctggtt gggcttacct tgcccgtcag ttccctgcca   1020

aatcatcccc aaagtggttt ggagcaacgg tgttgtcagt gtgcgaactc cagagaagcg   1080

cccacatctg aaggacctgc tcgcgagtat cagttcttcc ttgttgaatt cttacagttt   1140

ttagatggaa tttgctgcta taagaatgtc cagctaccat gggaacgcaa ggcagcaact   1200

ctctaattaa ccaggtcata aaaacgattc gtcttctatg tagacatcac tttcttacta   1260

taatttattt ttctacactt caatatgaac tgcccccccc acattaatat aaaaactact   1320

aatgcactga tatgaaacac ggcttacact aatgacattc tgaattcttg cttttaaaat   1380

tgcaattcct aagttgtaaa cataaaatat attaaagtta ctcttattgt atgtaaaaaa   1440

aaaa                                                                1444
```

<210> SEQ ID NO 86
<211> LENGTH: 2776
<212> TYPE: DNA
<213> ORGANISM: Homo sapiens
<220> FEATURE:
<221> NAME/KEY: misc_feature
<223> OTHER INFORMATION: Cd-18: Acc. No. M15395

<400> SEQUENCE: 86

```
cagggcagac tggtagcaaa gcccccacgc ccagccagga gcaccgccgc ggactccagc     60

acaccgaggg acatgctggg cctgcgcccc ccactgctcg ccctggtggg gctgctctcc    120

ctcgggtgcg tcctctctca ggagtgcacg aagttcaagg tcagcagctg ccgggaatgc    180

atcgagtcgg ggcccggctg cacctggtgc cagaagctga acttcacagg gccgggggat    240

cctgactcca ttcgctgcga cacccggcca cagctgctca tgaggggctg tgcggctgac    300

gacatcatgg accccacaag cctcgctgaa acccaggaag accacaatgg gggccagaag    360

cagctgtccc cacaaaaagt gacgctttac ctgcgaccag gccaggcagc agcgttcaac    420

gtgaccttcc ggcgggccaa gggctacccc atcgacctgt actatctgat ggacctctcc    480

tactccatgc ttgatgacct caggaatgtc aagaagctag gtggcgacct gctccgggcc    540

ctcaacgaga tcaccgagtc cggccgcatt ggcttcgggt ccttcgtgga caagaccgtg    600

ctgccgttcg tgaacacgca ccctgataag ctgcgaaacc catgccccaa caaggagaaa    660

gagtgccagc ccccgtttgc cttcaggcac gtgctgaagc tgaccaacaa ctccaaccag    720

tttcagaccg aggtcgggaa gcagctgatt tccggaaacc tggatgcacc cgagggtggg    780

ctggacgcca tgatgcaggt cgccgcctgc ccggaggaaa tcggctggcg caacgtcacg    840

cggctgctgg tgtttgccac tgatgacggc ttccatttcg cgggcgacgg aaagctgggc    900

gccatcctga cccccaacga cggccgctgt cacctggagg acaacttgta caagaggagc    960

aacgaattcg actacccatc ggtgggccag ctggcgcaca agctggctga aaacaacatc   1020

cagcccatct tcgcggtgac cagtaggatg gtgaagacct acgagaaact caccgagatc   1080
```

atccccaagt cagccgtggg ggagctgtct gaggactcca gcaatgtggt ccatctcatt 1140
aagaatgctt acaataaact ctcctccagg gtcttcctgg atcacaacgc cctccccgac 1200
accctgaaag tcacctacga ctccttctgc agcaatggag tgacgcacag gaaccagccc 1260
agaggtgact gtgatggcgt gcagatcaat gtcccgatca ccttccaggt gaaggtcacg 1320
gccacagagt gcatccagga gcagtcgttt gtcatccggg cgctgggctt cacggacata 1380
gtgaccgtgc aggttcttcc ccagtgtgag tgccggtgcc gggaccagag cagagaccgc 1440
agcctctgcc atggcaaggg cttcttggag tgcggcatct gcaggtgtga cactggctac 1500
attgggaaaa actgtgagtg ccagacacag ggccggagca gccaggagct ggaaggaagc 1560
tgccggaagg acaacaactc catcatctgc tcagggctgg gggactgtgt ctgcgggcag 1620
tgcctgtgcc acaccagcga cgtccccggc aagctgatat acgggcagta ctgcgagtgt 1680
gacaccatca actgtgagcg ctacaacggc caggtctgcg gcggcccggg gagggggctc 1740
tgcttctgcg ggaagtgccg ctgccacccg ggctttgagg gctcagcgtg ccagtgcgag 1800
aggaccactg agggctgcct gaacccgcgg cgtgttgagt gtagtggtcg tggccggtgc 1860
cgctgcaacg tatgcgagtg ccattcaggc taccagctgc ctctgtgcca ggagtgcccc 1920
ggctgcccct caccctgtgg caagtacatc tcctgcgccg agtgcctgaa gttcgaaaag 1980
ggcccctttg ggaagaactg cagcgcggcg tgtccgggcc tgcagctgtc gaacaacccc 2040
gtgaagggca ggacctgcaa ggagagggac tcagagggct gctgggtggc ctacacgctg 2100
gagcagcagg acgggatgga ccgctacctc atctatgtgg atgagagccg agagtgtgtg 2160
gcaggcccca acatcgccgc catcgtcggg ggcaccgtgg caggcatcgt gctgatcggc 2220
attctcctgc tggtcatctg gaaggctctg atccacctga gcgacctccg ggagtacagg 2280
cgctttgaga aggagaagct caagtcccag tggaacaatg ataatcccct tttcaagagc 2340
gccaccacga cggtcatgaa ccccaagttt gctgagagtt aggagcactt ggtgaagaca 2400
aggccgtcag gacccaccat gtctgcccca tcacgcggcc gagacatggc ttggccacag 2460
ctcttgagga tgtcaccaat taaccagaaa tccagttatt ttccgccctc aaaatgacag 2520
ccatggccgg ccggtgcttc tgggggctcg tcggggggac agctccactc tgactggcac 2580
agtctttgca tggagacttg aggagggctt gaggttggtg aggttaggtg cgtgtttcct 2640
gtgcaagtca ggacatcagt ctgattaaag gtggtgccaa tttatttaca tttaaacttg 2700
tcagggtata aaatgacatc ccattaatta tattgttaat caatcacgtg tatagaaaaa 2760
aaaataaaac ttcaat 2776

<210> SEQ ID NO 87
<211> LENGTH: 3387
<212> TYPE: DNA
<213> ORGANISM: Homo sapiens
<220> FEATURE:
<221> NAME/KEY: misc_feature
<223> OTHER INFORMATION: Cox2: Acc. No. M90100

<400> SEQUENCE: 87
gtccaggaac tcctcagcag cgcctccttc agctccacag ccagacgccc tcagacagca 60
aagcctaccc ccgcgccgcg ccctgcccgc cgctgcgatg ctcgcccgcg ccctgctgct 120
gtgcgcggtc ctggcgctca gccatacagc aaatccttgc tgttcccacc catgtcaaaa 180
ccgaggtgta tgtatgagtg tgggatttga ccagtataag tgcgattgta cccggacagg 240
attctatgga gaaaactgct caacaccgga atttttgaca agaataaaat tatttctgaa 300

-continued

```
acccactcca aacacagtgc actacatact tacccacttc aagggatttt ggaacgttgt    360
gaataacatt cccttccttc gaaatgcaat tatgagttat gtgttgacat ccagatcaca    420
tttgattgac agtccaccaa cttacaatgc tgactatggc tacaaaagct gggaagcctt    480
ctctaacctc tcctattata ctagagccct tcctcctgtg cctgatgatt gcccgactcc    540
cttgggtgtc aaaggtaaaa agcagcttcc tgattcaaat gagattgtgg gaaaattgct    600
tctaagaaga aagttcatcc ctgatcccca gggctcaaac atgatgtttg cattctttgc    660
ccagcacttc acgcatcagt tttcaagac agatcataag cgagggccag ctttcaccaa    720
cgggctgggc catggggtgg acttaaatca tatttacggt gaaactctgg ctagacagcg    780
taaactgcgc cttttcaagg atggaaaaat gaaatatcag ataattgatg gagagatgta    840
tcctcccaca gtcaaagata ctcaggcaga gatgatctac cctcctcaag tccctgagca    900
tctacggttt gctgtggggc aggaggtctt tggtctggtg cctggtctga tgatgtatgc    960
cacaatctgg ctgagggaac acaacagagt atgcgatgtg cttaaacagg agcatcctga   1020
atggggtgat gagcagttgt tccagacaag caggctaata ctgataggag agactattaa   1080
gattgtgatt gaagattatg tgcaacactt gagtggctat cacttcaaac tgaaatttga   1140
cccagaacta cttttcaaca aacaattcca gtaccaaaat cgtattgctg ctgaatttaa   1200
caccctctat cactggcatc cccttctgcc tgacaccttt caaattcatg accagaaata   1260
caactatcaa cagtttatct acaacaactc tatattgctg gaacatggaa ttacccagtt   1320
tgttgaatca ttcaccaggc aaattgctgg cagggttgct ggtggtagga atgttccacc   1380
cgcagtacag aaagtatcac aggcttccat tgaccagagc aggcagatga aataccagtc   1440
ttttaatgag taccgcaaac gctttatgct gaagccctat gaatcatttg aagaacttac   1500
aggagaaaag gaaatgtctg cagagttgga agcactctat ggtgacatcg atgctgtgga   1560
gctgtatcct gcccttctgg tagaaaagcc tcggccagat gccatctttg gtgaaaccat   1620
ggtagaagtt ggagcaccat tctccttgaa aggacttatg ggtaatgtta tatgttctcc   1680
tgcctactgg aagccaagca cttttggtgg agaagtgggt tttcaaatca tcaacactgc   1740
ctcaattcag tctctcatct gcaataacgt gaagggctgt ccctttactt cattcagtgt   1800
tccagatcca gagctcatta aaacagtcac catcaatgca agttcttccc gctccggact   1860
agatgatatc aatcccacag tactactaaa agaacgttcg actgaactgt agaagtctaa   1920
tgatcatatt tatttattta tatgaaccat gtctattaat ttaattattt aataatattt   1980
atattaaact ccttatgtta cttaacatct tctgtaacag aagtcagtac tcctgttgcg   2040
gagaaaggag tcatacttgt gaagactttt atgtcactac tctaaagatt ttgctgttgc   2100
tgttaagttt ggaaaacagt ttttattctg ttttataaac cagagagaaa tgagttttga   2160
cgtcttttta cttgaatttc aacttatatt ataaggacga aagtaaagat gtttgaatac   2220
ttaaacacta tcacaagatg ccaaaatgct gaaagttttt acactgtcga tgtttccaat   2280
gcatcttcca tgatgcatta gaagtaacta atgtttgaaa ttttaaagta cttttgggta   2340
tttttctgtc atcaaacaaa acaggtatca gtgcattatt aaatgaatat ttaaattaga   2400
cattaccagt aatttcatgt ctacttttta aaatcagcaa tgaaacaata atttgaaatt   2460
tctaaattca tagggtagaa tcacctgtaa aagcttgttt gatttcttaa agttattaaa   2520
cttgtacata taccaaaaag aagctgtctt ggatttaaat ctgtaaaatc agatgaaatt   2580
ttactacaat tgcttgttaa aatattttat aagtgatgtt cctttttcac caagagtata   2640
aacctttta gtgtgactgt taaaacttcc ttttaaatca aaatgccaaa tttattaagg   2700
```

```
tggtggagcc actgcagtgt tatctcaaaa taagaatatc ctgttgagat attccagaat   2760

ctgtttatat ggctggtaac atgtaaaaac cccataaccc cgccaaaagg ggtcctaccc   2820

ttgaacataa agcaataacc aaaggagaaa agcccaaatt attggttcca aatttagggt   2880

ttaaactttt tgaagcaaac tttttttag ccttgtgcac tgcagacctg gtactcagat   2940

tttgctatga ggttaatgaa gtaccaagct gtgcttgaat aacgatatgt tttctcagat   3000

tttctgttgt acagtttaat ttagcagtcc atatcacatt gcaaaagtag caatgacctc   3060

ataaaatacc tcttcaaaat gcttaaattc atttcacaca ttaattttat ctcagtcttg   3120

aagccaattc agtaggtgca ttggaatcaa gcctggctac ctgcatgctg ttccttttct   3180

tttcttcttt tagccatttt gctaagagac acagtcttct caaacacttc gtttctccta   3240

ttttgtttta ctagttttaa gatcagagtt cactttcttt ggactctgcc tatattttct   3300

tacctgaact tttgcaagtt ttcaggtaaa cctcagctca ggactgctat ttagctcctc   3360

ttaagaagat taaaaaaaaa aaaaaag                                        3387
```

<210> SEQ ID NO 88
<211> LENGTH: 4471
<212> TYPE: DNA
<213> ORGANISM: Homo sapiens
<220> FEATURE:
<221> NAME/KEY: misc_feature
<223> OTHER INFORMATION: HMG Co-A: Acc. No. NM_000859

<400> SEQUENCE: 88

```
ttcggtggcc tctagtgaga tctggaggat ccaaggattc tgtagctaca atgttgtcaa     60

gactttttcg aatgcatggc ctctttgtgg cctcccatcc ctgggaagtc atagtgggga    120

cagtgacact gaccatctgc atgatgtcca tgaacatgtt tactggtaac aataagatct    180

gtggttggaa ttatgaatgt ccaaagtttg aagaggatgt tttgagcagt gacattataa    240

ttctgacaat aacacgatgc atagccatcc tgtatattta cttccagttc cagaatttac    300

gtcaacttgg atcaaaatat attttgggta ttgctggcct tttcacaatt ttctcaagtt    360

ttgtattcag tacagttgtc attcacttct tagacaaaga attgacaggc ttgaatgaag    420

ctttgccctt tttcctactt ttgattgacc tttccagagc aagcacatta gcaaagtttg    480

ccctcagttc caactcacag gatgaagtaa gggaaaatat tgctcgtgga atggcaattt    540

taggtcctac gtttaccctc gatgctcttg ttgaatgtct tgtgattgga gttggtacca    600

tgtcaggggt acgtcagctt gaaattatgt gctgctttgg ctgcatgtca gttcttgcca    660

actacttcgt gttcatgact ttcttcccag cttgtgtgtc cttggtatta gagctttctc    720

gggaaagccg cgagggtcgt ccaatttggc agctcagcca ttttgcccga gttttagaag    780

aagaagaaaa taagccgaat cctgtaactc agagggtcaa gatgattatg tctctaggct    840

tggttcttgt tcatgctcac agtcgctgga tagctgatcc ttctcctcaa aacagtacag    900

cagatacttc taaggtttca ttaggactgg atgaaaatgt gtccaagaga attgaaccaa    960

gtgtttccct ctggcagttt tatctctcta aaatgatcag catggatatt gaacaagtta   1020

ttaccctaag tttagctctc cttctggctg tcaagtacat cttctttgaa caaacagaga   1080

cagaatctac actctcatta aaaaacccta tcacatctcc tgtagtgaca caaaagaaag   1140

tcccagacaa ttgttgtaga cgtgaaccta tgctggtcag aaataaccag aaatgtgatt   1200

cagtagagga agagacaggg ataaaccgag aaagaaaagt tgaggttata aaacccttag   1260

tggctgaaac agataacccca aacagagcta catttgtggt tggtaactcc tccttactcg   1320

atacttcatc agtactggtg acacaggaac ctgaaattga acttcccagg gaacctcggc   1380
```

-continued

```
ctaatgaaga atgtctacag atacttggga atgcagagaa aggtgcaaaa ttccttagtg   1440
atgctgagat catccagtta gtcaatgcta agcatatccc agcctacaag ttggaaactc   1500
tgatggaaac tcatgagcgt ggtgtatcta ttcgccgaca gttactttcc aagaagcttt   1560
cagaaccttc ttctctccag tacctacctt acagggatta taattactcc ttggtgatgg   1620
gagcttgttg tgagaatgtt attggatata tgcccatccc tgttggagtg gcaggacccc   1680
tttgcttaga tgaaaaagaa tttcaggttc caatggcaac aacagaaggt tgtcttgtgg   1740
ccagcaccaa tagaggctgc agagcaatag gtcttggtgg aggtgccagc agccgagtcc   1800
ttgcagatgg gatgactcgt ggcccagttg tgcgtcttcc acgtgcttgt gactctgcag   1860
aagtgaaagc ctggctcgaa acatctgaag ggttcgcagt gataaaggag gcatttgaca   1920
gcactagcag atttgcacgt ctacagaaac ttcatacaag tatagctgga cgcaaccttt   1980
atatccgttt ccagtccagg tcaggggatg ccatggggat gaacatgatt tcaaagggta   2040
cagagaaagc actttcaaaa cttcacgagt atttccctga aatgcagatt ctagccgtta   2100
gtggtaacta ttgtactgac aagaaacctg ctgctataaa ttggatagag ggaagaggaa   2160
aatctgttgt ttgtgaagct gtcattccag ccaaggttgt cagagaagta ttaaagacta   2220
ccacagaggc tatgattgag gtcaacatta acaagaattt agtgggctct gccatggctg   2280
ggagcatagg aggctacaac gcccatgcag caaacattgt caccgccatc tacattgcct   2340
gtggacagga tgcagcacag aatgttggta gttcaaactg tattacttta atggaagcaa   2400
gtggtcccac aaatgaagat ttatatatca gctgcaccat gccatctata gagataggaa   2460
cggtgggtgg tgggaccaac ctactacctc agcaagcctg tttgcagatg ctaggtgttc   2520
aaggagcatg caaagataat cctggggaaa atgcccggca gcttgcccga attgtgtgtg   2580
ggaccgtaat ggctggggaa ttgtcactta tggcagcatt ggcagcagga catcttgtca   2640
aaagtcacat gattcacaac aggtcgaaga tcaatttaca agacctccaa ggagcttgca   2700
ccaagaagac agcctgaata gcccgacagt tctgaactgg aacatgggca ttgggttcta   2760
aaggactaac ataaaatctg tgaattaaaa aagctcaatg cattgtcttg tggaggatga   2820
ataaatgtga tcactgagac agccacttgg tttttggctc tttcagagag gtctcaggtt   2880
ctttccatgc agactcctca gatctgaaca cagtttagtg ctttacatgc tgtgctcttt   2940
gaagagattt caacaagaat attgtatgtt aaagcatcag agatggtaat ctacagctca   3000
cctctgaaag caaatataag ctgggaaaaa agttttgatg aaattcttga agttcatggt   3060
gatcagtgca attgaccttc tccctcactc ctgccagttg aaaatggatt tttaaattat   3120
actgtagctg atgaaactcc tgattttgta gttaatttat taagtctggg atgtagaact   3180
tcaagaagta agagctaagt tctaagttca tgtttgtaaa ttaatacttc atttggtgct   3240
ggtctatttt gattttgggg ggtaatcagc attattcttc agaaggggac ctgttttctt   3300
caagggaaga aacactctta ttcccaaact acagaataat gtgttaaaca tgctaaatag   3360
ttctatcagg aaaacaaatc actgtattta tctccgcagg ctatttgttc agagaggcct   3420
tttgtttaaa tataaatgtt taaatataaa tgtttgtctg gattggctat aacatgtctt   3480
tcagcattag gcttttaaga aacacagggt tttgtattct ttactaaaga tatcagagct   3540
cttaatgttg cttagatgag ggtgactgtc aagtacaagc aagactggga ccttagaaat   3600
cattgtagaa acacagtttt gaaagatttt taccatgtct ctaagccaac tttaattgct   3660
taaaagacat ttttatttag ttgaaaaatc tagttttttt tgtaaactgt accaaatctg   3720
tatatgttgt aataaaactt atgctagttt attggaagtg ttcaagaaat aaaaatcaac   3780
```

```
ttgtgtactg ataaaatact ctagcctggg ccagagaaga taatgttctt taatgttgtc   3840

aggaaaccct ggcttgcttg ccgagcctaa tgaaagggaa agtcagcttt cagagccagt   3900

gaaggagcca cgtgaatggc cctagaactg tgcctagttc ctgtggccag gaggttggtg   3960

actgaaacat tcacacaggg ctcttggatg gacccacgaa cgctcttagc tttctcaggg   4020

ggtcagcaga gttattgaat cttaattttt tttaatgtac aagttttgta taaataataa   4080

agaactcctt attttgtatt acatctaatg cttaagtgtt gctcttggaa agctgatgat   4140

gtctcttgta gagatgactc tgaaaaacat tccaggaaac catggcagca tggagagcct   4200

cttagtgatt gtgtctgcat tgttattgtg gaagatttac cttttctgtt gtacgtaaag   4260

cttaaattac ttttgttgtg actttttagc cagtgacttt ttctgagctt ttcatggaag   4320

tggcagtgaa aaatatgttg agtgttcaaa aaagtgactg taattaatat cttgctggat   4380

taatgttttg tacaattact aaattgtata cattttgtta tagaatactt ttttctagtt   4440

tcagtaaata atgaaaagga agttaatacc a                                  4471
```

<210> SEQ ID NO 89
<211> LENGTH: 2444
<212> TYPE: DNA
<213> ORGANISM: Homo sapiens
<220> FEATURE:
<221> NAME/KEY: misc_feature
<223> OTHER INFORMATION: NM_021975

<400> SEQUENCE: 89

```
ggcacgaggc ggggccgggt cgcagctggg cccgcggcat ggacgaactg ttcccccctca     60

tcttcccggc agagcagccc aagcagcggg gcatgcgctt ccgctacaag tgcgaggggc    120

gctccgcggg cagcatccca ggcgagagga gcacagatac caccaagacc caccccacca    180

tcaagatcaa tggctacaca ggaccaggga cagtgcgcat ctccctggtc accaaggacc    240

ctcctcaccg gcctcacccc cacgagcttg taggaaagga ctgccgggat ggcttctatg    300

aggctgagct ctgcccggac cgctgcatcc acagtttcca gaacctggga atccagtgtg    360

tgaagaagcg ggacctggag caggctatca gtcagcgcat ccagaccaac aacaacccct    420

tccaagttcc tatagaagag cagcgtgggg actacgacct gaatgctgtg cggctctgct    480

tccaggtgac agtgcgggac ccatcaggca ggcccctccg cctgccgcct gtcctttctc    540

atcccatctt tgacaatcgt gcccccaaca ctgccgagct caagatctgc cgagtgaacc    600

gaaactctgg cagctgcctc ggtggggatg agatcttcct actgtgtgac aaggtgcaga    660

aagaggacat tgaggtgtat ttcacgggac caggctggga ggcccgaggc tccttttcgc    720

aagctgatgt gcaccgacaa gtggccattg tgttccggac ccctccctac gcagacccca    780

gcctgcaggc tcctgtgcgt gtctccatgc agctgcggcg gccttccgac cgggagctca    840

gtgagcccat ggaattccag tacctgccag atacagacga tcgtcaccgg attgaggaga    900

aacgtaaaag gacatatgag accttcaaga gcatcatgaa gaagagtcct ttcagcggac    960

ccaccgaccc ccggcctcca cctcgacgca ttgctgtgcc ttcccgcagc tcagcttctg   1020

tccccaagcc agcaccccag ccctatccct ttacgtcatc cctgagcacc atcaactatg   1080

atgagtttcc caccatggtg tttccttctg ggcagatcag ccaggcctcg gccttggccc   1140

cggcccctcc ccaagtcctg ccccaggctc cagcccctgc ccctgctcca gccatggtat   1200

cagctctggc ccaggcccca gcccctgtcc cagtcctagc cccaggccct cctcaggctg   1260

tggccccacc tgcccccaag cccacccagg ctggggaagg aacgctgtca gaggccctgc   1320
```

tgcagctgca gtttgatgat gaagacctgg gggccttgct tggcaacagc acagacccag 1380
ctgtgttcac agacctggca tccgtcgaca actccgagtt tcagcagctg ctgaaccagg 1440
gcatacctgt ggcccccac acaactgagc ccatgctgat ggagtaccct gaggctataa 1500
ctcgcctagt gacagcccag aggcccccg acccagctcc tgctccactg ggggccccgg 1560
ggctccccaa tggcctcctt tcaggagatg aagacttctc ctccattgcg gacatggact 1620
tctcagccct gctgagtcag atcagctcct aagggggtga cgcctgccct ccccagagca 1680
ctggttgcag gggattgaag ccctccaaaa gcacttacgg attctggtgg ggtgtgttcc 1740
aactgccccc aactttgtgg atgtcttcct tggagggggg agccatattt tattctttta 1800
ttgtcagtat ctgtatctct ctctcttttt ggaggtgctt aagcagaagc attaacttct 1860
ctggaaaggg gggagctggg gaaactcaaa cttttcccct gtcctgatgg tcagctccct 1920
tctctgtagg gaactgtggg gtcccccatc cccatcctcc agcttctggt actctcctag 1980
agacagaagc aggctggagg taaggccttt gagcccacaa agccttatca agtgtcttcc 2040
atcatggatt cattacagct taatcaaaat aacgccccag ataccagccc ctgtatggca 2100
ctggcattgt ccctgtgcct aacaccagcg tttgaggggc tgccttcctg ccctacagag 2160
gtctctgccg gctctttcct tgctcaacca tggctgaagg aaacagtgca acagcactgg 2220
ctctctccag gatccagaag ggtttggtc tggacttcct tgctctcccc tcttctcaag 2280
tgccttaata gtagggtaag ttgttaagag tgggggagag caggctggca gctctccagt 2340
caggaggcat agtttttagt gaacaatcaa agcacttgga ctcttgctct ttctactctg 2400
aactaataaa gctgttgcca agctggacgg cacgagctcg tgcc 2444

<210> SEQ ID NO 90
<211> LENGTH: 816
<212> TYPE: DNA
<213> ORGANISM: Homo sapiens

<400> SEQUENCE: 90
atgcactttc tttgccaaag gcaaacgcag aacgtttcag agccatgagg atgcttctgc 60
atttgagttt gctagctctt ggagctgcct acgtgtatgc catccccaca gaaattccca 120
caagtgcatt ggtgaaagag accttggcac tgctttctac tcatcgaact ctgctgatag 180
ccaatgagac tctgaggatt cctgttcctg tacataaaaa tcaccaactg tgcactgaag 240
aaatctttca gggaataggc acactggaga gtcaaactgt gcaagggggt actgtggaaa 300
gactattcaa aaacttgtcc ttaataaaga aatacattga cggccaaaaa aaaaagtgtg 360
gagaagaaag acggagagta aaccaattcc tagactacct gcaagagttt cttggtgtaa 420
tgaacaccga gtggataata gaaagttgag actaaactgg tttgttgcag ccaaagattt 480
tggaggagaa ggacatttta ctgcagtgag aatgagggcc aagaaagagt caggccttaa 540
ttttcaatat aatttaactt cagagggaaa gtaaatattt caggcatact gacactttgc 600
cagaaagcat aaaattctta aaatatattt cagatatcag aatcattgaa gtattttcct 660
ccaggcaaaa ttgatatact tttttcttat ttaacttaac attctgtaaa atgtctgtta 720
acttaatagt atttatgaaa tggttaagaa tttggtaaat tagtatttat ttaatgttat 780
gttgtgttct aataaaacaa aaatagacaa ctgttc 816

<210> SEQ ID NO 91
<211> LENGTH: 2484
<212> TYPE: DNA
<213> ORGANISM: Homo sapiens
<220> FEATURE:

<221> NAME/KEY: misc_feature
<223> OTHER INFORMATION: LO5: Acc. No. J03571

<400> SEQUENCE: 91

```
gggcccggcg ctcgctgctc ccgcggcccg cgccatgccc tcctacacgg tcaccgtggc     60
cactggcagc cagtggttcg ccggcactga cgactacatc tacctcagcc tcgtgggctc    120
ggcgggctgc agcgagaagc acctgctgga caagcccttc tacaacgact tcgagcgtgg    180
cgcggtggat tcatacgacg tgactgtgga cgaggaactg ggcgagatcc agctggtcag    240
aatcgagaag cgcaagtact ggctgaatga cgactggtac ctgaagtaca tcacgctgaa    300
gacgccccac ggggactaca tcgagttccc ctgctaccgc tggatcaccg gcgatgtcga    360
ggttgtcctg agggatggac gcgcaaagtt ggcccgagat gaccaaattc acattctcaa    420
gcaacaccga cgtaaagaac tggaaacacg gcaaaaacaa tatcgatgga tggagtggaa    480
ccctggcttc cccttgagca tcgatgccaa atgccacaag gatttacccc gtgatatcca    540
gtttgatagt gaaaaaggag tggactttgt tctgaattac tccaaagcga tggagaacct    600
gttcatcaac cgcttcatgc acatgttcca gtcttcttgg aatgacttcg ccgactttga    660
gaaaatcttt gtcaagatca gcaacactat ttctgagcgg gtcatgaatc actggcagga    720
agacctgatg tttggctacc agttcctgaa tggctgcaac cctgtgttga tccggcgctg    780
cacagagctg cccgagaagc tcccggtgac cacggagatg gtagagtgca gcctggagcg    840
gcagctcagc ttggagcagg aggtccagca agggaacatt ttcatcgtgg actttgagct    900
gctggatggc atcgatgcca acaaaaacaga cccctgcaca ctccagttcc tggccgctcc    960
catctgcttg ctgtataaga acctggccaa caagattgtc cccattgcca tccagctcaa   1020
ccaaatcccg ggagatgaga accctatttt cctcccttcg gatgcaaaat acgactggct   1080
tttggccaaa atctgggtgc gttccagtga cttccacgtc caccagacca tcacccacct   1140
tctgcgaaca catctggtgt ctgaggtttt tggcattgca atgtaccgcc agctgcctgc   1200
tgtgcacccc attttcaagc tgctggtggc acacgtgaga ttcaccattg caatcaacac   1260
caaggcccgt gagcagctca tctgcgagtg tggcctcttt gacaaggcca acgccacagg   1320
gggcggtggg cacgtgcaga tggtgcagag ggccatgaag gacctgacct atgcctccct   1380
gtgctttccc gaggccatca aggcccgggg catggagagc aaagaagaca tcccctacta   1440
cttctaccgg gacgacgggc tcctggtgtg ggaagccatc aggacgttca cggccgaggt   1500
ggtagacatc tactacgagg gcgaccaggt ggtggaggag gacccggagc tgcaggactt   1560
cgtgaacgat gtctacgtgt acggcatgcg gggccgcaag tcctcaggct tccccaagtc   1620
ggtcaagagc cgggagcagc tgtcggagta cctgaccgtg gtgatcttca ccgcctccgc   1680
ccagcacgcc gcggtcaact tcggccagta cgactggtgc tcctggatcc ccaatgcgcc   1740
cccaaccatg cgagccccgc caccgactgc caagggcgtg gtgaccattg agcagatcgt   1800
ggacacgctg cccgaccgcg gccgctcctg ctggcatctg ggtgcagtgt gggcgctgag   1860
ccagttccag gaaaacgagc tgttcctggg catgtaccca gaagagcatt ttatcgagaa   1920
gcctgtgaag gaagccatgg cccgattccg caagaacctc gaggccattg tcagcgtgat   1980
tgctgagcgc aacaagaaga agcagctgcc atattactac ttgtccccag accggattcc   2040
gaacagtgtg gccatctgag cacactgcca gtctcactgt gggaaggcca gctgccccag   2100
ccagatggac tccagcctgc ctggcaggtg tctggccagg cctcttggca gtcacatctc   2160
ttcctccgag gccagtacct ttccatttat tctttgatct tcagggaact gcatagattg   2220
atcaaagtgt aaacaccata gggacccatt ctacacagag caggactgca cagcgtcctg   2280
```

```
tccacaccca gctcagcatt tccacaccaa gcagcaacag caaatcacga ccactgatag   2340

atgtctattc ttgttggaga catgggatga ttattttctg ttctatttgt gcttagtcca   2400

attccttgca catagtaggt acccaattca attactattg aatgaattaa gaattggttg   2460

ccataaaaat aaatcagttc attt                                          2484
```

<210> SEQ ID NO 92
<211> LENGTH: 2437
<212> TYPE: DNA
<213> ORGANISM: Homo sapiens
<220> FEATURE:
<221> NAME/KEY: misc_feature
<223> OTHER INFORMATION: MPB: Acc. No.: M74047

<400> SEQUENCE: 92

```
gcggccaccg gcgaggaaca cggcgcgatg caggttcagt gccagcagag cccagtgctg     60

gcaggcagcg ccactttggt cgcccttggg gcactggcct tgtacgtcgc gaagccctcc    120

ggctacggga agcacacgga gagcctgaag ccggcggcta cccgcctgcc agcccgcgcc    180

gcctggttcc tgcaggagct gccttccttc gcggtgcccg cggggatcct cgcccggcag    240

cccctctccc tcttcgggcc acctgggacg gtacttctgg gcctcttctg cgtacattac    300

ttccacagga catttgtgta ctcactgctc aatcgaggga ggccttatcc agctatactc    360

attctcagag gcactgcctt ctgcactgga aatggagtcc ttcaaggcta ctatctgatt    420

tactgtgctg aataccctga tgggtggtac acagacatac ggtttagctt gggtgtcttc    480

ttatttattt tgggaatggg aataaacatt catagtgact atatattgcg ccagctcagg    540

aagcctggag aaatcagcta caggattcca caaggtggct tgtttacgta tgtttctgga    600

gccaatttcc tcggtgagat cattgaatgg atcggctatg ccctggccac ttggtccctc    660

ccagcacttg catttgcatt tttctcactt tgtttccttg ggctgcgagc ttttcaccac    720

cataggttct acctcaagat gtttgaggac taccccaaat ctcggaaagc ccttattcca    780

ttcatctttt aaaggaacca aattaaaaag gagcagagct cccacaatgc tgatgaaaac    840

tgtcaagctg ctgaaactgt aattttcatg atataatagt catatatata tatatatata    900

tatatatata tatatatatg tatatatgta atagtaggtc tcctggcgtt ctgccagctg    960

gcctggggat tctgagtggt gtctgcttag agtttactcc tacccttcca gggaccccta   1020

tcctgatccc caactgaagc ttcaaaaagc cacttttcca aatggcgaca gttgcttctt   1080

agctattgct ctgagaaagt acaaacttct cctatgtctt tcaccgggca atccaagtac   1140

atgtggcttc atacccactc cctgtcaatg caggacaact ctgtaatcaa gaatttttttg   1200

acttgaaggc agtacttata gaccttatta aaggtatgca ttttatacat gtaacagagt   1260

agcagaaatt taaactctga agccacaaag acccagagca aacccactcc caaatgaaaa   1320

ccccagtcat ggcttccttt ttcttggtta attaggaaag atgagaaatt attaggtaga   1380

ccttgaatac aggagccctc tcctcatagt gctgaaaaga tactgatgca ttgacctcat   1440

ttcaaatttg tgcagtgtct tagttgatga gtgcctctgt tttccagaag atttcacaat   1500

ccccggaaaa ctggtatggc tattcttgaa ggccaggttt taataaccac aaacaaaaag   1560

gcatgaacct gggtggctta tgagagagta gagaacaaca tgaccctgga tggctactaa   1620

gaggatagag aacagtttta caatagacat tgcaaactct catgtttttg gaaactggtg   1680

gcaatatcca aataatgagt agtgtaaaac aaagagaatt aatgatgagg ttacatgctg   1740

cttgcctcca ccagatgtcc acaacaatat gaagtacagc agaagcccca agcaactttc   1800
```

```
ctttcctgga gcttcttcct tgtagttctc aggacctgtt caagaaggtg tctcctaggg   1860

gcagcctgaa tgcctccctc aaaggacctg caggcagaga ctgaaaattg cagacagagg   1920

ggcacgtctg ggcagaaaac ctgttttgtt tggctcagac atatagtttt ttttttttta   1980

caaagtttca aaaacttaaa aatcaggaga ttccttcata aaactctagc attctagttt   2040

catttaaaaa gttggaggat ctgaacatac agagcccaca tttccacacc agaactggaa   2100

ctacgtagct agtaagcatt tgagtttgca aactcttgtg aaggggtcac cccagcatga   2160

gtgctgagat atggactctc taaggaaggg gccgaacgct tgtaattgga atacatggaa   2220

atatttgtct tctcaggcct atgtttgcgg aatgcattgt caatatttag caaactgttt   2280

tgacaaatga gcaccagtgg tactaagcac agaaactcac tatataagtc acataggaaa   2340

cttgaaaggt ctgaggatga tgtagattac tgaaaaatac aaattgcaat catataaata   2400

agtgtttttg ttgttcatta aataccttta aatcatg                            2437
```

```
<210> SEQ ID NO 93
<211> LENGTH: 5595
<212> TYPE: DNA
<213> ORGANISM: Homo sapiens
<220> FEATURE:
<221> NAME/KEY: misc_feature
<223> OTHER INFORMATION: NEP=CALLA:  Acc. No. NM_000902

<400> SEQUENCE: 93
```

```
gcggagatgt gcaagtggcg aagcttgacc gagagcaggc tggagcagcc gcccaactcc     60

tggcgcggga tctgctgagg ggtcacggat tttaggtgat gggcaagtca gaaagtcaga    120

tggatataac tgatatcaac actccaaagc caaagaagaa acagcgatgg actcgactgg    180

agatcagcct ctcggtcctt gtcctgctcc tcaccatcat agctgtgaga atgatcgcac    240

tctatgcaac ctacgatgat ggtatttgca agtcatcaga ctgcataaaa tcagctgctc    300

gactgatcca aaacatggat gccaccactg agccttgtag agactttttc aaatatgctt    360

gcggaggctg gttgaaacgt aatgtcattc ccgagaccag ctcccgttac ggcaactttg    420

acattttaag agatgaacta gaagtcgttt tgaaagatgt ccttcaagaa cccaaaactg    480

aagatatagt agcagtgcag aaagcaaaag cattgtacag gtcttgtata aatgaatctg    540

ctattgatag cagaggtgga gaacctctac tcaaactgtt accagacata tatgggtggc    600

cagtagcaac agaaaactgg gagcaaaaat atggtgcttc ttggacagct gaaaaagcta    660

ttgcacaact gaattctaaa tatgggaaaa aagtccttat taatttgttt gttggcactg    720

atgataagaa ttctgtgaat catgtaattc atattgacca acctcgactt ggcctccctt    780

ctagagatta ctatgaatgc actggaatct ataaagaggc ttgtacagca tatgtggatt    840

ttatgatttc tgtggccaga ttgattcgtc aggaagaaag attgcccatc gatgaaaacc    900

agcttgcttt ggaaatgaat aaagttatgg aattggaaaa agaaattgcc aatgctacgg    960

ctaaacctga agatcgaaat gatccaatgc ttctgtataa caagatgaga ttggcccaga   1020

tccaaaataa cttttcacta gagatcaatg ggaagccatt cagctggttg aatttcacaa   1080

atgaaatcat gtcaactgtg aatattagta ttacaaatga ggaagatgtg gttgtttatg   1140

ctccagaata tttaaccaaa cttaagccca ttcttaccaa atattctgcc agagatcttc   1200

aaaatttaat gtcctggaga ttcataatgg atcttgtaag cagcctcagc cgaacctaca   1260

aggagtccag aaatgctttc cgcaaggccc tttatggtac aacctcagaa acagcaactt   1320

ggagacgttg tgcaaactat gtcaatggga atatggaaaa tgctgtgggg aggctttatg   1380

tggaagcagc atttgctgga gagagtaaac atgtggtcga ggatttgatt gcacagatcc   1440
```

```
gagaagtttt tattcagact ttagatgacc tcacttggat ggatgccgag acaaaaaaga   1500
gagctgaaga aaaggcctta gcaattaaag aaaggatcgg ctatcctgat gacattgttt   1560
caaatgataa caaactgaat aatgagtacc tcgagttgaa ctacaaagaa gatgaatact   1620
tcgagaacat aattcaaaat ttgaaattca gccaaagtaa acaactgaag aagctccgag   1680
aaaaggtgga caaagatgag tggataagtg gagcagctgt agtcaatgca ttttactctt   1740
caggaagaaa tcagatagtc ttcccagccg gcattctgca gcccccctte tttagtgccc   1800
agcagtccaa ctcattgaac tatgggggca tcggcatggt cataggacac gaaatcaccc   1860
atggcttcga tgacaatggc agaaacttta acaaagatgg agacctcgtt gactggtgga   1920
ctcaacagtc tgcaagtaac tttaaggagc aatcccagtg catggtgtat cagtatggaa   1980
acttttcctg ggacctggca ggtggacagc accttaatgg aattaataca ctgggagaaa   2040
acattgctga taatggaggt cttggtcaag catacagagc ctatcagaat tatattaaaa   2100
agaatggcga agaaaaatta cttcctggac ttgacctaaa tcacaaacaa ctatttttct   2160
tgaactttgc acaggtgtgg tgtggaacct ataggccaga gtatgcggtt aactccatta   2220
aaacagatgt gcacagtcca ggcaatttca ggattattgg gactttgcag aactctgcag   2280
agttttcaga agcctttcac tgccgcaaga attcatacat gaatccagaa aagaagtgcc   2340
gggtttggtg atcttcaaaa gaagcattgc agcccttggc tagacttgcc aacaccacag   2400
aaatggggaa ttctctaatc gaaagaaaat gggccctagg ggtcactgta ctgacttgag   2460
ggtgattaac agagagggca ccatcacaat acagataaca ttaggttgtc ctagaaaggg   2520
tgtggaggga ggaagggggt ctaaggtcta tcaagtcaat catttctcac tgtgtacata   2580
atgcttaatt tctaaagata atattactgt ttatttctgt ttctcatatg gtctaccagt   2640
ttgctgatgt ccctagaaaa caatgcaaaa cctttgaggt agaccaggat ttctaatcaa   2700
aagggaaaag aagatgttga agaatagagt taggcaccag aagaagagta ggtgacacta   2760
tagtttaaaa cacattgcct aactactagt ttttactttt atttgcaaca tttacagtcc   2820
ttcaaaatcc ttccaaagaa ttcttataca cattggggcc ttggagctta catagtttta   2880
aactcatttt tgccatacat cagttattca ttctgtgatc atttatttta agcactctta   2940
aagcaaaaaa tgaatgtcta aaattgtttt ttgttgtacc tgctttgact gatgctgaga   3000
ttcttcaggc ttcctgcaat ttttctaagca atttcttgct ctatctctca aaacttggta   3060
tttttcagag atttatataa atgtaaaaat aataattttt atatttaatt attaactaca   3120
tttatgagta actattatta taggtaatca atgaatattg aagtttcagc ttaaaataaa   3180
cagttgtgaa ccaagatcta taaagcgata tacagatgaa aatttgagac tatttaaact   3240
tataaatcat attgatgaaa agatttaagc acaaacttta gggtaaaaat tgcgattgga   3300
cagttgtcta gagatatata tacttgtggt tttcaaattg gactttcaaa attaaatctg   3360
tccctgagag tgtctctgat aaaagggcaa atctgcacct atgtagctct gcatctcctg   3420
tcttttcagg tttgtcatca gatggaaata ttttgataat aaattgaaat tgtgaactca   3480
ttgctcccta agactgtgac aactgtctaa ctttagaagt gcatttctga atagaaatgg   3540
gaggcctctg atggaccttc tagaattata agtcacaaag agttctggaa aagaactgtt   3600
tactgcttga taggaattca tcttttgagg cttctgttcc tctcttttcc tgttgtattg   3660
actattttcg ttcattactt gattaagatt ttacaaaaga ggagcacttc caaaattctt   3720
atttttccta acaaaagatg aaagcaggga atttctatct aaatgatgag tattagttcc   3780
ctgtctcttg aaaaatgccc atttgccttt aaaaaaaaaa gttacagaaa tactataaca   3840
```

```
tatgtacata aattgcataa agcataagta tacagttcaa taaacttaac tttaactgaa   3900
caatggccct gtagccagca cctgtaagaa acagagcagt accagcgctc taaaagcacc   3960
tccttgtcac tttattactc ccagaacaac aactatcctg acttctaata tcattcacta   4020
gctttgcctg gttttgtctt ttatgcagat agaatcaatc agtatgtatt cttttgtgcc   4080
tggcttcttt ctctcagcct tacatttgtg agattcctct gtattgtgct gattgtggat   4140
cttttcattc tcattgcaga ataatgttct attgtgggac ttattacaat ttgttcatcc   4200
tattgttgat gggcacttga gaactttcca ttttggcgct attacaaata gtgcaactat   4260
gaatgtactg catgttacca tcttacttga gcctttaatg gacttatttc ttcaaatcct   4320
tccaaaaatt attataagca ttgaaattat agtttcaagc caactgtgga tacccttacc   4380
ctttcctcct ttatcacaac caccgttaca agtatactta tatttcccta aaatacattt   4440
aaaacttacc taagtgacat ttgtagttgg agtaatagga gcttccagct ctaataaaac   4500
agctgtctct aacttatttt atttccatca tgtcagagca ggtgaagagc cagaagtgaa   4560
gagtgactag tacaaattat aaaaagccac tagactcttc actgttagct ttttaaaaca   4620
ttaggctccc atccctatgg aggaacaact ctccagtgcc tggatcccct ctgtctacaa   4680
atataagatt ttctgggcct aaaggataga tcaaagtcaa aaatagcaat gcctccctat   4740
ccctcacaca tccagacatc atgaatttta catggtactc ttgttgagtt ctatagagcc   4800
ttctgatgtc tctaaagcac taccgattct ttggagttgt cacatcagat aagacatatc   4860
tctaattcca tccataaatc cagttctact atggctgagt tctggtcaaa gaaagaaagt   4920
ttagaagctg agacacaaag ggttgggagc tgatgaaact cacaaatgat ggtaggaaga   4980
agctctcgac aatacccgtt ggcaaggagt ctgcctccat gctgcagtgt tcgagtggat   5040
tgtaggtgca agatggaaag gattgtaggt gcaagctgtc cagagaaaag agtccttgtt   5100
ccagccctat tctgccactc ctgacagggt gaccttgggt atttgcaata ttcctttggg   5160
cctctgcttc tctcacctaa aaaaagagaa ttagattata ttggtggttc tcagcaagag   5220
aaggagtatg tgtccaatgc tgccttccca tgaatctgtc tcccagttat gaatcagtgg   5280
gcaggataaa ctgaaaactc ccatttaagt gtctgaatcg agtgagacaa aattttagtc   5340
caaataacaa gtaccaaagt tttatcaagt ttgggtctgt gctgctgtta ctgttaacca   5400
tttaagtggg gcaaaacctt gctaattttc tcaaaagcat ttatcattct tgttgccaca   5460
gctggagctc tcaaactaaa agacatttgt tattttggaa agaagaaaga ctctattctc   5520
aaagtttcct aatcagaaat ttttatcagt ttccagtctc aaaaatacaa aataaaaaca   5580
aacgttttta atact                                                    5595
```

<210> SEQ ID NO 94
<211> LENGTH: 551
<212> TYPE: DNA
<213> ORGANISM: Homo sapiens
<220> FEATURE:
<221> NAME/KEY: misc_feature
<223> OTHER INFORMATION: NPY: Acc. No. K01911

<400> SEQUENCE: 94

```
accccatccg ctggctctca cccctcggag acgctcgccc gacagcatag tacttgccgc     60
ccagccacgc ccgcgcgcca gccaccatgc taggtaacaa gcgactgggg ctgtccggac    120
tgaccctcgc cctgtccctg ctcgtgtgcc tgggtgcgct ggccgaggcg taccccctcca    180
agccggacaa cccgggcgag gacgcaccag cggaggacat ggccagatac tactcggcgc    240
```

```
tgcgacacta catcaacctc atcaccaggc agagatatgg aaaacgatcc agcccagaga    300

cactgatttc agacctcttg atgagagaaa gcacagaaaa tgttcccaga actcggcttg    360

aagaccctgc aatgtggtga tgggaaatga gacttgctct ctggcctttt cctattttca    420

gcccatattt catcgtgtaa aacgagaatc cacccatcct accaatgcat gcagccactg    480

tgctgaattc tgcaatgttt tcctttgtca tcattgtata tatgtgtgtt taaataaagt    540

atcatgcatt c                                                         551
```

<210> SEQ ID NO 95
<211> LENGTH: 4382
<212> TYPE: DNA
<213> ORGANISM: Homo sapiens
<220> FEATURE:
<221> NAME/KEY: misc_feature
<223> OTHER INFORMATION: SEG_AB00161S

<400> SEQUENCE: 95

```
aagcttgctg aatcacctct taattcttgt agttgctttg tgcattcctt tgggtattcc     60

tcatagatac tcatgtctgc aaatggagaa tgtttacttt ttcattttta tgccttatat    120

ttcttttttg tgtttttgct ttgttgcatt tgttttttct atttgtatga ccaaaatctt    180

tagcagtaca ggtaggtaac aaccaaataa tgtagaaccc cataagccac gttacagagt    240

ttgaatttta ttttagcaca gtgggaatac attgaaggtc tttagttaag ctgttgctca    300

tgagcaacaa atgagcaatg acatatatgt atgtatatac acatatatat cattgatttt    360

atatatatat atatatatat atatatatat atatatatat atatatctat cttagtccac    420

ttgtgttgca ataacaaaat accacagact gggtcattta caaaaattaa atatatatat    480

acatatacac acatatatat atcatacata tacacataca tacatcattg ctcatttgtt    540

tgttataaat agcattaaca gcatttttca agttatatcc tgggagtgtt tatgatttac    600

ttattcttca actaattcca taacaagatt tgaggtgctt agaacaattc atgccaagtt    660

aaaacaaaat aattgggcaa attgggataa agaataaaat ggagttgaaa aacaagaggc    720

ccaggtaatg tcagttcaaa atatgcttac ctttaactac tttaaattta caggaggtat    780

agttacacat tttggctgaa tctcccagag actagaactg tttgagacac ttctgttccc    840

caatcccttg tgatatgttt ctcaggtaat aggccttcac agtaactccc aaactatcat    900

atataccaca cagacttgag attcactatt gagagaatct atgtactgtt tttctttttt    960

tttctttttt gttatagagc cgggggtctt acactgtcac tgaggctgaa gtgcaatggc   1020

acgatcatgg ctcactgcag ccttgacctc ctgggctcaa tcctcttgcc tcagcctctc   1080

gaataactag gattacaggt gtgttccccc atgcctggct aatttttaaa aattttgtgt   1140

agagatgggg tcatgccatg tggcccaggc tggttcaaac tcctgagctc aagtatcctt   1200

ctacctctcc ctcccaaagt tctgagatta caggaatgag ccactgtgcc cagcctatag   1260

attgtttttc ttgaagcaat ttttcagaaa ccttcctggt ttctgataat ttaacccttt   1320

caggttagga gagaaaaatg aacattttga tattacccac tgtcttagtc catttgtgtt   1380

gctgtaataa aatatcacag actgggatat ttataaacaa tagaaattaa tttctctcag   1440

ttctggaggc tggaaactcc aaaatcaaag tgccagcaga tttggcaact ggtgagggct   1500

gctctttgct tacaaaatgg caccttgttg ctgcatcctc agcaagggtc agtgctgtgt   1560

cttcacatag tggaaagaat agaaggggcc aactgtctcc tttgggcctt tttttaaaaa   1620

ggcactaatg cattcacaaa ggcagagccc taatggtcta atcaccactt aaaggcacct   1680

cctcttaata ctgttgaatt agggattaag tttcaacatg aattttggag ggaatacaaa   1740
```

cattgaaatg attatacgtg tttatttaat caagtatcca acaaaagcaa ataattcaag 1800
ccccaaattc actgcatctt tagtagataa gcagagtttt aaattacgat tgatctcctg 1860
ttaggaggaa tgcatggatt tccacaagaa aaaactgtac tgaggagaaa ctttccacag 1920
taatgtgcca cttttcagtc aacgacagac cacatatatg agtcccataa gataatacta 1980
tatttttact gtaccttttc tatgtttaga tatgtttaga cacacaaata tcattgcatt 2040
acaattgcct acagtattca gtacagtaat atgctgtata gatttgtggt ctaggagcaa 2100
tagcctaagt gtgtagtagg ctgagccatc tattttgtgt tagtacactg tgatgttcag 2160
agaaggatga aattgcctaa ggatacattt ctcagaatgt atcctgttgt tcggtgacgc 2220
atgactgtat tccatgagca ctataatcac tatcatagta acacattagg agagaattct 2280
catttctaaa tccaatataa tttatcaccc attagttcat actctactgc tttgattgct 2340
tttctttggt tgtggctacc tgcatacagc agtaaagttt cagaaaaact gaagtcgcaa 2400
aaggtcaatt actcaatgaa ggaaagataa accattgcat tgggggacta gaagatactt 2460
ttaaaagttc tcagattatc aatttaatga tgtgtttcta tgtagtgaat aatgccttaa 2520
attcttgcca agagtattta gaaggaagtt gtcagaagta tatcagctaa ctcatttttt 2580
tttatatcac tgctaatggt gtcattcaca cattgtgcaa cccataattc cagatttaat 2640
tctaccaaaa aatataggtc attgcaaaat gccatattaa aactgccaat gcatgacagg 2700
aagatgggga tgcagacaaa gcaaaggatg acaccaattc ctttttttaaa gaagcaagat 2760
agggattgga caaaaaggct gagccatttt taatggatac ttttgaggga gtgttaattc 2820
caatttaatt aaaatgatgc attaatttaa aattgggata actggttgcc ctcgactgca 2880
cctgggttgc gccagtgctc tcggattaac ctaattgtac agaggtgccc ttgttttcta 2940
acttcatgca caaagcattg gaaattattt gtttgctttt tcttttccaa gtaaatcttt 3000
ttccagttat gcaaaaggga agtttgaggc aatggttaaa ggcacttaag ttataattat 3060
tgctgttatc attaacatta agcacgggta tggctttgtt gcaagttacc cacctacacc 3120
tgcaaatctc tcttgctagc acacgcccca gctctctcca cccgcagtgg tccgtggctg 3180
gaccgcttta agtcactgag cgggctgggc tctgaaggag gtcggtcccg ctcctcccag 3240
acccaagcgt agggctaggg aaaagctagg cgggaaggtc attgcactcc caggccccag 3300
gaaaagggcc cagggtctca tcatctctta ctttcgggca aaacttccca catcgcgacc 3360
ttccctccct ggggcactct gagaacacac ccagtcacct agcgcgctcc ccagaagtcg 3420
gcttggcaca cagcgcaccc cagcggccgc gcggcctcct tccagccgcc gccacttggc 3480
ttccggagag ctcgccgggc gctgccgccg ccgccgccgc cgccgccgcc tcctgggaac 3540
caggggactg aagagcctgc gagagcggaa cactgccgga ccccgggtgg gggggcgcag 3600
cagctgcgcc tggccccgcc caccacacct gggcgcccgt agaaccgcgc ggggcggggc 3660
ggggcaggag gctggcctgg cgctccggcc gctttgtcga aagccggccc gactggagca 3720
ggacgaaggg ggagggtctc gaggccgagt cctgttcttc tgagggacgg accccagctg 3780
gggtggaaaa gcagtaccag agagcctccg aggcgcgcgg tgccaaccat ggagcgggcc 3840
ggccccagct tcgggcagca gcgacagcag cagcagcccc agcagcagaa gcagcagcag 3900
agggatcagg actcggtcga agcatggctg gacgatcact gggactttac cttctcatac 3960
tttgttagaa aagccaccag gtaagaagag gacccacgga agacccgggg ctgatttctc 4020
tcccctgttg aattgtgccc ttcgttcacc cctgttccca ggccctttgc ttttgaagta 4080
ggtcctcggt cctgttacga ggtagaaacc tcaactctaa gcgagcacag tcgaaaaact 4140
caagtgtcgg atttgataca acttgctcac aaagttcaaa tacaaaaatg tacttggttc 4200
aaatacaaaa atgtacttgc cgacctccca ccctcacccc cgcccctctt ggtattcccc 4260
gggaacatga ttattttcat acatccgtgc tcacgggcct tcccctagcc cctctctagc 4320
cctctggttc cccaaaatcc aatcagcaaa acccaaacag tttctgagcc ccttccctgc 4380
ag 4382

<210> SEQ ID NO 96
<211> LENGTH: 3979
<212> TYPE: DNA
<213> ORGANISM: Homo sapiens
<220> FEATURE:
<221> NAME/KEY: misc_feature
<223> OTHER INFORMATION: Pde7a1: Acc. No. L12052

<400> SEQUENCE: 96
ggcggccgcg gcagggcggg cgccgcgcgg aggcagggcg ggcgtattca atggaagtgt 60
gttaccagct gccggtactg cccctggaca ggccggtccc ccagcacgtc ctcagccgcc 120
gaggagccat cagcttcagc tccagctccg ctctcttcgg ctgcccaat ccccggcagc 180 tctctcagag gcgtggagct atttcctatg acagttctga tcagactgca ttatacattc 240
gtatgctagg agatgtacgt gtaaggagcc gagcaggatt tgaatcagaa agaagaggtt 300
ctcacccata tattgatttt cgtattttcc actctcaatc tgaaattgaa gtgtctgtct 360
ctgcaaggaa tatcagaagg ctactaagtt tccagcgata tcttagatct tcacgctttt 420
ttcgtggtac tgcggtttca aattccctaa acattttaga tgatgattat aatggacaag 480
ccaagtgtat gctggaaaaa gttggaaatt ggaattttga tatctttcta tttgatagac 540
taacaaatgg aaatagtcta gtaagcttaa cctttcattt atttagtctt catggattaa 600
ttgagtactt ccatttagat atgatgaaac ttcgtagatt tttagttatg attcaagaag 660
attaccacag tcaaaatcct taccataacg cagtccacgc tgcggatgtt actcaggcca 720
tgcactgtta cttaaaggaa cctaagcttg ccaattctgt aactccttgg gatatcttgc 780
tgagcttaat tgcagctgcc actcatgatc tggatcatcc aggtgttaat caacctttcc 840
ttattaaaac taaccattac ttggcaactt tatacaagaa tacctcagta ctggaaaatc 900
accactggag atctgcagtg ggcttattga gagaatcagg cttattctca catctgccat 960
tagaaagcag gcaacaaatg gagacacaga taggtgctct gatactagcc acagacatca 1020
gtcgccagaa tgagtatctg tctttgttta ggtcccattt ggatagaggt gatttatgcc 1080
tagaagacac cagacacaga catttggttt tacagatggc tttgaaatgt gctgatattt 1140
gtaacccatg tcggacgtgg gaattaagca agcagtggag tgaaaaagta acggaggaat 1200
tcttccatca aggagatata gaaaaaaaat atcatttggg tgtgagtcca ctttgcgatc 1260
gtcacactga atctattgcc aacatccaga ttggttttat gacttaccta gtggagcctt 1320
tatttacaga atgggccagg ttttccaata caaggctatc ccagacaatg cttggacacg 1380
tggggctgaa taaagccagc tggaagggac tgcagagaga acagtcgagc agtgaggaca 1440
ctgatgctgc atttgagttg aactcacagt tattacctca ggaaaatcgg ttatcataac 1500
ccccagaacc agtgggacaa actgcctcct ggaggttttt agaaatgtga aatggggtct 1560
tgaggtgaga gaacttaact cttgactgcc aaggtttcca agtgagtgat gccagccagc 1620
attatttatt tccaagattt cctctgttgg atcatttgaa cccacttgtt aattgcaaga 1680
cccgaacata cagcaatatg aatttggctt tcatgtgaaa ccttgaatat aaagcccagc 1740

-continued

```
aggagagaat ccgaaaggag taacaaagga agttttgata tgtgccacga ctttttcaaa   1800
gcatctaatc ttcaaaacgt caaacttgaa ttgttcagca acaatctctt ggaatttaac   1860
cagtctgatg caacaatgtg tatcttgtac cttccactaa gttctctctg agaaaatgga   1920
aatgtgaagt gcccagcctc tgctgcctct ggcaagacaa tgtttacaaa tcaactctga   1980
aaatattggt tctaaattgc cttggagcat gattgtgaag gaaccactca aacaaattta   2040
aagatcaaac tttagactgc agctctttcc ccctggtttg ccttttttctt ctttggatgc   2100
caccaaagcc tcccatttgc tatagtttta tttcatgcac tggaaactga gcatttatcg   2160
tagagtaccg ccaagctttc actccagtgc cgtttggcaa tgcaattttt tttagcaatt   2220
agtttttaat ttggggtggg aggggaagaa caccaatgtc ctagctgtat tatgattctg   2280
cactcaagac attgcatgtt gttttcacta ctgtacactt gacctgcaca tgcgagaaaa   2340
aggtggaatg tttaaaacac cataatcagc tcaggtattt gccaatctga aataaaagtg   2400
ggatgggaga gcgtgtcctt cagatcaagg gtactaaagt ccctttcgct gcagtgagtg   2460
agaggtatgt tgtgtgtgaa tgtacggatg tgtgtttggt gatgtttgtg catgtgtgac   2520
gtgcatgtta tgtttctcca tgtgggcaaa gatttgaaag taagctttta tttattattt   2580
tagaatgtga cataatgagc agccacactc gggggagggg aaggttggta ggtaagctgt   2640
aacagattgc tccagttgcc ttaaactatg cacatagcta agtgaccaaa cttcttgttt   2700
tgatttgaaa aaagtgcatt gttttcttgt ccctcccttt gatgaaacgt taccctttga   2760
cgggcctttt gatgtgaaca gatgttttct aggacaaact ataaggacta attttaaact   2820
tcaaacattc cacttttgta atttgtttta aattgtttta tgtatagtaa gcacaactgt   2880
aatctagttt taagagaaac cggtgctttc ttttagttca tttgtatttc ccttgttact   2940
gtaaaagact gtttattaat tgtttacagt ttgttgcaac agccattttc ttgggagaaa   3000
gcttgagtgt aaagccattt gtaaaaggct ttgccatact cattttaata tgtgcctgtt   3060
gctgttaact tttgatgaat aaaaacctat cttttcatga aacttctctc tatacaaatt   3120
gaaatacata atgctttctg gttcttcttc aaaccaaaac ttgtcaaatt catagacaag   3180
ataacagtaa aactgatgaa agtgttccat tgttggtata ccaggaacaa ggttatagag   3240
atgaaacttc aaagcttcac tcttcagtaa gctataagcc atctctgtaa gattgattcc   3300
aactattgca taagaatacc ctaattttgg atgatttgaa cgggaaagaa tctgatgagc   3360
ttcactagtg taattttcac tgaaatacac aagattgatt aacccaagta tgcccatgcc   3420
tctgaagtct gtcttgggat catcaccctg aaaaccaatt tcagcccact gcttggagat   3480
tctagcgttt aacttcttcg tgggcattag aagattccaa agcttcatga gtagctcttc   3540
atgctgtagg ttatcagaat catatggcct tttcctcaca ctttctacat ccaaatacag   3600
ctgtttataa ccagttatct gcagtaagca catcttcatg catattttaa aactggcatc   3660
cttctcaggg ttaatattct tttccttcat aatatcatct acatatttgt ccacttcact   3720
ctgaacaaca tgtgtcgcct tctgtaaaac cttattcttg gagtatgtca aggaattttc   3780
tatcctgtgt gtcctttgtg cacctacata ggtatcaaat attcgctgca attcacactt   3840
cccagtcatc tgtcgtaata gccatttcat ccaaaatcga aaaaagtgcc catagaagaa   3900
ctcccacaaa gaaataaaca tttttttttc ctcacaggag cggaagaact agggggagca   3960
ggagctgcaa tgcggccgc                                                3979
```

<210> SEQ ID NO 97
<211> LENGTH: 2904
<212> TYPE: DNA

<213> ORGANISM: Homo sapiens
<220> FEATURE:
<221> NAME/KEY: misc_feature
<223> OTHER INFORMATION: Per-1: Acc. No. AB005293

<400> SEQUENCE: 97

```
ggcacgagct ctgtgagact gaggtggcgg tcagccggag tgagtgttgg ggtcctgggg     60
cacctgcctt acatggcttg tttatgaaca ttaaagggaa gaagttgaag cttgaggagc    120
gaggatggca gtcaacaaag gcctcacctt gctggatgga gacctccctg agcaggagaa    180
tgtgctgcag cgggtcctgc agctgccggt ggtgagtggc acctgcgaat gcttccagaa    240
gacctacacc agcactaagg aagcccaccc cctggtggcc tctgtgtgca atgcctatga    300
gaagggcgtg cagagcgcca gtagcttggc tgcctggagc atggagccgg tggtccgcag    360
gctgtccacc cagttcacag ctgccaatga gctggcctgc cgaggcttgg accacctgga    420
ggaaaagatc cccgccctcc agtacccccc tgaaaagatt gcttctgagc tgaaggacac    480
catctccacc cgcctccgca gtgccagaaa cagcatcagc gttcccatcg cgagcacttc    540
agacaaggtc ctgggggccg ctttggccgg gtgcgagctt gcctgggggg tggccagaga    600
cactgcggaa tttgctgcca acactcgagc tggccgactg gcttctggag ggggccgactt   660
ggccttgggc agcattgaga aggtggtgga gtacctcctc cctgcagaca aggaagagtc    720
agcccctgct cctggacacc agcaagccca gaagtctccc aaggccaagc caagcctctt    780
gagcagggtt ggggctctga ccaacaccct ctctcgatac accgtgcaga ccatggcccg    840
ggccctggag cagggccaca ccgtggccat gtggatccca ggcgtggtgc ccctgagcag    900
cctggcccag tggggtgcct cagtggccat gcaggcggtg tcccggcgga ggagcgaagt    960
gcgggtaccc tggctgcaca gcctcgcagc cgcccaggag gaggatcatg aggaccagac   1020
agacacggag ggagaggaca cggaggagga ggaagaattg gagactgagg agaacaagtt   1080
cagtgaggta gcagccctgc caggccctcg aggcctcctg ggtggtgtgg cacataccct   1140
gcagaagacc ctccagacca ccatctcggc tgtgacatgg gcacctgcag ctgtgctggg   1200
catggcaggg agggtgctgc acctcacacc agccccccgct gtctcctcaa ccaaggggag  1260
ggccatgtcc ctatcagatg ccctgaaggg cgttactgac aacgtggtgg acacagtggt   1320
gcattacgtg ccgctcccca ggctgtcgct gatggagccc gagagcgaat tccgggacat   1380
cgacaaccca ccagccgagg tcgagcgccg ggaggcggag cgcagagcgt ctggggcgcc   1440
gtccgccggc ccggagcccg ccccgcgtct cgcacagccc cgccgcagcc tgcgcagcgc   1500
gcagagcccc ggcgcgcccc ccggcccggg cctggaggac gaagtcgcca cgcccgcagc   1560
gccgcgcccg ggcttcccgg ccgtgccccg cgagaagcca aagcgcaggg tcagcgacag   1620
cttcttccgg cccagcgtca tggagcccat cgtgggccgc acgcattaca gccagctgcg   1680
caagaagagc tgagtcgccg caccagccgc cgcgccccgg gccggcgggt ttctctaaca   1740
aataaacaga acccgcactg cccaggcgag cgttgccact ttcaaagtgg tcccctgggg   1800
agctcagcct catcctgatg atgctgccaa ggcgcacttt ttatttttat tttattttta   1860
ttttttttt agcatccttt tggggcttca ctctcagagc cagtttttaa gggacaccag   1920
agccgcagcc tgctctgatt ctatggcttg gttgttacta taagagtaat tgcctaactt   1980
gatttttcat ctctttaacc aaacttgtgg ccaaaagata tttgaccgtt tccaaaattc   2040
agattctgcc tctgcggata aatatttgcc acgaatgagt aactcctgtc accactctga   2100
aggtccagac agaaggtttt gacacattct tagcactgaa ctcctctgtg atctaggatg   2160
atctgttccc cctctgatga acatcctctg atgatcaagg ctcccagcag gctactttga   2220
```

```
agggaacaat cagatgcaaa agctcttggg tgtttattta aaatactagt gtcactttct   2280

gagtacccgc cgcttcacag gctgagtcca ggcctgtgtg ctttgtagag ccagctgctt   2340

gctcacagcc acatttccat ttgcatcatt actgccttca cctgcatagt cactcttttg   2400

atgctgggga accaaaatgg tgatgatata tagactttat gtatagccac agttcatccc   2460

caaccctagt cttcgaaatg ttaatatttg ataaatctag aaaatgcatt catacaatta   2520

cagaattcaa atattgcaaa aggatgtgtg tctttctccc cgagctcccc tgttcccctt   2580

cattgaaaac caccacggtg ccatctcttg tgtatgcagg gctatgcacc tgcaggcacg   2640

tgtgtatgca ctccccgctt gtgtttacac aagctgtggg gtgttacgca tgcctgcttt   2700

tttcacttaa taatacagct tggagagatt tttgtatcac attataaatc ccactcgctc   2760

tttttgatgg ccacataata actactgcat aatatggata cgccttattt gatttaacta   2820

gttccctaat gatggacttt taagttgttt cctttttttt tctttttttgc tactgcaaac   2880

gatgctataa taaatgtcct tatc                                          2904
```

<210> SEQ ID NO 98
<211> LENGTH: 4626
<212> TYPE: DNA
<213> ORGANISM: Homo sapiens
<220> FEATURE:
<221> NAME/KEY: misc_feature
<223> OTHER INFORMATION: TPP II: Acc. No. M73047

<400> SEQUENCE: 98

```
gaattcccct ccatcctgcg tccatggcca ccgctgcgac tgaggagccc ttccctttc     60

acggtctcct gccgaagaag gagaccggag ccgcctcctt cctctgccgc tacccggagt    120

atgatgggcg gggggtgctc atcgcagtcc tggacacggg ggtcgacccg ggggctccgg    180

gcatgcaggt tacaactgat ggaaaaccaa aaatcgttga tatcattgat acaacaggaa    240

gtggcgatgt gaatactgct acagaagtag agccaaagga tggtgagatt gttggccttt    300

caggaagagt gcttaagatt cctgcaagct ggacaaatcc ctcaggcaaa tatcatattg    360

gcataaaaaa tggctatgac ttctatccta aggcactcaa ggaaaggata cagaaagaac    420

ggaaggaaaa aatctgggac cctgttcaca gagtggccct tgcagaagcc tgtagaaaac    480

aggaagaatt tgatgttgcc aacaacggct cttctcaagc aaataaacta atcaaggagg    540

aacttcaaag tcaagtggaa ttgctaaatt cttttgagaa gaaatacagc gatcctggcc    600

ctgtatatga ctgcttggta tggcatgatg gcgaagtctg gagagcctgc attgattcta    660

atgaagatgg ggacttgagt aaatctaccg tgttgagaaa ctacaaagaa gcccaagaat    720

atggctcttt tggcacagct gagatgttga attactccgt taatatatac gatgatagaa    780

acctgctctc cattgtgacc agtggaggag ctcatgggac acatgtagct agtatagctg    840

ctggacactt tccagaagaa cctgaacgga atggggtagc tcctggtgct caaattcttt    900

ccatcaagat tggtgataca agactaagca caatggaaac aggcacaggc ctcataagag    960

ctatgataga agttataaat cataagtgtg atcttgtcaa ctacagttac ggagaagcaa   1020

ctcactggcc aaattctggg agaatttgtg aagtaattaa tgaagcagta tggaagcata   1080

atataattta tgtttcaagt gctggaaata atggtccatg cctgtctaca gttggttgtc   1140

caggtggaac tacatcaagt gtgataggtg ttggtgctta tgtttctcct gatatgatgg   1200

ttgctgagta ttcactgaga gagaaattac ctgcaaatca atatacttgg tcttctagag   1260

gacctagtgc tgacggggcc cttggtgtga gtatcagtgc gccaggagga gccattgctt   1320
```

```
ctgttcctaa ctggacactg agagggacgc agctgatgaa tggaacatct atgtcttccc   1380
ccaatgcatg tggaggcatt gccctgatcc tttcaggtct gaaagctaat aacattgact   1440
acacagttca ttcagtcaga agagctctag aaaacactgc agtgaaggct gacaatatag   1500
aagtatttgc tcaaggacat ggtattattc aggttgataa agcctatgac tacctcgttc   1560
agaatacatc atttgctaat aaattaggtt ttactgttac tgttggaaat aaccgtggca   1620
tctacctccg agatcctgtt caggtggctg caccttcaga tcatggcgtt ggcattgaac   1680
ctgtatttcc ggagaacaca gaaaactctg aaaaaatatc ccttcagctt catttagctc   1740
tgacttcaaa ttcatcttgg gttcagtgtc ccagccattt ggaactcatg aatcaatgta   1800
gacacataaa catacgtgtg gatcccaggg gcttaagaga aggattgcat tatacagagg   1860
tatgtggcta tgatatagca tcccctaacg caggtccgct cttcagagtt ccgatcactg   1920
cagttatagc agcaaaagta aatgaatcat cacattatga tctagccttt acagatgtac   1980
actttaaacc tggtcaaatt cgaaggcatt ttattgaggt tcctgagggt gcaacatggg   2040
ctgaagtgac agtgtgttcg tgttcttctg aggtgtcagc aaagtttgtt ctacatgcag   2100
tccagcttgt gaagcaaaga gcatatcgaa gccatgaatt ctataagttt tgttctcttc   2160
cagagaaagg aacactgact gaagcttttc ctgtcctagg tggaaaagca attgaatttt   2220
gcattgctcg ttggtgggca agtctcagtg atgtcaacat tgattatacc atttctttcc   2280
atgggatagt gtgtactgct cctcagttaa acattcatgc atcggaagga atcaaccgct   2340
ttgatgttca gtcctccttg aaatacgaag atctggctcc ctgcataact ttgaagaact   2400
gggtccaaac actgcgccca gtgagtgcaa aaacaaaacc tttaggatca agagatgttt   2460
tgccaaataa ccgtcaactt tatgagatgg tcctgacata taactttcat caacccaaga   2520
gtggggaagt aactccaagc tgcccactac tttgtgaact attatatgaa tctgaatttg   2580
acagccaact gtggattatt tttgaccaga acaaaagaca gatgggttca ggcgatgcct   2640
atccacatca gtattctttg aaactggaga aaggagatta tacaattcga ctacagattc   2700
gccatgagca aatcagtgat ttggaacgcc ttaaagacct tccatttatt gtttctcata   2760
gattgtctaa taccttgagc ttagatattc atgaaaatca tagttttgca cttctaggga   2820
agaagaaatc aagcaatttg acattaccac ccaaatataa ccagccattc tttgttactt   2880
ccttacctga tgataaaata cctaaagggg caggacctgg atgctatctt gcaggatcct   2940
taacattgtc aaagactgaa ctaggaaaga aagctgatgt aatccctgtt cattactact   3000
taatacctcc accaacaaag actaagaatg gcagcaaaga taaggaaaaa gattcagaaa   3060
aagagaaaga tttaaaagaa gagtttactg aagcattacg agatcttaaa attcagtgga   3120
tgacaaagct ggattctagt gacatttata acgaattgaa agaaacatat cctaattatc   3180
ttcctctgta cgttgcacga cttcatcaat tggatgctga aaaggaacga atgaaaagac   3240
ttaatgaaat tgttgatgcg gcaaatgctg ttatttctca tatagatcaa acagccctag   3300
cagtttatat tgcaatgaag actgatccca ggcctgatgc agctactata aaaaatgaca   3360
tggacaaaca aaaatccacc ctcgtagatg ccctttgtag gaaaggttgt gccctggcag   3420
accatcttct tcacacccag gctcaagacg gagccatttc cactgatgca gaaggaaagg   3480
aggaggaagg agaaagtcct ttggattctc tggcagaaac attttgggaa actactaaat   3540
ggactgatct ctttgacaat aaggttttga catttgcata taaacatgca ttagtaaata   3600
aaatgtatgg gagaggcctt aaatttgcaa ctaaacttgt ggaagaaaaa ccaacaaaag   3660
aaaactggaa aaattgtatt caactgatga agttacttgg atggacccat tgtgcatctt   3720
```

```
ttactgaaaa ctggctcccc atcatgtatc ctcccgatta ttgcgtattc taaaatagga   3780

aacaagactt taaattttaa aaaaggaagt tttatagtga atgggtataa aaacaaattt   3840

gtggcatttt tagtctaatg catgttttca tccactatcc agtactgatt attaaaatga   3900

catgtattta tcagagaatt cactgacgtg tggcttaata catgtaaatc tagacctctg   3960

acatcatggt gttttcttaa tgcctcacat tgctggcacg ggatgtgcc ctgcctgcca   4020

gcacctagga cttcgagttg ggttgcagct tatgacatgc atgataggtt ttggaaggta   4080

acttttaact gcaaacctat aaagtactat tttttatttt ataaatgaac agggttttaa   4140

cgtgctcaac tttaattttt ttcaattgta tgaaggcctt aaaaaagcta cattaagcgt   4200

agctaaaatt atttattgga ctaaaaacta acagaacttc atttccagaa ttttttttt   4260

ttttttttt ttggcaaatg tttacattca attaagggga aaaagtagaa ccagcacaaa   4320

tgagtggcag ttgctggagc ataactgctt caataaatct tcatcttggg gtaattacag   4380

gcaagtcatt ttcacatcct cttgaggttc agagcatcag aatgaactct atgaatacat   4440

gtgtaagtgc cagacagctg aatctttatc aggtattgta aagatacaca tatgatatgt   4500

ttattaaaat tgaaataatg taaaacacat gaataaattt gcaaaaccaa gatcacagta   4560

caccatatgc actctggtac cttaattttt ttttataaat aataaaagtg aatattgaag   4620

cttctt                                                              4626
```

<210> SEQ ID NO 99
<211> LENGTH: 3224
<212> TYPE: DNA
<213> ORGANISM: Homo sapiens
<220> FEATURE:
<221> NAME/KEY: misc_feature
<223> OTHER INFORMATION: MTP: Acc. No. X59657

<400> SEQUENCE: 99

```
actccctcac tggctgccat tgaaagagtc cacttctcag tgactcctag ctgggcactg     60

gatgcagttg aggattgctg gtcaatatga ttcttcttgc tgtgcttttt ctctgcttca    120

tttcctcata ttcagcttct gttaaaggtc acacaactgg tctctcatta aataatgacc    180

ggctgtacaa gctcacgtac tccactgaag ttcttcttga tcggggcaaa ggaaaactgc    240

aagacagcgt gggctaccgc atttcctcca acgtggatgt ggccttacta tggaggaatc    300

ctgatggtga tgatgaccag ttgatccaaa taacgatgaa ggatgtaaat gttgaaaatg    360

tgaatcagca gagaggagag aagagcatct tcaaaggaaa aagcccatct aaaataatgg    420

gaaaggaaaa cttggaagct ctgcaaagac ctacgctcct tcatctaatc catggaaagg    480

tcaaagagtt ctactcatat caaaatgagg cagtggccat agaaaatatc aagagaggtc    540

tggctagcct atttcagaca cagttaagct ctggaaccac caatgaggta gatatctctg    600

gaaattgtaa agtgacctac caggctcatc aagacaaagt gatcaaaatt aaggccttgg    660

attcatgcaa aatagcgagg tctggattta cgaccccaaa tcaggtcttg ggtgtcagtt    720

caaaagctac atctgtcacc acctataaga tagaagacag ctttgttata gctgtgcttg    780

ctgaagaaac acacaatttt ggactgaatt tcctacaaac cattaagggg aaaatagtat    840

cgaagcagaa attagagctg aagacaaccg aagcaggccc aagattgatg tctggaaagc    900

aggctgcagc cataatcaaa gcagttgatt caaagtacac ggccattccc attgtggggc    960

aggtcttcca gagccactgt aaaggatgtc cttctctctc ggagctctgg cggtccacca   1020

ggaaatacct gcagcctgac aacctttcca aggctgaggc tgtcagaaac ttcctggcct   1080

tcattcagca cctcaggact gcgaagaaag aagagatcct tcaaatacta aagatggaaa   1140
```

```
ataaggaagt attacctcag ctggtggatg ctgtcacctc tgctcagacc tcagactcat   1200
tagaagccat tttggacttt ttggatttca aaagtgacag cagcattatc ctccaggaga   1260
ggtttctcta tgcctgtgga tttgcttctc atcccaatga agaactcctg agagccctca   1320
ttagtaagtt caaaggttct attggtagca gtgacatcag agaaactgtt atgatcatca   1380
ctgggacact tgtcagaaag ttgtgtcaga atgaaggctg caaactcaaa gcagtagtgg   1440
aagctaagaa gttaatcctg ggaggacttg aaaaagcaga gaaaaaagag gacaccagga   1500
tgtatctgct ggctttgaag aatgccctgc ttccagaagg catcccaagt cttctgaagt   1560
atgcagaagc aggagaaggg cccatcagcc acctggctac cactgctctc cagagatatg   1620
atctcccttt cataactgat gaggtgaaga agaccttaaa cagaatatac caccaaaacc   1680
gtaaagttca tgaaaagact gtgcgcactg ctgcagctgc tatcatttta aataacaatc   1740
catcctacat ggacgtcaag aacatcctgc tgtctattgg ggagcttccc caagaaatga   1800
ataaatacat gctcgccatt gttcaagaca tcctacgttt ggaaatgcct gcaagcaaaa   1860
ttgtccgtcg agttctgaag gaaatggtcg ctcacaatta tgaccgtttc tccaggagtg   1920
gatcttcttc tgcctacact ggctacatag aacgtagtcc ccgttcggca tctacttaca   1980
gcctagacat tctctactcg ggttctggca ttctaaggag aagtaacctg aacatctttc   2040
agtacattgg gaaggctggt cttcacggta gccaggtggt tattgaagcc caaggactgg   2100
aagccttaat cgcagccacc cctgacgagg gggaggagaa ccttgactcc tatgctggta   2160
tgtcagccat cctctttgat gttcagctca gacctgtcac ctttttcaac ggatacagtg   2220
atttgatgtc caaaatgctg tcagcatctg gcgaccctat cagtgtggtg aaaggactta   2280
ttctgctaat agatcattct caggaacttc agttacaatc tggactaaaa gccaatatag   2340
aggtccaggg tggtctagct attgatattt caggtgcaat ggagtttagc ttgtggtatc   2400
gtgagtctaa aacccgagtg aaaaataggg tgactgtggt aataaccact gacatcacag   2460
tggactcctc ttttgtgaaa gctggcctgg aaaccagtac agaaacagaa gcaggcttgg   2520
agtttatctc cacagtgcag ttttctcagt acccattctt agtttgcatg cagatggaca   2580
aggatgaagc tccattcagg caatttgaga aaaagtacga aaggctgtcc acaggcagag   2640
gttatgtctc tcagaaaaga aaagaaagcg tattagcagg atgtgaattc ccgctccatc   2700
aagagaactc agagatgtgc aaagtggtgt ttgcccctca gccggatagt acttccagcg   2760
gatggttttg aaactgacct gtgatatttt acttgaattt gtctccccga aagggacaca   2820
atgtggcatg actaagtact tgctctctga gagcacagcg tttacatatt tacctgtatt   2880
taagattttt gtaaaaagct acaaaaaact gcagtttgat caaatttggg tatatgcagt   2940
atgctaccca cagcgtcatt ttgaatcatc atgtgacgct ttcaacaacg ttcttagttt   3000
acttatacct ctctcaaatc tcatttggta cagtcagaat agttattctc taagaggaaa   3060
ctagtgtttg ttaaaaacaa aaataaaaac aaaaccacac aaggagaacc caattttgtt   3120
tcaacaattt ttgatcaatg tatatgaagc tcttgatagg acttccttaa gcatgacggg   3180
aaaaccaaac acgttcccta atcaggaaaa aaaaaaaaaa aaaa                    3224
```

<210> SEQ ID NO 100
<211> LENGTH: 5856
<212> TYPE: DNA
<213> ORGANISM: Homo sapiens
<220> FEATURE:
<221> NAME/KEY: misc_feature
<223> OTHER INFORMATION: HisR: Acc. No. D14436

<400> SEQUENCE: 100

```
gagctcatca tttttatgg ctgcatagta ttccatggtg tatatgtgcc acattttctt     60
aatccagtct atcattgttg gacagttggg ttggttccaa gtctttgcta ctgtgaatag    120
tgcctcaata aacatatgtg tgcatgtgtc tttatagcag caagatttat agtcctttgg    180
gtatatacc agtaatggga tggctgggtc aaatggtatt tctagttcta catccctgag    240
gaatcgccac accgacttcc acaatggttg aactagttta cagtcccacc aaaagtgtaa    300
aaatgttcct atttctccac ttcctctcca gcatctgttg tttcctgact ttttaatgat    360
tgctattcta actggtgtga gatggtatct cattgtggtt ttgatttgca tttctctgat    420
ggccagtgat ggtgagcatt ttttcatgtg tttttggat gcataaatgt cttcttttga    480
gaagtgtctg ttcatgtcct tcgcccactt tttgatgggg atgttttttt cttgtaaatt    540
tgtttgagtt cattgtagat tctggatatt agccctttgt cagatgagta ggttgtgaaa    600
attttctccc attttgtagg ttgcctgttc actctgatgg tagtttcttt tgctgtgcag    660
aaaatcttta gtttaattag atcccatttg tcaattttgg cttttgttgc cattgttttt    720
ggtgttttag acatgaagtc cttgcccatg cctatgtcct gaatggtaat gcctaggatt    780
tcttctgggg gttttatggt tttaggtcta atgtttaagt ctttaatcca tcttgaatta    840
atttttgtat aaggtgtaag gaagggatcc agtttcagct ttctacatat ggctagccag    900
ttttcccagc actttttatt aaatagagaa tcctttcccc attgcttttc tcaggtttgt    960
caaagatcag atagttgtag atatgcaatg ctatttctga gggctctgtt ctgttccatt   1020
gatctatatc tctgttttgg taccagtacc atgctgtttt ggttactgtg gccttgtagt   1080
atagtttgaa gtcaggtagc atgatgcctc cagctttgtt cttttggctt aggattgact   1140
tggcgatgtg ggctcttttt ggttccatat gaactttaaa gtagtttttt ccaattctgt   1200
gaagaaagtc attggtagct tgatggggat ggcattgaat ctatcaatta ccttgggcag   1260
tatggccatt ttcaagatat tgattcttcc tacccatgag catggaatgt tcttccattt   1320
gtttgtatcc tcttttattt ccttgagcag tggtttgtag ttctcctcga agaggtcctt   1380
cacatccctt gtaagttgga ttcctaggta ttttattctc tttgaagcaa ttgtgaatgg   1440
gagttcactc atgatttggc tctctgtttg tctgttattg gtgtattaga atgcttgtga   1500
tttttgtaca ttgattttgt atcctgagac tttgctgaag ttgcttatca gcttaaggag   1560
attttgggct gagacaatgg ggttttctag atatacaatc atgtcatctg caaacaggga   1620
caatttgact tcctcttttc ctaattgagt accctttatt tccttctcct gcctaattgc   1680
cctggccaga acttccaaca ctatgttgaa taggagtggt gagagagggc atccctgtct   1740
tgtgccagtt ttcaaaggga atgcttgcag tttttgccca ttcagtatga tactggctgt   1800
gggtttgtca tagatagctc ttattatttt gagatacgtc ccatgaatac ctaatttatt   1860
gagagttttt agcatgaagg gttgttgaat tttgtcaaag gccttttctg catctattga   1920
gataatcatg tggtttttgt ctttggttct gtttacatgc tggattacat ttattgattt   1980
gcatatattg aaccagcctt gcatcccagg gatgaagtcc acttgatcac ccccaacagc   2040
atacaactcc agtctgatga acatcatgct actaagtggc cactcatcac ccaagtctct   2100
gaccttactt tttctctctt ttctcccagg gagtgagcca taactggcgg ctgctcttgc   2160
gccaatgagc ctccccaatt cctcctgcct cttagaagac aagatgtgtg agggcaacaa   2220
gaccactatg gccagccccc agctgatgcc cctggtggtg gtcctgagca ctatctgctt   2280
ggtcacagta gggctcaacc tgctggtgct gtatgccgta cggagtgagc ggaagctcca   2340
```

```
cactgtgggg aacctgtaca tcgtcagcct ctcggtggcg gacttgatcg tgggtgccgt   2400
cgtcatgcct atgaacatcc tctacctgct catgtccaag tggtcactgg gccgtcctct   2460
ctgcctcttt tggctttcca tggactatgt ggccagcaca gcgtccattt tcagtgtctt   2520
catcctgtgc attgatcgct accgctctgt ccagcagccc ctcaggtacc ttaagtatcg   2580
taccaagacc cgagcctcgg ccaccattct gggggcctgg tttctctctt ttctgtgggt   2640
tattcccatt ctaggctgga atcacttcat gcagcagacc tcggtgcgcc gagaggacaa   2700
gtgtgagaca gacttctatg atgtcacctg gttcaaggtc atgactgcca tcatcaactt   2760
ctacctgccc accttgctca tgctctggtt ctatgccaag atctacaagg ccgtacgaca   2820
acactgccag caccgggagc tcatcaatag gtccctccct tccttctcag aaattaagct   2880
gaggccagag aaccccaagg gggatgccaa gaaaccaggg aaggagtctc cctgggaggt   2940
tctgaaaagg aagccaaaag atgctggtgg tggatctgtc ttgaagtcac catcccaaac   3000
ccccaaggag atgaaatccc cagttgtctt cagccaagag gatgatagag aagtagacaa   3060
actctactgc tttccacttg atattgtgca catgcaggct gcggcagagg ggagtagcag   3120
ggactatgta gccgtcaacc ggagccatgg ccagctcaag acagatgagc agggcctgaa   3180
cacacatggg gccagcgaga tatcagagga tcagatgtta ggtgatagcc aatccttctc   3240
tcgaacggac tcagatacca ccacagagac agcaccaggc aaaggcaaat tgaggagtgg   3300
gtctaacaca ggcctggatt acatcaagtt tacttggaag aggctccgct cgcattcaag   3360
acagtatgta tctgggttgc acatgaaccg cgaaaggaag gccgccaaac agttgggttt   3420
tatcatggca gccttcatcc tctgctggat cccttatttc atcttcttca tggtcattgc   3480
cttctgcaag aactgttgca atgaacattt gcacatgttc accatctggc tgggctacat   3540
caactccaca ctgaaccccc tcatctaccc cttgtgcaat gagaacttca agaagacatt   3600
caagagaatt ctgcatattc gctcctaagg gaggctctga ggggatgcaa caaaatgatc   3660
cttatgatgt ccaacaagga aatagaggac gaaggcctgt gtgttgccag gcaggcacct   3720
gggctttctg gaatccaaac cacagtctta ggggcttggt agtttggaaa gttcttaggc   3780
accatagaag aacagcagat ggcggtgatc agcagagaga ttgaactttg aggaggaagc   3840
agaatctttg caagaaagtc agacctgttt cttgtaactg ggttcaaaaa gaaaaaaata   3900
ataaaaataa aagagagaga gaatcagacc tgggtggaac tctcctgctc ctcaggaact   3960
atgggagcct cagactcatt gtaattcaag ctttccgagt caagtgattg acaactgaag   4020
agacacgtgg ctagggttcc actggagaat tgaaaaggac tcttgagccc tcctggaatg   4080
gagctgtata actgtgcaga gactttatcc atgccaatag ttgctgtccc cttccagggg   4140
tcaccttgag aggcatgaca gctgttccac aggggctatc ccttctcaga aaacttctct   4200
tctgagcctc tttaacagct ttctccagaa ccagtgtctg aaccaccctg gaaattctgc   4260
cttattattt cttactcaaa catgtttaga gtggatagaa aattatgcag cttgcacacc   4320
catcatcttt aaccccaaat ttcctttggc tattaaaaaa gtggtggcaa aaggcatcct   4380
caaaagaaag agaaatgaaa tatttttgaa tggttgcacg ttaaaaatta aaagaaggaa   4440
tgggggcaga atgccatatt tttgagggct gtactaggtt tatctcattt aagcccccaca   4500
acaccccaca ggagggtaat tttctaactc tagtttgcag aggagcaaat tgaggttcag   4560
caaggtgaga gaggtaccca aggtcacata gctagttatg tgagaaagtt agagtacaga   4620
tcctctgggg tttcagctta ttgtagcata ttttctccga aaggcaaaaa tgtgcccttt   4680
tggccgggca tggtagctca agcctataat cccagcatgt tgagaggctg aggtgggcag   4740
```

```
atcatttgag gccaggagtt caagaccagt ctggccaata tggagaaacc ttgtctctac   4800

taaaaacaca aaaattatct gggcatggtg gggcatgcct gtagtcccac ttacttggga   4860

ggccgaggca cgagaatcgc ttgaacccgg gaggtggagg ttgccgtgag ccaagatcac   4920

gccactgcac tccagcctgg gcaacagagc aagactctgt ctcaaaaaaa aaaatacaat   4980

attttaacaa tgtgccctct taagtgtgca cagatacaca tacacggtat tcccaagagt   5040

ggtggcagct caaaatgata tgtttgagta gacgaacagc tgacatggag ttcccgtgca   5100

cctacggaag gggacgcttt gaaggaacca agtgcatttt tatctgtgag ttctgttgtg   5160

tttgtcaaaa agtcattgta atctttcata gccatacctg gtaagcaaaa actagtaaag   5220

acataggaac atgtagtttt acttggtgtt tatgttgcaa tctggttgtg atttatattt   5280

taaagcttgg tgctaaacca caatatgtat agcacatgga gtgcctgtac aagctgatgt   5340

tttgtatttt gtgttcctct ttgcatgatc tgtcaaagtg agatattttt acctgcctaa   5400

aatatgatgt ttaaaagcat actctatgtg atttatttat ttctaccttt ctgagtctct   5460

tggactaaga agatgttttg aaatgtacca tcaaatgtta acagagtttg atatgggctt   5520

tctctttggt ttctcatcac atttgtaaat gtcttttcaa aaggatttac tttttgtaaa   5580

aagcttcatt ctcactctgc tttgcatccc ccaaacttct tgttcaaaac gggggggagtt  5640

taggagactt taatcccggt ttcagaagct gcagctggtc tgtttccagg tcagaaacca   5700

ttgttcagaa gacctccctg tgagagagtt gctcctcagg gtccctcagg accaaagaac   5760

actcgaaaag agcacttcac acagacaagt ggctaagtgt ccattattta ccttgaacaa   5820

tcaaggcaac tagtggagag aactgattgt gagctc                             5856
```

<210> SEQ ID NO 101
<211> LENGTH: 2438
<212> TYPE: DNA
<213> ORGANISM: Homo sapiens
<220> FEATURE:
<221> NAME/KEY: misc_feature
<223> OTHER INFORMATION: CRP: Acc. No. M11880

<400> SEQUENCE: 101

```
aataaataac tcacattgat ttctctggtc tgaaataatt ttgcttcccc tcttcccgaa     60

gctctgacac ctgccccaac aagcaatgtt ggaaaattat ttacatagtg gcgcaaactc    120

ccttactgct ttggatataa atccaggcag gaggaggtag ctctaaggca agagatctag    180

gacttctagc ccctgaactt tcagccgaat acatcttttc caaaggagtg aattcaggcc    240

cttgtatcac tggcagcagg acgtgaccat ggagaagctg ttgtgtttct tggtcttgac    300

cagcctctct catgcttttg gccagacagg taagggccac cccaggctat gggagagttt    360

tgatctgagg tatgggggtg gggtctaaga ctgcatgaac agtctcaaaa aaaaaaaaaa    420

aagactgtat gaacagaaca gtggagcatc cttcatggtg tgtgtgtgtg tgtgtgtgtg    480

tgtgtgtggt gtgtaactgg agaaggggtc agtctgtttc tcaatcttaa attctatacg    540

taagtgaggg gatagatctg tgtgatctga gaaacctctc acatttgctt gtttttctgg    600

ctcacagaca tgtcgaggaa ggcttttgtg tttcccaaag agtcggatac ttcctatgta    660

tccctcaaag caccgttaac gaagcctctc aaagccttca ctgtgtgcct ccacttctac    720

acggaactgt cctcgacccg tgggtacagt attttctcgt atgccaccaa gagacaagac    780

aatgagattc tcatattttg gtctaaggat ataggataca gttttacagt gggtgggtct    840

gaaatattat tcgaggttcc tgaagtcaca gtagctccag tacacatttg tacaagctgg    900

gagtccgcct cagggatcgt ggagttctgg gtagatggga agcccagggt gaggaagagt    960
```

```
ctgaagaagg gatacactgt gggggcagaa gcaagcatca tcttggggca ggagcaggat   1020

tccttcggtg ggaactttga aggaagccag tccctagtgg gagacattgg aaatgtgaac   1080

atgtgggact ttgtgctgtc accagatgag attaacacca tctatcttgg cgggcccttc   1140

agtcctaatg tcctgaactg gcgggcactg aagtatgaag tgcaaggcga agtgttcacc   1200

aaaccccagc tgtggccctg aggcccagct gtgggtcctg aaggtacctc ccggtttttt   1260

acaccgcatg ggccccacgt ctctgtctct ggtacctccc gctttttttac actgcatggt   1320

tcccacgtct ctgtctctgg gcctttgttc ccctatatgc attgaggcct gctccaccct   1380

cctcagcgcc tgagaatgga ggtaaagtgt ctggtctggg agctcgttaa ctatgctggg   1440

aaatggtcca aaagaatcag aatttgaggt gttttgtttt catttttatt tcaagttgga   1500

cagatcttgg agataatttc ttacctcaca tagatgagaa aactaacacc cagaaaggag   1560

aaatgatgtt ataaaaaact cataaggcaa gagctgagaa ggaagcgctg atcttctatt   1620

taattcccca cccatgaccc ccagaaagca ggagcattgc ccacattcac agggctcttc   1680

agtatcagaa tcaggacact ggccaggtgt ctggtttggg tccagagtgc tcatcatcat   1740

gtcatagaac tgctgggccc aggtctcctg aaatgggaag cccagcaata ccacgcagtc   1800

cctccacttt ctcaaagcac actggaaagg ccattagaat tgccccagca gagcagatct   1860

gcttttttttc cagagcaaaa tgaagcacta ggtataaata tgttgttact gccaagaact   1920

taaatgactg gtttttgttt gcttgcagtg ctttcttaat tttatggctc ttctgggaaa   1980

ctcctcccct tttccacacg aaccttgtgg ggctgtgaat tctttcttca tccccgcatt   2040

cccaatatac ccaggccaca agagtggacg tgaaccacag ggtgtcctgt cagaggagcc   2100

catctcccat ctccccagct ccctatctgg aggatagttg gataggtacg tgttcctagc   2160

aggaccaact acagtcttcc caaggattga gttatggact ttgggagtga gacatcttct   2220

tgctgctgga tttccaagct gagaggacgt gaacctggga ccaccagtag ccatcttgtt   2280

tgccacatgg agagagactg tgaggacaga agccaaactg gaagtggagg agccaaggga   2340

ttgacaaaca acagagcctt gaccacgtgg agtctctgaa tcagccttgt ctggaaccag   2400

atctacacct ggactgccca ggtctataag ccaataaa                           2438
```

<210> SEQ ID NO 102
<211> LENGTH: 1457
<212> TYPE: DNA
<213> ORGANISM: Homo sapiens
<220> FEATURE:
<221> NAME/KEY: misc_feature
<223> OTHER INFORMATION: CETP: Acc. No. XM_008050

<400> SEQUENCE: 102

```
cctggccctg ctgggcaatg cccatgcctg ctccaaaggc acctcgcacg aggcaggcat     60

cgtgtgccgc atcaccaagc ctgccctcct ggtgttgaac cacgagactg ccaaggtgat    120

ccagaccgcc ttccagcgag ccagctaccc agatatcacg ggcgagaagg ccatgatgct    180

ccttggccaa gtcaagtatg ggttgcacaa catccagatc agccacttgt ccatcgccag    240

cagccaggtg gagctggtgg aagccaagtc cattgatgtc tccattcaga acgtgtctgt    300

ggtcttcaag gggaccctga agtatggcta caccactgcc tggtggctgg gtattgatca    360

gtccattgac ttcgagatcg actctgccat tgacctccag atcaacacac agctgacctg    420

tgactctggt agagtgcgga ccgatgcccc tgactgctac ctgtctttcc ataagctgct    480

cctgcatctc caaggggagc gagagcctgg gtggatcaag cagctgttca caaatttcat    540
```

ctccttcacc ctgaagctgg tcctgaaggg acagatctgc aaagagatca acgtcatctc 600
taacatcatg gccgattttg tccagacaag ggctgccagc atcctttcag atggagacat 660
tggggtggac atttccctga caggtgatcc cgtcatcaca gcctcctacc tggagtccca 720
tcacaaggca gtgctggaga cctggggctt caacaccaac caggaaatct tccaagaggt 780
tgtcggcggc ttccccagcc aggcccaagt caccgtccac tgcctcaaga tgcccaagat 840
ctcctgccaa aacaagggag tcgtggtcaa ttcttcagtg atggtgaaat tcctctttcc 900
acgcccagac cagcaacatt ctgtagctta cacatttgaa gaggatatcg tgactaccgt 960
ccaggcctcc tattctaaga aaaagctctt cttaagcctc ttggatttcc agattacacc 1020
aaagactgtt tccaacttga ctgagagcag ctccgagtcc gtccagagct tcctgcagtc 1080
aatgatcacc gctgtgggca tccctgaggt catgtctcgg ctcgaggtag tgtttacagc 1140
cctcatgaac agcaaaggcg tgagcctctt cgacatcatc aaccctgaga ttatcactcg 1200
agatggcttc ctgctgctgc agatggactt tggcttccct gagcacctgc tggtggattt 1260
cctccagagc ttgagctaga agtctccaag gaggtcggga tggggcttgt agcagaaggc 1320
aagcaccagg ctcacagctg gaaccctggt gtctcctcca gcgtggtgga agttgggtta 1380
ggagtacgga gatggagatt ggctcccaac tcctccctat cctaaaggcc cactggcatt 1440
aaagtgctgt atccaag 1457

<210> SEQ ID NO 103
<211> LENGTH: 2986
<212> TYPE: DNA
<213> ORGANISM: Homo sapiens
<220> FEATURE:
<221> NAME/KEY: misc_feature
<223> OTHER INFORMATION: ICAM: Acc. No. J03132

<400> SEQUENCE: 103
gcgccccagt cgacgctgag ctcctctgct actcagagtt gcaacctcag cctcgctatg 60
gctcccagca gcccccggcc cgcgctgccc gcactcctgg tcctgctcgg ggctctgttc 120
ccaggacctg gcaatgccca gacatctgtg tccccctcaa aagtcatcct gccccgggga 180
ggctccgtgc tggtgacatg cagcacctcc tgtgaccagc ccaagttgtt gggcatagag 240
accccgttgc ctaaaaagga gttgctcctg cctgggaaca accggaaggt gtatgaactg 300
agcaatgtgc aagaagatag ccaaccaatg tgctattcaa actgccctga tgggcagtca 360
acagctaaaa ccttcctcac cgtgtactgg actccagaac gggtggaact ggcacccctc 420
ccctcttggc agccagtggg caagaacctt accctacgct gccaggtgga gggtggggca 480
ccccgggcca acctcaccgt ggtgctgctc cgtggggaga aggagctgaa acgggagcca 540
gctgtggggg agcccgctga ggtcacgacc acggtgctgg tgaggagaga tcaccatgga 600
gccaatttct cgtgccgcac tgaactggac ctgcggcccc aagggctgga gctgtttgag 660
aacacctcgg ccccctacca gctccagacc tttgtcctgc cagcgactcc cccacaactt 720
gtcagccccc gggtcctaga ggtggacacg caggggaccg tggtctgttc cctggacggg 780
ctgttcccag tctcggaggc ccaggtccac ctggcactgg gggaccagag gttgaacccc 840
acagtcacct atggcaacga ctccttctcg gccaaggcct cagtcagtgt gaccgcagag 900
gacgagggca cccagcggct gacgtgtgca gtaatactgg ggaaccagag ccaggagaca 960
ctgcagacag tgaccatcta cagctttccg gcgcccaacg tgattctgac gaagccagag 1020
gtctcagaag ggaccgaggt gacagtgaag tgtgaggccc accctagagc caaggtgacg 1080
ctgaatgggg ttccagccca gccactgggc ccgagggccc agctcctgct gaaggccacc 1140
ccagaggaca acgggcgcag cttctcctgc tctgcaaccc tggaggtggc cggccagctt 1200
atacacaaga accagacccg ggagcttcgt gtcctgtatg gcccccgact ggacgagagg 1260
gattgtccgg gaaactggac gtggccagaa aattcccagc agactccaat gtgccaggct 1320
tgggggaacc cattgcccga gctcaagtgt ctaaaggatg gcactttccc actgcccatc 1380
ggggaatcag tgactgtcac tcgagatctt gagggcacct acctctgtcg ggccaggagc 1440
actcaagggg aggtcacccg cgaggtgacc gtgaatgtgc tctccccccg gtatgagatt 1500
gtcatcatca ctgtggtagc agccgcagtc ataatgggca ctgcaggcct cagcacgtac 1560
ctctataacc gccagcggaa gatcaagaaa tacagactac aacaggccca aaaagggacc 1620
cccatgaaac cgaacacaca agccacgcct ccctgaacct atcccgggac agggcctctt 1680
cctcggcctt cccatattgg tggcagtggt gccacactga acagagtgga agacatatgc 1740
catgcagcta cacctaccgg ccctgggacg ccggaggaca gggcattgtc ctcagtcaga 1800
tacaacagca tttggggcca tggtacctgc acacctaaaa cactaggcca cgcatctgat 1860
ctgtagtcac atgactaagc caagaggaag gagcaagact caagacatga ttgatggatg 1920
ttaaagtcta gcctgatgag aggggaagtg gtgggggaga catagcccca ccatgaggac 1980
atacaactgg gaaatactga aacttgctgc ctattgggta tgctgaggcc cacagactta 2040
cagaagaagt ggccctccat agacatgtgt agcatcaaaa cacaaaggcc cacacttcct 2100
gacggatgcc agcttgggca ctgctgtcta ctgaccccaa cccttgatga tatgtattta 2160
ttcatttgtt attttaccag ctatttattg agtgtctttt atgtaggcta aatgaacata 2220
ggtctctggc ctcacggagc tcccagtcca tgtcacattc aaggtcacca ggtacagttg 2280
tacaggttgt acactgcagg agagtgcctg gcaaaaagat caaatggggc tgggacttct 2340
cattggccaa cctgcctttc cccagaagga gtgatttttc tatcggcaca aaagcactat 2400
atggactggt aatggttcac aggttcagag attacccagt gaggccttat tcctcccttc 2460
cccccaaaac tgacaccttt gttagccacc tccccaccca catacatttc tgccagtgtt 2520
cacaatgaca ctcagcggtc atgtctggac atgagtgccc agggaatatg cccaagctat 2580
gccttgtcct cttgtcctgt ttgcatttca ctgggagctt gcactattgc agctccagtt 2640
tcctgcagtg atcagggtcc tgcaagcagt ggggaagggg gccaaggtat tggaggactc 2700
cctcccagct ttggaagggt catccgcgtg tgtgtgtgtg tgtatgtgta gacaagctct 2760
cgctctgtca cccaggctgg agtgcagtgg tgcaatcatg gttcactgca gtcttgacct 2820
tttgggctca agtgatcctc ccacctcagc ctcctgagta gctgggacca taggctcaca 2880
acaccacacc tggcaaattt gatttttttt ttttttttca gagacggggt ctcgcaacat 2940
tgcccagact tcctttgtgt tagttaataa agctttctca actgcc 2986

<210> SEQ ID NO 104
<211> LENGTH: 3634
<212> TYPE: DNA
<213> ORGANISM: Homo sapiens
<220> FEATURE:
<221> NAME/KEY: misc_feature
<223> OTHER INFORMATION: X02910

<400> SEQUENCE: 104
gaattccggg tgatttcact cccggctgtc caggcttgtc ctgctacccc acccagcctt 60
tcctgaggcc tcaagcctgc caccaagccc ccagctcctt ctccccgcag gacccaaaca 120
caggcctcag gactcaacac agcttttccc tccaacccgt ttctctccc tcaacggact 180

-continued

```
cagctttctg aagcccctcc cagttctagt tctatctttt tcctgcatcc tgtctggaag    240
ttagaaggaa acagaccaca gacctggtcc ccaaaagaaa tggaggcaat aggttttgag    300
gggcatgggg acggggttca gcctccaggg tcctacacac aaatcagtca gtggcccaga    360
agaccccccct cggaatcgga gcagggagga tggggagtgt gaggggtatc cttgatgctt    420
gtgtgtcccc aactttccaa atccccgccc ccgcgatgga gaagaaaccg agacagaagg    480
tgcagggccc actaccgctt cctccagatg agctcatggg tttctccacc aaggaagttt    540
tccgctggtt gaatgattct ttccccgccc tcctctcgcc ccagggacat ataaaggcag    600
ttgttggcac acccagccag cagacgctcc ctcagcaagg acagcagagg accagctaag    660
agggagagaa gcaactacag acccccccctg aaaacaaccc tcagacgcca catcccctga    720
caagctgcca ggcaggttct cttcctctca catactgacc cacggcttca ccctctctcc    780
cctggaaagg acaccatgag cactgaaagc atgatccggg acgtggagct ggccgaggag    840
gcgctcccca agaagacagg ggggccccag ggctccaggc ggtgcttgtt cctcagcctc    900
ttctccttcc tgatcgtggc aggcgccacc acgctcttct gcctgctgca ctttggagtg    960
atcggccccc agagggaaga ggtgagtgcc tggccagcct tcatccactc tcccacccaa   1020
ggggaaatga gagacgcaag agagggagag agatgggatg ggtgaaagat gtgcgctgat   1080
agggagggat gagagagaaa aaaacatgga gaaagacggg gatgcagaaa gagatgtggc   1140
aagagatggg gaagagagag agagaaagat ggagagacag gatgtctggc acatggaagg   1200
tgctcactaa gtgtgtatgg agtgaatgaa tgaatgaatg aatgaacaag cagatatata   1260
aataagatat ggagacagat gtggggtgtg agaagagaga tgggggaaga aacaagtgat   1320
atgaataaag atggtgagac agaaagagcg ggaaatatga cagctaagga gagagatggg   1380
ggagataagg agagaagaag atagggtgtc tggcacacag aagacactca gggaaagagc   1440
tgttgaatgc tggaaggtga atacacagat gaatggagag agaaaaccag acacctcagg   1500
gctaagagcg caggccagac aggcagccag ctgttcctcc tttaagggtg actccctcga   1560
tgttaaccat tctccttctc cccaacagtt ccccagggac ctctctctaa tcagccctct   1620
ggcccaggca gtcagtaagt gtctccaaac ctctttccta attctgggtt tgggtttggg   1680
ggtagggtta gtaccggtat ggaagcagtg ggggaaattt aaagttttgg tcttgggga    1740
ggatggatgg aggtgaaagt aggggggtat tttctaggaa gtttaagggt ctcagctttt   1800
tcttttctct ctcctcttca ggatcatctt ctcgaacccc gagtgacaag cctgtagccc   1860
atgttgtagg taagagctct gaggatgtgt cttggaactt ggagggctag gatttgggga   1920
ttgaagcccg gctgatggta ggcagaactt ggagacaatg tgagaaggac tcgctgagct   1980
caagggaagg gtggaggaac agcacaggcc ttagtgggat actcagaacg tcatggccag   2040
gtgggatgtg ggatgacaga cagagaggac aggaaccgga tgtggggtgg gcagagctcg   2100
agggccagga tgtggagagt gaaccgacat ggccacactg actctcctct ccctctctcc   2160
ctccctccag caaaccctca agctgagggg cagctccagt ggctgaaccg ccgggccaat   2220
gccctcctgg ccaatggcgt ggagctgaga gataaccagc tggtggtgcc atcagagggc   2280
ctgtacctca tctactccca ggtcctcttc aagggccaag gctgcccctc cacccatgtg   2340
ctcctcaccc acaccatcag ccgcatcgcc gtctcctacc agaccaaggt caacctcctc   2400
tctgccatca agagcccctg ccagagggag accccagagg gggctgaggc caagccctgg   2460
tatgagccca tctatctggg aggggtcttc cagctggaga agggtgaccg actcagcgct   2520
gagatcaatc ggcccgacta tctcgacttt gccgagtctg ggcaggtcta ctttgggatc   2580
```

```
attgccctgt gaggaggacg aacatccaac cttcccaaac gcctcccctg ccccaatccc   2640

tttattaccc cctccttcag acaccctcaa cctcttctgg ctcaaaaaga gaattggggg   2700

cttagggtcg gaacccaagc ttagaacttt aagcaacaag accaccactt cgaaacctgg   2760

gattcaggaa tgtgtggcct gcacagtgaa gtgctggcaa ccactaagaa ttcaaactgg   2820

ggcctccaga actcactggg gcctacagct ttgatccctg acatctggaa tctggagacc   2880

agggagcctt tggttctggc cagaatgctg caggacttga gaagacctca cctagaaatt   2940

gacacaagtg gaccttaggc cttcctctct ccagatgttt ccagacttcc ttgagacacg   3000

gagcccagcc ctccccatgg agccagctcc ctctatttat gtttgcactt gtgattattt   3060

attatttatt tattatttat ttatttacag atgaatgtat ttatttggga gaccggggta   3120

tcctggggga cccaatgtag gagctgcctt ggctcagaca tgttttccgt gaaaacggag   3180

ctgaacaata ggctgttccc atgtagcccc ctggcctctg tgccttcttt tgattatgtt   3240

ttttaaaata tttatctgat taagttgtct aaacaatgct gatttggtga ccaactgtca   3300

ctcattgctg agcctctgct ccccagggga gttgtgtctg taatcgccct actattcagt   3360

ggcgagaaat aaagtttgct tagaaaagaa acatggtctc cttcttggaa ttaattctgc   3420

atctgcctct tcttgtgggt gggaagaagc tccctaagtc ctctctccac aggctttaag   3480

atccctcgga cccagtccca tccttagact cctagggccc tggagaccct acataaacaa   3540

agcccaacag aatattcccc atcccccagg aaacaagagc ctgaacctaa ttacctctcc   3600

ctcagggcat gggaatttcc aactctggga attc                               3634
```

<210> SEQ ID NO 105
<211> LENGTH: 11233
<212> TYPE: DNA
<213> ORGANISM: Homo sapiens

<400> SEQUENCE: 105

```
gaattccttc cgtagcttca ccagacacct aattggccaa gaaggtttga agacctgatg     60

tggttcttaa ttggggatgg ggaattaagg gctactgtat ctataggatt atcttttcac    120

ttgcatagac ctatttggtg tgttcagggc atagtgatac tataattgcc atatttaaca    180

gtttataaag ttcaagccca gcatattctt tgcctgttta atgatgtctt ggtatcagcc    240

ttttaatggt acttatcagc atagaaaatg gaaacaaaat aacttttaaa acagtagctc    300

tcaagcttta gtgtgctcag aatgaccaga gaaccttgtg aaatatacag atttctgggt    360

ccagatctgg ggcaggacca ggaagtctgc atttcatctg caccccccacc ctactctgag    420

gcttatagtc ctgagaacat gctttgaaaa aggctgtccc aagggctcgc agacaggcta    480

ttgaccagct actctttctt gatgttctcc aggaaaaacc caacaaagga atgcctttca    540

ttgagtagta gcagcatagg agcaatagtt gctcctgaat tatggtgggt ttcccctctt    600

catcaatgtg ctttaagggt acagtttcat ttggtctatc taccatgttc tataaaaaca    660

tgaaaattca caggtaagtt tgagatacag aaaataacta aactgattct tctcacgaac    720

tctgatcact aggctgtggt tgatttagct ctctaaccaa caagtaattt gttctttggc    780

atgagtaagg ggggaaaagg aggagtgggt aaaagcagct gataacagat ggcttgcgcc    840

catctaaaat gtggggagag aaataaagct gtcccaagag aactaaagct gagttctctc    900

gtcatatatc tgaagattca tatcaggggt ctaaacatgg tatgtcgggt agcttaattg    960

gaaactcctg gactgtgagt gtcacagact catggatggg ccaatcagtg gccactttag   1020

tgtctgggct gcagcaaaat gagacaatag ctgtcattca caaacctttg gaattaaaaa   1080
```

```
aaccccgaaa tgacattggt gctttaaagt aaaataaagt cctgccttta agtccagcat   1140
atcactgttg tttctgagtt taaatattaa gaaccacatt tcgttaatga ttaaaacaac   1200
agtgattgat ttaggggctc agtgagcatt taatctgtcc tgacttcagg taccatgcta   1260
aaggagcaca atgcctgatg ctgcaggaga aacattaggt aactatttaa tggagtttta   1320
atttctgtt attattttta ataattaatt gtgattttga ctatttggaa gctacaggta   1380
tattttgtcc tccttttggg gtggtgttat tgccctgccc tgttttaatc agtggttctt   1440
agagaaagtg aactcaggag tgacttaaaa tgaaggaaga cggactttgg ctaaaattac   1500
aattaaataa tcaaatcatt ttcaaatata aagggagcat gcagatgatc tggcccaatc   1560
ctttcattct gcagatgaga aaactgagac tcataggaat gaaaagactt gcccaaagcc   1620
atacagcttg tttctgttgt ttggtgcatt aggccaaaag acctaggcct aatagatgga   1680
aaagatggca ggatgtcttg gccttgctct gacagttgct tctctgatct cagatatttc   1740
ccaccctttg taatctgtgt tccacacagg aagtagttct tgtttttaa atatcgaagg   1800
tgtataaacg taaagttttt atagatgagc cacccagggc caatatctgt ttaagtaaag   1860
acctaaatgc tttgcagaga cagtaaagtg tcatgtctgt cccagggaaa gaaatccagg   1920
acaggaaatg ctcagtcttc cagcactcct ctggctacct ggagctcagg ctatgagcct   1980
caacccctcc ctgaagcatt agctctggag cagaggctgt gatttacttc agagatctgg   2040
gcaagtccct ttaacctggt agtccttcct ttccttgttt gtaaaacaga gagatgaggc   2100
tgatagctcc ctcacagctc catcagaggc agtgtgtgaa attagttcct gtttgggaag   2160
gtttaaaagc caccacattc cacctccctg ctaatatgat tactaaaatg tttttatatg   2220
aaagggccaa ttcctcatct cccctcttcc tttaaaaaca gaccaagggg catcttttct   2280
tgtctccctg tggcctaaaa ggttactgct tctgtggtta tctccttgga aagacagagt   2340
gtcaggactc ttaggtacac caaaaatgaa caaaaaaatc aacaacaacc ataacaccaa   2400
caaaaataac tgctgtgtcg gttcttaaga cggcttctga gctagaaaca gatttttcta   2460
actgtaaaaa acgtggcccc agcctgtctg caggccacct ctgtctttag gccttggggg   2520
gaggagggaa gtgagctcat ttactggggt ctacctcagg gtcatcacca aggtgttcta   2580
caaaacgcac tttaagaatg ttttggaagg aaattcacct tttaacagcc caagaggtat   2640
ctctctctgg cacacagttc tgcacacagc ctgtttctca acgtttggaa atcttttaac   2700
agtttatgga aggccacctt ttaaaccgat ccaacagctc ctttctccat aacctgattt   2760
tagaggtgtt tcattatctc taattactca gggtaaatgg tgattactca gtgttttaat   2820
catcagtttg ggcagcagtt acactaaact cagggaagcc cagactccca tgggtatttt   2880
tggaaggtac ggcgactagt cggtgcatgc tttctagtac ctccgcacgt ggtccccagg   2940
tgagccccag ccgcttccca gagctggagg cagcggcgtc ccagctccga cggcagctgc   3000
ggactcgggc gctgcctggg cttccgggac ccgggcctgc taggcgaggt cgggcggctg   3060
gaggggagga tgtgggcggg gctcccatcc ccagaaaggg aggcgagcga gggaggaggg   3120
aaggagggag gggccgccgg ggaagaggag gaggaaggaa agaaagaaag cgagggaggg   3180
aaagaggagg aaggaagatg cgagaaggca gaggaggagg gagggaggga aggagcgcgg   3240
agcccggccc ggaagctagg tgagtgtggc atccgagctg agggacgcga gcctgagacg   3300
ccgctgctgc tccggctgag tatctagctt gtctccccga tgggattccc gtccaagcta   3360
tctcgagcct gcagcgccac agtccccggc cctcgcccag gttcactgca accgttcaga   3420
ggtccccagg agctgctgct ggcgagcccg ctactgcagg gacctatggt gagcaaggct   3480
```

```
acctggtgag gggagacagg cagagggggt ctaggagcct ccttgggggg aagaagctgg   3540
tcacaggctg tgaccgaggc aaaaggtggc ctaattattt tccaatagtg gtgctggagg   3600
tggggatgct ggcgctgaaa gacctttaaa tatcggctac tgcccctgcc caggccttct   3660
ctgtccagca gtccctggga gattctcacc tttgggaagt gcggggcagg agagcagaaa   3720
caagagaagc ccttggtagg ggggtcgttg ggaaaaactg tggggtcttg ggctgaacgc   3780
gttgcccacg ggctggaggt tgcgatcccc ggacggaaag cgcgggagga ggaaggagag   3840
aaccggctct gaggtccaga gagagtgagg gggcagagcg acggcgagat ggggagagaa   3900
cacctagctg gagcaggttc tgcggtagag agcgcagtcc tgctggcctc tggagagtgc   3960
gcgccgctac ggaggctgcg tcgaggggag tgtcacccaa tctggccccc agctggcggg   4020
gcgccctgag agcttgcgaa ctgcagttgc aggacgcgcc ttctccacga gctattttcg   4080
tcgacttgcg gaacccaagg aacctcgcct ctatcatttc acggtgtagg gtccctagag   4140
acgacagcca agatcccagg ggctcccagg acgcttgttc ctgcggtgtc gtgtcctatg   4200
gggagttcct ggcgggacga aaggcggacg cgcggctctt cctggccctc caggcccgga   4260
accgacggga aaggttcccg tgattcccga gtccctgcag gcttcttcca gcgggagttg   4320
gtccgggggc cttagaggcc tccaagcact gctttggagg atggtttcca aggatcgcgg   4380
tttgtgagtt gaaggctttg tgagaggtta aacccccaaa agatacatac ttggtaaact   4440
gaggctacct gtaaacacat ttcggcatta ggagaagatt cgagtaggga agtgaaggac   4500
aaccaccccg agttacattc ctttccccca ataaaaagct ctggggatga aagttctttt   4560
ggcttttatc ttttcgattt aaaaatttga gaagaaaaat gtgactagag atgaatcctg   4620
gtgaatccga aattgaaaca caactccccc ttccccttcc tatcctctcg gttttagaac   4680
cgcgctctcc cgccccagga gattccttgg ggccgagggt tttccgggga acccgggcgc   4740
ccgccccttc tactgtccct ttgccccgcg ggcacagctt gcctccgtct gctttctcta   4800
cttctggacc tctcctcgcc gggcttttta aagggcttct gcgtctcaaa acaaaacaaa   4860
aaaacccttt gctcttccca acccttttcgc agcccgcccc agcggtggcg cgggaccagc   4920
aaaggcgaaa gccgcgcggc tcttgccggg cgcggacggt cgcgcagggg cgcccgcggc   4980
ctccgcaccc ggacctgagg tgttggtcga ctccgggcat ccacggtcgg gagggagggc   5040
tgagctgttc gatcctttac ttttcttcct caaagtctac ctgccaatgc ccctaagaag   5100
aaaaccaagt atgtgcgtgg agagtggggc ggcaggcaac ccgagttctt gagctccgga   5160
gcgacccaaa gcagcaactg ggaacagcct caggaaaggg aggtcgggtg gagtgggctt   5220
tggggcagga gtcatggggc ccgggccccg gggacgacct ggcgctcccg gccctgctga   5280
acgctgagtt gcgcctagtc gggttttcga agaggccctt gcgcagagcg acccacgcgc   5340
gcggcagcat cttcgattag tcaggacatc ccagtaactg cttgaactgt aggtaggtaa   5400
aattcttgaa ggagtatttg ctgcgtgcga ctctgctgct ggtgcaacgg aggaaggggg   5460
tgggggaagg aagtggcggg ggaaggagtg tggtggtggt ttaaaaaata agggaagccg   5520
aggcgagaga gacgcagacg cagaggtcga gcgcaggccg aaagctgttc accgttttct   5580
cgactccggg gaacatggtg ggatttcctt tctgcgccgg gtcgggagtt gtaaaacctc   5640
ggccacatta agatctgaaa actgtgatgc gtcctttctg cagagacgcc tctttctgaa   5700
tctgcccgga gcttcgagcc ccggcgtctg tccctcagcc tggcatggct tcttcggggg   5760
tctgctttgc atggggagag gggccacgca gcggcggact aggtttgggg attctcggta   5820
atggacccgg agcaatgact aacagccgct ccctctcact ttcccacagc gatcaccctc   5880
```

-continued

```
taacaccctc cctcccattc ccggccccgc gcgtgacaag gtcggctgct ttcagccggg   5940
agctagatcg gtggcccggc tcttcggagc cttagcaggc gttcgccaag ggtgactgg    6000
ctgtcattgg gagcaatatt tggccttgag gagaccctgg ggaggaagtg gcggggagct   6060
cgtgtttgct tgtgtgtgtg tggggggggg ggtgtgtgta cacgcgcgtg ggcagggtcc   6120
ctctgcgctt tcctttttaa gtgcctctcg gtggtgaggc tttgggcggg tgagactttc   6180
ccgacctcgc tcccggcccc acttaagccg ggttcgagct gggagacgca gtcccttcag   6240
tgcgccccaa atcctctggc ttcaggtggc ccggcgcggg ggcccagcac gacgcaccgc   6300
gccgagaacc gggttctccg tgcgctgcgc cagtagccct gggagcgcgg cggccgcggg   6360
gcaccggccg agggctctgc cgagcgccgc cgggagctcc tcccggaccg ctgaggctcg   6420
ggcggcgggc gcggaggttg gcctcgcctg gaggggcggg cccgcgaggg gcggggggct   6480
gtggaggagg ggagggcgcg caggcccttt cgccgcctgc cgcgggaggg gcctcggcgc   6540
tcacgtgact ccgaggggct ggaagaaaaa cagagcctgt ctgcggtgga gtctcattat   6600
attcaaatat tccttttagg agccattccg tagtgccatc ccgagcaacg cactgctgca   6660
gcttccctga gcctttccag caagtttgtt caagattggc tgtcaagaat catggactgt   6720
tattatatgc cttgttttct gtcagtgagt agacacctct tccttccccc tctccggaat   6780
tcactctgcc ctcaccaccc ctgctcgccg gctgtccctt ccgtcggacc tcctttacaa   6840
tatccacact ctgctccctg gcagcactgt cgctcccttc ttggcccggc agccggggcg   6900
ctggaagcgt acgggttcct tttaaagtgc tgctagcgcg cactcgccct ctcagcgttg   6960
caagaaaggg gagcgcgagg gagctaaaga gatgaaagcc cggggttgta ccttgagggc   7020
taaccactcc cttcccctat ccaacttgtc tgggagagcc cccagtgtct ccgtggcgcg   7080
ttcccactct cttgtcaaaa ctcacagagg tctctccgga atcgtctctc acccccttccc  7140
tggggatgag cgggcacgat caggcacttt tggctgaata tttcaaactc atcggccaca   7200
ataaaataag ccctcaagcc acccggttag ctcccagacc accttctcgg cttctggacc   7260
ctgtcgccct ctgtcttcgc ccagccccctg cctctcactt tccctccctc tggctctgaa  7320
ccaactggaa gttgtgaaag ttgggctctg agggtggagg aaaagggaga gaagctgaag   7380
gtctaaagtg gagagcaatg ccattttaat tctccctccc ccaccccttt tcacccccctc  7440
aatgttaact gtttatcctt caagaagcca cgctgagatc atggcccaga tagcagttag   7500
gacaaaaaaa gattaacagg atggaggcta tctgatttgg ggttatttga ctgtaaacaa   7560
gttagaccaa gtaattacag ggcaattctt actttcaggc cgtgcatggc tgcagctggt   7620
gggtgggcgg gtggtgtgag ggagaagaca caaacttgat ctttctgacc tgctttccat   7680
cttgcccctc catttctagc cctaaatgca tatgcagaca catctctatt tctccctatt   7740
tattggtgtt tgtttattct ttaaccttcc actcccctcc ccctccccag agacaccatg   7800
attcctggta accgaatgct gatggtcgtt ttattatgcc aagtcctgct aggaggcgcg   7860
agccatgcta gtttgatacc tgagacgggg aagaaaaaag tcgccgagat tcagggccac   7920
gcgggaggac gccgctcagg gcagagccat gagctcctgc gggacttcga ggcgacactt   7980
ctgcagatgt ttgggctgcg ccgccgcccg cagcctagca agagtgccgt cattccggac   8040
tacatgcggg atctttaccg gcttcagtct ggggaggagg aggaagagca gatccacagc   8100
actggtcttg agtatcctga gcgcccggcc agccgggcca acaccgtgag gagcttccac   8160
cacgaaggtc agtctcttcc cccagtctgc gtgggggagg gctggtggga ctggctagag   8220
gggcagtgaa agccctgggg aagaagagtt cgggttacat caaaccccag tccaggaggc   8280
```

-continued

```
tgaggaacag agctgcttac ctccaagaat ttgcagagct gccgccgaac ttattttttg   8340
gagacagagg gggaggtgtt caggggaagg ggaatgacag cactcagacg tgggctagcc   8400
ccagcggtgt gtttttgcta tatcaaagcc ttttctgcta ggttttctgc ccgttttttt   8460
caaagcacct actgaattta atattacagc tgtgtgtttg tcgggtttat tcaatagggg   8520
ccttgtaatc cgatctgaat gtttcctagc ggatgtttct tttccaaagt aaatctgagt   8580
tattaatcca ccagcatcat tactgtgttg gaatttattt tcccctctgt aacatgatca   8640
acaaggcatg ctctgtgttt ccaagatcgc tggggaaatg tttagtaaca tactcaatag   8700
tggaagaggg agagggtggt tgtctccatg tttcctcctg cctgtgctct gttggcccct   8760
ctttttcttt acaaccactt gtaaagaaaa ctgtggacac aaagccaagg tggggggttt   8820
aaaagaggag tctgattgtg gtgccataga ggagttgaca catagaaatt attagacata   8880
tcaaggaggc tggatatagt ttctgtcttt ggtgcttgag aaatgctagc tacattttgc   8940
tggtttgtta gctgccccac ttatctgctc cttcaaatta aggggtatgc ttattttccc   9000
ccagtaggtt tcccctgcat aagcagaatt caccattcat tgcccaaccc tgagctatct   9060
cttgactctt ccatctttga aaaaagttca tatgcttttt cttttcccct tccttcctaa   9120
ctgtgcctag aacatctgga gaacatccca gggaccagtg aaaactctgc ttttcgtttc   9180
ctctttaacc tcagcagcat ccctgagaac gaggcgatct cctctgcaga gcttcggctc   9240
ttccgggagc aggtggacca gggccctgat tgggaaaggg gcttccaccg tataaacatt   9300
tatgaggtta tgaagccccc agcagaagtg gtgcctgggc acctcatcac acgactactg   9360
gacacgagac tggtccacca caatgtgaca cggtgggaaa cttttgatgt gagccctgcg   9420
gtccttcgct ggacccggga gaagcagcca aactatgggc tagccattga ggtgactcac   9480
ctccatcaga ctcggaccca ccagggccag catgtcagga ttagccgatc gttacctcaa   9540
gggagtggga attgggccca gctccggccc ctcctggtca cctttggcca tgatggccgg   9600
ggccatgcct tgacccgacg ccggagggcc aagcgtagcc ctaagcatca ctcacagcgg   9660
gccaggaaga agaataagaa ctgccggcgc cactcgctct atgtggactt cagcgatgtg   9720
ggctggaatg actggattgt ggccccacca ggctaccagg ccttctactg ccatggggac   9780
tgcccctttc cactggctga ccacctcaac tcaaccaacc atgccattgt gcagaccctg   9840
gtcaattctg tcaattccag tatccccaaa gcctgttgtg tgcccactga actgagtgcc   9900
atctccatgc tgtacctgga tgagtatgat aaggtggtac tgaaaaatta tcaggagatg   9960
gtagtagagg gatgtgggtg ccgctgagat caggcagtcc ttgaggatag acagatatac  10020
acaccacaca cacacaccac atacaccaca cacacacgtt cccatccact cacccacaca  10080
ctacacagac tgcttcctta tagctggact tttatttaaa aaaaaaaaaa aaaaaatgga  10140
aaaaatccct aaacattcac cttgacctta tttatgactt tacgtgcaaa tgttttgacc  10200
atattgatca tatattttga caaaatatat ttataactac gtattaaaag aaaaaaataa  10260
aatgagtcat tattttaaag gtaaatcatg attttttttt ctccttaatc ctttctcttt  10320
tccttcgggc tcatctcttt tgaatgaggc ttttttctgt tcaggtgagt tggaggctgg  10380
atggaagtca aaaggtggta cctggaggtg gttaagttgt agggacagga agtaaactgt  10440
tggcagagag agatggtaat tgccagcatg aattgttttc tatttctatt taatgttaac  10500
aaggatgcag tatcctctcc catctggatg acacatgcct tggagaaaca ctgggatgaa  10560
aggagtgtag gtcagattaa agacttcatt tcaggcccct tgtacatctt ctgtttcact  10620
cacctgttga ggtgtatcac agctgagcgt gatgaggtct caaccctaga aaaatgatac  10680
```

```
ccacctctgc tttcatgata cctcagggta tctccagtta ttacaggtac caatgtgata  10740

tttccaaatc aaaactaatt tgtacactaa catcataatg tgtgtgtgaa ggcatgtttt  10800

taaacttatt ttttttttct ccaggtagga ctcttttgtt ttttcttttg tctttttttt  10860

tttgaaacaa gttctctctt tgttgcccca ggctggtctt gaactcctgg gctcaagcaa  10920

tcttctcatt tcggcctctt tgggattaca ggcatgcact gctattttgt cttttttttt  10980

tttttgtaac aaataatgta ccctaccttc aaaaagtttg atgactactg ttttaatatg  11040

ccacttgata gaatttccca ttgtttcttg actttttccc ttgtcctctt ttcccaatgt  11100

gaaggccttc atcaagttta ggatcccaac agattgggct gggtgggggt tgacaatggg  11160

gtcagatact aaagggtcag aatttctaag caggcactgt gaaggtgtcc cactattata  11220

cagaaatctc gag                                                      11233
```

<210> SEQ ID NO 106
<211> LENGTH: 1723
<212> TYPE: DNA
<213> ORGANISM: Homo sapiens
<220> FEATURE:
<221> NAME/KEY: misc_feature
<223> OTHER INFORMATION: BB1=BAR1 Acc. No. NM_000684

<400> SEQUENCE: 106

```
tgctacccgc gcccgggctt ctggggtgtt ccccaaccac ggcccagccc tgccacaccc    60

cccgcccccg gcctccgcag ctcggcatgg gcgcgggggt gctcgtcctg ggcgcctccg   120

agcccggtaa cctgtcgtcg gccgcaccgc tccccgacgg cgcggccacc gcggcgcggc   180

tgctggtgcc cgcgtcgccg cccgcctcgt tgctgcctcc cgccagcgaa agccccgagc   240

cgctgtctca gcagtggaca gcgggcatgg gtctgctgat ggcgctcatc gtgctgctca   300

tcgtggcggg caatgtgctg gtgatcgtgg ccatcgccaa gacgccgcgg ctgcagacgc   360

tcaccaacct cttcatcatg tccctggcca gcgccgacct ggtcatgggg ctgctggtgg   420

tgccgttcgg ggccaccatc gtggtgtggg gccgctggga gtacggctcc ttcttctgcg   480

agctgtggac ctcagtggac gtgctgtgcg tgacggccag catcgagacc ctgtgtgtca   540

ttgccctgga ccgctacctc gccatcacct cgcccttccg ctaccagagc ctgctgacgc   600

gcgcgcgggc gcggggcctc gtgtgcaccg tgtgggccat ctcggccctg gtgtccttcc   660

tgcccatcct catgcactgg tggcgggcgg agagcgacga ggcgcgccgc tgctacaacg   720

accccaagtg ctgcgacttc gtcaccaacc gggcctacgc catcgcctcg tccgtagtct   780

ccttctacgt gcccctgtgc atcatggcct tcgtgtacct gcgggtgttc cgcgaggccc   840

agaagcaggt gaagaagatc gacagctgcg agcgccgttt cctcggcggc ccagcgcggc   900

cgccctcgcc ctcgccctcg cccgtccccg cgcccgcgcc gccgcccgga cccccgcgcc   960

ccgccgccgc cgccgccacc gccccgctgg ccaacgggcg tgcgggtaag cggcggccct  1020

cgcgcctcgt ggccctacgc gagcagaagg cgctcaagac gctgggcatc atcatgggcg  1080

tcttcacgct ctgctggctg cccttcttcc tggccaacgt ggtgaaggcc ttccaccgcg  1140

agctggtgcc cgaccgcctc ttcgtcttct tcaactggct gggctacgcc aactcggcct  1200

tcaaccccat catctactgc cgcagccccg acttccgcaa ggccttccag ggactgctct  1260

gctgcgcgcg cagggctgcc cgccggcgcc acgcgaccca cggagaccgg ccgcgcgcct  1320

cgggctgtct ggcccggccc ggacccccgc catcgcccgg ggccgcctcg gacgacgacg  1380

acgacgatgt cgtcggggcc acgccgcccg cgcgcctgct ggagccctgg gccggctgca  1440

acggcggggc ggcggcggac agcgactcga gcctggacga gccgtgccgc cccggcttcg  1500
```

cctcggaatc caaggtgtag ggcccggcgc ggggcgcgga ctccgggcac ggcttcccag 1560
gggaacgagg agatctgtgt ttacttaaga ccgatagcag gtgaactcga agcccacaat 1620
cctcgtctga atcatccgag gcaaagagaa aagccacgga ccgttgcaca aaaaggaaag 1680
tttgggaagg gatgggagag tggcttgctg atgttccttg ttg 1723

<210> SEQ ID NO 107
<211> LENGTH: 1145
<212> TYPE: DNA
<213> ORGANISM: Homo sapiens
<220> FEATURE:
<221> NAME/KEY: misc_feature
<223> OTHER INFORMATION: IL-6: Acc. No. X04430

<400> SEQUENCE: 107
aggactggag atgtctgagg ctcattctgc cctcgagccc accgggaacg aaagagaagc 60
tctatctccc ctccaggagc ccagctatga actccttctc cacaagcgcc ttcggtccag 120
ttgccttctc cctggggctg ctcctggtgt tgcctgctgc cttccctgcc ccagtacccc 180
caggagaaga ttccaaagat gtagccgccc cacacagaca gccactcacc tcttcagaac 240
gaattgacaa acaaattcgg tacatcctcg acggcatctc agccctgaga aaggagacat 300
gtaacaagag taacatgtgt gaaagcagca aagaggcact ggcagaaaac aacctgaacc 360
ttccaaagat ggctgaaaaa gatggatgct tccaatctgg attcaatgag gagacttgcc 420
tggtgaaaat catcactggt cttttggagt ttgaggtata cctagagtac ctccagaaca 480
gatttgagag tagtgaggaa caagccagag ctgtccagat gagtacaaaa gtcctgatcc 540
agttcctgca gaaaaaggca aagaatctag atgcaataac cacccctgac ccaaccacaa 600
atgccagcct gctgacgaag ctgcaggcac agaaccagtg gctgcaggac atgacaactc 660
atctcattct gcgcagcttt aaggagttcc tgcagtccag cctgagggct cttcggcaaa 720
tgtagcatgg gcacctcaga ttgttgttgt taatgggcat tccttcttct ggtcagaaac 780
ctgtccactg ggcacagaac ttatgttgtt ctctatggag aactaaaagt atgagcgtta 840
ggacactatt ttaattattt ttaatttatt aatatttaaa tatgtgaagc tgagttaatt 900
tatgtaagtc atattttata tttttaagaa gtaccacttg aaacatttta tgtattagtt 960
ttgaaataat aatggaaagt ggctatgcag tttgaatatc ctttgtttca gagccagatc 1020
atttcttgga aagtgtaggc ttacctcaaa taaatggcta actttataca tatttttaaa 1080
gaaatattta tattgtattt atataatgta taaatggttt ttataccaat aaatggcatt 1140
ttaaa 1145

<210> SEQ ID NO 108
<211> LENGTH: 2063
<212> TYPE: DNA
<213> ORGANISM: Homo sapiens
<220> FEATURE:
<221> NAME/KEY: misc_feature
<223> OTHER INFORMATION: U82535

<400> SEQUENCE: 108
tgccgggcgg taggcagcag caggctgaag ggatcatggt gcagtacgag ctgtgggccg 60
cgctgcctgg cgcctccggg gtcgccctgg cctgctgctt cgtggcggcg gccgtggccc 120
tgcgctggtc cgggcgccgg acggcgcggg gcgcggtggt ccgggcgcga cagaagcagc 180
gagcgggcct ggagaacatg gacagggcgg cgcagcgctt ccggctccag aacccagacc 240
tggactcaga ggcgctgcta gccctgcccc tgcctcagct ggtgcagaag ttacacagta 300

```
gagagctggc ccctgaggcc gtgctcttca cctatgtggg aaaggcctgg gaagtgaaca    360
aagggaccaa ctgtgtgacc tcctatctgg ctgactgtga gactcagctg tctcaggccc    420
caaggcaggg cctgctctat ggcgtccctg tgagcctcaa ggagtgcttc acctacaagg    480
gccaggactc cacgctgggc ttgagcctga atgaaggggt gccggcggag tgcgacagcg    540
tagtggtgca tgtgctgaag ctgcagggtg ccgtgccctt cgtgcacacc aatgttccac    600
agtccatgtt cagctatgac tgcagtaacc ccctctttgg ccagaccgtg aacccatgga    660
agtcctccaa aagcccaggg ggctcctcag gggtgaagg ggccctcatc gggtctggag    720
gctccccct gggcttaggc actgatatcg gaggcagcat ccgcttcccc tcctccttct    780
gcggcatctg cggcctcaag cccacaggga accgcctcag caagagtggc ctgaagggct    840
gtgtctatgg acaggaggca gtgcgtctct ccgtgggccc catggcccgg gacgtggaga    900
gcctggcact gtgcctgcga gccctgctgt gcgaggacat gttccgcttg gaccccactg    960
tgcctccctt gcccttcaga gaagaggtct acaccagctc tcagcccctg cgtgtggggt   1020
actatgagac tgacaactat accatgccct ccccggccat gaggcgggcc gtgctggaga   1080
ccaaacagag ccttgaggct gcggggcaca cgctggttcc cttcttgcca agcaacatac   1140
cccatgctct ggagaccctg tcaacaggtg ggctcttcag tgatggtggc cacaccttcc   1200
tacagaactt caaaggtgat ttcgtggacc cctgcctggg ggacctggtc tcaattctga   1260
agcttcccca atggcttaaa ggactgctgg ccttcctggt gaagcctctg ctgccaaggc   1320
tgtcagcttt cctcagcaac atgaagtctc gttcggctgg aaaactctgg gaactgcagc   1380
acgagatcga ggtgtaccgc aaaaccgtga ttgcccagtg gagggcgctg gacctggatg   1440
tggtgctgac cccatgctg gcccctgctc tggacttgaa tgccccaggc agggccacag   1500
gggccgtcag ctacactatg ctgtacaact gcctggactt ccctgcaggg gtggtgcctg   1560
tcaccacggt gactgctgag gacgaggccc agatggaaca ttacaggggc tactttgggg   1620
atatctggga caagatgctg cagaagggca tgaagaagag tgtggggctg ccggtggccg   1680
tgcagtgtgt ggctctgccc tggcaagaag agttgtgtct gcggttcatg cgggaggtgg   1740
agcgactgat gacccctgaa aagcagtcat cctgatggct ctggctccag aggacctgag   1800
actcacactc tctgcagccc agcctagtca gggcacagct gccctgctgc cacagcaagg   1860
aaatgtcctg catggggcag aggcttccgt gtcctctccc ccaaccccct gcaagaagcg   1920
ccgactccct gagtctggac ctccatccct gctctggtcc cctctcttcg tcctgatccc   1980
tccacccca tgtggcagcc catgggtatg acataggcca aggcccaact aacagtcaag   2040
aaacaaaaaa aaaaaaaaaa aaa                                          2063
```

<210> SEQ ID NO 109
<211> LENGTH: 2729
<212> TYPE: DNA
<213> ORGANISM: Homo sapiens
<220> FEATURE:
<221> NAME/KEY: misc_feature
<223> OTHER INFORMATION: ACAT-1: Acc. No. XM_031119

<400> SEQUENCE: 109

```
agcttagcag gcgacgttgc gggccctggg cgccaggaga gcttcccgga gtcgaccttc     60
ctgctggctg ctctgtgacc gcttcccggc tctgccctct tggccgaagt gcccgctgcc    120
gggcgcgggc ctcagacaat acaatggtgg gtgaagagaa gatgtctcta agaaaccggc    180
tgtcaaagtc cagggaaaat cctgaggaag atgaagacca gagaaaccct gcaaaggagt    240
```

```
ccctagagac acctagtaat ggtcgaattg acataaaaca gttgatagca aagaagataa    300
agttgacagc agaggcagag gaattgaagc catttttat gaaggaagtt ggcagtcact    360
ttgatgattt tgtgaccaat ctcattgaaa agtcagcatc attagataat ggtgggtgcg    420
ctctcacaac cttttctgtt cttgaaggag agaaaaacaa ccatagagcg aaggatttga    480
gagcacctcc agaacaagga aagattttta ttgcaaggcg ctctctctta gatgaactgc    540
ttgaagtgga ccacatcaga acaatatatc acatgtttat tgccctcctc attctcttta    600
tcctcagcac acttgtagta gattacattg atgaaggaag gctggtgctt gagttcagcc    660
tcctgtctta tgcttttggc aaatttccta ccgttgtttg gacctggtgg atcatgttcc    720
tgtctacatt ttcagttccc tattttctgt ttcaacattg ggccactggc tatagcaaga    780
gttctcatcc gctgatccgt tctctcttcc atggctttct tttcatgatc ttccagattg    840
gagttctagg ttttggacca acatatgttg tgttagcata tacactgcca ccagcttccc    900
ggttcatcat tatattcgag cagattcgtt ttgtaatgaa ggcccactca tttgtcagag    960
agaacgtgcc tcgggtacta aattcagcta aggagaaatc aagcactgtt ccaataccta   1020
cagtcaacca gtatttgtac ttcttatttg ctcctaccct tatctaccgt gacagctatc   1080
ccaggaatcc cactgtaaga tggggttatg tcgctatgaa gtttgcacag gtctttggtt   1140
gctttttcta tgtgtactac atctttgaaa ggctttgtgc cccccttgttt cggaatatca   1200
aacaggagcc cttcagcgct cgtgttctgg tcctatgtgt atttaactcc atcttgccag   1260
gtgtgctgat tctcttcctt actttttttg cctttttgca ctgctggctc aatgcctttg   1320
ctgagatgtt acgctttggt gacaggatgt tctataagga ttggtggaac tccacgtcat   1380
actccaacta ttatagaacc tggaatgtgg tggtccatga ctggctatat tactatgctt   1440
acaaggactt tctctggttt ttctccaaga gattcaaatc tgctgccatg ttagctgtct   1500
ttgctgtatc tgctgtagta cacgaatatg ccttggctgt ttgcttgagc tttttctatc   1560
ccgtgctctt cgtgctcttc atgttctttg gaatggcttt caacttcatt gtcaatgata   1620
gtcggaaaaa gccgatttgg aatgttctga tgtggacttc tcttttcttg ggcaatggag   1680
tcttactctg cttttattct caagaatggt atgcacgtca gcactgtcct ctgaaaaatc   1740
ccacattttt ggattatgtc cggccacgtt cctggacttg tcgttacgtg ttttagaagc   1800
ttggactttg tttcctcctt gtcactgaag attgggtagc tccctgattt ggagccagct   1860
gtttccagtt gttactgaag ttatctgtgt tatttggacc actccaggct ttacagatga   1920
ctcactccat tcctaggtca cttgaagcca aactgttgga agttcactgg agtcttgtac   1980
acttaagcag agcagaactt tttttgtggg gctgggtggg gggagaagac cgactaacag   2040
ctgaagtaat gacagattgt tgctgggtca tatcagcttt atcccttggt aattatatct   2100
gttttgtttc ttgactctgt ccaatcagag aataaacatc atagtttctt ggccactgaa   2160
ttagccaaaa cacttaggaa gaaatcactt aaatacctct ggcttagaaa ttttttcatg   2220
cacactgttg gaatgtatgc taattgaaca tgcaattggg gaagaaaaaa tgtagaatga   2280
tttttgctat ttctagtaga aagaaaatgt ctgttttcca aagataatgt tatacatcct   2340
attttgtaat ttttttgaaa aaagttcaat gttcagtttt ccttagtttt taccttgttt   2400
tctctatagg tcatgatttc tgtgaagcaa aaagatgcct tttaccatga attcttgagt   2460
ttacatcaat aatattgtat attaagggga tcagaagtag gaaggaaaaa ataagagata   2520
gcagaggaaa aagaaaaaca tttcctctta taacttctga agtaatttgt aaaaaagatt   2580
tgtagagtca atcatgtgtt taaattattt tatcacaaac ttaacatgga agatattcct   2640
```

```
ttttaacttt gtggtaactt ctttgaagtt atttagaaat atcctttgga acaattattt   2700

tattgtctaa taaatattga cttctcttg                                     2729


<210> SEQ ID NO 110
<211> LENGTH: 3779
<212> TYPE: DNA
<213> ORGANISM: Homo sapiens
<220> FEATURE:
<221> NAME/KEY: misc_feature
<223> OTHER INFORMATION: IBAT:  Acc. No. NM_000452

<400> SEQUENCE: 110

ttctattgaa agggaaatgg gagaacaata tgtgttccta tggctcagtc cctataagat     60

tctgtactat tcagagttga ttttaagtgt cacttaactg aaattatcca acaaaccttc    120

atggcatgaa acattaacac agctcttttt atatggcatg gttcctatgg ctcaatccct    180

ataagattct gtactagttc agagttgatt ttaaaagtca cttaactgaa attatccaac    240

aaaccctcga ggacattaaa cattaacgtg gctcttttta tatggcatgg ttcattatca    300

tgccaataaa tgattaatcg taactctctg tcttgaccaa taattttgct ggacttttgt    360

gattcacaac gtgctctgtg ttgtaatgct acctcttgaa actgacatcc tagctttatt    420

gtttttttatt acttccctaa ggtggctttc aaaagagaca ccaagtgaca tatttttagg    480

aggggtttaa aagtttgatg ggtagaagt aaacgttgct taactcaacc agcagcagag    540

ccagggccca gggaccagcg cttctgtgga cttggccttt ccagcagcag acccagcaat    600

gaatgatccg aacagctgtg tggacaatgc aacagtttgc tctggtgcat cctgtgtggt    660

acctgagagc aatttcaata acatcctaag tgtggtccta agtacggtgc tgaccatcct    720

gttggccttg gtgatgttct ccatgggatg caacgtggaa atcaagaaat ttctagggca    780

cataaagcgg ccgtggggca tttgtgttgg cttcctctgt cagtttggaa tcatgcccct    840

cacaggattc atcctgtcgg tggcctttga catcctcccg ctccaggccg tagtggtgct    900

cattatagga tgctgccctg gaggaactgc ctccaatatc ttggcctatt gggtcgatgg    960

cgacatggac ctgagcgtca gcatgaccac atgctccaca ctgcttgccc tcggaatgat   1020

gccgctgtgc ctccttatct ataccaaaat gtgggtcgac tctgggagca tcgtaattcc   1080

ctatgataac ataggtacat ctctggttgc tctcgttgtt cctgtttcca ttggaatgtt   1140

tgttaatcac aaatggcccc aaaaagcaaa gatcatactt aaaattgggt ccatcgcggg   1200

cgccatcctc attgtgctca tagctgtggt tggaggaata ttgtaccaaa gcgcctggat   1260

cattgctccc aaactgtgga ttataggaac aatatttcct gtggcgggtt actccctggg   1320

gtttcttctg gctagaattg ctggtctacc ctggtacagg tgccgaacgg ttgcttttga   1380

aacggggatg cagaacacgc agctatgttc caccatcgtt cagctctcct tcactcctga   1440

ggagctcaat gtcgtattca ccttcccgct catctacagc attttccagc tcgcctttgc   1500

cgcaatattc ttaggatttt atgtggcata caagaaatgt catggaaaaa acaaggcaga   1560

aattccagag agcaaagaaa atggaacgga gccagagtca tcgttttata aggcaaatgg   1620

aggatttcaa cctgacgaaa agtagacatc aagtggacaa aacagacgag ttccaaatta   1680

cgttcttaaa ccgtaactat atttaattat ttgttttggt aggacagttg gcagaaaaga   1740

gttaaagtga aaattggaat ttcattggaa ttcatgtatt ggtttcagta ccaagtgact   1800

ggtggcccaa ttctttaatg ggacaaatat tgtttcctat atatatgtat atgttttata   1860

tatgtatgta tactcatata gatatattgt cattgaaata ttcccccaaa atattctcag   1920

actaaacctg acatagggaa caccgagaat gaaaacatcg ttaacaccaa aactgaattc   1980
```

```
ttatgcagaa tttcctagcc catagatgac aacctgagtt tctgtatgtt aaagtagatg   2040

taatgaatta ttattattac agtggtcacg attttcttca gtgtttatga ttataaaaat   2100

tgacatgaac atctttcact gacattttaa tcattatttt aaaagctttg caacctatat   2160

atttatataa ctttgtaata taacatgggc aaatatctga cttcagtatt tttaaaaagt   2220

tgccttctcc agtggcagtc caaaagcaga aatgagagga aattattaca aaatagaatt   2280

caataaccat attggatgca ggctcttaac tcagcaggga tatcgtacat ctattgctct   2340

acctcagggg tccagtgata cccactagat cttccaagga aaaacataat tctttcaaac   2400

ggtgtgtatt tggcaaagag ctcttcaaat ctgggagagg gacttcctca aggttttcct   2460

gtgtgcagtg gatccacata gctaatatga cagctagtca gttgacaggg accacccaca   2520

gtaagcacca tggtcaggga ggtggcagga ggtgcaaaga cagaagtatt gagagaaaca   2580

ccaagactct agtggaggaa ttaattcaat gggagatagt ataaaataca tagaaaacac   2640

aagtaacaga aacctggttg aaatgcttaa ctagagtcaa ttagatgtgc aggagtaagt   2700

agtataagaa gaatcaagtc cgagagtgat caggaaatga gtattaaaca gtatttgaaa   2760

cagagaacgt gtcccagggc ccaaaagtca gaagggcccc accagccagg aaagttgttt   2820

caatgctgta agtaggtgta gccaagggaa gccaggacta tctgatatac ggtagcaggg   2880

gtttacggct gccaggggaa aataactcat caagtgttgg actttcaatt ataagatcga   2940

atttaatttc ctttccctca ttctgcagca atcagaatac acaatcttaa ccactcggtc   3000

cttagtggtt ttgttccatt ttgcattggg tattttcact gcctcataga gtctatttca   3060

agtgtttggc tgaaagggct tttgcattt gcatgttctg agttcagatt ctgctggtgc   3120

acccaagcat tatgggaaca ggaactcaac ttagctcttc cagtagaggg gtgagggatt   3180

ctgcttttca aattcataac attgatcttt ttatgcaaga tttccattta cagttgaata   3240

agtacttcat atttttccat cattagacaa atacaaaatg gactaaataa ttttaagaga   3300

tagtggaggc agcagggggt acagacttcc ttcttagaga gtgtcagaga atatgctccc   3360

aatggtggaa aggaagattt acagtctagc ggctaagtac ctcctacaca tttcccatca   3420

atcagaaaat agacaggtac actaaaggga cctgagaact cctcttgtaa tttcaacaca   3480

cccaaaatca agggcctgga tgccagcagc tgcagcaagc aggtttttcc tccctgttga   3540

gcaagacagg tgaggcaaga taggacttgg ctttcttaca tgatgcggta acttgtgact   3600

tgagtctttt tccctaattt gctagtggga agaaaaatag ctgagctttc taaaatgata   3660

gctctctatt tttaaatgaa tttgaaaagt cgattaaatt atgtatttta ttgcctctga   3720

gtatcatatt aaatgaatat tttattttaa aggcttaaat aaatgaaaat gatttttgt    3779
```

<210> SEQ ID NO 111
<211> LENGTH: 4067
<212> TYPE: DNA
<213> ORGANISM: Homo sapiens
<220> FEATURE:
<221> NAME/KEY: misc_feature
<223> OTHER INFORMATION: U28749

<400> SEQUENCE: 111

```
cttgaatctt ggggcaggaa ctcagaaaac ttccagcccg ggcagcgcgc gcttggtgca     60

agactcagga gctagcagcc cgtccccctc cgactctccg gtgccgccgc tgcctgctcc    120

cgccacccta ggaggcgcgg tgccacccac tactctgtcc tctgcctgtg ctccgtgccc    180

gaccctatcc cggcggagtc tccccatcct cctttgcttt ccgactgccc aaggcacttt    240
```

-continued

```
caatctcaat ctcttctctc tctctctctc tctctctgtc tctctctctc tctctctctc    300
tctctctctc gcagggtggg gggaagagga ggaggaattc tttccccgcc taacatttca    360
agggacacaa ttcactccaa gtctcttccc tttccaagcc gcttccgaag tgctcccggt    420
gcccgcaact cctgatccca acccgcgaga ggagcctctg cgacctcaaa gcctctcttc    480
cttctccctc gcttccctcc tcctcttgct acctccacct ccaccgccac ctccacctcc    540
ggcacccacc caccgccgcc gccgccaccg gcagcgcctc ctcctctcct cctcctcctc    600
ccctcttctc tttttggcag ccgctggacg tccggtgttg atggtggcag cggcggcagc    660
ctaagcaaca gcagccctcg cagcccgcca gctcgcgctc gccccgccgg cgtccccagc    720
cctatcacct catctcccga aaggtgctgg gcagctccgg ggcggtcgag gcgaagcggc    780
tgcagcggcg gtagcggcgg cgggaggcag gatgagcgca cgcggtgagg gcgcggggca    840
gccgtccact tcagcccagg gacaacctgc cgccccagcg cctcagaaga gaggacgcgg    900
ccgccccagg aagcagcagc aagaaccaac cggtgagccc tctcctaaga gacccagggg    960
aagacccaaa ggcagcaaaa acaagagtcc ctctaaagca gctcaaaaga aagcagaagc   1020
cactggagaa aaacggccaa gaggcagacc taggaaatgg ccacaacaag ttgttcagaa   1080
gaagcctgct caggaggaaa ctgaagagac atcctcacaa gagtctgccg aagaggacta   1140
gggggcgcaa cgttcgattt ctacctcagc agcagttgga tcttttgaag ggagaagaca   1200
ctgcagtgac cacttattct gtattgccat ggtctttcca ctttcatctg gggtggggtg   1260
gggtggggtg ggggaggggg gggtggggtg gggagaaatc acataacctt aaaaaggact   1320
atattaatca ccttctttgt aatcccttca cagtcccagg tttagtgaaa aactgctgta   1380
aacacagggg acacagctta acaatgcaac ttttaattac tgttttcttt tttcttaacc   1440
tactaatagt ttgttgatct gataagcaag agtgggcggg tgagaaaaac cgaattgggt   1500
ttagtcaatc actgcactgc atgcaaacaa gaaacgtgtc acacttgtga cgtcgggcat   1560
tcatatagga agaacgcggt gtgtaacact gtgtacacct caaataccac cccaacccac   1620
tccctgtagt gaatcctctg tttagaacac caaagataag gactagatac tactttctct   1680
ttttcgtata atcttgtaga cacttacttg atgattttta actttttatt tctaaatgag   1740
acgaaatgct gatgtatcct ttcattcagc taacaaacta gaaaaggtta tgttcatttt   1800
tcaaaaaggg aagtaagcaa acaaatattg ccaactcttc tatttatgga tatcacacat   1860
atcagcagga gtaataaatt tactcacagc acttgttttc aggacaacac ttcattttca   1920
ggaaatctac ttcctacaga gccaaaatgc catttagcaa taaataacac ttgtcagcct   1980
cagagcattt aaggaaacta gacaagtaaa attatcctct ttgtaattta atgaaaaggt   2040
acaacagaat aatgcatgat gaactcacct aattatgagg tgggaggagc gaaatctaaa   2100
tttcttttgc tatagttata catcaattta aaaagcaaaa aaaaaaaggg gggggcaatc   2160
tctctctgtg tctttctctc tctctctccc tctccctctc tcttttcatg tgtatcagtt   2220
tccatgaaag acctgaatac cacttacctc aaattaagca tatgtgttac ttcaagtaat   2280
acgttttgac ataagatggt tgaccaaggt gcttttcttc ggcttgagtt caccatctct   2340
tcattcaaac tgcactttta gccagagatg caatatatcc ccactactca atactacctc   2400
tgaatgttac aacgaattta cagtctagta cttattacat gctgctatac acaagcaatg   2460
caagaaaaaa acttactggg taggtgattc taatcatctg cagttctttt tgtacactta   2520
attacagtta aagaagcaat ctccttactg tgtttcagca tgactatgta tttttctatg   2580
tttttttaat taaaaatttt taaaatactt gtttcagctt ctctgctaga tttctacatt   2640
```

```
aacttgaaaa ttttttaacc aagtcgctcc taggttctta aggataattt tcctcaatca   2700

cactacacat cacacaagat ttgactgtaa tatttaaata ttaccctcca agtctgtacc   2760

tcaaatgaat tctttaagga gatggactaa ttgacttgca aagacctacc tccagacttc   2820

aaaaggaatg aacttgttac ttgcagcatt catttgtttt ttcaatgttt gaaatagttc   2880

aaactgcagc taaccctagt caaaactatt tttgtaaaag acatttgata gaaaggaaca   2940

cgtttttaca tacttttgca aaataagtaa ataataaata aaataaagcc aaccttcaaa   3000

gaacttgaag ctttgtaggt gagatgcaac aagccctgct tttgcataat gcaatcaaaa   3060

atatgtgttt ttaagattag ttgaatataa gaaaatgctt gacaaatatt ttcatgtatt   3120

ttacacaaat gtgatttttg taatatgtct caaccagatt tattttaaac gcttcttatg   3180

tagagttttt atgcctttct ctcctagtga gtgtgctgac tttttaacat ggtattatca   3240

actgggccag gaggtagttt ctcatgacgg cttttgtcag tatggctttt agtactgaag   3300

ccaaatgaaa ctcaaaacca tctctcttcc agctgcttca gggaggtagt ttcaaaggcc   3360

acatacctct ctgagactgg cagatcgctc actgttgtga atcaccaaag gagctatgga   3420

gagaattaaa actcaacatt actgttaact gtgcgttaaa taagcaaata aacagtggct   3480

cataaaaata aaagtcgcat tccatatctt tggatgggcc ttttagaaac ctcattggcc   3540

agctcataaa atggaagcaa ttgctcatgt tggccaaaca tggtgcaccg agtgatttcc   3600

atctctggta aagttacact tttatttcct gtatgttgta caatcaaaac acactactac   3660

ctcttaagtc ccagtatacc tcatttttca tactgaaaaa aaaagcttgt ggccaatgga   3720

acagtaagaa catcataaaa tttttatata tatagtttat ttttgtggga gataaatttt   3780

ataggactgt tctttgctgt tgttggtcgc agctacataa gactggacat ttaacttttc   3840

taccatttct gcaagttagg tatgtttgca ggagaaaagt atcaagacgt ttaactgcag   3900

ttgactttct ccctgttcct ttgagtgtct tctaacttta ttctttgttc tttatgtaga   3960

attgctgtct atgattgtac tttgaatcgc ttgcttgttg aaaatatttc tctagtgtat   4020

tatcactgtc tgttctgcac aataaacata acagcctctg tgatccc                 4067
```

<210> SEQ ID NO 112
<211> LENGTH: 511
<212> TYPE: DNA
<213> ORGANISM: Homo sapiens
<220> FEATURE:
<221> NAME/KEY: misc_feature
<223> OTHER INFORMATION: NM_016362

<400> SEQUENCE: 112

```
gcaggcccac ctgtctgcaa cccagctgag gccatgccct ccccagggac cgtctgcagc     60

ctcctgctcc tcggcatgct ctggctggac ttggccatgg caggctccag cttcctgagc    120

cctgaacacc agagagtcca gcagagaaag gagtcgaaga agccaccagc caagctgcag    180

ccccgagctc tagcaggctg gctccgcccg gaagatggag gtcaagcaga aggggcagag    240

gatgaactgg aagtccggtt caacgccccc tttgatgttg gaatcaagct gtcaggggtt    300

cagtaccagc agcacagcca ggccctgggg aagtttcttc aggacatcct ctgggaagag    360

gccaaagagg ccccagccga caagtgatcg ccccacaagcc ttactcacct ctctctaagt   420

ttagaagcgc tcatctggct tttcgcttgc ttctgcagca actcccacga ctgttgtaca    480

agctcaggag gcgaataaat gttcaaactg t                                   511
```

<210> SEQ ID NO 113
<211> LENGTH: 2268

<212> TYPE: DNA
<213> ORGANISM: Homo sapiens
<220> FEATURE:
<221> NAME/KEY: misc_feature
<223> OTHER INFORMATION: S77410

<400> SEQUENCE: 113

```
accccaggca gcagcgagtg acaggacgtc tggaccggcg cgccgctagc agctctgccg     60

ggccgcggcg gtgatcgatg gggagcggct ggagcggacc cagcgagtga gggcgcacag    120

ccgggacgcc gaggcggcgg gcgggagacc cgcaccagcg cagccggccc tcggcgggac    180

gtgacgcagc gcccggggcg cgggtttgat atttgacaaa ttgatctaaa atggctgggt    240

ttttatctga ataactcact gatgccatcc cagaaagtcg gcaccaggtg tatttgatat    300

agtgtttgca acaaattcga cccaggtgat caaaatgatt ctcaactctt ctactgaaga    360

tggtattaaa agaatccaag atgattgtcc caaagctgga aggcataatt acatatttgt    420

catgattcct actttataca gtatcatctt tgtggtggga atatttggaa acagcttggt    480

ggtgatagtc atttactttt atatgaagct gaagactgtg gccagtgttt ttcttttgaa    540

tttagcactg gctgacttat gctttttact gactttgcca ctatgggctg tctacacagc    600

tatggaatac cgctggccct ttggcaatta cctatgtaag attgcttcag ccagcgtcag    660

tttcaacctg tacgctagtg tgtttctact cacgtgtctc agcattgatc gatacctggc    720

tattgttcac ccaatgaagt cccgccttcg acgcacaatg cttgtagcca aagtcacctg    780

catcatcatt tggctgctgg caggcttggc cagtttgcca gctataatcc atcgaaatgt    840

atttttcatt gagaacacca atattacagt ttgtgctttc cattatgagt cccaaaattc    900

aacccttccg atagggctgg gcctgaccaa aaatatactg ggtttcctgt ttcctttttct    960

gatcattctt acaagttata ctcttatttg gaaggcccta aagaaggctt atgaaattca   1020

gaagaacaaa ccaagaaatg atgatatttt taagataatt atggcaattg tgcttttctt   1080

tttcttttcc tggattcccc accaaatatt cacttttctg gatgtattga ttcaactagg   1140

catcatacgt gactgtagaa ttgcagatat tgtggacacg gccatgccta tcaccatttg   1200

tatagcttat tttaacaatt gcctgaatcc tctttttat ggctttctgg ggaaaaaatt   1260

taaaagatat tttctccagc ttctaaaata tattcccccca aaagccaaat cccactcaaa   1320

cctttcaaca aaaatgagca cgctttccta ccgcccctca gataatgtaa gctcatccac   1380

caagaagcct gcaccatgtt ttgaggttga gtgacatgtt cgaaacctgt ccataaagta   1440

attttgtgaa agaaggagca agagaacatt cctctgcagc acttcactac caaatgagca   1500

ttagctactt ttcagaattg aaggagaaaa tgcattatgt ggactgaacc gacttttcta   1560

aagctctgaa caaaagcttt tctttccttt tgcaacaaga caaagcaaag ccacattttg   1620

cattagacag atgacggctg ctcgaagaac aatgtcagaa actcgatgaa tgtgttgatt   1680

tgagaaattt tactgacaga aatgcaatct ccctagcctg cttttgtcct gttatttttt   1740

atttccacat aaaggtattt agaatatatt aaatcgttag aggagcaaca ggagatgaga   1800

gttccagatt gttctgtcca gtttccaaag ggcagtaaag ttttcgtgcc ggttttcagc   1860

tattagcaac tgtgctacac ttgcacctgg tactgcacat tttgtacaaa gatatgctaa   1920

gcagtagtcg tcaagttgca gatctttttg tgaaattcaa cctgtgtctt ataggtttac   1980

actgccaaaa caatgcccgt aagatggctt atttgtataa tggtgttact aaagtcacat   2040

ataaaagtta aactacttgt aaaggtgctg cactggtccc aagtagtagt gtcctcctag   2100

tatattagtt tgatttaata tctgagaagt gtatatagtt tgtggtaaaa agattatata   2160
```

tcataaagta tgccttcctg tttaaaaaaa gtatatattc tacacatata tatatatgta 2220
tatctatatc tctaaactgc tgttaattga ttaaaatctg gcaaagtt 2268

<210> SEQ ID NO 114
<211> LENGTH: 785
<212> TYPE: DNA
<213> ORGANISM: Homo sapiens
<220> FEATURE:
<221> NAME/KEY: misc_feature
<223> OTHER INFORMATION: XM_166457

<400> SEQUENCE: 114
gcgcgagccg cgccggcccc ggtcgggcct ccgaaaccat gaactttctg ctgtcttggg 60
tgcattggag ccttgccttg ctgctctacc tccaccatgc caagtggtcc caggctgcac 120
ccatggcaga aggaggaggg cagaatcatc acgaagtggt gaagttcatg gatgtctatc 180
agcgcagcta ctgccatcca atcgagaccc tggtggacat cttccaggag taccctgatg 240
agatcgagta catcttcaag ccatcctgtg tgcccctgat gcgatgcggg ggctgctgca 300
atgacgaggg cctggagtgt gtgcccactg aggagtccaa catcaccatg cagattatgc 360
ggatcaaacc tcaccaaggc cagcacatag gagagatgag cttcctacag cacaacaaat 420
gtgaatgcag accaaagaaa gatagagcaa gacaagaaaa aaaatcagtt cgaggaaagg 480
gaaaggggca aaaacgaaag cgcaagaaat cccggtataa gtcctggagc gtgtacgttg 540
gtgcccgctg ctgtctaatg ccctggagcc tccctggccc ccatccctgt gggccttgct 600
cagagcggag aaagcatttg tttgtacaag atccgcagac gtgtaaatgt tcctgcaaaa 660
acacagactc gcgttgcaag gcgaggcagc ttgagttaaa cgaacgtact tgcagatgtg 720
acaagccgag gcggtgagcc gggcaggagg aaggagcctc cctcagggtt tcgggaacca 780
gatct 785

<210> SEQ ID NO 115
<211> LENGTH: 8460
<212> TYPE: DNA
<213> ORGANISM: Homo sapiens
<220> FEATURE:
<221> NAME/KEY: misc_feature
<223> OTHER INFORMATION: U29344
<220> FEATURE:
<221> NAME/KEY: misc_feature
<222> LOCATION: (1)..(8460)
<223> OTHER INFORMATION: n can be a or c or g or t

<400> SEQUENCE: 115
cggccgtcga cacggcagcg gccccggcct ccctctccgc cgcgcttcag cctcccgctc 60
cgccgcgctc cagcctcgct ctccgccgcc cgcaccgccg cccgcgccct caccagagca 120
gccatggagg aggtggtgat tgccggcatg tccgggaagc tgccagagtc ggagaacttg 180
caggagttct gggacaacct catcggcggt gtggacatgg tcacggacga tgaccgtcgc 240
tggaaggcgg ggctctacgg cctgccccgg cggtccggca agctgaagga cctgtctagg 300
tttgatgcct ccttcttcgg agtccacccc aagcaggcac acacgatgga ccctcagctg 360
cggctgctgc tggaagtcac ctatgaagcc atcgtggacg gaggcatcaa cccagattca 420
ctccgaggaa cacacactgg cgtctgggtg ggcgtgagcg gctctgagac ctcggaggcc 480
ctgagccgag accccgagac actcgtgggc tacagcatgg tgggctgcca gcgagcgatg 540
atggccaacc ggctctcctt cttcttcgac ttcagagggc ccagcatcgc actggacaca 600
gcctgctcct ccagcctgat ggccctgcag aacgcctacc aggccatcca cagcgggcag 660

```
tgccctgccg ccatcgtggg gggcatcaat gtcctgctga agcccaacac ctccgtgcag    720
ttcttgaggc tggggatgct cagccccgag ggcacctgca aggccttcga cacagcgggg    780
aatgggtact gccgctcgga gggtgtggtg gccgtcctgc tgaccaagaa gtccctggcc    840
cggcgggtgt acgccaccat cctgaacgcc ggcaccaata cagatggctt caaggagcaa    900
ggcgtgacct tcccctcagg ggatatccag gagcagctca tccgctcgtt gtaccagtcg    960
gccggagtgg cccctgagtc atttgaatac atcgaagccc acggcacagg caccaaggtg   1020
ggcgaccccc aggagctgaa tggcatcacc cgagccctgt gcgccacccg ccaggagccg   1080
ctgctcatcg gctccaccaa gtccaacatg ggccacccgg agccagcctc ggggctggca   1140
gccctggcca aggtgctgct gtccctggag cacgggctct gggcccccaa cctgcacttc   1200
catagcccca accctgagat cccagcgctg ttggatgggc ggctgcaggt ggtggaccag   1260
cccctgcccg tccgtggcgg caacgtgggc atcaactcct ttggcttcgg gggctccaac   1320
gtgcacatca tcctgaggcc caacacgcag ccgccccccg cacccgcccc acatgccacc   1380
ctgccccgtc tgctgcgggc cagcggacgc acccctgagg ccgtgcagaa gctgctggag   1440
cagggcctcc ggcacagcca ggacctggct ttcctgagca tgctgaacga catcgcgctg   1500
tccccgacca ccgccatgcc cttccgtggc tacgctgtgc tgggtggtga gcgcggtggc   1560
ccagaggtgc agcaggtgcc cgctggcgag cgcccgctct ggttcatctg ctctgggatg   1620
ggcacacagt ggcgcgggat ggggctgagc ctcatgcgcc tggaccgctt ccgagattcc   1680
atcctacgct ccgatgaggc tgtgaaccga ttcggcctga aggtgtcaca gctgctgctg   1740
agcacagacg agagcacctt tgatgacatc gtccattcgt ttgtgagcct gactgccatc   1800
cagataggcc tcatagacct gctgagctgc atggggctga ggccagatgg catcgtcggc   1860
cactccctgg gggaggtggc ctgtggctac gccgacggct gcctgtccca ggaggaggcc   1920
gtcctcgctg cctactggag ggacagtgc atcaaagaag cccatctccc gccgggcgcc   1980
atggcagccg tgggcttgtc ctgggaggag tgtaaacagc gctgcccccc ggcggtggtg   2040
cccgcctgcc acaactccaa ggacacagtc accatctcgg gacctcaggc cccggtgttt   2100
gagttcgtgg agcagctgag gaaggagggt gtgtttgcca aggaggtgcg gaccggcggt   2160
atggccttcc actcctactt catggaggcc atcgcacccc cactgctgca ggagctcaag   2220
aaggtgatcc gggagccgaa gccacgttca gcccgctggc tcagcacctc tatccccgag   2280
gcccagtggc acagcagcct ggcacgcacg tcctccgccg agtacaatgt caacaacctg   2340
gtgagccctg tgctgttcca ggaggccctg tggcacgtgc ctgagcacgc ggtggtgctg   2400
gagatcgcgc cccacgccct gctgcaggct gtcctgaagc gtggcctgaa gccgagctgc   2460
accatcatcc ccctgatgaa gaaggatcac agggacaacc tggagttctt cctggccggc   2520
atccggaggc tgcacctctc aggcatcgac gccaacccca atgccttgtt cccacctgtg   2580
gagttcccag ctccccgagg aactcccctc atctccccac tcatcaagtg ggaccacagc   2640
ctggcctggg acgtgccggc cgccgaggac ttccccaacg gttcaggttc cccctcagcc   2700
gccatctaca acatcgacac cagctccgag tctcctgacc actacctggt ggaccacacc   2760
ctcgacggtc gcgtcctctt ccccgccact ggctacctga gcatagtgtg gaagacgctg   2820
gcccgacccc tgggcctggg cgtcgagcag ctgcctgtgg tgtttgagga tgtggtgctg   2880
caccaggcca ccatcctgcc caagactggg acagtgtccc tggaggtacg gctcctggag   2940
gcctcccgtg ccttcgaggt gtcagagaac ggcaacctgg tagtgagtgg gaaggtgtac   3000
cagtgggatg accctgaccc caggctcttc gaccacccgg aaagccccac ccccaacccc   3060
```

```
acggagcccc tcttcctggc ccaggctgaa gtttacaagg agctgcgtct gcgtggctac   3120
gactacggcc ctcatttcca gggcatcctg gaggccagcc tggaaggtga ctcggggagg   3180
ctgctgtgga aggataactg ggtgagcttc atggacacca tgctgcagat gtccatcctg   3240
ggctcggcca agcacggcct gtacctgccc acccgtgtca ccgccatcca catcgaccct   3300
gccacccaca ggcagaagct gtacacactg caggacaagg cccaagtggc tgacgtggtg   3360
gtgagcaggt ggctgagggt cacagtggcc ggaggcgtcc acatctccgg gctccacact   3420
gagtcggccc cgcggcggca gcaggagcag caggtgccca tcctggagaa gttttgcttc   3480
acttcccaca cggaggaggg gtgcctgtct gagcgcgctg ccctgcagga ggagctgcaa   3540
ctgtgcaagg ggctggtgca ggcactgcag accaaggtga cccagcaggg gctgaagatg   3600
gtggtgcccg gactggatgg ggcccagatc cccagggacc cctcacagca ggaactgccc   3660
cggctgttgt cggctgcctg caggcttcag ctcaacggga acctgcagct ggagctggcg   3720
caggtgctgg cccaggagag gcccaagctg ccagaggacc ctctgctcag cggcctcctg   3780
gactccccgg cactcaaggc ctgcctggac actgccgtgg agaacatgcc cagcctgaag   3840
atgaaggtgg tggaggtgct ggccggccac ggtcacctgt attcccgcat cccaggcctg   3900
ctcagccccc atcccctgct gcagctgagc tacacggcca ccgaccgcca cccccaggcc   3960
ctggaggctg cccaggccga gctgcagcag cacgacgttg cccagggcca gtgggatccc   4020
gcagaccctg cccccagcgc cctgggcagc gccgacctcc tggtgtgcaa ctgtgctgtg   4080
gctgccctcg ggacccggc ctcagctctc agcaacatgg tggctgccct gagagaaggg   4140
ggctttctgc tcctgcacac actgctccgg gggcacccct cgggacatgt ggccttcctc   4200
acctccactg agccgcagta tggccagggc atcctgagcc aggacgcgtg ggagagcctc   4260
ttctccaggg tgtccgtgcg cctggtgggc ctgaagaagt ccttctacgg ctccacgctc   4320
ttcctgtgcc gccggcccac cccgcaggac agccccatct tcctgccggt ggacgatacc   4380
agcttccgct gggtggagtc tctgaagggc atcctggctg acgaagactc ttcccggcct   4440
gtgtggctga aggccatcaa ctgtgccacc tcgggcgtgg tgggcttggt gaactgtctc   4500
cgccgagagc ccggcggaac gctccggtgt gtgctgctct ccaacctcag cagcacctcc   4560
cacgtcccgg aggtggaccc gggctccgca gaactgcaga aggtgttgca gggagacctg   4620
gtgatgaacg tctaccgcga cggggcctgg ggggctttcc gccacttcct gctggaggag   4680
gacaagcctg aggagccgac ggcacatgcc tttgtgagca ccctcacccg gggggacctg   4740
tcctccatcc gctgggtctg ctcctcgctg cgccatgccc agcccacctg ccctggcgcc   4800
cagctctgca cggtctacta cgcctccctc aacttccgcg acatcatgct ggccactggc   4860
aagctgtccc ctgatgccat cccagggaag tggacctccc aggacagcct gctaggtatg   4920
gagttctcgg gccgagacgc cagcggcaag cgtgtgatgg gactggtgcc tgccaagggc   4980
ctggccacct ctgtcctgct gtcaccggac ttcctctggg atgtgccttc caactggacg   5040
ctggaggagg cggcctcggt gcctgtcgtc tacagcacgg cctactacgc gctggtggtg   5100
cgtgggcggg tgcgccccgg ggagacgctg ctcatccact cgggctcggg cggcgtgggc   5160
caggccgcca tcgccatcgc cctcagtctg ggctgccgcg tcttcaccac cgtggggtcg   5220
gctgagaagc gggcgtacct ccaggccagg ttcccccagc tcgacagcac cagcttcgcc   5280
aactcccggg acacatcctt cgagcagcat gtgctgtggc acacgggcgg gaagggcgtt   5340
gacctggtct tgaactcctt ggcggaagag aagctgcagg ccagcgtgag gtgcttggct   5400
acgcacggtc gcttcctgga aattggcaaa ttcgaccttt ctcagaacca cccgctcggc   5460
```

```
atggctatct tcctgaagaa cgtgacattc cacggggtcc tactggatgc gttcttcaac   5520
gagagcagtg ctgactggcg ggaggtgtgg gcgcttgtgc aggccggcat ccgggatggg   5580
gtggtacggc ccctcaagtg cacggtgttc catggggccc aggtggagga cgccttccgc   5640
tacatggccc aagggaagca cattggcaaa gtcgtcgtgc aggtgcttgc ggaggagccg   5700
gaggcagtgc tgaagggggc caaacccaag ctgatgtcgg ccatctccaa gaccttctgc   5760
ccggcccaca agagctacat catcgctggt ggtctgggtg gcttcggcct ggagttggcg   5820
cagtggctga tacagcgtgg ggtgcagaag ctcgtgttga cttctcgctc cgggatccgg   5880
acaggctacc aggccaagca ggtccgccgg tggagggccc agggcgtaca ggtgcaggtg   5940
tccaccagca acatcagctc actggagggg gcccggggcc tcattgccga ggcggcgcag   6000
cttgggcccg tgggcggcgt cttcaacctg gccgtggtct tgagagatgg cttgctggag   6060
aaccagaccc cagagttctt ccaggacgtc tgcaagccca agtacagcgg caccctgaac   6120
ctggacaggg tgacccgaga ggcgtgccct gagctggact actttgtggt cttctcctct   6180
gtgagctgcg ggcgtggcaa tgcgggacag agcaactacg gctttgccaa ttccgccatg   6240
gagcgtatct gtgagaaacg ccggcacgaa ggcctcccag gcctggccgt gcagtggggc   6300
gccatcggcg acgtgggcat tttggtggag acgatgagca ccaacgacac gatcgtcagt   6360
ggcacgctgc cccaggccat ggcgtcctgc ctggaggtgc tggacctctt cctgaaccag   6420
ccccacatgg tcctgagcag ctttgtgctg gctgagaagg ctgcggccta tagggacagg   6480
gacagccagc gggacctggt ggaggccgtg gcacacatcc tgggcatccg cgacttggct   6540
gctgtcaacc tggacagctc actggcggac ctgggcctgg actcgctcat gagcgtggag   6600
gtgcgccaga cgctggagcg tgagctcaac ctggtgctgt ccgtgcgcga ggtgcggcaa   6660
ctcacgctcc ggaaactgca ggagctgtcc tcaaaggcgg atgaggccag cgagctggca   6720
tgccccacgc ccaaggagga tggtctggcc cagcagcaga ctcagctgaa cctgcgctcc   6780
ctgctggtga acccggaggg ccccaccctg atgcggctca actccgtgca gagctcggag   6840
cggcccctgt tcctggtgca cccaatcgag ggctccacca ccgtgttcca cagcctggcc   6900
tcccggctca gcatccccac ctatggcctg cagtgcaccc gagctgcgcc ccttgacagc   6960
atccacagcc tggctgccta ctacatcgac tgcatcaggc aggtgcagcc cgagggcccc   7020
taccgcgtgg ccggctactc ctacggggcc tgcgtggcct ttgaaatgtg ctcccagctg   7080
caggcccagc agagcccagc ccccacccac aacagcctct tcctgttcga cggctcgccc   7140
acctacgtac tggcctacac ccagagctac cgggcaaagc tgaccccagg ctgtgaggct   7200
gaggctgaga cggaggccat atgcttcttc gtgcagcagt tcacggacat ggagcacaac   7260
agggtgctgg aggcgctgct gccgctgaag ggcctagagg agcgtgtggc agccgccgtg   7320
gacctgatca tcaagagcca ccagggcctg gaccgccagg agctgagctt tgcggcccgg   7380
tccttctact acaagctcgg tgccgctgag cagtacacac ccaaggccaa gtaccatggc   7440
aacgtgatgc tactgcgcgc caagacgggt ggcgcctacg gcgaggacct gggcgcggat   7500
tacaacctct cccaggtatg cgacgggaaa gtatccgtcc acgtcatcga gggtgaccac   7560
cgcacgctgc tggagggcag cggcctggag tccatcatca gcatcatcca cagctccctg   7620
gctgagccac gcgtgagcgt gcgggagggc taggcccgtg cccccgcctg ccaccggagg   7680
tcactccacc atccccaccc caccccaccc cacccccgcc atgcaacggg attgaagggt   7740
cctgccggtg ggaccctgtc cggcccagtg ccactgcccc ccgaggctgc tagatgtagg   7800
tgttaggcat gtcccaccca cccgccgcct cccacggcac ctcggggaca ccagagctgc   7860
```

```
cgacttggag actcctggtc tgtgaagagc cggtggtgcc cgttcccgca ggaactgggc   7920

tgggcctcgt gcgcccgtgg ggtctgcgct tggtctttct gtgcttggat ttgcatattt   7980

attgcattgc tggtagagac ccccaggcct gtccaccctg ccaagactcc tcaggcagcg   8040

tgtgggtccc gcactctgcc cccatttccc cgatgtcccc tgcgggcgcg ggcagccacc   8100

caagcctgct ggctgcggcc ccctctcggc caggcattgg ctcagccngc tgagtggggg   8160

gtcgtgggcc agtccccgag gagctgggcc cctgcacagg cacacagggc ccggccacac   8220

ccagcggccc cccgcacagc cacccgtggg gtgctgccct tatcgcccgg cgccgggcac   8280

caactccatg tttggtgttt gtctgtgttt gtttttcaag aaatgattca aattgctgct   8340

tggattttga aatttactgt aactgtcagt gtacacgtct ggaccccgtt tcatttttac   8400

accaatttgg taaaaatgct gctctcagcc tcccacaatt aaaccgcatg tgatctcccc   8460


<210> SEQ ID NO 116
<211> LENGTH: 959
<212> TYPE: DNA
<213> ORGANISM: Homo sapiens
<220> FEATURE:
<221> NAME/KEY: misc_feature
<223> OTHER INFORMATION: NM_001639

<400> SEQUENCE: 116

gggcatgaat atcagacgct agggggacag ccactgtgtt gtctgctacc ctcatcctgg     60

tcactgcttc tgctataaca gccctaggcc aggaatatga acaagccgct gctttggatc    120

tctgtcctca ccagcctcct ggaagccttt gctcacacag acctcagtgg gaaggtgttt    180

gtatttccta gagaatctgt tactgatcat gtaaacttga tcacaccgct ggagaagcct    240

ctacagaact ttaccttgtg ttttcgagcc tatagtgatc tctctcgtgc ctacagcctc    300

ttctcctaca atacccaagg cagggataat gagctactag tttataaaga aagagttgga    360

gagtatagtc tatacattgg aagacacaaa gttacatcca aagttatcga aaagttcccg    420

gctccagtgc acatctgtgt gagctgggag tcctcatcag gtattgctga attttggatc    480

aatgggacac ctttggtgaa aaagggtctg cgacagggtt actttgtgga agctcagccc    540

aagattgtcc tggggcagga acaggattcc tatgggggca agtttgatag gagccagtcc    600

tttgtgggag agattgggga tttgtacatg tgggactctg tgctgccccc agaaaatatc    660

ctgtctgcct atcagggtac ccctctccct gccaatatcc tggactggca ggctctgaac    720

tatgaaatca gaggatatgt catcatcaaa cccttggtgt gggtctgagg tcttgactca    780

acgagagcac ttgaaaatga aatgactgtc taagagatct ggtcaaagca actggatact    840

agatcttaca tctgcagtct ttcttctttg aatttcctat ctgtatgtct gcctaattaa    900

aaaaatatat attgtattat gctacctgca aaaaaaaaaa aaaaaaaaaa aaaaaaaaa     959


<210> SEQ ID NO 117
<211> LENGTH: 1471
<212> TYPE: DNA
<213> ORGANISM: Homo sapiens
<220> FEATURE:
<221> NAME/KEY: misc_feature
<223> OTHER INFORMATION: NM_000936

<400> SEQUENCE: 117

ggaactgcca cgatgctgcc actttggact ctttcactgc tgctgggagc agtagcagga     60

aaagaagttt gctacgaaag actcggctgc ttcagtgatg actccccatg gtcaggaatt    120

acggaaagac ccctccatat attgccttgg tctccaaaag atgtcaacac ccgcttcctc    180
```

```
ctatatacta atgagaaccc aaacaacttt caagaagttg ccgcagattc atcaagcatc    240

agtggctcca atttcaaaac aaatagaaaa actcgcttta ttattcatgg attcatagac    300

aagggagaag aaaactggct ggccaatgtg tgcaagaatc tgttcaaggt ggaaagtgtg    360

aactgtatct gtgtggactg gaaaggtggc tcccgaactg gatacacaca agcctcgcag    420

aacatcagga tcgtgggagc agaagtggca tattttgttg aatttcttca gtcggcgttc    480

ggttactcac cttccaacgt gcatgtcatt ggccacagcc tgggtgccca cgctgctggg    540

gaggctggaa ggagaaccaa tgggaccatt ggacgcatca cagggttgga cccagcagaa    600

ccttgctttc agggcacacc tgaattagtc cgattggacc ccagcgatgc caaatttgtg    660

gatgtaattc acacggatgg tgcccccata gtccccaatt tggggtttgg aatgagccaa    720

gtcgtgggcc acctagattt ctttccaaat ggaggagtgg aaatgcctgg atgtaaaaag    780

aacattctct ctcagattgt ggacatagac ggaatctggg aagggactcg agactttgcg    840

gcctgtaatc acttaagaag ctacaaatat tacactgata gcatcgtcaa ccctgatggc    900

tttgctggat tcccctgtgc ctcttacaac gtcttcactg caaacaagtg tttcccttgt    960

ccaagtggag gctgcccaca gatgggtcac tatgctgata gatatcctgg gaaaacaaat   1020

gatgtgggcc agaaatttta tctagacact ggtgatgcca gtaattttgc acgttggagg   1080

tataaggtat ctgtcacact gtctggaaaa aaggttacag gacacatact agtttctttg   1140

ttcggaaata aaggaaactc taagcagtat gaaattttca agggcactct caaaccagat   1200

agtactcatt ccaatgaatt tgactcagat gtggatgttg gggacttgca gatggttaaa   1260

tttatttggt ataacaatgt gatcaaccca actttaccta gagtgggagc atccaagatt   1320

atagtggaga caaatgttgg aaaacagttc aacttctgta gtccagaaac cgtcagggag   1380

gaagttctgc tcaccctcac accgtgttag gagactactg ttatttgacc aatgaattga   1440

cttctaataa aatctagtgg tgatgcaaaa a                                  1471
```

```
<210> SEQ ID NO 118
<211> LENGTH: 7452
<212> TYPE: DNA
<213> ORGANISM: Homo sapiens
<220> FEATURE:
<221> NAME/KEY: misc_feature
<223> OTHER INFORMATION: U89344

<400> SEQUENCE: 118
```

```
atggtcttgc ttctttgtct atcttgtctg attttctcct gtctgacctt ttcctggtta     60

aaaatctggg agaaaatgac ggactccaag ccgatcacca agagtaaatc agaagcaaac    120

ctcatcccga gccaggagcc ctttccagcc tctgataact caggggagac accgcagaga    180

aatggggagg gccacactct gcacaaagac acccagccag gccgagccca gcctcccaca    240

aaggcccaaa gatccggtcg gcggagaaac tccctaccac cctcccgcca gaagcccccca    300

agaaaccccc tttcttccag tgacgcagca ccctccccag agcttcaagc caacgggact    360

gggacacaag gtctggaggc cacagatacc aatggcctgt cctcctcagc caggccccag    420

ggcagcaagc tggtcccctc caaagaagac aagaagcagg caaacatcaa gaggcagctg    480

atgaccaact tcatcctggg ctcttttgat gactactcct ccgacgagga ctctgttgct    540

ggctcatctc gtgagtctac ccggaagggc agccgggcca gcttgggggc cctgtccctg    600

gaggcttatc tgaccacagg tgaagctgag acccgcgtcc ccactatgag gccgagcatg    660

tcgggactcc acctggtgaa gaggggacgg gaacacaaga agctggacct gcacagagac    720

tttaccgtgg cttctcccgc tgagtttgtc acacgctttg ggggggatcg ggtcatcgag    780
```

```
aaggtgctta ttgccaacaa cgggattgcc gctgtgaagt gcatgcgctc catccgcagg    840
tgggcctatg agatgttccg caacgagcgg gccatccggt ttgttcgcat ggtgaccccc    900
gaggacctta aggccaacgc agagtacatc aagatggcgg atcattacgg gcccgcccca    960
ggagggccca ataacaacaa ctatgccaac gtggagctga ttgtggacat tgccaagaga   1020
atcccgttgc aggcggtgtg ggctggctgg ggccatgctt tagaaaaccc taaacttccg   1080
gagctgctgt gcaagaatgg agttgctttc ttaggccctc ccaggttgag gccaatggtg   1140
ggtctaggag ataagatcgc ctccaccgtt gtcgcccaga cgctacaggt cccaaccctg   1200
cccaggagtg gaagcgccct gacagtggag tggacagaag atgatctgca gcagggaaaa   1260
agaatcagtg tcccagaaga tgtttatgac aagggttgcg tgaaagacgt agatgagggc   1320
ttggaggcag cagaaagaat tggttttcca ttgatgatca aagcttctga aggtggcgga   1380
gggaagggaa tccgggaaac tgagagtgcg gaggacttcc cgatcctttt cagacaagta   1440
cagagtgaga tcccaggctc gcccatcttt ctcatgaagc tggcccagca cgcccgtcac   1500
ctggaagttc agatcctcgc tgaccagtat gggaatgctg tgtctctgtt tggtcgcgac   1560
tgctccatcc agcggcggca tcagaagatc gttgaggaag caccggccac catcgcgccg   1620
ctggccatat tcgagttcat ggagcagtgt gccattcgcc tggccaagac cgtgggctat   1680
gtgagtgcag ggacagtgga atacctctat agtcaggatg gtagcttcca cttcttggag   1740
ctgaatcctc gcttgcaggt ggaacatccc tgcacagaaa tgattgctga cgttaatctg   1800
ccggccgccc agctacagat cgccatgggt gccccactgc accggctgaa agatatccgg   1860
cttctgtatg gagagtcacc ctggggagac tccccaattt cttttgaaaa ctcagctcat   1920
ctcccctgcc cccgaggcca cgtcattgcc accagaatca ccagcgaaaa cccagacgag   1980
ggttttaagc cgagctccgg gactgtccag gaactgaatt tccggagcag caagaacgtc   2040
tggggttact tcacggtggc cgctactgga ggcctgcacg agtttgcgat ttcccagttt   2100
gggcactgct tctcctgggg agagaaccgg aaagaggcca tttcgaacat ggtggtggct   2160
ttgaaggaac tgtccctccg aggcgacttt aggactaccg tggaatacct cattaacctc   2220
ctggagaccg agagcttcca gaacaactac atcgacaccg ggtggttgga ctacctcatt   2280
gctgagaaag tgcaaaagaa accgaatatc atgcttgggg tggtatgcgg ggcccttgaa   2340
cgtggagatg cgatgttcag aacgtgcatg acagatttct tacactccct ggaaaggggc   2400
caggtcctcc cagcggattc actactgaac ctcgtagatg tggaattaat ttacgagggt   2460
gtaaagtaca ttctaaaggt gacccggcag tctctgacca tgttcgttct catcatgaat   2520
ggctgccaca tcgagattga tgcccaccgg ctgaatgatg gggggctcct gctctcctac   2580
aatgggaaca gctacaccac ctacatgaag gaagaggttg acagttaccg taccatcggc   2640
aataagacgt gtgtttttga gaaggagaac gatcctacag tcctgagatc cccctcggct   2700
gggaagctga cacagatcac agtggaggat gggggccacg ttgaggctgg gagacgctac   2760
gctgagatgg aggtgatgaa gatgatcatg accctgaacg ttcaggaaag aggccgggtg   2820
aagtacatca agcgtccagg tgcggtgctg gaagcaggct gcgtggtggc caggctggag   2880
ctcgatgacc cttctaaagt ccacccggct gaaccgttca caggagaact ccctgcccag   2940
cagaacactg ccgacctcgg aaagaaactg cacagggtct tccacagcgt cctgggaagc   3000
ctcaccaacg tcatgagtgg cttttgtctg ccagagccgt tttttagcat aaagctgaag   3060
gagtgggtgc agaagctcat gatgaccctc cggcacccgt cactgctgct ggacgtgcag   3120
gagatcatga ccagtcgtgc aggccgcatc cccccccctg ttgagaagtc tgtccgcaag   3180
```

```
gtgatggccc agtatgccag caacatcacc tcggtgctgt gccagttccc cagccagcag   3240
atagccacca tcctggactg ccatgcagcc accctgcagc ggaaggctga tcgagaggtc   3300
ttcttcatca acacccagag catggtgcag ttggtccaga ggtaccgaag tggaatccgc   3360
ggtcatatga aaacagtggt gatcgatctc ttgagaagat acttgcgtgt tgagaccatt   3420
ttcggcaagg caagagatgc tgatgccaac tccagtggga tggtgggggg cgtgaggagc   3480
ctgagcttta cctctgtgtg ggtggttttg tctcccccag cccactacga caagtgtgtg   3540
ataaacctca gggaacagtt caagccagac atgtcccagg tgctggactg catcttctcc   3600
cacgcacagg tgaccaagaa gaaccagctg gtgatcatgt tgatcgatga gctgtgtggc   3660
ccagaccctt ccctgtcgga cgagctgatc tccatcctca acgagctcac tcagctgagc   3720
aaaagcgagc actgcaaagt ggccctcaga gcccggcaga tcctgatcgc ctccccctcc   3780
tacgagctgc ggcataacca ggtggagtcc attttcctgt ctgccattga catgtacggc   3840
caccagttct gccccgagaa cctccagaaa ttaatacttt cggaaacaac catcttcgac   3900
gtcctgaata ctttcttcta tcacgcaaac aaagtcgtgt gcatggcgtc cttggaggtt   3960
tacgtggggg gggcttacat cgcctatgtg ttaaacagcc tgcagcaccg gcagctcccg   4020
gacggcacct gcgtggtaga attccagttc atgctgccgt cctcccaccc aaaccggatg   4080
accgtgccca tcagcatcac caaccctgac ctgctgaggc acacgacaga gctcttcatg   4140
gacagcggct tctccccact gtgccagcgc atgggagcca tggtagcctt caggagattc   4200
gaggacttca ccagaaattt tgatgaagtc atctcttgct tcgccaacgt gccgaaagac   4260
cccccctct tcagcgaggc ccgcacctcc ctatactccg aggatgactg caagagcctc   4320
agagaagagc ccatccacat tctgaatgtg tccatccagt gtgcggacca cctggaggat   4380
gaggcactgg tgccgatttt acgtacattc gtacagtcca agaaaaatat ccttgtggat   4440
tatggactcc gacgaatccc attcttgatt gcccaagaga aagaatttcc caagtttttc   4500
acattcagag caagagatga gtttgcagaa gatcgcattt accgtcactt ggaacctgcc   4560
ctggctttcc agctggaact caaccggatg cgtaacttcg atctgaccgc cgtgccctgt   4620
gccaaccaca agatgcacct ttacctgggt gctgccaagg tggaaggaag gtatgaagtg   4680
acggaccata ggttcttcat ccgtgccatc atcaggcact ctgacctgat cacaaaggaa   4740
gcctccttcg aatacctgca gaacgagggt gagcggctgc tcctggaggc catggacgag   4800
ctggaggtgg cgttcaataa caccaacgtg cgcaccgact gcaaccacat cttcctcaac   4860
ttcgtgccca ctgtcatcat ggaccccaac aagatcgagg agtccgtgcg ctacatggtt   4920
atgcgctacg gcagccggct gtggaaactc cgtgtgctac aggctgaggt caagatcaac   4980
atccgccaga ccaccaccgg cagtgccgtt cccatccgcc tgttcatcac caatgagtcg   5040
ggctactacc tggacatcag cctctacaaa gaagtgactg actccagatc tggaaatatc   5100
atgtttcact ccttcggcaa caagcaaggg ccccagcacg ggatgctgat caatactccc   5160
tacgtcacca aggatctgct ccaggccaag cgattccagg cccagaccct gggaaccacc   5220
tacatctatg acttcccgga aatgttcagg caggctctct ttaaactgtg gggctcccca   5280
gacaagtatc ccaaagacat cctgacatac actgaattag tgttggactc tcagggccag   5340
ctggtggaga tgaaccgact tcctggtgga aatgaggtgg gcatggtggc cttcaaaatg   5400
aggtttaaga cccaggagta cccggaagga cgggatgtga tcgtcatcgg caatgacatc   5460
acctttcgca ttggatcctt tggccctgga gaggaccttc tgtacctgcg ggcatccgag   5520
atggcccggg cagaggcgat tcccaaaatt tacgtggcag ccaacagtgg cgcccgtatt   5580
```

ggcatggcag aggagatcaa acacatgttc cacgtggctt gggtggaccc agaagacccc 5640
cacaaaggat ttaaatacct gtacctgact ccccaagact acaccagaat cagctccctg 5700
aactccgtcc actgtaaaca catcgaggaa ggaggagagt ccagatacat gatcacggat 5760
atcatcggga aggatgatgg cttgggcgtg gagaatctga ggggctcagg catgattgct 5820
ggggagtcct ctctggctta cgaagagatc gtcaccatta gcttggtgac ctgccgagcc 5880
attgggattg gggcctactt ggtgaggctg ggccagcgag tgatccaggt ggagaattcc 5940
cacatcatcc tcacaggagc aagtgctctc aacaaggtcc tgggaagaga ggtctacaca 6000
tccaacaacc agctgggtgg cgttcagatc atgcattaca atggtgtctc ccacatcacc 6060
gtgccagatg actttgaggg ggtttatacc atcctggagt ggctgtccta tatgccaaag 6120
gataatcaca gccctgtccc tatcatcaca cccactgacc ccattgacag agaaattgaa 6180
ttcctcccat ccagagctcc ctacgacccc cggtggatgc ttgcaggaag gcctcaccca 6240
actctgaagg gaacgtggca gagcggattc tttgaccacg gcagtttcaa ggaaatcatg 6300
gcaccctggg cgcagaccgt ggtgacagga cgagcaaggc ttgggggggat tcccgtggga 6360 gtgattgctg tggagacacg gactgtggag gtggcagtcc ctgcagaccc tgccaacctg 6420
gattctgagg ccaagataat tcagcaggca ggacaggtgt ggttcccaga ctcagcctac 6480
aaaaccgccc aggccatcaa ggacttcaac cgggagaagt tgcccctgat gatctttgcc 6540
aactggaggg ggttctccgg tggcatgaaa gacatgtatg accaggtgct gaagtttgga 6600
gcctacatcg tggacggcct tagacaatac aaacagccca tcctgatcta tatccgccct 6660
atgcgggagc tccggggagg ctcctgggtg gtcatagatg ccaccatcaa cccgctgtgc 6720
atagaaatgt atgcagacaa agagagcagg ggtggtgttc tggaaccaga ggggacagtg 6780
gagattaagt tccgaaagga agatctgata aagtccatga gaaggatcga tccagcttac 6840
aagaagctca tggaacagct aggggaacct gatctctccg acaaggaccg aaaggacctg 6900
gagggccggc taaaggctcg cgaggacctg ctgctcccca tctaccacca ggtggcggtg 6960
cagttcgccg acttccatga cacacccggc cggatgctgg agaagggcgt catatctgac 7020
atcctggagt ggaagaccgc acgcaccttc ctgtattggc gtctgcgccg cctcctcctg 7080
gaggaccagg tcaagcagga gatcctgcag gccagcgggg agctgagtca cgtgcatatc 7140
cagtccatgc tgcgtcgctg gttcgtggag acggaggggg ctgtcaaggc ctacttgtgg 7200
gacaacaacc aggtggttgt gcagtggctg gaacagcact ggcaggcagg ggatggcccg 7260
cgctccacca tccgtgagaa catcacgtac ctgaagcacg actctgtcct caagaccatc 7320
cgaggcctgg ttgaagaaaa ccccgaggtg gccgtggact gtgtgatata cctgagccag 7380
cacatcagcc cagctgagcg ggcgcaggtc gttcacctgc tgtctaccat ggacagcccg 7440
gcctccacct ga 7452

<210> SEQ ID NO 119
<211> LENGTH: 3259
<212> TYPE: DNA
<213> ORGANISM: Homo sapiens
<220> FEATURE:
<221> NAME/KEY: misc_feature
<223> OTHER INFORMATION: M31158

<400> SEQUENCE: 119
gacgcgcgcc gggagccggc ggccgggcca gccggcgccg gggcccagtg cgccgcgctc 60
gcagccggta gcgcgccagc cgtaggcgtc gctcggcagc cgcggggccc taggcgtgcc 120

```
gggggagggggg cgagggcggc caggcgcctg ccgccccgga ggcaggatga gcatcgagat    180
cccggcggga ctgacggagc tgctgcaggg cttcacggtg gaggtgctga ggcaccagcc    240
cgcggacctg ctggagttcg cgctgcagca cttcacccgc ctgcagcagg agaacgagcg    300
caaaggcacc gcgcgcttcg gccatgaggg caggacctgg ggggacctgg gcgccgctgc    360
cgggggcggc acccccagca agggggtcaa cttcgccgag gagcccatgc agtccgactc    420
cgaggacggg gaggaggagg aggcggcgcc cgcggacgca ggggcgttca atgctccagt    480
aataaaccga ttcacaaggc gtgcctcagt atgtgcagaa gcttataatc ctgatgaaga    540
agaagatgat gcagagtcca ggattataca tccaaaaact gatgatcaaa gaaataggtt    600
gcaagaggct tgcaaagaca tcctgctgtt taagaatctg gatccggagc agatgtctca    660
agtattagat gccatgtttg aaaaattggt caaagatggg gagcatgtaa ttgatcaagg    720
tgacgatggt gacaactttt atgtaattga tagaggcaca tttgatattt atgtgaaatg    780
tgatggtgtt ggaagatgtg ttggtaacta tgataatcgt gggagtttcg gcgaactggc    840
cttaatgtac aatacaccca gagcagctac aatcactgct acctctcctg gtgctctgtg    900
ggtttggacc agggtaacct tcaggagaat aattgtgaaa aacaatgcca aaaagagaaa    960
aatgtatgaa agctttattg agtcactgcc attccttaaa tctttggagt tttctgaacg   1020
cctgaaagta gtagatgtga taggcaccaa agtatacaac gatggagaac aaatcattgc   1080
tcagggagat tcggctgatt ctttttttcat tgtagaatct ggagaagtga aaattactat   1140
gaaaagaaag ggtaaatcag aagtggaaga gaatggtgca gtagaaatgc ctcgatgctc   1200
gcggggacag tactttggag agcttgccct ggtaactaac aaacctcgag cagcttctgc   1260
ccacgccatt gggactgtca aatgtttagc aatggatgtg caagcatttg aaaggcttct   1320
gggaccttgc atggaaatta tgaaaaggaa catcgctacc tatgaagaac agttagttgc   1380
cctgtttgga acgaacatgg atattgttga acccactgca tgaagcaaaa gtatggagca   1440
agacctgtag tgacaaaatt acacagtagt ggttagtcca ctgagaatgt gtttgtgtag   1500
atgccaagca ttttctgtga tttcaggttt tttcctttt ttacatttac aacgtatcaa   1560
taaacagtag tgatttaata gtcaataggc tttaacatca ctttctaaag agtagttcat   1620
aaaaaaatca acatactgat aaaatgactt tgtactccac aaaattatga ctgaaaggtt   1680
tattaaaatg attgtaatat atagaaagta tctgtgttta agaagataat taaaggatgt   1740
tatcataggc tatatgtgtt ttacttattc agactgataa tcatattagt gactatcccc   1800
atgtaagagg gcacttggca attaaacatg ctacacagca tggcatcact tttttttata   1860
actcattaaa cacagtaaaa ttttaatcat ttttgtttta aagttttcta gcttgataag   1920
ttatgtgctg ccttggccta ttggtgaaat ggtataaaat atcatatgca gttttaaaac   1980
tttttatatt tttgcaataa agtacatttt gactttgttg gcataatgtc agtaacatac   2040
atattccagt ggttttatgg acaggcaatt tagtcattat gataataagg aaaacagtgt   2100
tttagatgag agatcattaa tgcatttttc cctcatcaag catatatctg cttttttttta   2160
ttttgcaatt ctctgtattc tatgtcttta aaaatttgat cttgacattt aatgtcacaa   2220
agttttgttt ttttaaaaag tgatttaaac ttaagatccg acattttttg tattctttaa   2280
gattttacac ctaaaaaatc tctcctatcc caaaaataat gtgggatcct tatcagcatg   2340
cccacagttt atttctttgt tcttcactag gcctgcataa tacagtccta tgtagacatc   2400
tgttcccttg ggtttccgtt ctttcttagg atggttgcca acccacaatc tcattgatca   2460
gcagccaata tgggtttgtt tggttttttt aattcttaaa aacatcctct agaggaatag   2520
```

```
aaacaaattt ttatgagcat aaccctatat aaagacaaaa tgaatttctg accttaccat   2580

atataccatt aggccttgcc attgctttaa tgtagactca tagttgaaat tagtgcagaa   2640

agaactcaga tgtactagat tttcattgtt cattgatatg ctcagtatgc tgccacataa   2700

gatgaattta attatattca accaaagcaa tatactctta catgatttct aggccccatg   2760

acccagtgtc tagagacatt aattctaacc agttgtttgc ttttaaatga gtgatttcat   2820

tttgggaaac aggtttcaaa tgaatatata tacatgggta aaattactct gtgctagtgt   2880

agtcttacta gagaatgttt atggtcccac ttgtatatga aaatgtggtt agaatgttaa   2940

ttggataatg tatatataag aagttaaagt atgtaaagta taacttcagc cacattttta   3000

gaacactgtt taacattttt gcaaaacctt cttgtaggaa aagagagctc tctacatgaa   3060

gatgacttgt tttatatttc agattttatt ttaaaagcca tgtctgttaa acaagaaaaa   3120

acacaaaaga actccagatt cctggttcat cattctgtat tcttactcac tttttcaagt   3180

tatctatttt gttgcataaa ctaattgtta actattcatg gaacagcaaa cgcctgttta   3240

ataaagaact ttgaccaag                                                3259


<210> SEQ ID NO 120
<211> LENGTH: 3261
<212> TYPE: DNA
<213> ORGANISM: Homo sapiens
<220> FEATURE:
<221> NAME/KEY: misc_feature
<223> OTHER INFORMATION: XM_008512

<400> SEQUENCE: 120

gcccgggacc ccacggaggc ggggagacca ctcttctccc acacgagccc agctctccct     60

tcgagtagca accgccttca agctcacaag cacccgtggg cctggggtgt gcctgcgtct    120

agctggttgc acactgggcc acagaggatc cagcaaggat gaagaaatgg agcagcacag    180

acttgggggc agctgcggac ccactccaaa aggacacctg cccagacccc ctggatggag    240

accctaactc caggccacct ccagccaagc cccagctctc cacggccaag agccgcaccc    300

ggctctttgg gaagggtgac tcggaggagg ctttcccggt ggattgccct cacgaggaag    360

gtgagctgga ctcctgcccg accatcacag tcagccctgt tatcaccatc cagaggccag    420

gagacggctc caccggtgcc aggctgctgt cccaggactc tgtcgccgcc agcaccgaga    480

agaccctcag gctctatgat cgcaggagta tctttgaagc cgttgctcag aataactgcc    540

aggatctgga gagcctgctg ctcttcctgc agaagagcaa gaagcacctc acagacaacg    600

agttcaaaga ccctgagaca gggaagacct gtctgctgaa agccatgctc aacctgcatg    660

acggacagaa caccaccatc cccctgctcc tggagatcgc gcggcaaacg gacagcctga    720

aggagcttgt caacgccagc tacacggaca gctactacaa gggccagaca gcactgcaca    780

tcgccatcga gagacgcaac atggccctgg tgaccctcct ggtggagaac ggagcagacg    840

tccaggctgc ggcccatggg gacttcttta agaaaaccaa agggcggcct ggattctact    900

tcggtgaact gcccctgtcc ctggccgcgt gcaccaacca gctgggcatc gtgaagttcc    960

tgctgcagaa ctcctggcag acggccgaca tcagcgccag ggactcggtg ggcaacacgg   1020

tgctgcacgc cctggtggag gtggccgaca acacggccga caacacgaag tttgtgacga   1080

gcatgtacaa tgagattctg atcctggggg ccaaactgca cccgacgctg aagctggagg   1140

agctcaccaa caagaaggga atgacgccgc tggctctggc agctgggacc gggaagatcg   1200

ggtcttggc ctatattctc cagcgggaga tccaggagcc cgagtgcagg cacctgtcca   1260

ggaagttcac cgagtgggcc tacgggcccg tgcactcctc gctgtacgac ctgtcctgca   1320
```

```
tcgacacctg cgagaagaac tcggtgctgg aggtgatcgc ctacagcagc agcgagaccc   1380
ctaatcgcca cgacatgctc ttggtggagc cgctgaaccg actcctgcag gacaagtggg   1440
acagattcgt caagcgcatc ttctacttca acttcctggt ctactgcctg tacatgatca   1500
tcttcaccat ggctgcctac tacaggcccg tggatggctt gcctcccttt aagatggaaa   1560
aaattggaga ctatttccga gttactggag agatcctgtc tgtgttagga ggagtctact   1620
tctttttccg agggattcag tatttcctgc agaggcggcc gtcgatgaag accctgtttg   1680
tggacagcta cagtgagatg cttttctttc tgcagtcact gttcatgctg gccaccgtgg   1740
tgctgtactt cagccacctc aaggagtatg tggcttccat ggtattctcc ctggccttgg   1800
gctggaccaa catgctctac tacacccgcg gtttccagca gatgggcatc tatgccgtca   1860
tgatagagaa gatgatcctg agagacctgt gccgtttcat gtttgtctac atcgtcttct   1920
tgttcgggtt ttccacagcg gtggtgacgc tgattgaaga cgggaagaat gactccctgc   1980
cgtctgagtc cacgtcgcac aggtggcggg ggcctgcctg caggcccccc gatagctcct   2040
acaacagcct gtactccacc tgcctggagc tgttcaagtt caccatcggc atgggcgacc   2100
tggagttcac tgagaactat gacttcaagg ctgtcttcat catcctgctg ctggcctatg   2160
taattctcac ctacatcctc ctgctcaaca tgctcatcgc cctcatgggt gagactgtca   2220
acaagatcgc acaggagagc aagaacatct ggaagctgca gagagccatc accatcctgg   2280
acacggagaa gagcttcctt aagtgcatga ggaaggcctt ccgctcaggc aagctgctgc   2340
aggtggggta cacacctgat ggcaaggacg actaccggtg gtgcttcagg gtggacgagg   2400
tgaactggac cacctggaac accaacgtgg gcatcatcaa cgaagacccg ggcaactgtg   2460
agggcgtcaa gcgcaccctg agcttctccc tgcggtcaag cagagtttca ggcagacact   2520
ggaagaactt tgccctggtc cccctttttaa gagaggcaag tgctcgagat aggcagtctg   2580
ctcagcccga ggaagtttat ctgcgacagt tttcagggtc tctgaagcca gaggacgctg   2640
aggtcttcaa gagtcctgcc gcttccgggg agaagtgagg acgtcacgca gacagcactg   2700
tcaacactgg gccttaggag accccgttgc cacgggggc tgctgaggga acaccagtgc   2760
tctgtcagca gcctggcctg gtctgtgcct gcccagcatg ttcccaaatc tgtgctggac   2820
aagctgtggg aagcgttctt ggaagcatgg ggagtgatgt acatccaacc gtcactgtcc   2880
ccaagtgaat ctcctaacag actttcaggt ttttactcac tttactaaac agtttggatg   2940
gtcagtctct actgggacat gttaggccct tgttttcttt gattttattc tttttttga   3000
gacagaattt cactcttctc acccaggctg gaatgcagtg gcacaatttt ggctccctgc   3060
aacctccgcc tcctggattc cagcaattct cctgcctcgg cttcccaagt agctgggatt   3120
acaggcacgt gccaccatgt ctggctaatt ttttgtattt ttttaataga tatggggttt   3180
cgccatgttg gccaggctgg tctcgaactc ctgacctcag gtgatccgcc cacctcggcc   3240
tcccaaagtg ctgggattac a                                              3261
```

<210> SEQ ID NO 121
<211> LENGTH: 4307
<212> TYPE: DNA
<213> ORGANISM: Homo sapiens
<220> FEATURE:
<221> NAME/KEY: misc_feature
<223> OTHER INFORMATION: NM_005099

<400> SEQUENCE: 121

```
cacagacaca tatgcacgag agagacagag gaggaaagag acagagacaa aggcacagcg     60
```

-continued gaagaaggca gagacagggc aggcacagaa gcggcccaga cagagtccta cagagggaga 120
ggccagagaa gctgcagaag acacaggcag ggagagacaa agatccagga aaggagggct 180
caggaggaga gtttggagaa gccagacccc tgggcacctc tcccaagccc aaggactaag 240
ttttctccat ttcctttaac ggtcctcagc ccttctgaaa actttgcctc tgaccttggc 300
aggagtccaa gcccccaggc tacagagagg agctttccaa agctagggtg tggaggactt 360
ggtgccctag acggcctcag tccctcccag ctgcagtacc agtgccatgt cccagacagg 420
ctcgcatccc gggaggggct tggcagggcg ctggctgtgg ggagcccaac cctgcctcct 480
gctccccatt gtgccgctct cctggctggt gtggctgctt ctgctactgc tggcctctct 540
cctgccctca gcccggctgg ccagccccct cccccgggag gaggagatcg tgtttccaga 600
gaagctcaac ggcagcgtcc tgcctggctc gggcacccct gccaggctgt tgtgccgctt 660
gcaggccttt ggggagacgc tgctactaga gctggagcag gactccggtg tgcaggtcga 720
ggggctgaca gtgcagtacc tgggccaggc gcctgagctg ctgggtggag cagagcctgg 780
cacctacctg actggcacca tcaatggaga tccggagtcg gtggcatctc tgcactggga 840
tgggggagcc ctgttaggcg tgttacaata tcggggggct gaactccacc tccagcccct 900
ggagggaggc accccctaact ctgctggggg acctggggct cacatcctac gccggaagag 960
tcctgccagc ggtcaaggtc ccatgtgcaa cgtcaaggct cctcttggaa gccccagccc 1020
cagaccccga agagccaagc gctttgcttc actgagtaga tttgtggaga cactggtggt 1080
ggcagatgac aagatggccg cattccacgg tgcggggcta aagcgctacc tgctaacagt 1140
gatggcagca gcagccaagg ccttcaagca cccaagcatc cgcaatcctg tcagcttggt 1200
ggtgactcgg ctagtgatcc tggggtcagg cgaggagggg ccccaagtgg ggcccagtgc 1260
tgcccagacc ctgcgcagct tctgtgcctg gcagcggggc ctcaacaccc ctgaggactc 1320
ggaccctgac cactttgaca cagccattct gtttacccgt caggacctgt gtggagtctc 1380
cacttgcgac acgctgggta tggctgatgt gggcaccgtc tgtgacccgg ctcggagctg 1440
tgccattgtg gaggatgatg ggctccagtc agccttcact gctgctcatg aactgggtca 1500
tgtcttcaac atgctccatg acaactccaa gccatgcatc agtttgaatg ggcctttgag 1560
cacctctcgc catgtcatgg cccctgtgat ggctcatgtg gatcctgagg agccctggtc 1620
cccctgcagt gcccgcttca tcactgactt cctggacaat ggctatgggc actgtctctt 1680
agacaaacca gaggctccat tgcatctgcc tgtgactttc cctggcaagg actatgatgc 1740
tgaccgccag tgccagctga ccttcgggcc cgactcacgc cattgtccac agctgccgcc 1800
gccctgtgct gccctctggt gctctggcca cctcaatggc catgccatgt gccagaccaa 1860
acactcgccc tgggccgatg gcacaccctg cgggcccgca caggcctgca tgggtggtcg 1920
ctgcctccac atggaccagc tccaggactt caatattcca caggctggtg gctggggtcc 1980
ttggggacca tggggtgact gctctcggac ctgtgggggt ggtgtccagt tctcctcccg 2040
agactgcacg aggcctgtcc cccggaatgg tggcaagtac tgtgagggcc gccgtacccg 2100
cttccgctcc tgcaacactg aggactgccc aactggctca gccctgacct tccgcgagga 2160
gcagtgtgct gcctacaacc accgcaccga cctcttcaag agcttcccag ggcccatgga 2220
ctgggttcct cgctacacag gcgtggcccc ccaggaccag tgcaaactca cctgccaggc 2280
ccgggcactg ggctactact atgtgctgga gccacgggtg gtagatggga ccccctgttc 2340
cccggacagc tcctcggtct gtgtccaggg ccgatgcatc catgctggct gtgatcgcat 2400
cattggctcc aagaagaagt ttgacaagtg catggtgtgc ggaggggacg gttctggttg 2460

```
cagcaagcag tcaggctcct tcaggaaatt caggtacgga tacaacaatg tggtcactat   2520

ccccgcgggg gccacccaca ttcttgtccg gcagcaggga aaccctggcc accggagcat   2580

ctacttggcc ctgaagctgc cagatggctc ctatgccctc aatggtgaat acacgctgat   2640

gccctccccc acagatgtgg tactgcctgg ggcagtcagc ttgcgctaca gcggggccac   2700

tgcagcctca gagacactgt caggccatgg gccactggcc cagcctttga cactgcaagt   2760

cctagtggct ggcaaccccc aggacacacg cctccgatac agcttcttcg tgccccggcc   2820

gaccccttca acgccacgcc ccactcccca ggactggctg caccgaagag cacagattct   2880

ggagatcctt cggcggcgcc cctgggcggg caggaaataa cctcactatc ccggctgccc   2940

tttctgggca ccggggcctc ggacttagct gggagaaaga gagagcttct gttgctgcct   3000

catgctaaga ctcagtgggg aggggctgtg ggcgtgagac ctgcccctcc tctctgccct   3060

aatgcgcagg ctggccctgc cctggtttcc tgccctggga ggcagtgatg ggttagtgga   3120

tggaaggggc tgacagacag ccctccatct aaactgcccc ctctgccctg cgggtcacag   3180

gagggagggg gaaggcaggg agggcctggg ccccagttgt atttatttag tatttattca   3240

cttttattta gcaccaggga aggggacaag gactagggtc ctggggaacc tgacccctga   3300

cccctcatag ccctcaccct ggggctagga aatccagggt ggtggtgata ggtataagtg   3360

gtgtgtgtat gcgtgtgtgt gtgtgtgtga aaatgtgtgt gtgcttatgt atgaggtaca   3420

acctgttctg ctttcctctt cctgaatttt atttttgggg aaaagaaaag tcaagggtag   3480

ggtgggcctt cagggagtga gggattatct tttttttttt ttctttcttt ctttcttttt   3540

ttttttgag acagaatctc gctctgtcgc ccaggctgga gtgcaatggc acaatctcgg   3600

ctcactgcat cctccgcctc ccgggttcaa gtgattctca tgcctcagcc tcctgagtag   3660

ctgggattac aggctcctgc caccacgccc agctaatttt tgttttgttt tgtttggaga   3720

cagagtctcg ctattgtcac cagggctgga atgatttcag ctcactgcaa ccttcgccac   3780

ctgggttcca gcaattctcc tgcctcagcc tcccgagtag ctgagattat aggcacctac   3840

caccacgccc ggctaatttt tgtattttta gtagagacgg ggtttcacca tgttggccag   3900

gctggtctcg aactcctgac cttaggtgat ccactcgcct tcatctccca aagtgctggg   3960

attacaggcg tgagccaccg tgcctggcca cgcccaacta atttttgtat ttttagtaga   4020

gacagggttt caccatgttg gccaggctgc tcttgaactc ctgacctcag gtaatcgacc   4080

tgcctcggcc tcccaaagtg ctgggattac aggtgtgagc caccacgccc ggtacatatt   4140

ttttaaattg aattctacta tttatgtgat ccttttggag tcagacagat gtggttgcat   4200

cctaactcca tgtctctgag cattagattt ctcatttgcc aataataata cctcccttag   4260

aagtttgttg tgaggattaa ataatgtaaa taaagaacta gcataac                4307
```

<210> SEQ ID NO 122
<211> LENGTH: 1423
<212> TYPE: DNA
<213> ORGANISM: Homo sapiens
<220> FEATURE:
<221> NAME/KEY: misc_feature
<223> OTHER INFORMATION: U94320

<400> SEQUENCE: 122

```
gaaaggctat cggtaacaac tgacctgcca caaagttaga agaaaggatt gattcaagaa     60

agactataat atggatttag agctcgacga gtattataac aagacacttg ccacagagaa    120

taatactgct gccactcgga attctgattt cccagtctgg gatgactata aaagcagtgt    180

agatgactta cagtattttc tgattgggct ctatacattt gtaagtcttc ttggctttat    240
```

```
ggggaatcta cttattttaa tggctctcat gaaaaagcgt aatcagaaga ctacggtaaa    300

cttcctcata ggcaatctgg ccttttctga tatcttggtt gtgctgtttt gctcaccttt    360

cacactgacg tctgtcttgc tggatcagtg gatgtttggc aaagtcatgt gccatattat    420

gccttttctt caatgtgtgt cagttttggt ttcaacttta attttaatat caattgccat    480

tgtcaggtat catatgataa aacatcccat atctaataat ttaacagcaa accatggcta    540

ctttctgata gctactgtct ggacactagg ttttgccatc tgttctcccc ttccagtgtt    600

tcacagtctt gtggaacttc aagaaacatt tggttcagca ttgctgagca gcaggtattt    660

atgtgttgag tcatggccat ctgattcata cagaattgcc tttactatct ctttattgct    720

agttcagtat attctgccct tagtttgtct tactgtaagt catacaagtg tctgcagaag    780

tataagctgt ggattgtcca acaaagaaaa cagacttgaa gaaaatgaga tgatcaactt    840

aactcttcat ccatccaaaa agagtgggcc tcaggtgaaa ctctctggca gccataaatg    900

gagttattca ttcatcaaaa aacacagaag aagatatagc aagaagacag catgtgtgtt    960

acctgctcca gaaagacctt ctcaagagaa ccactccaga atacttccag aaaactttgg   1020

ctctgtaaga agtcagctct cttcatccag taagttcata ccaggggtcc ccacttgctt   1080

tgagataaaa cctgaagaaa attcagatgt tcatgaattg agagtaaaac gttctgttac   1140

aagaataaaa aagagatctc gaagtgtttt ctacagactg accatactga tattagtatt   1200

tgctgttagt tggatgccac tacacctttt ccatgtggta actgatttta atgacaatct   1260

tatttcaaat aggcatttca agttggtgta ttgcatttgt catttgttgg gcatgatgtc   1320

ctgttgtctt aatccaattc tatatgggtt tcttaataat gggattaaag ctgatttagt   1380

gtcccttata cactgtcttc atatgtaata attctcactg ttt                     1423
```

<210> SEQ ID NO 123
<211> LENGTH: 5078
<212> TYPE: DNA
<213> ORGANISM: Homo sapiens
<220> FEATURE:
<221> NAME/KEY: misc_feature
<223> OTHER INFORMATION: NM_002410

<400> SEQUENCE: 123

```
taatactcct ttattccctg ttttaaaaat ttttttaaat ttgatacaat aattatacat     60

aataatggag taccatgtga gattcaatcc acatatacat tgtgaaatga tcaaattagg    120

atagttagca tgcacatcac ccccaaataa ttattacttt tgtggtgaga acacttaaaa    180

ttgtctcttt tagaaatata cgttattatt aaccatagtc acctcgctgt gcaatagaac    240

accagaactt attcctccta aatgtaactt tttacccatt gaccactccc tcctcacccc    300

cctctctcct ccccacccct ggtaaccact gttctgttat ctcctatgat agcaactttt    360

tagcttctgc atgtgagatt gtacggtagt tgcctttctg tgcctggatt atttcattta    420

gcataatgtc cttcgggtat atccctgttg ctgcaaaaga caggatttct ctctcttttt    480

ctggttgaat agtattccat tgtcagagaa tgttgtaaga ctaggaaagg aacactgcag    540

gctggagccc tggggaaatg gtctgaggca ggtggtggga ctagagctgg ggtctggcaa    600

acaggctggg tttgattgtc agcataatag agagcactca tgtgccagct gggtgggagg    660

agcagccgag tgaagaaggg gaagcctctc aggaagcatg tgcagggttt atggtaatga    720

gcagaccagc aggtacgtag tgggagaggg gtgtgatggg gcagaggaac ttacgttatg    780

atagtacaag acagaggttg agcctcattt taataggcat tgtggtgggt gttgaatagt    840
```

-continued

```
gatggaatgt atgggtctgg aatcaggctg cctggtcaag ggctctgaaa catgagtgtg    900
catcagaatc acctcgaggc ttgttaaagg ataggctgtg gaccacatct cctcagttgc    960
tgattcagtg ggtgtgggtg gggcctgaga attcacattt cccactggtg atgctgctgt   1020
tactgattgg gaccacattt ggggaacact ggtctagaat tgagaggttg gcaaaccttc   1080
tctgttaaga ggtagatagt aaatatttta ggccttctgg gctacaaaga gtatctgtta   1140
catatttttt attgcttttc atgacccatt aagcatatat atatcattct ctgccatata   1200
caaacaggct gttgggggag tgaggatgat gtagggaagg tggggcatgg tttaataacc   1260
cctgggccat gcctagatga tcagtcctct gccacatagc tggctgacct ttgccaagtt   1320
aatcaccttt tacctttatt ttctcatgtt tctaataaaa cagagacgat aatattcata   1380
cttcttacca tatagaactt ctgaggattc agtgagcaaa gccacaaaag atggtatgtc   1440
acaatatctg ggatatagct agaatttata atttattttt actctgttga taggcaatgg   1500
gaaaacagta agaggcagac caacagtgat ccagggctct gaaagctaat tgcttcaaga   1560
tcctgctacc attttctttt gggccgcttg caaagaagaa tcctttgact gaagcatgta   1620
tgtacactct gaagtacagc ctgggttagt ctcttataag ggatcggatc attgctcagc   1680
tctcccttga gtggcactta gaaaatggcg ctattcgtaa gctgactggt attgggccca   1740
ggactctggc tgaaggggtg ggcatgctgg taaccatttg caacctatgc tcaggtccta   1800
cttgttggga agccctgatt gagaagagtg gcctggtctg tgctggcatt agataggatc   1860
tggctgcatt aatattgaaa ctactctgcc ttttaatgtc tcattttgcc tcatggtggg   1920
agtgaaagtg agaaccacag aaaatctgcc tgccaggtgt tccacatttc ttgtgctaca   1980
gcatgcaagt gagcagtgag gtgtaccttt tcctcatgta gctgggaaag caatacccct   2040
gcttgtacct ctggcatatc ttctctgtgc tggtgcacct agagaggttg cctggtggcc   2100
ctgagagagc catctcatca ctaaacactg atggtgaaaa gctggccatg ctcaaataag   2160
atgtagcaat ctacctcttc tttgtctagt tacccccaag gggcatccca ctttcttgct   2220
cacctcacca gttgcatgtt ctagtccttg ccagaagcac ataataatga ctttgtaagc   2280
ttaagttaca ggcacacaaa agggcctgat ggtgatatga ctccaccctc cccgtttttg   2340
ctgacattcc gccaaatatc cttctgtctc ctccccacct tgcaaaacaa acttcctgtt   2400
ttgaatttgg tccaggctgg aacagcccca ccacacctgt taacacacgc agacgcacac   2460
ttccccccttc ataattgctt agcttcttgt tgcctagcca gatttcccct cagcttacag   2520
ttcctgaatc ataagatatt gaaccagcaa atttaagagt tgacatttta cttagaggta   2580
ttcaagtgaa aacatggctt ctggtttatt ttgctgtatt gtgccatgac cacttggcta   2640
attcttctcc tccttcacat cagaatggaa gtgaggaaag gcaaccagct gacacaggag   2700
ccagagtgag accagcagac tctcacactc aacctacacc atgaatttgt gtctatcttc   2760
tacgcgttaa gagccaagga caggtgaagt tgccagagag caatggctct cttcactccg   2820
tggaagttgt cctctcagaa gctgggcttt ttcctggtga cttttggctt catttggggt   2880
atgatgcttc tgcactttac catccagcag cgaactcagc ctgaaagcag ctccatgctg   2940
cgcgagcaga tcctggacct cagcaaaagg tacatcaagg cactggcaga agaaaacagg   3000
aatgtggtgg atgggccata cgctggagtc atgacagctt atgatctgaa gaaaaccctt   3060
gctgtgttat tagataacat tttgcagcgc attggcaagt tggagtcgaa ggtggacaat   3120
cttgttgtca atggcaccgg aacaaactca accaactcca ctacagctgt tcccagcttg   3180
gttgcacttg agaaaattaa tgtggcagat atcattaacg gagctcaaga aaaatgtgta   3240
```

```
ttgcctccta tggacggcta ccctcactgt gagggaaaga tcaagtggat gaaagacatg   3300
tggcgttcag atccctgcta cgcagactat ggagtggatg gatccacctg ctcttttttt   3360
atttacctca gtgaggttga aaattggtgt cctcatttac cttggagagc aaaaaatccc   3420
tacgaagaag ctgatcataa ttcattggcg gaaattcgta cagattttaa tattctctac   3480
agtatgatga aaaagcatga agaattccgg tggatgagac tacggatccg gcgaatggct   3540
gacgcatgga tccaagcaat caagtccctg gcagaaaagc agaaccttga aaagagaaag   3600
cggaagaaag tcctcgttca cctgggactc ctgaccaagg aatctggatt taagattgca   3660
gagacagctt tcagtggtgg ccctcttggt gaattagttc aatggagtga tttaattaca   3720
tctctgtact tactgggcca tgacattagg atttcagctt cactggctga gctcaaggaa   3780
atcatgaaga aggttgtagg aaaccgatct ggctgcccaa ctgtaggaga cagaattgtt   3840
gagctcattt acattgatat tgtaggactt gctcaattca agaaaactct tggaccatcc   3900
tgggttcatt accagtgcat gctccgagtc cttgattcat ttggtactga acccgaattt   3960
aatcatgcaa attatgccca atcgaaaggc cacaagaccc cttgggggaa atggaatctg   4020
aaccctcagc agttttatac catgttccct catacccccag acaacagctt tctggggttt   4080
gtggttgagc agcacctgaa ctccagtgat atccaccaca ttaatgaaat caaaaggcag   4140
aaccagtccc ttgtgtatgg caaagtggat agcttctgga agaataagaa gatctacttg   4200
gacattattc acacatacat ggaagtgcat gcaactgttt atggctccag cacaaagaat   4260
attcccagtt acgtgaaaaa ccatggtatc ctcagtggac gggacctgca gttccttctt   4320
cgagaaacca agttgtttgt tggacttggg ttcccttacg agggcccagc tcccctggaa   4380
gctatcgcaa atggatgtgc ttttctgaat cccaagttca acccacccaa aagcagcaaa   4440
aacacagact tttcattgg caagccaact ctgagagagc tgacatccca gcatccttac   4500
gctgaagttt tcatcgggcg gccacatgtg tggactgttg acctcaacaa tcaggaggaa   4560
gtagaggatg cagtgaaagc aattttaaat cagaagattg agccatacat gccatatgaa   4620
tttacgtgcg aggggatgct acagagaatc aatgctttca ttgaaaaaca ggacttctgc   4680
catgggcaag tgatgtggcc acccctcagc gccctacagg tcaagcttgc tgagcccggg   4740
cagtcctgca agcaggtgtg ccaggagagc cagctcatct gcgagccttc tttcttccag   4800
cacctcaaca aggacaagga catgctgaag tacaaggtga cctgccaaag ctcagagctg   4860
gccaaggaca tcctggtgcc ctcctttgac cctaagaata agcactgtgt gtttcaaggt   4920
gacctcctgc tcttcagctg tgcaggcgcc caccccaggc accagagggt ctgcccctgc   4980
cgggacttca tcaagggcca ggtggctctc tgcaaagact gcctatagca gctacctgct   5040
cagccctgca ccatgctgct ggggaagaca gtggcccc                           5078
```

<210> SEQ ID NO 124
<211> LENGTH: 887
<212> TYPE: DNA
<213> ORGANISM: Homo sapiens
<220> FEATURE:
<221> NAME/KEY: misc_feature
<223> OTHER INFORMATION: X16863

<400> SEQUENCE: 124

```
tctttggtga cttgtccact ccagtgtggc atcatgtggc agctgctcct cccaactgct     60
ctgctacttc tagtttcagc tggcatgcgg actgaagatc tcccaaaggc tgtggtgttc    120
ctggagcctc aatggtacag cgtgcttgag aaggacagtg tgactctgaa gtgccaggga    180
gcctactccc ctgaggacaa ttccacacag tggtttcaca atgagagcct catctcaagc    240
```

```
caggcctcga gctacttcat tgacgctgcc acagtcaacg acagtggaga gtacaggtgc    300

cagacaaacc tctccaccct cagtgacccg gtgcagctag aagtccatat cggctggctg    360

ttgctccagg cccctcggtg ggtgttcaag gaggaagacc ctattcacct gaggtgtcac    420

agctggaaga acactgctct gcataaggtc acatatttac agaatggcaa agacaggaag    480

tattttcatc ataattctga cttccacatt ccaaaagcca cactcaaaga tagcggctcc    540

tacttctgca gggggcttgt tgggagtaaa aatgtgtctt cagagactgt gaacatcacc    600

atcactcaag gtttggcagt gtcaaccatc tcatcattct ctccacctgg gtaccaagtc    660

tctttctgct tggtgatggt actccttttt gcagtggaca caggactata tttctctgtg    720

aagacaaaca tttgaagctc aacaagagac tggaaggacc ataaacttaa atggagaaag    780

gaccctcaag acaaatgacc cccatcccat gggagtaata agagcagtgg cagcagcatc    840

tctgaacatt tctctggatt tgcaacccca tcatcctcag gcctctc                  887
```

<210> SEQ ID NO 125
<211> LENGTH: 1800
<212> TYPE: DNA
<213> ORGANISM: Homo sapiens
<220> FEATURE:
<221> NAME/KEY: misc_feature
<223> OTHER INFORMATION: XM_042961

<400> SEQUENCE: 125

```
cttctctgcc agaagatacc atttcaactt taacacagca tgatcgaaac atacaaccaa     60

acttctcccc gatctgcggc cactggactg cccatcagca tgaaaatttt tatgtattta    120

cttactgttt ttcttatcac ccagatgatt gggtcagcac tttttgctgt gtatcttcat    180

agaaggttgg acaagataga agatgaaagg aatcttcatg aagattttgt attcatgaaa    240

acgatacaga gatgcaacac aggagaaaga tccttatcct tactgaactg tgaggagatt    300

aaaagccagt ttgaaggctt tgtgaaggat ataatgttaa acaaagagga gacgaagaaa    360

gaaaacagct ttgaaatgca aaaaggtgat cagaatcctc aaattgcggc acatgtcata    420

agtgaggcca gcagtaaaac aacatctgtg ttacagtggg ctgaaaaagg atactacacc    480

atgagcaaca acttggtaac cctggaaaat gggaaacagc tgaccgttaa aagacaagga    540

ctctattata tctatgccca agtcaccttc tgttccaatc gggaagcttc gagtcaagct    600

ccatttatag ccagcctctg cctaaagtcc cccggtagat tcgagagaat cttactcaga    660

gctgcaaata cccacagttc cgccaaacct tgcgggcaac aatccattca cttgggagga    720

gtatttgaat tgcaaccagg tgcttcggtg tttgtcaatg tgactgatcc aagccaagtg    780

agccatggca ctggcttcac gtcctttggc ttactcaaac tctgaacagt gtcaccttgc    840

aggctgtggt ggagctgacg ctgggagtct tcataataca gcacagcggt taagcccacc    900

ccctgttaac tgcctattta taaccctagg atcctcctta tggagaacta tttattatac    960

actccaaggc atgtagaact gtaataagtg aattacaggt cacatgaaac caaaacgggc   1020

cctgctccat aagagcttat atatctgaag cagcaacccc actgatgcag acatccagag   1080

agtcctatga aaagacaagg ccattatgca caggttgaat tctgagtaaa cagcagataa   1140

cttgccaagt tcagttttgt ttctttgcgt gcagtgtctt tccatggata atgcatttga   1200

tttatcagtg aagatgcaga agggaaatgg ggagcctcag ctcacattca gttatggttg   1260

actctgggtt cctatggcct tgttggaggg ggccaggctc tagaacgtct aacacagtgg   1320

agaaccgaaa cccccccccc ccccccgcca ccctctcgga cagttattca ttctctttca   1380
```

```
atctctctct ctccatctct ctctttcagt ctctctctct caacctcttt cttccaatct   1440

ctctttctca atctctctgt ttccctttgt cagtctcttc cctcccccag tctctcttct   1500

caatccccct ttctaacaca cacacacaca cacacacaca cacacacaca cacacacaca   1560

cacacacaga gtcaggccgt tgctagtcag ttctcttctt tccaccctgt ccctatctct   1620

accactatag atgagggtga ggagtaggga gtgcagccct gagcctgccc actcctcatt   1680

acgaaatgac tgtatttaaa ggaaatctat tgtatctacc tgcagtctcc attgtttcca   1740

gagtgaactt gtaattatct tgttatttat tttttgaata ataaagacct cttaacatta   1800
```

<210> SEQ ID NO 126
<211> LENGTH: 1450
<212> TYPE: DNA
<213> ORGANISM: Homo sapiens
<220> FEATURE:
<221> NAME/KEY: misc_feature
<223> OTHER INFORMATION: J04101

<400> SEQUENCE: 126

```
ttgggaagaa agtcggattt cccccgtccc cttccccctg ttactaatcc tcattaaaaa     60

gaaaaacaac aataactgca aacttgctac catcccgtac gtcccccact cctggcacca    120

tgaaggcggc cgtcgatctc aagccgactc tcaccatcat caagacggaa aaagtcgatc    180

tggagctttt cccctccccg gatatggaat gtgcagatgt ccccactatta actccaagca    240

gcaaagaaat gatgtctcaa gcattaaaag ctactttcag tggtttcact aaagaacagc    300

aacgactggg gatcccaaaa gacccccggc agtggacaga aacccatgtt cgggactggg    360

tgatgtgggc tgtgaatgaa ttcagcctga aaggtgtaga cttccagaag ttctgtatga    420

atggagcagc cctctgcgcc ctgggtaaag actgctttct cgagctggcc ccagactttg    480

ttggggacat cttatgggaa catctagaga tcctgcagaa agaggatgtg aaaccatatc    540

aagttaatgg agtcaaccca gcctatccag aatcccgcta tacctcggat tacttcatta    600

gctatggtat tgagcatgcc cagtgtgttc caccatcgga gttctcagag cccagcttca    660

tcacagagtc ctatcagacg ctccatccca tcagctcgga agagctcctc tccctcaagt    720

atgagaatga ctacccctcg gtcattctcc gagaccctct ccagacagac accttgcaga    780

atgactactt tgctatcaaa caagaagtcg tcaccccaga caacatgtgc atggggagga    840

ccagtcgtgg taaactcggg ggccaggact cttttgaaag catagagagc tacgatagtt    900

gtgatcgcct cacccagtcc tggagcagcc agtcatcttt caacagcctg cagcgtgttc    960

cctcctatga cagcttcgac tcagaggact atccggctgc cctgcccaac cacaagccca   1020

agggcacctt caaggactat gtgcgggacc gtgctgacct caataaggac aagcctgtca   1080

ttcctgctgc tgccctagct ggctacacag gcagtggacc aatccagcta tggcagtttc   1140

ttctggaatt actcactgat aaatcctgtc agtcttttat cagctggaca ggagatggct   1200

gggaattcaa actttctgac ccagatgagg tggccaggag atggggaaag aggaaaaaca   1260

aacctaagat gaattatgag aaactgagcc gtggcctacg ctactattac gacaaaaaca   1320

tcatccacaa gacagcgggg aaacgctacg tgtaccgctt tgtgtgtgac ctgcagagcc   1380

tgctggggta cacccctgag gagctgcacg ccatgctgga cgtcaagcca gatgccgacg   1440

agtgatggca                                                          1450
```

<210> SEQ ID NO 127
<211> LENGTH: 6069
<212> TYPE: DNA
<213> ORGANISM: Homo sapiens
<220> FEATURE:
<221> NAME/KEY: misc_feature
<223> OTHER INFORMATION: XM_047802

<400> SEQUENCE: 127

```
gcagctgccg actggggatg acggcgggca ggaggagacc gcagccgaag ggacacagac     60
acgccgcttc accagctcgc ctcaggctgc ccccctgcat ttttgtttta atttttacgg    120
ctttttcccc tctctttctt cccttcctcc tggtcccagc agagccaagg aaacccacaa    180
aataagaaag gaagtgggcc ccggagcttg gaacctccac agccggcttg tccagcgcag    240
cgcgggggcg ggaggctgcg cgcaccagtt gccagcccgg tgcgcggtac ctttccttac    300
ttttcttgaa acagcgatcg tgcctgcatt tggtggtttt ttggtttttg tttttttcct    360
tttcccgtat ttgctgaatc tccactatcc gacttttttt ttttaatctt ttctttcccc    420
cccccccac cccacctctt tctggagcac gaatccaaac attttcccaa gcaacaaaga    480
aaagttcgca cgctggcacc gcagcccgga caggctggcg ctgctgccgg gcccccctcc    540
ctccgacact tgactcaatc ctgcaagcaa gtgtgtgtgt gtccccatcc cccgccccgt    600
taacttcata gcaaataaca aatacccata aagtcccagt cgcgcagccc ctccccgcgg    660
gcagcgcact atgctgctcg ggtgggcgtc cctgctgctg tgcgcgttcc gcctgcccct    720
ggccgcggtc ggccccgccg cgacacctgc ccaggataaa gccgggcagc ctccgactgc    780
tgcagcagcc gcccagcccc gccggcggca gggggaggag gtgcaggagc gagccgagcc    840
tcccggccac ccgcaccccc tggcgcagcg gcgcaggagc aaggggctgg tgcagaacat    900
cgaccaactc tactccggcg gcggcaaggt gggctacctc gtctacgcgg gcggccggag    960
gttcctcttg gacctggagc gagatggttc ggtgggcatt gctggcttcg tgcccgcagg   1020
aggcgggacg agtgcgccct ggcgccaccg gagccactgc ttctatcggg gcacagtgga   1080
cggtagtccc cgctctctgg ctgtctttga cctctgtggg ggtctcgacg gcttcttcgc   1140
ggtcaagcac gcgcgctaca ccctaaagcc actgctgcgc ggaccctggg cggaggaaga   1200
aaaggggcgc gtgtacgggg atgggtccgc acggatcctg cacgtctaca cccgcgaggg   1260
cttcagcttc gaggccctgc cgccgcgcgc cagctgcgaa acccccgcgt ccacaccgga   1320
ggcccacgag catgctccgg cgcacagcaa cccgagcgga cgcgcagcac tggcctcgca   1380
gctcttggac cagtccgctc tctcgcccgc tgggggctca ggaccgcaga cgtggtggcg   1440
gcggcggcgc cgctccatct cccgggcccg ccaggtggag ctgcttctgg tggctgacgc   1500
gtccatggcg cggttgtatg gccggggcct gcagcattac ctgctgaccc tggcctccat   1560
cgccaatagg ctgtacagcc atgctagcat cgagaaccac atccgcctgg ccgtggtgaa   1620
ggtggtggtg ctaggcgaca aggacaagag cctggaagtg agcaagaacg ctgccaccac   1680
actcaagaac ttttgcaagt ggcagcacca acacaaccag ctgggagatg accatgagga   1740
gcactacgat gcagctatcc tgtttactcg ggaggattta tgtgggcatc attcatgtga   1800
caccctggga atggcagacg ttgggaccat atgttctcca gagcgcagct gtgctgtgat   1860
tgaagacgat ggcctccacg cagccttcac tgtggctcac gaaatcggac atttacttgg   1920
cctctcccat gacgattcca aattctgtga agagaccttt ggttccacag aagataagcg   1980
cttaatgtct tccatcctta ccagcattga tgcatctaag ccctggtcca aatgcacttc   2040
agccaccatc acagaattcc tggatgatgg ccatggtaac tgtttgctgg acctaccacg   2100
aaagcagatc ctgggccccg aagaactccc aggacagacc tacgatgcca cccagcagtg   2160
caacctgaca ttcgggcctg agtactccgt gtgtcccggc atggatgtct gtgctcgcct   2220
```

-continued

```
gtggtgtgct gtggtacgcc agggccagat ggtctgtctg accaagaagc tgcctgcggt   2280
ggaagggacg ccttgtggaa aggggagaat ctgcctgcag ggcaaatgtg tggacaaaac   2340
caagaaaaaa tattattcaa cgtcaagcca tggcaactgg ggatcttggg gatcctgggg   2400
ccagtgttct cgctcatgtg gaggaggagt gcagtttgcc tatcgtcact gtaataaccc   2460
tgctcccaga aacaacggac gctactgcac agggaagagg gccatctacc gctcctgcag   2520
tctcatgccc tgcccaccca atggtaaatc atttcgtcat gaacagtgtg aggccaaaaa   2580
tggctatcag tctgatgcaa aaggagtcaa aacttttgtg gaatgggttc ccaaatatgc   2640
aggtgtcctg ccagcggatg tgtgcaagct gacctgcaga gccaagggca ctggctacta   2700
tgtggtattt tctccaaagg tgaccgatgg cactgaatgt aggctgtaca gtaattccgt   2760
ctgcgtccgg gggaagtgtg tgagaactgg ctgtgacggc atcattggct caaagctgca   2820
gtatgacaag tgcggagtat gtggaggaga caactccagc tgtacaaaga ttgttggaac   2880
ctttaataag aaaagtaagg gttacactga cgtggtgagg attcctgaag ggcaacccca   2940
cataaaagtt cgacagttca aagccaaaga ccagactaga ttcactgcct atttagccct   3000
gaaaaagaaa aacggtgagt accttatcaa tggaaagtac atgatctcca cttcagagac   3060
tatcattgac atcaatggaa cagtcatgaa ctatagcggt tggagccaca gggatgactt   3120
cctgcatggc atgggctact ctgccacgaa ggaaattcta atagtgcaga ttcttgcaac   3180
agaccccact aaaccattag atgtccgtta tagctttttt gttcccaaga agtccactcc   3240
aaaagtaaac tctgtcacta gtcatggcag caataaagtg ggatcacaca cttcgcagcc   3300
gcagtgggtc acgggcccat ggctcgcctg ctctaggacc tgtgacacag gttggcacac   3360
cagaacggtg cagtgccagg atggaaaccg gaagttagca aaaggatgtc ctctctccca   3420
aaggccttct gcgtttaagc aatgcttgtt gaagaaatgt tagcctgtgg ttatgatctt   3480
atgcacaaag ataactggag gattcagcac tgatgcagtc gtggtgaaca ggaggtctac   3540
ctaacgcaca gaaagtcatg cttcagtgac attgtcaaca ggagtccaat tatgggcaga   3600
atctgctctc tgtgaccaaa agaggatgtg cactgcttca cgtgacagtg gtgaccttgc   3660
aatatagaaa aacttgggag ttattgaaca tcccctgggc ttacaagaaa cactgatgaa   3720
tgtaaaatca ggggacattt gaagatggca gaactgtctc cccttgtca cctacctctg   3780
atagaatgtc tttaatggta tcataatcat tttcacccat aatacacagt agcttcttct   3840
tactgtttgt aaatacattc tcccttggta tgtcacttta tatcccctgg ttctattaaa   3900
atatccatat atatttctat aaaaaaagtg tttgaccaaa gtaggtctgc agctatttca   3960
acttccttcc gtttccagaa agagctgtgg atattttact ggaaattaag aacttgctgc   4020
tgttttaata agatgtagta tattttctga ctacaggaga taaaatttca gtcaaaaaac   4080
cattttgaca gcaagtatct tctgagaaat tttgaaaagt aaatagatct cagtgtatct   4140
agtcacttaa atacatacac gggttcattt acttaaacct ttgactgcct gtattttttt   4200
caggtagcta gccaaattaa tgcataattt cagatgtaga agtagggttt gcgtgtgtgt   4260
gtgtgatcat actcaagagt ctaaaaacta gtttccttgt gttggaaatt taaaaggaaa   4320
aaaatcgtat ttcactgtgt tttcaattta tattttcaca actactttct ctctccagag   4380
ctttcatctg atatctcaca atgtatgata tacgtacaaa acacacagca agttttctat   4440
catgtccaac acattcaaca ctggtatacc tcctaccagc aagcctttaa aatgcattg    4500
tgtttgctta tttgttttgt tcaagggttc agtaagacct acaatgtttt gtatttcttg   4560
acttatttta ttagaaacat taaagatcac ttggtagtta gccacattga gaagtggtta   4620
```

```
tcattgttaa tgtggttaat gccaaaaagt ggttaatatt aataagactg tttccacacc   4680

ataggcaata atttcttaat ttaaaaaatc taagtatatt cctattgtac taaatatttt   4740

tcccaactgg aaagcacttg attgtacccg taagtgtttg agtgatgaca tgtgatgatt   4800

ttcagaaagt tgttgttttt gtttccatag cctgtttaag taggttgtaa gtttgaatag   4860

ttagacatgg aaattatttt ataagcacac acctaaagat atctttttag atgataaaat   4920

gtacaccccc ccatcaccaa cctcacaact tagaaaatct aagttgtttg atttctttgg   4980

gatttctttt gttgtgaaac actgcaaagc caatttttct ttataaaaat tcatagtaat   5040

cctgccaaat gtgcctattg ttaaagattt gcatgtgaag atcttaggga accactgttt   5100

gagttctaca agctcatgag agtttatttt tattataaga tgtttttaat ataaaagaat   5160

tatgtaactg atcactatat tacatcattt cagtgggcca ggaaaataga tgtcttgctg   5220

ttttcagtat tttcttaaga aattgctttt aaaacaaata attgttttac aaaaccaata   5280

attatccttt gaattttcat agactgactt tgcttttgac gtagaaattt tttttctcaa   5340

taaattatca ctttgagaaa tgaggcctgt acaaggctga taacctatat gtgatggaga   5400

tcacccaatg ccaagggcag aaagcaaacc tagttaaata ggtgagaaaa aaaataataa   5460

tcccagtgcc atttgtctgt gcaaagagaa ttaggagaga ggttaatgtt actttttttcc   5520

attttggaaa taattttaat caagtaactc aaatgtgaca aaatttattt ttattttttg   5580

tggttatatt cccaacaaca ttaaaaaata ctcgaggcat aaatgtagtt gtctcctact   5640

ctgcttctct tactatactc atacattttt aatatggttt atcaatgatt catgtttccc   5700

tcaaatagtg atggtttaca cctgtcatgg aaacaatcct agagagctca gagcaattaa   5760

accactattc catgctttta agtagttttc tccacctttt tcttatgagt ctcactagat   5820

tgactgagga atgtatgtct aaattcctgg agaagatgat atggattgga aactgaaatt   5880

cagagaaatg gagtgttcaa tagataccac gaattgtgaa caaagggaaa attctataca   5940

actcaatcta agtcagtcca ctttgacttc gtactgtctt tcacctttcc attgttgcat   6000

cttgaatttt ttaaaatgtc tagaattcag gatgctaggg gctacttctt taaaaaaaaa   6060

aaaaaaaaa                                                           6069
```

<210> SEQ ID NO 128
<211> LENGTH: 3318
<212> TYPE: DNA
<213> ORGANISM: Homo sapiens
<220> FEATURE:
<221> NAME/KEY: misc_feature
<223> OTHER INFORMATION: NM_002827

<400> SEQUENCE: 128

```
gtgatgcgta gttccggctg ccggttgaca tgaagaagca gcagcggcta gggcggcggt     60

agctgcaggg gtcggggatt gcagcgggcc tcggggctaa gagcgcgacg cggcctagag    120

cggcagacgg cgcagtgggc cgagaaggag gcgcagcagc cgccctggcc cgtcatggag    180

atggaaaagg agttcgagca gatcgacaag tccgggagct gggcggccat ttaccaggat    240

atccgacatg aagccagtga cttcccatgt agagtggcca agcttcctaa gaacaaaaac    300

cgaaataggt acagagacgt cagtcccttt gaccatagtc ggattaaact acatcaagaa    360

gataatgact atatcaacgc tagtttgata aaaatggaag aagcccaaag gagttacatt    420

cttacccagg gccctttgcc taacacatgc ggtcactttt gggagatggt gtgggagcag    480

aaaagcaggg gtgtcgtcat gctcaacaga gtgatggaga aaggttcgtt aaaatgcgca    540

caatactggc cacaaaaaga agaaaaagag atgatctttg aagacacaaa tttgaaatta    600
```

```
acattgatct ctgaagatat caagtcatat tatacagtgc gacagctaga attggaaaac    660
cttacaaccc aagaaactcg agagatctta catttccact ataccacatg gcctgacttt    720
ggagtccctg aatcaccagc ctcattcttg aactttcttt tcaaagtccg agagtcaggg    780
tcactcagcc cggagcacgg gcccgttgtg gtgcactgca gtgcaggcat cggcaggtct    840
ggaaccttct gtctggctga tacctgcctc ttgctgatgg acaagaggaa agacccttct    900
tccgttgata tcaagaaagt gctgttagaa atgaggaagt ttcggatggg gctgatccag    960
acagccgacc agctgcgctt ctcctacctg gctgtgatcg aaggtgccaa attcatcatg   1020
ggggactctt ccgtgcagga tcagtggaag gagctttccc acgaggacct ggagccccca   1080
cccgagcata tccccccacc tccccggcca cccaaacgaa tcctggagcc acacaatggg   1140
aaatgcaggg agttcttccc aaatcaccag tgggtgaagg aagagaccca ggaggataaa   1200
gactgcccca tcaaggaaga aaaaggaagc cccttaaatg ccgcacccta cggcatcgaa   1260
agcatgagtc aagacactga agttagaagt cgggtcgtgg ggggaagtct tcgaggtgcc   1320
caggctgcct ccccagccaa aggggagccg tcactgcccg agaaggacga ggaccatgca   1380
ctgagttact ggaagccctt cctggtcaac atgtgcgtgg ctacggtcct cacggccggc   1440
gcttacctct gctacaggtt cctgttcaac agcaacacat agcctgaccc tcctccactc   1500
cacctccacc cactgtccgc ctctgcccgc agagcccacg cccgactagc aggcatgccg   1560
cggtaggtaa gggccgccgg accgcgtaga gagccgggcc ccggacggac gttggttctg   1620
cactaaaacc catcttcccc ggatgtgtgt ctcacccctc atccttttac tttttgcccc   1680
ttccactttg agtaccaaat ccacaagcca tttttttgagg agagtgaaag agagtaccat   1740
gctggcggcg cagagggaag gggcctacac ccgtcttggg gctcgcccca cccagggctc   1800
cctcctggag catcccaggc gggcggcacg ccaacagccc ccccccttgaa tctgcaggga   1860
gcaactctcc actccatatt tatttaaaca attttttccc caaaggcatc catagtgcac   1920
tagcattttc ttgaaccaat aatgtattaa aatttttttga tgtcagcctt gcatcaaggg   1980
ctttatcaaa aagtacaata ataaatcctc aggtagtact gggaatggaa ggctttgcca   2040
tgggcctgct gcgtcagacc agtactggga aggaggacgg ttgtaagcag ttgttattta   2100
gtgatattgt gggtaacgtg agaagataga acaatgctat aatatataat gaacacgtgg   2160
gtatttaata agaaacatga tgtgagatta ctttgtcccg cttattctcc tccctgttat   2220
ctgctagatc tagttctcaa tcactgctcc cccgtgtgta ttagaatgca tgtaaggtct   2280
tcttgtgtcc tgatgaaaaa tatgtgcttg aaatgagaaa ctttgatctc tgcttactaa   2340
tgtgccccat gtccaagtcc aacctgcctg tgcatgacct gatcattaca tggctgtggt   2400
tcctaagcct gttgctgaag tcattgtcgc tcagcaatag ggtgcagttt tccaggaata   2460
ggcatttgcc taattcctgg catgacactc tagtgacttc ctggtgaggc ccagcctgtc   2520
ctggtacagc agggtcttgc tgtaactcag acattccaag ggtatgggaa gccatattca   2580
cacctcacgc tctggacatg atttagggaa gcagggacac cccccgcccc ccacctttgg   2640
gatcagcctc cgccattcca agtcaacact cttcttgagc agaccgtgat ttggaagaga   2700
ggcacctgct ggaaaccaca cttcttgaaa cagcctgggt gacggtcctt taggcagcct   2760
gccgccgtct ctgtcccggt tcaccttgcc gagagaggcg cgtctgcccc accctcaaac   2820
cctgtggggc ctgatggtgc tcacgactct tcctgcaaag ggaactgaag acctccacat   2880
taagtggctt tttaacatga aaaacacggc agctgtagct cccgagctac tctcttgcca   2940
gcattttcac attttgcctt tctcgtggta gaagccagta cagagaaatt ctgtggtggg   3000
```

```
aacattcgag gtgtcaccct gcagagctat ggtgaggtgt ggataaggct taggtgccag   3060

gctgtaagca ttctgagctg ggcttgttgt ttttaagtcc tgtatatgta tgtagtagtt   3120

tgggtgtgta tatatagtag catttcaaaa tggacgtact ggtttaacct cctatccttg   3180

gagagcagct ggctctccac cttgttacac attatgttag agaggtagcg agctgctctg   3240

ctatatgcct taagccaata tttactcatc aggtcattat tttttacaat ggccatggaa   3300

taaaccattt ttacaaaa                                                 3318
```

<210> SEQ ID NO 129
<211> LENGTH: 1973
<212> TYPE: DNA
<213> ORGANISM: Homo sapiens
<220> FEATURE:
<221> NAME/KEY: misc_feature
<223> OTHER INFORMATION: NM_002421

<400> SEQUENCE: 129

```
gggatattgg agtagcaaga ggctgggaag ccatcactta ccttgcactg agaaagaaga     60

caaaggccag tatgcacagc tttcctccac tgctgctgct gctgttctgg ggtgtggtgt    120

ctcacagctt cccagcgact ctagaaacac aagagcaaga tgtggactta gtccagaaat    180

acctggaaaa atactacaac ctgaagaatg atgggaggca agttgaaaag cggagaaata    240

gtggcccagt ggttgaaaaa ttgaagcaaa tgcaggaatt ctttgggctg aaagtgactg    300

ggaaaccaga tgctgaaacc ctgaaggtga tgaagcagcc cagatgtgga gtgcctgatg    360

tggctcagtt tgtcctcact gaggggaacc ctcgctggga gcaaacacat ctgacctaca    420

ggattgaaaa ttacacgcca gatttgccaa gagcagatgt ggaccatgcc attgagaaag    480

ccttccaact ctggagtaat gtcacacctc tgacattcac caaggtctct gagggtcaag    540

cagacatcat gatatctttt gtcaggggag atcatcggga caactctcct tttgatggac    600

ctggaggaaa tcttgctcat gcttttcaac caggcccagg tattggaggg gatgctcatt    660

ttgatgaaga tgaaaggtgg accaacaatt tcagagagta caacttacat cgtgttgcgg    720

ctcatgaact cggccattct cttggactct cccattctac tgatatcggg gctttgatgt    780

accctagcta caccttcagt ggtgatgttc agctagctca ggatgacatt gatggcatcc    840

aagccatata tggacgttcc caaaatcctg tccagcccat cggcccacaa accccaaaag    900

cgtgtgacag taagctaacc tttgatgcta taactacgat tcggggagaa gtgatgttct    960

ttaaagacag attctacatg cgcacaaatc ccttctaccc ggaagttgag ctcaatttca   1020

tttctgtttt ctggccacaa ctgccaaatg ggcttgaagc tgcttacgaa tttgccgaca   1080

gagatgaagt ccggtttttc aaagggaata agtactgggc tgttcaggga cagaatgtgc   1140

tacacggata ccccaaggac atctacagct cctttggctt ccctagaact gtgaagcata   1200

tcgatgctgc tctttctgag gaaaacactg gaaaaaccta cttctttgtt gctaacaaat   1260

actggaggta tgatgaatat aaacgatcta tggatccagg ttatcccaaa atgatagcac   1320

atgactttcc tggaattggc cacaaagttg atgcagtttt catgaaagat ggatttttct   1380

atttctttca tggaacaaga caatacaaat ttgatcctaa aacgaagaga attttgactc   1440

tccagaaagc taatagctgg ttcaactgca ggaaaaattg aacattacta atttgaatgg   1500

aaaacacatg gtgtgagtcc aaagaaggtg ttttcctgaa gaactgtcta ttttctcagt   1560

catttttaac ctctagagtc actgatacac agaatataat cttatttata cctcagtttg   1620

catatttttt tactatttag aatgtagccc tttttgtact gatataattt agttccacaa   1680
```

```
atggtgggta caaaaagtca agtttgtggc ttatggattc atataggcca gagttgcaaa   1740

gatcttttcc agagtatgca actctgacgt tgatcccaga gagcagcttc agtgacaaac   1800

atatcctttc aagacagaaa gagacaggag acatgagtct ttgccggagg aaaagcagct   1860

caagaacaca tgtgcagtca ctggtgtcac cctggatagg caagggataa ctcttctaac   1920

acaaaataag tgttttatgt ttggaataaa gtcaaccttg tttctactgt ttt          1973


<210> SEQ ID NO 130
<211> LENGTH: 2279
<212> TYPE: DNA
<213> ORGANISM: Homo sapiens
<220> FEATURE:
<221> NAME/KEY: misc_feature
<223> OTHER INFORMATION: NM_001752

<400> SEQUENCE: 130

tgcctgctga gggtggagac ccacgagccg aggcctcctg cagtgttctg cacagcaaac     60

cgcacgctat ggctgacagc cgggatcccg ccagcgacca gatgcagcac tggaaggagc    120

agcgggccgc gcagaaagct gatgtcctga ccactggagc tggtaaccca gtaggagaca    180

aacttaatgt tattacagta gggccccgtg ggcccccttct tgttcaggat gtggttttca    240

ctgatgaaat ggctcatttt gaccgagaga gaattcctga gagagttgtg catgctaaag    300

gagcaggggc ctttggctac tttgaggtca cacatgacat taccaaatac tccaaggcaa    360

aggtatttga gcatattgga aagaagactc ccatcgcagt tcggttctcc actgttgctg    420

gagaatcggg ttcagctgac acagttcggg accctcgtgg gtttgcagtg aaattttaca    480

cagaagatgg taactgggat ctcgttggaa ataacacccc cattttcttc atcagggatc    540

ccatattgtt tccatctttt atccacagcc aaaagagaaa tcctcagaca catctgaagg    600

atccggacat ggtctgggac ttctggagcc tacgtcctga gtctctgcat caggtttctt    660

tcttgttcag tgatcggggg attccagatg gacatcgcca catgaatgga tatggatcac    720

atactttcaa gctggttaat gcaaatgggg aggcagttta ttgcaaattc cattataaga    780

ctgaccaggg catcaaaaac ctttctgttg aagatgcggc gagactttcc caggaagatc    840

ctgactatgg catccgggat ctttttaacg ccattgccac aggaaagtac ccctcctgga    900

ctttttacat ccaggtcatg acatttaatc aggcagaaac ttttccattt aatccattcg    960

atctcaccaa ggtttggcct cacaaggact accctctcat cccagttggt aaactggtct   1020

taaaccggaa tccagttaat tactttgctg aggttgaaca gatagccttc gacccaagca   1080

acatgccacc tggcattgag gccagtcctg acaaaatgct tcagggccgc ctttttgcct   1140

atcctgacac tcaccgccat cgcctgggac ccaattatct tcatatacct gtgaactgtc   1200

cctaccgtgc tcgagtggcc aactaccagc gtgatggccc gatgtgcatg caggacaatc   1260

agggtggtgc tccaaattac taccccaaca gctttggtgc tccggaacaa cagccttctg   1320

ccctggagca cagcatccaa tattctggag aagtgcggag attcaacact gccaatgatg   1380

ataacgttac tcaggtgcgg gcattctatg tgaacgtgct gaatgaggaa cagaggaaac   1440

gtctgtgtga gaacattgcc ggccacctga aggatgcaca aattttcatc cagaagaaag   1500

cggtcaagaa cttcactgag gtccaccctg actacgggag ccacatccag gctcttctgg   1560

acaagtacaa tgctgagaag cctaagaatg cgattcacac ctttgtgcag tccggatctc   1620

acttggcggc aagggagaag gcaaatctgt gaggccgggg ccctgcacct gtgcagcgaa   1680

gcttagcgtt catccgtgta acccgctcat cactggatga agattctcct gtgctagatg   1740

tgcaaatgca agctagtggc ttcaaaatag agaatcccac tttctatagc agattgtgta   1800
```

```
acaattttaa tgctatttcc ccaggggaaa atgaaggtta ggatttaaca gtcatttaaa   1860

aaaaaaattt gttttgacgg atgattggat tattcattta aaatgattag aaggcaagtt   1920

tctagctaga aatatgattt tatttgacaa aatttgttga aattatgtat gtttacatat   1980

cacctcatgg cctattatat taaaatatgg ctataaatat ataaaaagaa aagataaaga   2040

tgatctactc agaaattttt atttttctaa ggttctcata ggaaaagtac atttaataca   2100

gcagtgtcat cagaagataa cttgagcacc gtcatggctt aatgtttatt cctgataata   2160

attgatcaaa ttcatttttt tcactggagt tacattaatg ttaattcagc actgatttca   2220

caacagatca atttgtaatt gcttacattt ttacaataaa taatctgtac gtaagaaca    2279


<210> SEQ ID NO 131
<211> LENGTH: 2438
<212> TYPE: DNA
<213> ORGANISM: Homo sapiens
<220> FEATURE:
<221> NAME/KEY: misc_feature
<223> OTHER INFORMATION: NM_016155

<400> SEQUENCE: 131

ccggcggggg cgccgcggag agcggagggc gccgggctgc ggaacgcgaa gcggagggcg     60

cgggaccctg cacgccgccc gcgggcccat gtgagcgcca tgcggcgccg cgcagcccgg    120

ggacccggcc cgccgccccc agggcccgga ctctcgcggt tgccgctgct gccgctgccg    180

ctgctgctgc tgctggcgct ggggacccgc gggggctgcg ccgcgcccgc acccgcgccg    240

cgcgccgagg acctcagcct gggagtggag tggctaagca ggttcggtta cctgcccccg    300

gctgacccca caacagggca gctgcagacg caagaggagc tgtctaaggc catcacagcc    360

atgcagcagt ttggtggcct ggaggccacc ggcatcctgg acgaggccac cctggccctg    420

atgaaaaccc cacgctgctc cctgccagac ctccctgtcc tgacccaggc tcgcaggaga    480

cgccaggctc cagcccccac caagtggaac aagaggaacc tgtcgtggag ggtccggacg    540

ttcccacggg actcaccact ggggcacgac acggtgcgtg cactcatgta ctacgccctc    600

aaggtctgga gcgacattgc gcccctgaac ttccacgagg tggcgggcag caccgccgac    660

atccagatcg acttctccaa ggccgaccat aacgacggct accccttcga cggccccggc    720

ggcaccgtgg cccacgcctt cttccccggc caccaccaca ccgccgggga cacccacttt    780

gacgatgacg aggcctggac cttccgctcc tcggatgccc acgggatgga cctgtttgca    840

gtggctgtcc acgagtttgg ccacgccatt gggttaagcc atgtggccgc tgcacactcc    900

atcatgcggc cgtactacca gggcccggtg ggtgacccgc tgcgctacgg gctcccctac    960

gaggacaagg tgcgcgtctg gcagctgtac ggtgtgcggg agtctgtgtc tcccacggcg   1020

cagcccgagg agcctcccct gctgccggag cccccagaca accggtccag cgccccgccc   1080

aggaaggacg tgccccacag atgcagcact cactttgacg cggtggccca gatccgcggt   1140

gaagctttct tcttcaaagg caagtacttc tggcggctga cgcgggaccg gcacctggtg   1200

tccctgcagc cggcacagat gcaccgcttc tggcggggcc tgccgctgca cctggacagc   1260

gtggacgccg tgtacgagcg caccagcgac cacaagatcg tcttctttaa aggagacagg   1320

tactgggtgt tcaaggacaa taacgtagag gaaggatacc cgcgccccgt ctccgacttc   1380

agcctcccgc ctggcggcat cgacgctgcc ttctcctggg cccacaatga caggacttat   1440

ttctttaagg accagctgta ctggcgctac gatgaccaca cgaggcacat ggaccccggc   1500

taccccgccc agagcccccct gtggaggggt gtccccagca cgctggacga cgccatgcgc   1560
```

tggtccgacg gtgcctccta cttcttccgt ggccaggagt actggaaagt gctggatggc 1620
gagctggagg tggcacccgg gtacccacag tccacggccc gggactggct ggtgtgtgga 1680
gactcacagg ccgatggatc tgtggctgcg ggcgtggacg cggcagaggg gccccgcgcc 1740
cctccaggac aacatgacca gagccgctcg gaggacggtt acgaggtctg ctcatgcacc 1800
tctggggcat cctctccccc gggggcccca ggcccactgg tggctgccac catgctgctg 1860
ctgctgccgc cactgtcacc aggcgccctg tggacagcgg cccaggccct gacgctatga 1920
cacacagcgc gagcccatga gaggacagag gcggtgggac agcctggcca cagagggcaa 1980
ggactgtgcc ggagtccctg ggggaggtgc tggcgcggga tgaggacggg ccaccctggc 2040
accggaaggc cagcagaggg cacggcccgc cagggctggg caggctcagg tggcaaggac 2100
ggagctgtcc cctagtgagg gactgtgttg actgacgagc cgaggggtgg ccgctccaga 2160
agggtgccca gtcaggccgc accgccgcca gcctcctccg gccctggagg gagcatctcg 2220
ggctgggggc ccacccctct ctgtgccggc gccaccaacc ccacccacac tgctgcctgg 2280
tgctcccgcc ggcccacagg gcctccgtcc ccaggtcccc agtggggcag ccctccccac 2340
agacgagccc cccacatggt gccgcggcac gtcccccctg tgacgcgttc cagaccaaca 2400
tgacctctcc ctgctttgta aaaaaaaaaa aaaaaaaa 2438

<210> SEQ ID NO 132
<211> LENGTH: 1356
<212> TYPE: DNA
<213> ORGANISM: Homo sapiens
<220> FEATURE:
<221> NAME/KEY: misc_feature
<223> OTHER INFORMATION: U94332

<400> SEQUENCE: 132
gtatatataa cgtgatgagc gtacgggtgc ggagacgcac cggagcgctc gcccagccgc 60
cgyctccaag cccctgaggt ttccggggac cacaatgaac aagttgctgt gctgcgcgct 120
cgtgtttctg gacatctcca ttaagtggac cacccaggaa acgtttcctc caaagtacct 180
tcattatgac gaagaaacct ctcatcagct gttgtgtgac aaatgtcctc ctggtaccta 240
cctaaaacaa cactgtacag caaagtggaa gaccgtgtgc gccccttgcc ctgaccacta 300
ctacacagac agctggcaca ccagtgacga gtgtctatac tgcagccccg tgtgcaagga 360
gctgcagtac gtcaagcagg agtgcaatcg cacccacaac cgcgtgtgcg aatgcaagga 420
agggcgctac cttgagatag agttctgctt gaaacatagg agctgccctc ctggatttgg 480
agtggtgcaa gctggaaccc cagagcgaaa tacagtttgc aaaagatgtc cagatgggtt 540
cttctcaaat gagacgtcat ctaaagcacc ctgtagaaaa cacacaaatt gcagtgtctt 600
tggtctcctg ctaactcaga aaggaaatgc aacacacgac aacatatgtt ccggaaacag 660
tgaatcaact caaaaatgtg gaatagatgt taccctgtgt gaggaggcat tcttcaggtt 720
tgctgttcct acaaagttta cgcctaactg gcttagtgtc ttggtagaca atttgcctgg 780
caccaaagta aacgcagaga gtgtagagag gataaaacgg caacacagct cacaagaaca 840
gactttccag ctgctgaagt tatggaaaca tcaaaacaaa gcccaagata tagtcaagaa 900
gatcatccaa gatattgacc tctgtgaaaa cagcgtgcag cggcacattg gacatgctaa 960
cctcaccttc gagcagcttc gtagcttgat ggaaagctta ccgggaaaga aagtgggagc 1020
agaagacatt gaaaaaacaa taaaggcatg caaacccagt gaccagatcc tgaagctgct 1080
cagtttgtgg cgaataaaaa atggcgacca agacaccttg aagggcctaa tgcacgcact 1140
aaagcactca aagacgtacc actttcccaa aactgtcact cagagtctaa agaagaccat 1200

-continued

```
caggttcctt cacagcttca caatgtacaa attgtatcag aagttatttt tagaaatgat   1260

aggtaaccag gtccaatcag taaaaataag ctgcttataa ctggaaatgg ccattgagct   1320

gtttcctcac aattggcgag atcccatgga tgataa                             1356
```